United States Patent
Loumaye et al.

(10) Patent No.: US 11,980,621 B2
(45) Date of Patent: May 14, 2024

(54) GONADOTROPIN-RELEASING HORMONE ANTAGONIST DOSING REGIMENS FOR THE TREATMENT OF ENDOMETRIOSIS

(71) Applicant: ObsEva S.A., Plan-les-Ouates (CH)

(72) Inventors: Ernest Loumaye, Cologny (CH); Jean-Pierre Gotteland, Geneva (CH)

(73) Assignee: Kissei Pharmaceutical Co., Ltd., Matsumoto (JP)

( * ) Notice: Subject to any disclaimer, the term of this patent is extended or adjusted under 35 U.S.C. 154(b) by 646 days.

(21) Appl. No.: 16/619,776

(22) PCT Filed: Jun. 5, 2018

(86) PCT No.: PCT/EP2018/064768
§ 371 (c)(1),
(2) Date: Dec. 5, 2019

(87) PCT Pub. No.: WO2018/224498
PCT Pub. Date: Dec. 13, 2018

(65) Prior Publication Data
US 2020/0138819 A1 May 7, 2020

Related U.S. Application Data

(60) Provisional application No. 62/515,268, filed on Jun. 5, 2017.

(51) Int. Cl.
*A61K 31/519* (2006.01)
*A61K 38/09* (2006.01)
*A61P 15/00* (2006.01)

(52) U.S. Cl.
CPC ............ *A61K 31/519* (2013.01); *A61K 38/09* (2013.01); *A61P 15/00* (2018.01)

(58) Field of Classification Search
CPC ........ A61K 31/519; A61K 38/09; A61P 15/00
See application file for complete search history.

(56) References Cited

U.S. PATENT DOCUMENTS

| 9,040,693 | B2 * | 5/2015 | Ohno ..................... A61P 25/20 544/278 |
| 9,169,266 | B2 | 10/2015 | Jo et al. |
| 9,737,539 | B2 | 8/2017 | Jo et al. |
| 10,016,433 | B2 | 7/2018 | Jo et al. |
| 2017/0056403 | A1 | 3/2017 | Goss et al. |

(Continued)

FOREIGN PATENT DOCUMENTS

| CA | 3025760 A1 | 2/2018 |
| EP | 2535342 A1 | 12/2012 |

(Continued)

OTHER PUBLICATIONS

Franke et al., Fertility and Sterility, 2000, 74(3): 534-539 (Year: 2000).*

(Continued)

*Primary Examiner* — San Ming R Hui
(74) *Attorney, Agent, or Firm* — Clark & Elbing LLP

(57) ABSTRACT

The invention provides methods of treating endometriosis in a patient by administration of a gonadotropin-releasing hormone (GnRH) antagonist, for instance, according to dosing regimens predicated on the patient's level of anti-Müllerian hormone (AMH) or β17-estradiol (E2).

20 Claims, 3 Drawing Sheets

(56) References Cited

U.S. PATENT DOCUMENTS

| | | |
|---|---|---|
| 2019/0134038 A1 | 5/2019 | Jo et al. |
| 2019/0175600 A1 | 6/2019 | Dan et al. |
| 2020/0138819 A1 | 5/2020 | Loumaye et al. |
| 2020/0179390 A1 | 6/2020 | Loumaye et al. |

FOREIGN PATENT DOCUMENTS

| | | |
|---|---|---|
| EP | 3498280 A1 | 6/2019 |
| JP | 2003-525249 A | 8/2003 |
| JP | 2016-513708 A | 5/2016 |
| WO | WO-2007/046392 A1 | 4/2007 |
| WO | WO-2011/099507 A1 | 8/2011 |
| WO | WO-2014/042176 A1 | 3/2014 |
| WO | WO-2014/143669 A1 | 9/2014 |
| WO | WO-2018/030317 A1 | 2/2018 |
| WO | WO-2018/060501 A2 | 4/2018 |
| WO | WO-2018/224497 A1 | 12/2018 |
| WO | WO-2018/224498 A1 | 12/2018 |
| WO | WO-2020/094698 A2 | 5/2020 |

OTHER PUBLICATIONS

Struthers et al., J Clin Endocrinol Metab. Feb. 2009; 94(2): 545-551 (Year: 2009).*

U.S. Appl. No. 17/291,192, Loumaye et al.

U.S. Appl. No. 17/289,418, Gotteland et al.

Abbvie, "AbbVie Announces Positive Topline Results from Phase 3 Extension Study Evaluating Investigational Elagolix in Women with Uterine Fibroids," dated Aug. 22, 2018, <retrieved from https://news.abbvie.com/news/abbvie-announces-positive-topline-results-from-phase-3-extension-study-evaluating-investigational-elagolix-in-women-with-uterine-fibroids.htm> on Oct. 1, 2020 (6 pages).

Lewis et al., "A Comprehensive Review of the Pharmacologic Management of Uterine Leiomyoma," Biomed Res Int. 2018:2414609 (2018) (11 pages).

International Search Report and Written Opinion for International Application No. PCT/EP2019/080362, dated Jul. 7, 2020 (20 pages).

Invitation to Pay Additional Fees for International Application No. PCT/EP2019/079448, dated Feb. 12, 2020 (14 pages).

International Search Report and Written Opinion for International Application No. PCT/EP2019/079448, dated May 19, 2020 (20 pages).

Communication pursuant to Article 94(3) for European Patent Application No. 18731976.9, dated May 17, 2021 (6 pages).

ObsEva, "ObsEva SA Announces the Completion of a Phase 1 PK/PD Clinical Trial Evaluating Different Doses of OBE2109 and Add-Back Therapy," dated Jun. 7, 2017, retrieved on Jul. 28, 2021 (5 pages).

ObsEva, "Building a Leader by Innovating Women's Reproductive Health and Pregnancy Therapeutics," dated Nov. 1, 2017, retrieved on Jul. 28, 2021 (35 pages).

"Late-Stage Women's Health Co. w/ Potentially Best-in-Class Lead Asset; Outperform, $27 TP," ObsEva S.A., <https://research-doc.credit-suisse.com/docView?language=ENG&format=PDF&sourceid=csplusresearchcp&document_id=1071589801&serialid=w5tUz5ckZojLgop%2BFQZCZvq2JSqlpv%2FqYEO7ASCs3s0%3D>, (Feb. 21, 2017) (44 pages).

WHO Drug Information, "International Nonproprietary Names for Pharmaceutical Substances (INN)," vol. 31, No. 4, published Jan. 19, 2018 (36 pages).

"United States Securities Exchange Commission—Annual Report Persuant to Section 13 or 15(d) of the Securities Exchange Act of 1934—Myovant Sciences Ltd.," Published Jun. 7, 2018, (40 pages).

"Informed Consent and Authorization Form," ObsEva S.A., <https://proslc.com/wp-content/uploads/2013/06/EDEWEISS-ENDO-ICF.pdf>, (2016) (21 pages).

U.S. Appl. No. 16/619,702, Loumaye et al.

Donnez et al., "Partial suppression of estradiol: a new strategy in endometriosis management?," Fertil Steril. 107(3):568-70 (2017).

Hamdine et al., "Ovarian response prediction in GnRH antagonist treatment for IVF using anti-Müllerian hormone," Hum Reprod. 30(1):170-8 (2015).

International Search Report and Written Opinion for International Application No. PCT/EP2018/064768, dated Oct. 17, 2018 (20 pages).

Signorile et al., "A tissue specific magnetic resonance contrast agent, Gd-AMH, for diagnosis of stromal endometriosis lesions: a phase I study," J Cell Physiol. 230(6):1270-5 (2015).

ObsEva S.A., "Annual Report 2016," <http://investors.obseva.com/phoenix.zhtml?c=254482&p=irol-reportsannual>, (114 pages).

Archer et al., "Elagolix for the management of heavy menstrual bleeding associated with uterine fibroids: results from a phase 2a proof-of-concept study," Fertil Steril. 108(1):152-160.e4 (includes supplemental content) (2017) (13 pages).

"ObsEva SA Announces the Completion of a Phase 1 PK/PD Clinical Trial Evaluating Different Doses of OBE2109 and Add-Back Therapy," ObsEva, retrieved from, <http://www.obseva.com/news/obseva-sa-announces-the-completion-of-a-phase-1-pk-pd-clinical-trial-evaluating-different-doses-of-obe2109-and-add-back-therapy> on Mar. 8, 2018 (2017) (7 pages).

"Building a Leader by Innovating Women's Reproductive Health and Pregnancy Therapeutics," ObsEva, Nov. 2017, <http://www.jefferies.com/CMSFiles/Jefferies.com/files/ObsEva.pdf> (35 pages).

International Search Report and Written Opinion for International Application No. PCT/EP2018/064767, dated Aug. 24, 2018 (16 pages).

"Metrofibroma," Medical Dictionary, <https://medical-dictionary.thefreedictionary.com/metrofibroma>, retrieved on Nov. 3, 2021 (1 page).

"Fibroma," Medical Dictionary, <https://medical-dictionary.thefreedictionary.com/fibroma>, retrieved on Nov. 3, 2021 (2 pages).

PubChem, "Compound Summary for CID 5757, Estradiol," <https://pubchem.ncbi.nlm.nih.gov/compound/Estradiol>, retrieved on Feb. 23, 2022 (64 pages).

Pohl et al., "Gonadotropin-Releasing Hormone Receptor Antagonist Mono- and Combination Therapy With Estradiol/Norethindrone Acetate Add-Back: Pharmacodynamics and Safety of OBE2109," J Clin Endocrinol Metab. 103(2):497-504 (Feb. 2018).

Franke et al., "Gonadotropin-releasing hormone agonist plus "add-back" hormone replacement therapy for treatment of endometriosis: a prospective, randomized, placebo-controlled, double-blind trial," Fertil Steril. 74(3):534-9 (2000).

Struthers et al., "Suppression of gonadotropins and estradiol in premenopausal women by oral administration of the nonpeptide gonadotropin-releasing hormone antagonist elagolix," J Clin Endocrinol Metab. 94(2):545-51 (2009) (14 pages).

U.S. Appl. No. 17/291,192, filed May 4, 2021 (270 pages).

WHO, "Proposed INN: List 118," WHO Drug Inf. 31(4):719-54 (2017).

Chen et al., "Discovery of sodium R-(+)-4-{2-[5-(2-fluoro-3-methoxyphenyl)-3-(2-fluoro-6-[trifluoromethyl]benzyl)-4-methyl-2,6-dioxo-3,6-dihydro-2H-pyrimidin-1-yl]-1-phenylethylamino} butyrate (elagolix), a potent and orally available nonpeptide antagonist of the human gonadotropin-releasing hormone receptor" J Med Chem. 51(23):7478-85. (Dec. 2008).

Donnez et al., "Linzagolix with and without hormonal add-back therapy for the treatment of symptomatic uterine fibroids: two randomised, placebo-controlled, phase 3 trials," Lancet. 400(10356):896-907 (Sep. 17, 2022).

Donnez et al., "Treatment of endometriosis-associated pain with linzagolix, an oral gonadotropin-releasing hormone-antagonist: a randomized clinical trial," Fertil Steril. 114(1):44-55 (Jul. 2020).

Rafique et al., "Medical Management of Endometriosis," Clin Obstet Gynecol. 60(3):485-496 (Sep. 2017).

Taylor et al., "Treatment of Endometriosis-Associated Pain with Elagolix, an Oral GnRH Antagonist," N Engl J Med. 377(1): 28-40, S1-S41 (includes supplemental content) (May 2017) (55 pages).

(56) References Cited

OTHER PUBLICATIONS

Donnez et al., "Profile of Linzagolix in the Management of Endometriosis, Including Design, Development and Potential Place in Therapy: A Narrative Review," Drug Des Devel Ther. 17:369-380 (Feb. 2023).

Küpker et al., "Use of GnRH antagonists in the treatment of endometriosis," Reprod Biomed Online. 5(1):12-16 (2002).

* cited by examiner

GONADOTROPIN-RELEASING HORMONE ANTAGONIST DOSING REGIMENS FOR THE TREATMENT OF ENDOMETRIOSIS

FIELD OF THE INVENTION

The invention relates to methods of determining dosing regimens for gonadotropin-releasing hormone antagonists for the treatment of endometriosis.

BACKGROUND OF THE INVENTION

Endometriosis is an estrogen-dependent gynecological condition, characterized by the presence of endometrial-like tissue outside the uterus, and is one of the most common sex hormone-dependent diseases. The condition is predominantly observed in women in their reproductive years and disappears spontaneously after menopause. A chronic inflammatory reaction induced by the ectopic endometrial cells, endometriosis may result in infertility and a variety of pain symptoms including dysmenorrhea, dyspareunia, chronic pelvic pain, dysuria, and dyschezia, among others.

A principal objective in treating endometriosis is achieving symptomatic relief. Treatment options for women with endometriosis-associated pain are diverse and include analgesic therapies, hormonal therapies, conservative or minimal invasive surgery, or a combination of these treatment options. Hormonal therapies aim at inhibition of ovulation, prevention of cyclic endometrium growth, and abolition of menstruation through achievement of a stable steroid hormone milieu. These strategies are predicated on the concept that the response of the eutopic and ectopic endometrium to steroid hormones is substantially similar.

Combined oral contraceptives (COCs), although not currently approved for the treatment of endometriosis-associated pain, are often used as initial therapy. Their intake results in anovulation, reduction of menstrual blood flow, decidualization of endometriotic lesions, attenuation of cell proliferation, and enhanced apoptosis in the endometrium. However, over time many women taking COCs no longer experience adequate pain relief and often require second-line therapy.

Progestin monotherapy can be efficacious for the reduction in endometriosis-associated pain as it induces anovulation and a hypoestrogenic state via suppression of pituitary gonadotropin release. Progestins also exert direct effects on the endometrium, causing decidualization of eutopic and ectopic endometrium leading to atrophy of the endometriotic implants. However, progestin monotherapy is often associated with breakthrough bleeding, alterations in mood, weight gain, and breast tenderness.

Other therapies with proven efficacy for the treatment of endometriosis-associated pain are often limited by undesirable side effects. For example, GnRH agonists induce a constant stimulation of the GnRH receptor at the pituitary level, thus desensitizing this receptor and ultimately causing suppression of ovulation and reduced serum estrogen levels. The use of GnRH receptor agonists is thus associated with significant hypoestrogenic side effects. Short-term effects include menopausal symptoms such as hot flashes, vaginal dryness, loss of libido, and emotional lability, and their long-term use is limited by substantial bone mineral density (BMD) reduction.

GnRH antagonists represent a therapeutic modality for the treatment of endometriosis that enables dose-dependent control of β17-estradiol (E2) levels. There remains a need for improved GnRH antagonist dosing regimens capable of reducing endometriosis implants and endometriosis-associated pain without inducing hypo-estrogenic side effects, such as hot flashes and BMD loss, as well as methods of determining such dosing schedules on the basis of the concentration of one or more endogenous hormones in a patient.

SUMMARY OF THE INVENTION

The invention provides compositions and methods for dosing a patient with a gonadotropin-releasing hormone (GnRH) receptor antagonist for the treatment of endometriosis based on the level of one or more endogenous substances within the patient. In some embodiments of the invention, GnRH antagonist dosing regimens are determined by analyzing the concentration of anti-Müllerian hormone (AMH) in a sample isolated from the patient. In some embodiments, GnRH antagonist dosing regimens are determined by analyzing the concentration of β17-estradiol (E2) in a sample isolated from the patient. The GnRH antagonist may be a thieno[3,4d]pyrimidine derivative or variant, such as 3-[2-fluoro-5-(2,3-difluoro-6-methoxybenzyloxy)4-methoxyphenyl]-2,4-dioxo-1,2,3,4-tetrahydrothieno[3,4d]pyrimidine-5-carboxylic acid or the choline salt thereof. In some embodiments, the GnRH antagonist is elagolix, relugolix, ASP-1707, SKI2670, BAY-784, or a derivative or variant thereof, among others.

In a first aspect, the invention features a method of treating endometriosis in a patient (e.g., a female human patient, such as a premenopausal female human patient). In another aspect, the invention features a method of reducing the concentration of E2, follicle-stimulating hormone (FSH), and/or luteinizing hormone (LH) in the blood of a patient (e.g., a female human patient, such as a premenopausal female human patient). In another aspect, the invention features a method of reducing pain (e.g., endometriosis-associated pain) in a patient (e.g., a female human patient, such as a premenopausal female human patient).

In any of the above aspects of the invention, the method may include the step of determining the concentration of AMH in a sample (e.g., a blood sample) isolated from the patient. In some embodiments, the concentration of AMH in a sample (e.g., a blood sample) isolated from the patient has previously been determined. The method may include:
a. comparing the concentration of AMH to an AMH reference range; and
b. administering a higher quantity (e.g., a higher daily dosage or an elevated dosing frequency) of a GnRH antagonist to the patient if the concentration of AMH in the sample isolated from the patient is above the AMH reference range;
c. administering a lower quantity (e.g., a lower daily dosage or a reduced dosing frequency) of a GnRH antagonist to the patient if the concentration of AMH in the sample isolated from the patient is below the AMH reference range; or
d. administering an intermediate quantity (e.g., intermediate daily dosage or intermediate dosing frequency) of a GnRH antagonist to the patient if the concentration of AMH in the sample isolated from the patient is within the AMH reference range.

In some embodiments, the method includes determining that the concentration of AMH in the sample isolated from the patient is greater than an AMH reference range, and may further include administering a higher quantity (e.g., a higher daily dosage or an elevated dosing frequency) of a GnRH antagonist to the patient accordingly.

In some embodiments, the method includes determining that the concentration of AMH in the sample isolated from the patient is less than an AMH reference range, and may further include administering a lower quantity (e.g., a lower daily dosage or a reduced dosing frequency) of a GnRH antagonist to the patient accordingly.

In some embodiments, the method includes determining that the concentration of AMH in the sample isolated from the patient is within an AMH reference range, and may further include administering an intermediate quantity (e.g., an intermediate daily dosage or an intermediate dosing frequency) of a GnRH antagonist to the patient accordingly.

In some embodiments, the method includes administering from 5 to 700 mg/day of a GnRH antagonist to the patient if the concentration of AMH in the sample isolated from the patient is above the AMH reference range.

For instance, in some embodiments, the method includes administering from 10 to 600 mg/day, from 20 to 590 mg/day, from 30 to 580 mg/day, from 40 to 570 mg/day, from 50 to 560 mg/day, from 60 to 550 mg/day, from 70 to 540 mg/day, from 80 to 530 mg/day, from 90 to 520 mg/day, from 100 to 510 mg/day, or from 110 to 500 mg/day (e.g., 5 mg/day, 10 mg/day, 15 mg/day, 20 mg/day, 25 mg/day, 30 mg/day, 35 mg/day, 40 mg/day, 45 mg/day, 50 mg/day, 55 mg/day, 60 mg/day, 65 mg/day, 70 mg/day, 75 mg/day, 80 mg/day, 85 mg/day, 90 mg/day, 95 mg/day, 100 mg/day, 105 mg/day, 110 mg/day, 115 mg/day, 120 mg/day, 125 mg/day, 130 mg/day, 135 mg/day, 140 mg/day, 145 mg/day, 150 mg/day, 155 mg/day, 160 mg/day, 165 mg/day, 170 mg/day, 175 mg/day, 180 mg/day, 185 mg/day, 190 mg/day, 195 mg/day, 200 mg/day, 205 mg/day, 210 mg/day, 215 mg/day, 220 mg/day, 225 mg/day, 230 mg/day, 235 mg/day, 240 mg/day, 245 mg/day, 250 mg/day, 255 mg/day, 260 mg/day, 265 mg/day, 270 mg/day, 275 mg/day, 280 mg/day, 285 mg/day, 290 mg/day, 295 mg/day, 300 mg/day, 305 mg/day, 310 mg/day, 315 mg/day, 320 mg/day, 325 mg/day, 330 mg/day, 335 mg/day, 340 mg/day, 345 mg/day, 350 mg/day, 355 mg/day, 360 mg/day, 365 mg/day, 370 mg/day, 375 mg/day, 380 mg/day, 385 mg/day, 390 mg/day, 395 mg/day, 400 mg/day, 405 mg/day, 410 mg/day, 415 mg/day, 420 mg/day, 425 mg/day, 430 mg/day, 435 mg/day, 440 mg/day, 445 mg/day, 450 mg/day, 455 mg/day, 460 mg/day, 465 mg/day, 470 mg/day, 475 mg/day, 480 mg/day, 485 mg/day, 490 mg/day, 495 mg/day, 500 mg/day, 505 mg/day, 510 mg/day, 515 mg/day, 520 mg/day, 525 mg/day, 530 mg/day, 535 mg/day, 540 mg/day, 545 mg/day, 550 mg/day, 555 mg/day, 560 mg/day, 565 mg/day, 570 mg/day, 575 mg/day, 580 mg/day, 585 mg/day, 590 mg/day, 595 mg/day, 600 mg/day, 605 mg/day, 610 mg/day, 615 mg/day, 620 mg/day, 625 mg/day, 630 mg/day, 635 mg/day, 640 mg/day, 645 mg/day, 650 mg/day, 655 mg/day, 660 mg/day, 665 mg/day, 670 mg/day, 675 mg/day, 680 mg/day, 685 mg/day, 690 mg/day, 695 mg/day, or 700 mg/day) of a GnRH antagonist to the patient if the concentration of AMH in the sample isolated from the patient is above the AMH reference range.

In some embodiments, the method includes administering more than 10 mg/day of a GnRH antagonist to the patient if the concentration of AMH in the sample isolated from the patient is above the AMH reference range. For instance, the method may include administering more than 10 mg/day of ASP-1707 to the patient if the concentration of AMH in the sample isolated from the patient is above the AMH reference range.

In some embodiments, the method includes administering more than 40 mg/day of a GnRH antagonist to the patient if the concentration of AMH in the sample isolated from the patient is above the AMH reference range. For instance, the method may include administering more than 40 mg/day of relugolix to the patient if the concentration of AMH in the sample isolated from the patient is above the AMH reference range.

In some embodiments, the method includes administering from 75 mg/day to 200 mg/day of a GnRH antagonist to the patient if the concentration of AMH in the sample isolated from the patient is above the AMH reference range. For instance, the method may include administering 75 mg/day, 100 mg/day, or 200 mg/day of a thieno[3,4d]pyrimidine derivative or variant, such as 3-[2-fluoro-5-(2,3-difluoro-6-methoxybenzyloxy)4-methoxyphenyl]-2,4-dioxo-1,2,3,4-tetrahydrothieno[3,4d]pyrimidine-5-carboxylic acid or the choline salt thereof to the patient if the concentration of AMH in the sample isolated from the patient is above the AMH reference range.

In some embodiments, the method includes administering more than 150 mg/day of a GnRH antagonist to the patient if the concentration of AMH in the sample isolated from the patient is above the AMH reference range. For instance, the method may include administering more than 150 mg/day of elagolix to the patient if the concentration of AMH in the sample isolated from the patient is above the AMH reference range. In some embodiments, the method includes administering more than 400 mg/day of a GnRH antagonist to the patient if the concentration of AMH in the sample isolated from the patient is above the AMH reference range. For instance, the method may include administering more than 400 mg/day of elagolix to the patient if the concentration of AMH in the sample isolated from the patient is above the AMH reference range.

In some embodiments, the method includes administering from 5 to 400 mg/day of a GnRH antagonist to the patient if the concentration of AMH in the sample isolated from the patient is below the AMH reference range.

For instance, in some embodiments, the method includes administering from 5 to 190 mg/day, from 15 to 180 mg/day, from 35 to 170 mg/day, from 50 to 160 mg/day, from 60 to 150 mg/day, from 70 to 140 mg/day, from 80 to 130 mg/day, from 90 to 120 mg/day, from 100 to 110 mg/day, from 200 to 400 mg/day, from 225 to 375 mg/day, from 250 to 350 mg/day, or from 275 to 325 mg/day (e.g., 5 mg/day, 10 mg/day, 15 mg/day, 20 mg/day, 25 mg/day, 30 mg/day, 35 mg/day, 40 mg/day, 45 mg/day, 50 mg/day, 55 mg/day, 60 mg/day, 65 mg/day, 70 mg/day, 75 mg/day, 80 mg/day, 85 mg/day, 90 mg/day, 95 mg/day, 100 mg/day, 105 mg/day, 110 mg/day, 115 mg/day, 120 mg/day, 125 mg/day, 130 mg/day, 135 mg/day, 140 mg/day, 145 mg/day, 150 mg/day, 155 mg/day, 160 mg/day, 165 mg/day, 170 mg/day, 175 mg/day, 180 mg/day, 185 mg/day, 190 mg/day, 195 mg/day, 200 mg/day, 205 mg/day, 210 mg/day, 215 mg/day, 220 mg/day, 225 mg/day, 230 mg/day, 235 mg/day, 240 mg/day, 245 mg/day, 250 mg/day, 255 mg/day, 260 mg/day, 265 mg/day, 270 mg/day, 275 mg/day, 280 mg/day, 285 mg/day, 290 mg/day, 295 mg/day, 300 mg/day, 305 mg/day, 310 mg/day, 315 mg/day, 320 mg/day, 325 mg/day, 330 mg/day, 335 mg/day, 340 mg/day, 345 mg/day, 350 mg/day, 355 mg/day, 360 mg/day, 365 mg/day, 370 mg/day, 375 mg/day, 380 mg/day, 385 mg/day, 390 mg/day, 395 mg/day, or 400 mg/day) of a GnRH antagonist to the patient if the concentration of AMH in the sample isolated from the patient is below the AMH reference range.

In some embodiments, the method includes administering less than 10 mg/day of a GnRH antagonist to the patient if the concentration of AMH in the sample isolated from the patient is below the AMH reference range. For instance, the method may include administering less than 10 mg/day of ASP-1707 to the patient if the concentration of AMH in the sample isolated from the patient is below the AMH reference range.

In some embodiments, the method includes administering less than 40 mg/day of a GnRH antagonist to the patient if the concentration of AMH in the sample isolated from the patient is below the AMH reference range. For instance, the method may include administering less than 40 mg/day of relugolix to the patient if the concentration of AMH in the sample isolated from the patient is below the AMH reference range.

In some embodiments, the method includes administering from 50 mg/day to 200 mg/day of a GnRH antagonist to the patient if the concentration of AMH in the sample isolated from the patient is below the AMH reference range. For instance, the method may include administering 50 mg/day, 75 mg/day, 100 mg/day, or 200 mg/day of a thieno[3,4d] pyrimidine derivative or variant, such as 3-[2-fluoro-5-(2, 3-difluoro-6-methoxybenzyloxy)4-methoxyphenyl]-2,4-di-oxo-1,2,3,4-tetrahydrothieno[3,4d]pyrimidine-5-carboxylic acid or the choline salt thereof to the patient if the concentration of AMH in the sample isolated from the patient is below the AMH reference range.

In some embodiments, the method includes administering less than 150 mg/day of a GnRH antagonist to the patient if the concentration of AMH in the sample isolated from the patient is below the AMH reference range. For instance, the method may include administering less than 150 mg/day of elagolix to the patient if the concentration of AMH in the sample isolated from the patient is below the AMH reference range. In some embodiments, the method includes administering less than 400 mg/day of a GnRH antagonist to the patient if the concentration of AMH in the sample isolated from the patient is below the AMH reference range. For instance, the method may include administering less than 400 mg/day of elagolix to the patient if the concentration of AMH in the sample isolated from the patient is below the AMH reference range.

In some embodiments, the method includes administering from 10 to 500 mg/day of a GnRH antagonist to the patient if the concentration of AMH in the sample isolated from the patient is within the AMH reference range.

For instance, in some embodiments, the method includes administering from 10 to 490 mg/day, from 25 to 480 mg/day, from 50 to 470 mg/day, or from 100 to 450 mg/day (e.g., 10 mg/day, 15 mg/day, 20 mg/day, 25 mg/day, 30 mg/day, 35 mg/day, 40 mg/day, 45 mg/day, 50 mg/day, 55 mg/day, 60 mg/day, 65 mg/day, 70 mg/day, 75 mg/day, 80 mg/day, 85 mg/day, 90 mg/day, 95 mg/day, 100 mg/day, 105 mg/day, 110 mg/day, 115 mg/day, 120 mg/day, 125 mg/day, 130 mg/day, 135 mg/day, 140 mg/day, 145 mg/day, 150 mg/day, 155 mg/day, 160 mg/day, 165 mg/day, 170 mg/day, 175 mg/day, 180 mg/day, 185 mg/day, 190 mg/day, 195 mg/day, 200 mg/day, 205 mg/day, 210 mg/day, 215 mg/day, 220 mg/day, 225 mg/day, 230 mg/day, 235 mg/day, 240 mg/day, 245 mg/day, 250 mg/day, 255 mg/day, 260 mg/day, 265 mg/day, 270 mg/day, 275 mg/day, 280 mg/day, 285 mg/day, 290 mg/day, 295 mg/day, 300 mg/day, 305 mg/day, 310 mg/day, 315 mg/day, 320 mg/day, 325 mg/day, 330 mg/day, 335 mg/day, 340 mg/day, 345 mg/day, 350 mg/day, 355 mg/day, 360 mg/day, 365 mg/day, 370 mg/day, 375 mg/day, 380 mg/day, 385 mg/day, 390 mg/day, 395 mg/day, 400 mg/day, 405 mg/day, 410 mg/day, 415 mg/day, 420 mg/day, 425 mg/day, 430 mg/day, 435 mg/day, 440 mg/day, 445 mg/day, 450 mg/day, 455 mg/day, 460 mg/day, 465 mg/day, 470 mg/day, 475 mg/day, 480 mg/day, 485 mg/day, 490 mg/day, 495 mg/day, or 500 mg/day) of a GnRH antagonist to the patient if the concentration of AMH in the sample isolated from the patient is within the AMH reference range.

In some embodiments, the method includes administering 10 mg/day of a GnRH antagonist to the patient if the concentration of AMH in the sample isolated from the patient is within the AMH reference range. For instance, the method may include administering 10 mg/day of ASP-1707 to the patient if the concentration of AMH in the sample isolated from the patient is within the AMH reference range.

In some embodiments, the method includes administering 40 mg/day of a GnRH antagonist to the patient if the concentration of AMH in the sample isolated from the patient is within the AMH reference range. For instance, the method may include administering 40 mg/day of relugolix to the patient if the concentration of AMH in the sample isolated from the patient is within the AMH reference range.

In some embodiments, the method includes administering from 50 mg/day to 200 mg/day of a GnRH antagonist to the patient if the concentration of AMH in the sample isolated from the patient is within the AMH reference range. For instance, the method may include administering 50 mg/day, 75 mg/day, 100 mg/day, or 200 mg/day of a thieno[3,4d] pyrimidine derivative or variant, such as 3-[2-fluoro-5-(2, 3-difluoro-6-methoxybenzyloxy)4-methoxyphenyl]-2,4-di-oxo-1,2,3,4-tetrahydrothieno[3,4d]pyrimidine-5-carboxylic acid or the choline salt thereof to the patient if the concentration of AMH in the sample isolated from the patient is within the AMH reference range.

In some embodiments, the method includes administering 150 mg/day of a GnRH antagonist to the patient if the concentration of AMH in the sample isolated from the patient is within the AMH reference range. For instance, the method may include administering 150 mg/day of elagolix to the patient if the concentration of AMH in the sample isolated from the patient is within the AMH reference range. In some embodiments, the method includes administering 400 mg/day of a GnRH antagonist to the patient if the concentration of AMH in the sample isolated from the patient is within the AMH reference range. For instance, the method may include administering 400 mg/day of elagolix to the patient if the concentration of AMH in the sample isolated from the patient is within the AMH reference range.

In another aspect, the invention features a method of determining a dosing regimen for the treatment of endometriosis in a patient (e.g., a female human patient, such as a premenopausal female human patient). In another aspect, the invention features a method of determining a dosing regimen for reducing pain (e.g., endometriosis-associated pain) in a patient (e.g., a female human patient, such as a premenopausal female human patient).

In any of the above aspects of the invention, the method may include the step of determining the concentration of AMH in a sample (e.g., a blood sample) isolated from the patient. In some embodiments, the concentration of AMH in a sample (e.g., a blood sample) isolated from the patient has previously been determined. The method may include:

a. comparing the concentration of AMH to an AMH reference range;
b. determining that the patient be administered a higher quantity (e.g., a higher daily dosage or an elevated dosing frequency) of a GnRH antagonist to the patient if the concentration of AMH in the sample isolated from the patient is above the AMH reference range;
c. determining that the patient be administered a lower quantity (e.g., a lower daily dosage or a reduced dosing frequency) of a GnRH antagonist to the patient if the concentration of AMH in the sample isolated from the patient is below the AMH reference range; or d. determining that the patient be administered an intermediate quantity (e.g., intermediate daily dosage or intermediate dosing frequency) of a GnRH antagonist to the patient if the concentration of AMH in the sample isolated from the patient is within the AMH reference range.

In some embodiments, the method includes administering the GnRH antagonist to the patient at the determined dose.

For instance, in some embodiments, the method includes determining that the patient be administered from 10 to 600 mg/day, from 20 to 590 mg/day, from 30 to 580 mg/day, from 40 to 570 mg/day, from 50 to 560 mg/day, from 60 to 550 mg/day, from 70 to 540 mg/day, from 80 to 530 mg/day, from 90 to 520 mg/day, from 100 to 510 mg/day, or from 110 to 500 mg/day (e.g., 5 mg/day, 10 mg/day, 15 mg/day, 20 mg/day, 25 mg/day, 30 mg/day, 35 mg/day, 40 mg/day, 45 mg/day, 50 mg/day, 55 mg/day, 60 mg/day, 65 mg/day, 70 mg/day, 75 mg/day, 80 mg/day, 85 mg/day, 90 mg/day, 95 mg/day, 100 mg/day, 105 mg/day, 110 mg/day, 115 mg/day, 120 mg/day, 125 mg/day, 130 mg/day, 135 mg/day, 140 mg/day, 145 mg/day, 150 mg/day, 155 mg/day, 160 mg/day, 165 mg/day, 170 mg/day, 175 mg/day, 180 mg/day, 185 mg/day, 190 mg/day, 195 mg/day, 200 mg/day, 205 mg/day, 210 mg/day, 215 mg/day, 220 mg/day, 225 mg/day, 230 mg/day, 235 mg/day, 240 mg/day, 245 mg/day, 250 mg/day, 255 mg/day, 260 mg/day, 265 mg/day, 270 mg/day, 275 mg/day, 280 mg/day, 285 mg/day, 290 mg/day, 295 mg/day, 300 mg/day, 305 mg/day, 310 mg/day, 315 mg/day, 320 mg/day, 325 mg/day, 330 mg/day, 335 mg/day, 340 mg/day, 345 mg/day, 350 mg/day, 355 mg/day, 360 mg/day, 365 mg/day, 370 mg/day, 375 mg/day, 380 mg/day, 385 mg/day, 390 mg/day, 395 mg/day, 400 mg/day, 405 mg/day, 410 mg/day, 415 mg/day, 420 mg/day, 425 mg/day, 430 mg/day, 435 mg/day, 440 mg/day, 445 mg/day, 450 mg/day, 455 mg/day, 460 mg/day, 465 mg/day, 470 mg/day, 475 mg/day, 480 mg/day, 485 mg/day, 490 mg/day, 495 mg/day, 500 mg/day, 505 mg/day, 510 mg/day, 515 mg/day, 520 mg/day, 525 mg/day, 530 mg/day, 535 mg/day, 540 mg/day, 545 mg/day, 550 mg/day, 555 mg/day, 560 mg/day, 565 mg/day, 570 mg/day, 575 mg/day, 580 mg/day, 585 mg/day, 590 mg/day, 595 mg/day, 600 mg/day, 605 mg/day, 610 mg/day, 615 mg/day, 620 mg/day, 625 mg/day, 630 mg/day, 635 mg/day, 640 mg/day, 645 mg/day, 650 mg/day, 655 mg/day, 660 mg/day, 665 mg/day, 670 mg/day, 675 mg/day, 680 mg/day, 685 mg/day, 690 mg/day, 695 mg/day, or 700 mg/day) of a GnRH antagonist if the concentration of AMH in the sample isolated from the patient is above the AMH reference range.

In some embodiments, the method includes determining that the patient be administered more than 10 mg/day of a GnRH antagonist if the concentration of AMH in the sample isolated from the patient is above the AMH reference range. For instance, the method may include determining that the patient be administered more than 10 mg/day of ASP-1707 if the concentration of AMH in the sample isolated from the patient is above the AMH reference range.

In some embodiments, the method includes determining that the patient be administered more than 40 mg/day of a GnRH antagonist if the concentration of AMH in the sample isolated from the patient is above the AMH reference range. For instance, the method may include determining that the patient be administered more than 40 mg/day of relugolix if the concentration of AMH in the sample isolated from the patient is above the AMH reference range.

In some embodiments, the method includes determining that the patient be administered from about 50 mg/day to about 200 mg/day of a GnRH antagonist if the concentration of AMH in the sample isolated from the patient is above the AMH reference range. For instance, the method may include determining that the patient be administered about 50 mg/day, 75 mg/day, 100 mg/day, or 200 mg/day of a thieno[3,4d]pyrimidine derivative or variant, such as 3-[2-fluoro-5-(2,3-difluoro-6-methoxybenzyloxy)4-methoxyphenyl]-2,4-dioxo-1,2,3,4-tetrahydrothieno[3,4d]pyrimidine-5-carboxylic acid or the choline salt thereof if the concentration of AMH in the sample isolated from the patient is above the AMH reference range.

In some embodiments, the method includes determining that the patient be administered more than 150 mg/day of a GnRH antagonist if the concentration of AMH in the sample isolated from the patient is above the AMH reference range. For instance, the method may include determining that the patient be administered more than 150 mg/day of elagolix if the concentration of AMH in the sample isolated from the patient is above the AMH reference range. In some embodiments, the method includes determining that the patient be administered more than 400 mg/day of a GnRH antagonist if the concentration of AMH in the sample isolated from the patient is above the AMH reference range. For instance, the method may include determining that the patient be administered more than 400 mg/day of elagolix if the concentration of AMH in the sample isolated from the patient is above the AMH reference range.

In some embodiments, the method includes determining that the patient be administered from 5 to 400 mg/day of a GnRH antagonist if the concentration of AMH in the sample isolated from the patient is below the AMH reference range. For instance, in some embodiments, the method includes determining that the patient be administered from 5 to 190 mg/day, from 15 to 180 mg/day, from 35 to 170 mg/day, from 50 to 160 mg/day, from 60 to 150 mg/day, from 70 to 140 mg/day, from 80 to 130 mg/day, from 90 to 120 mg/day, from 100 to 110 mg/day, from 200 to 400 mg/day, from 225 to 375 mg/day, from 250 to 350 mg/day, or from 275 to 325 mg/day (e.g., 5 mg/day, 10 mg/day, 15 mg/day, 20 mg/day, 25 mg/day, 30 mg/day, 35 mg/day, 40 mg/day, 45 mg/day, 50 mg/day, 55 mg/day, 60 mg/day, 65 mg/day, 70 mg/day, 75 mg/day, 80 mg/day, 85 mg/day, 90 mg/day, 95 mg/day, 100 mg/day, 105 mg/day, 110 mg/day, 115 mg/day, 120 mg/day, 125 mg/day, 130 mg/day, 135 mg/day, 140 mg/day, 145 mg/day, 150 mg/day, 155 mg/day, 160 mg/day, 165 mg/day, 170 mg/day, 175 mg/day, 180 mg/day, 185 mg/day, 190 mg/day, 195 mg/day, 200 mg/day, 205 mg/day, 210 mg/day, 215 mg/day, 220 mg/day, 225 mg/day, 230 mg/day, 235 mg/day, 240 mg/day, 245 mg/day, 250 mg/day, 255 mg/day, 260 mg/day, 265 mg/day, 270 mg/day, 275 mg/day, 280 mg/day, 285 mg/day, 290 mg/day, 295 mg/day, 300 mg/day, 305 mg/day, 310 mg/day, 315 mg/day, 320 mg/day, 325 mg/day, 330 mg/day, 335 mg/day, 340 mg/day, 345 mg/day, 350 mg/day, 355 mg/day, 360 mg/day, 365 mg/day, 370 mg/day, 375 mg/day, 380 mg/day, 385 mg/day, 390 mg/day, 395 mg/day, or 400 mg/day) of a GnRH antagonist if the concentration of AMH in the sample isolated from the patient is below the AMH reference range.

In some embodiments, the method includes determining that the patient be administered less than 10 mg/day of a GnRH antagonist if the concentration of AMH in the sample isolated from the patient is below the AMH reference range. For instance, the method may include determining that the patient be administered less than 10 mg/day of ASP-1707 if the concentration of AMH in the sample isolated from the patient is below the AMH reference range.

In some embodiments, the method includes determining that the patient be administered less than 40 mg/day of a GnRH antagonist if the concentration of AMH in the sample isolated from the patient is below the AMH reference range. For instance, the method may include determining that the patient be administered less than 40 mg/day of relugolix if the concentration of AMH in the sample isolated from the patient is below the AMH reference range.

In some embodiments, the method includes determining that the patient be administered from about 50 mg/day to about 200 mg/day of a GnRH antagonist if the concentration of AMH in the sample isolated from the patient is below the AMH reference range. For instance, the method may include determining that the patient be administered about 50 mg/day, 75 mg/day, 100 mg/day, or 200 mg/day of a thieno[3,4d]pyrimidine derivative or variant, such as 3-[2-fluoro-5-(2,3-difluoro-6-methoxybenzyloxy)4-methoxyphenyl]-2,4-dioxo-1,2,3,4-tetrahydrothieno[3,4d]pyrimidine-5-carboxylic acid or the choline salt thereof if the concentration of AMH in the sample isolated from the patient is below the AMH reference range.

In some embodiments, the method includes determining that the patient be administered less than 150 mg/day of a GnRH antagonist if the concentration of AMH in the sample isolated from the patient is below the AMH reference range. For instance, the method may include determining that the patient be administered less than 150 mg/day of elagolix if the concentration of AMH in the sample isolated from the patient is below the AMH reference range. In some embodiments, the method includes determining that the patient be administered less than 400 mg/day of a GnRH antagonist if the concentration of AMH in the sample isolated from the patient is below the AMH reference range. For instance, the method may include determining that the patient be administered less than 400 mg/day of elagolix if the concentration of AMH in the sample isolated from the patient is below the AMH reference range. In some embodiments, the method includes administering the GnRH antagonist to the patient at the determined dose.

In some embodiments, the method includes determining that the patient be administered from 10 to 500 mg/day of a GnRH antagonist if the concentration of AMH in the sample isolated from the patient is within the AMH reference range. For instance, in some embodiments, the method includes determining that the patient be administered from 10 to 490 mg/day, from 25 to 480 mg/day, from 50 to 470 mg/day, or from 100 to 460 mg/day (e.g., 10 mg/day, 15 mg/day, 20 mg/day, 25 mg/day, 30 mg/day, 35 mg/day, 40 mg/day, 45 mg/day, 50 mg/day, 55 mg/day, 60 mg/day, 65 mg/day, 70 mg/day, 75 mg/day, 80 mg/day, 85 mg/day, 90 mg/day, 95 mg/day, 100 mg/day, 105 mg/day, 110 mg/day, 115 mg/day, 120 mg/day, 125 mg/day, 130 mg/day, 135 mg/day, 140 mg/day, 145 mg/day, 150 mg/day, 155 mg/day, 160 mg/day, 165 mg/day, 170 mg/day, 175 mg/day, 180 mg/day, 185 mg/day, 190 mg/day, 195 mg/day, 200 mg/day, 205 mg/day, 210 mg/day, 215 mg/day, 220 mg/day, 225 mg/day, 230 mg/day, 235 mg/day, 240 mg/day, 245 mg/day, 250 mg/day, 255 mg/day, 260 mg/day, 265 mg/day, 270 mg/day, 275 mg/day, 280 mg/day, 285 mg/day, 290 mg/day, 295 mg/day, 300 mg/day, 305 mg/day, 310 mg/day, 315 mg/day, 320 mg/day, 325 mg/day, 330 mg/day, 335 mg/day, 340 mg/day, 345 mg/day, 350 mg/day, 355 mg/day, 360 mg/day, 365 mg/day, 370 mg/day, 375 mg/day, 380 mg/day, 385 mg/day, 390 mg/day, 395 mg/day, 400 mg/day, 405 mg/day, 410 mg/day, 415 mg/day, 420 mg/day, 425 mg/day, 430 mg/day, 435 mg/day, 440 mg/day, 445 mg/day, 450 mg/day, 455 mg/day, 460 mg/day, 465 mg/day, 470 mg/day, 475 mg/day, 480 mg/day, 485 mg/day, 490 mg/day, 495 mg/day, or 500 mg/day) of a GnRH antagonist if the concentration of AMH in the sample isolated from the patient is within the AMH reference range.

In some embodiments, the method includes determining that the patient be administered 10 mg/day of a GnRH antagonist if the concentration of AMH in the sample isolated from the patient is within the AMH reference range. For instance, the method may include determining that the patient be administered 10 mg/day of ASP-1707 if the concentration of AMH in the sample isolated from the patient is within the AMH reference range.

In some embodiments, the method includes determining that the patient be administered 40 mg/day of a GnRH antagonist if the concentration of AMH in the sample isolated from the patient is within the AMH reference range. For instance, the method may include determining that the patient be administered 40 mg/day of relugolix if the concentration of AMH in the sample isolated from the patient is within the AMH reference range.

In some embodiments, the method includes determining that the patient be administered from about 50 mg/day to about 200 mg/day of a GnRH antagonist if the concentration of AMH in the sample isolated from the patient is within the AMH reference range. For instance, the method may include determining that the patient be administered about 50 mg/day, 75 mg/day, 100 mg/day, or 200 mg/day of a thieno[3,4d]pyrimidine derivative or variant, such as 3-[2-fluoro-5-(2,3-difluoro-6-methoxybenzyloxy)4-methoxyphenyl]-2,4-dioxo-1,2,3,4-tetrahydrothieno[3,4d]pyrimidine-5-carboxylic acid or the choline salt thereof if the concentration of AMH in the sample isolated from the patient is within the AMH reference range.

In some embodiments, the method includes determining that the patient be administered 150 mg/day of a GnRH antagonist if the concentration of AMH in the sample isolated from the patient is within the AMH reference range. For instance, the method may include determining that the patient be administered 150 mg/day of elagolix if the concentration of AMH in the sample isolated from the patient is within the AMH reference range. In some embodiments, the method includes determining that the patient be administered 400 mg/day of a GnRH antagonist if the concentration of AMH in the sample isolated from the patient is within the AMH reference range. For instance, the method may include determining that the patient be administered 400 mg/day of elagolix if the concentration of AMH in the sample isolated from the patient is within the AMH reference range. In some embodiments, the method includes administering the GnRH antagonist to the patient at the determined dose.

In some embodiments, the AMH reference range is from 15 to 35 pM. Thus, it will be appreciated that an AMH concentration of less than 15 pM (e.g., 1 pM, 2 pM, 3 pM, 4 pM, 5 pM, 6 pM, 7 pM, 8 pM, 9 pM, 10 pM, 11 pM, 12 pM, 13 pM, or 14 pM) is considered below an AMH reference range of from 15 to 35 pM. Likewise, an AMH concentration of greater than 35 pM (e.g., 36 pM, 37 pM, 38 pM, 39 pM, 40 pM, 50 pM, 55 pM, or greater) is considered above an AMH reference range of from 15 to 35 pM.

In some embodiments, the method includes administering the GnRH antagonist to the patient in an amount sufficient to reduce or alleviate a symptom of the endometriosis.

In some embodiments, the method includes administering the GnRH antagonist to the patient in an amount sufficient to reduce the serum concentration of β17-estradiol (E2) in the patient to between about 20 and about 50 pg/ml (e.g., to about 20 pg/ml, 25 pg/ml, 30 pg/ml, 35 pg/ml, 40 pg/ml, 45 pg/ml, or 50 pg/ml). In some embodiments, the serum concentration of E2 is reduced to between about 20 and about 50 pg/ml within about 4 to about 36 weeks of administering the GnRH antagonist to the patient (e.g., within about 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, or 36 weeks of administering the GnRH antagonist to the patient). In some embodiments, the serum concentration of E2 is reduced to between about 20 and about 50 pg/ml within about 4 weeks of administering the GnRH antagonist to the patient. In some embodiments, the serum concentration of E2 is reduced to between about 20 and about 50 pg/ml within about 12 weeks of administering the GnRH antagonist to the patient. In some embodiments, the serum concentration of E2 is reduced to between about 20 and about 50 pg/ml within about 24 weeks of administering the GnRH antagonist to the patient.

In some embodiments, the method includes administering the GnRH antagonist to the patient in an amount sufficient to reduce the serum concentration of follicle stimulating hormone (FSH) in the patient to between about 0.1 and about 10 mIU/ml (e.g., to about 0.1, 0.2, 0.3, 0.4, 0.5, 0.6, 0.7, 0.8, 0.9, 1, 2, 3, 4, 5, 6, 7, 8, 9, or 10 mIU/ml). In some embodiments, the serum concentration of FSH is reduced to between about 0.1 and about 10 mIU/ml within about 4 to about 36 weeks of administering the GnRH antagonist to the patient (e.g., within about 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, or 36 weeks of administering the GnRH antagonist to the patient). In some embodiments, the serum concentration of FSH is reduced to between about 0.1 and about 10 mIU/mL within about 4 weeks of administering the GnRH antagonist to the patient. In some embodiments, the serum concentration of FSH is reduced to between about 0.1 and about 10 mIU/mL within about 12 weeks of administering the GnRH antagonist to the patient. In some embodiments, the serum concentration of FSH is reduced to between about 0.1 and about 10 mIU/mL within about 24 weeks of administering the GnRH antagonist to the patient.

In some embodiments, the method includes administering the GnRH antagonist to the patient in an amount sufficient to reduce the serum concentration of luteinizing hormone (LH) in the patient to between about 0.1 and about 10 mIU/ml (e.g., to about 0.1, 0.2, 0.3, 0.4, 0.5, 0.6, 0.7, 0.8, 0.9, 1, 2, 3, 4, 5, 6, 7, 8, 9, or 10 mIU/ml). In some embodiments, the serum concentration of LH is reduced to between about 0.1 and about 10 mIU/mL within about 4 to about 36 weeks of administering the GnRH antagonist to the patient (e.g., within about 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, or 36 weeks of administering the GnRH antagonist to the patient). In some embodiments, the serum concentration of LH is reduced to between about 0.1 and about 10 mIU/mL within about 4 weeks of administering the GnRH antagonist to the patient. In some embodiments, the serum concentration of LH is reduced to between about 0.1 and about 10 mIU/mL within about 12 weeks of administering the GnRH antagonist to the patient. In some embodiments, the serum concentration of LH is reduced to between about 0.1 and about 10 mIU/mL within about 24 weeks of administering the GnRH antagonist to the patient.

In some embodiments, the method includes administering the GnRH antagonist to the patient in an amount sufficient to reduce endometriosis-associated pain in the patient. In some embodiments, the endometriosis-associated pain is reduced within about 4 to about 36 weeks of administering the GnRH antagonist to the patient (e.g., within about 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, or 36 weeks of administering the GnRH antagonist to the patient). In some embodiments, the endometriosis-associated pain is reduced within about 4 weeks of administering the GnRH antagonist to the patient. In some embodiments, the endometriosis-associated pain is reduced within about 12 weeks of administering the GnRH antagonist to the patient. In some embodiments, the endometriosis-associated pain is reduced within about 24 weeks of administering the GnRH antagonist to the patient. The endometriosis-associated pain is selected from the group consisting of pelvic pain, dyspareunia, and dyschezia.

In some embodiments, the endometriosis-associated pain is assessed by determining a Numerical Rating Score (NRS) for the patient. In some embodiments, the NRS is reduced by from about 1% to about 50% (e.g., by about 1%, 2%, 3%, 4%, 5%, 6%, 7%, 8%, 9%, 10%, 15%, 20%, 25%, 30%, 35%, 40%, 45%, or 50%). In some embodiments the NRS is reduced by about 30%.

In some embodiments, the endometriosis-associated pain is assessed by determining a Verbal Rating Score (VRS) for the patient. In some embodiments, the VRS is reduced by from about 1% to about 50% (e.g., by about 1%, 2%, 3%, 4%, 5%, 6%, 7%, 8%, 9%, 10%, 15%, 20%, 25%, 30%, 35%, 40%, 45%, or 50%). In some embodiments the VRS is reduced by about 30%.

In some embodiments, the method includes administering the GnRH antagonist to the patient in an amount sufficient to alleviate a symptom selected from the group consisting of dysmenorrhea, non-menstrual pelvic pain, and dyspareunia. In some embodiments, the symptom is alleviated within about 4 to about 36 weeks of administering the GnRH antagonist to the patient (e.g., within about 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, or 36 weeks of administering the GnRH antagonist to the patient). In some embodiments, the symptom is alleviated within about 4 weeks of administering the GnRH antagonist to the patient. In some embodiments, the symptom is alleviated within about 12 weeks of administering the GnRH antagonist to the patient. In some embodiments, the symptom is alleviated within about 24 weeks of administering the GnRH antagonist to the patient.

In some embodiments, the symptom is assessed by determining a Biberoglu and Behrman (B&B) scale score for the patient. In some embodiments, the B&B score is reduced by from about 1% to about 50% (e.g., by about 1%, 2%, 3%, 4%, 5%, 6%, 7%, 8%, 9%, 10%, 15%, 20%, 25%, 30%, 35%, 40%, 45%, or 50%).

In some embodiments, the method includes administering the GnRH antagonist to the patient in an amount sufficient to reduce an Endometriosis Health Profile-5 (EHP-5) score determined for the patient. In some embodiments, the EHP-5 score is reduced within about 4 to about 36 weeks of administering the GnRH antagonist to the patient (e.g., within about 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, or 36 weeks of administering the GnRH antagonist to the patient). In some embodiments, the EHP-5 score is reduced within about 4 weeks of administering the GnRH antagonist to the patient. In some embodiments, the EHP-5 score is reduced within about 12 weeks of administering the GnRH antagonist to the patient. In some embodiments, the EHP-5 score is reduced within about 24 weeks of administering the GnRH antagonist to the patient. In some embodiments, the EHP-5 score is reduced by from about 1% to about 50% (e.g., by about 1%, 2%, 3%, 4%, 5%, 6%, 7%, 8%, 9%, 10%, 15%, 20%, 25%, 30%, 35%, 40%, 45%, or 50%).

In some embodiments, the method includes administering the GnRH antagonist to the patient in an amount that does not cause a reduction in bone mineral density (BMD) in the patient of greater than 5%. In some embodiments, the method includes administering the GnRH antagonist to the patient in an amount that does not cause a reduction in BMD in the patient of greater than 1%.

In some embodiments, the method includes administering add-back therapy to the patient. The add-back therapy may be administered to the patient concurrently with the GnRH antagonist, prior to administration of the GnRH antagonist, or following administration of the GnRH antagonist. In some embodiments, add-back therapy is administered as a fixed dose combination containing a GnRH antagonist, estrogen, and one or more additional agents, such as a progestin, in a single pharmaceutical composition. For instance, add-back therapy may be administered as a fixed dose combination of a GnRH antagonist, estrogen (e.g., in the form of β17-estradiol, ethinyl estradiol, or a conjugated estrogen, such as a conjugated equine estrogen) and/or a progestin (e.g., norethindrone or a compound that is metabolized in vivo to produce norethindrone, such as an ester of norethindrone that is de-esterified in vivo to produce norethindrone, for instance, norethindrone acetate (also referred to herein as "NETA"), among other agents, such as progesterone, norgestimate, medroxyprogesterone, and drospirenone) in the form of a single pharmaceutical composition, such as a single tablet, capsule, gel cap, powder, liquid solution, or liquid suspension. In some embodiments, the add-back therapy is administered orally, transdermally, or intravaginally.

In some embodiments, the add-back therapy is administered to the patient in one or more doses per day, week, month, or year, such as daily, for example, from 1 to 10 times daily, or more (e.g., 1, 2, 3, 4, 5, 6, 7, 8, 9, 10, or more, times daily). In some embodiments, the add-back therapy is administered to the patient once daily, for example, concurrently with the GnRH antagonist. For example, the GnRH antagonist may be administered to the patient orally, and concurrently with oral administration of the GnRH antagonist, the add-back therapy may be administered to the patient orally, transdermally, or intravaginally. In some embodiments, the add-back therapy is administered to the patient in the form of a pharmaceutical composition that further includes the GnRH antagonist, such as a single tablet, capsule, gel cap, powder, liquid solution, or liquid suspension, for instance, as described above and herein.

In some embodiments, the add-back therapy is administered to the patient once daily, following administration of the compound. For example, the GnRH antagonist may be administered to the patient orally, and following oral administration of the GnRH antagonist, the add-back therapy may be administered to the patient orally, transdermally, or intravaginally.

In some embodiments, the add-back therapy is administered to the patient once daily, prior to administration of the compound. For example, the GnRH antagonist may be administered to the patient orally, and prior to oral administration of the GnRH antagonist, the add-back therapy may be administered to the patient orally, transdermally, or intravaginally.

In some embodiments, the add-back therapy includes an estrogen. In some embodiments, the estrogen is selected from the group consisting of β17-estradiol, ethinyl estradiol, and conjugated estrogens, such as conjugated equine estrogens.

In some embodiments, the estrogen is β17-estradiol. The β17-estradiol may be administered to the patient, for example, at a dose of from about 0.1 mg to about 2.5 mg, such as at a dose of about 0.1 mg, 0.2 mg, 0.3 mg, 0.4 mg, 0.5 mg, 0.6 mg, 0.7 mg, 0.8 mg, 0.9 mg, 1.0 mg, 1.1 mg, 1.2 mg, 1.3 mg, 1.4 mg, 1.5 mg, 1.6 mg, 1.7 mg, 1.8 mg, 1.9 mg, 2.0 mg, 2.1 mg, 2.2 mg, 2.3 mg, 2.4 mg, or 2.5 mg, for instance, by oral administration. In some embodiments, the β17-estradiol is administered to the patient at a dose of 1.0 mg, for instance, by oral administration. In some embodiments, the β17-estradiol is administered to the patient at a dose of 0.5 mg, for instance, by oral administration.

The β17-estradiol may be administered to the patient one or more times per day, week, or month. The β17-estradiol may be administered to the patient, for example, at a dose of from about 0.1 mg/day to about 2.5 mg/day, such as at a dose of about 0.1 mg/day, 0.2 mg/day, 0.3 mg/day, 0.4 mg/day, 0.5 mg/day, 0.6 mg/day, 0.7 mg/day, 0.8 mg/day, 0.9 mg/day, 1.0 mg/day, 1.1 mg/day, 1.2 mg/day, 1.3 mg/day, 1.4 mg/day, 1.5 mg/day, 1.6 mg/day, 1.7 mg/day, 1.8 mg/day, 1.9 mg/day, 2.0 mg/day, 2.1 mg/day, 2.2 mg/day, 2.3 mg/day, 2.4 mg/day, or 2.5 mg/day, for instance, by oral administration. In some embodiments, the β17-estradiol is administered to the patient at a dose of 1.0 mg/day, for instance, by oral administration. In some embodiments, the β17-estradiol is administered to the patient at a dose of 0.5 mg/day, for instance, by oral administration.

In some embodiments, the estrogen is ethinyl estradiol. The ethinyl estradiol may be administered to the patient, for example, at a dose of from about 1.0 µg to about 6.0 µg, such as at a dose of about 1.0 µg, 1.1 µg, 1.2 µg, 1.3 µg, 1.4 µg, 1.5 µg, 1.6 µg, 1.7 µg, 1.8 µg, 1.9 µg, 2.0 µg, 2.1 µg, 2.2 µg, 2.3 µg, 2.4 µg, 2.5 µg, 2.6 µg, 2.7 µg, 2.8 µg, 2.9 µg, 3.0 µg, 3.1 µg, 3.2 µg, 3.3 µg, 3.4 µg, 3.5 µg, 3.6 µg, 3.7 µg, 3.8 µg, 3.9 µg, 4.0 µg, 4.1 µg, 4.2 µg, 4.2 µg, 4.3 µg, 4.4 µg, 4.5 µg, 4.6 µg, 4.7 µg, 4.8 µg, 4.9 µg, 5.0 µg, 5.1 µg, 5.2 µg, 5.3 µg, 5.4 µg, 5.5 µg, 5.6 µg, 5.7 µg, 5.8 µg, 5.9 µg, or 6.0 µg, for instance, by oral administration. In some embodiments, the ethinyl estradiol is administered to the patient at a dose of 5.0 µg, for instance, by oral administration. In some embodiments, the ethinyl estradiol is administered to the patient at a dose of 2.5 µg, for instance, by oral administration.

The ethinyl estradiol may be administered to the patient one or more times per day, week, or month. The ethinyl estradiol may be administered to the patient, for example, at a dose of from about 1.0 µg/day to about 6.0 µg/day, such as at a dose of about 1.0 µg/day, 1.1 µg/day, 1.2 µg/day, 1.3 µg/day, 1.4 µg/day, 1.5 µg/day, 1.6 µg/day, 1.7 µg/day, 1.8 µg/day, 1.9 µg/day, 2.0 µg/day, 2.1 µg/day, 2.2 µg/day, 2.3 µg/day, 2.4 µg/day, 2.5 µg/day, 2.6 µg/day, 2.7 µg/day, 2.8 µg/day, 2.9 µg/day, 3.0 µg/day, 3.1 µg/day, 3.2 µg/day, 3.3 µg/day, 3.4 µg/day, 3.5 µg/day, 3.6 µg/day, 3.7 µg/day, 3.8 µg/day, 3.9 µg/day, 4.0 µg/day, 4.1 µg/day, 4.2 µg/day, 4.3 µg/day, 4.4 µg/day, 4.5 µg/day, 4.6 µg/day, 4.7 µg/day, 4.8 µg/day, 4.9 µg/day, 5.0 µg/day, 5.1 µg/day, 5.2 µg/day, 5.3 µg/day, 5.4 µg/day, 5.5 µg/day, 5.6 µg/day, 5.7 µg/day, 5.8 µg/day, 5.9 µg/day, or 6.0 µg/day, for instance, by oral administration. In some embodiments, the ethinyl estradiol is administered to the patient at a dose of 5.0 µg/day, for instance, by oral administration. In some embodiments, the ethinyl estradiol is administered to the patient at a dose of 2.5 µg/day, for instance, by oral administration.

In some embodiments, the estrogen is a conjugated estrogen, such as a conjugated equine estrogen. The conjugated estrogen may be administered to the patient, for example, at a dose of from about 0.1 mg to about 2.0 mg, such as at a dose of about 0.1 mg, 0.2 mg, 0.3 mg, 0.4 mg, 0.5 mg, 0.6 mg, 0.7 mg, 0.8 mg, 0.9 mg, 1.0 mg, 1.1 mg, 1.2 mg, 1.3 mg, 1.4 mg, 1.5 mg, 1.6 mg, 1.7 mg, 1.8 mg, 1.9 mg, or 2.0 mg, for instance, by oral administration. In some embodiments, the conjugated estrogen is administered to the patient at a dose of 0.625 mg, for instance, by oral administration. In some embodiments, the conjugated estrogen is administered to the patient at a dose of 0.45 mg, for instance, by oral administration. In some embodiments, the conjugated estrogen is administered to the patient at a dose of 0.3 mg, for instance, by oral administration.

The conjugated estrogen may be administered to the patient one or more times per day, week, or month. The conjugated estrogen may be administered to the patient, for example, at a dose of from about 0.1 mg/day to about 2.0 mg/day, such as at a dose of about 0.1 mg/day, 0.2 mg/day, 0.3 mg/day, 0.4 mg/day, 0.5 mg/day, 0.6 mg/day, 0.7 mg/day, 0.8 mg/day, 0.9 mg/day, 1.0 mg/day, 1.1 mg/day, 1.2 mg/day, 1.3 mg/day, 1.4 mg/day, 1.5 mg/day, 1.6 mg/day, 1.7 mg/day, 1.8 mg/day, 1.9 mg/day, or 2.0 mg/day, for instance, by oral administration. In some embodiments, the conjugated estrogen is administered to the patient at a dose of 0.625 mg/day, for instance, by oral administration. In some embodiments, the conjugated estrogen is administered to the patient at a dose of 0.45 mg/day, for instance, by oral administration. In some embodiments, the conjugated estrogen is administered to the patient at a dose of 0.3 mg/day, for instance, by oral administration.

In some embodiments, the add-back therapy includes a progestin. In some embodiments, the progestin is selected from the group consisting of norethindrone or an ester thereof, such as norethindrone acetate, or another agent such as progesterone, norgestimate, medroxyprogesterone, or drospirenone.

In some embodiments, the progestin is norethindrone or a compound that is metabolized in vivo to produce norethindrone, such as an ester of norethindrone that is de-esterified in vivo to produce norethindrone, for instance, norethindrone acetate.

In some embodiments, the progestin is norethindrone. The norethindrone may be administered to the patient, for example, at a dose of from about 0.05 mg to about 5.0 mg, such as at a dose of about 0.05 mg, 0.06 mg, 0.07 mg, 0.08 mg, 0.09 mg, 0.1 mg, 0.2 mg, 0.3 mg, 0.4 mg, 0.5 mg, 0.6 mg, 0.7 mg, 0.8 mg, 0.9 mg, 1.0 mg, 1.1 mg, 1.2 mg, 1.3 mg, 1.4 mg, 1.5 mg, 1.6 mg, 1.7 mg, 1.8 mg, 1.9 mg, 2.0 mg, 2.1 mg, 2.2 mg, 2.3 mg, 2.4 mg, 2.5 mg, 2.6 mg, 2.7 mg, 2.8 mg, 2.9 mg, 3.0 mg, 3.1 mg, 3.2 mg, 3.3 mg, 3.4 mg, 3.5 mg, 3.6 mg, 3.7 mg, 3.8 mg, 3.9 mg, 4.0 mg, 4.1 mg, 4.2 mg, 4.3 mg, 4.4 mg, 4.5 mg, 4.6 mg, 4.7 mg, 4.8 mg, 4.9 mg, or 5.0 mg, for instance, by oral administration. In some embodiments, the norethindrone is administered to the patient at a dose of 1.0 mg, for instance, by oral administration. In some embodiments, the norethindrone is administered to the patient at a dose of 0.5 mg, for instance, by oral administration. In some embodiments, the norethindrone is administered to the patient at a dose of 0.1 mg, for instance, by oral administration.

The norethindrone may be administered to the patient one or more times per day, week, or month. The norethindrone may be administered to the patient, for example, at a dose of from about 0.05 mg/day to about 5.0 mg/day, such as at a dose of about 0.05 mg/day, 0.06 mg/day, 0.07 mg/day, 0.08 mg/day, 0.09 mg/day, 0.1 mg/day, 0.2 mg/day, 0.3 mg/day, 0.4 mg/day, 0.5 mg/day, 0.6 mg/day, 0.7 mg/day, 0.8 mg/day, 0.9 mg/day, 1.0 mg/day, 1.1 mg/day, 1.2 mg/day, 1.3 mg/day, 1.4 mg/day, 1.5 mg/day, 1.6 mg/day, 1.7 mg/day, 1.8 mg/day, 1.9 mg/day, 2.0 mg/day, 2.1 mg/day, 2.2 mg/day, 2.3 mg/day, 2.4 mg/day, 2.5 mg/day, 2.6 mg/day, 2.7 mg/day, 2.8 mg/day, 2.9 mg/day, 3.0 mg/day, 3.1 mg/day, 3.2 mg/day, 3.3 mg/day, 3.4 mg/day, 3.5 mg/day, 3.6 mg/day, 3.7 mg/day, 3.8 mg/day, 3.9 mg/day, 4.0 mg/day, 4.1 mg/day, 4.2 mg/day, 4.3 mg/day, 4.4 mg/day, 4.5 mg/day, 4.6 mg/day, 4.7 mg/day, 4.8 mg/day, 4.9 mg/day, or 5.0 mg/day, for instance, by oral administration. In some embodiments, the norethindrone is administered to the patient at a dose of 1.0 mg/day, for instance, by oral administration. In some embodiments, the norethindrone is administered to the patient at a dose of 0.5 mg/day, for instance, by oral administration. In some embodiments, the norethindrone is administered to the patient at a dose of 0.1 mg/day, for instance, by oral administration.

In some embodiments, the progestin is norethindrone acetate. The norethindrone acetate may be administered to the patient, for example, at a dose of from about 0.05 mg to about 5.0 mg, such as at a dose of about 0.05 mg, 0.06 mg, 0.07 mg, 0.08 mg, 0.09 mg, 0.1 mg, 0.2 mg, 0.3 mg, 0.4 mg, 0.5 mg, 0.6 mg, 0.7 mg, 0.8 mg, 0.9 mg, 1.0 mg, 1.1 mg, 1.2 mg, 1.3 mg, 1.4 mg, 1.5 mg, 1.6 mg, 1.7 mg, 1.8 mg, 1.9 mg, 2.0 mg, 2.1 mg, 2.2 mg, 2.3 mg, 2.4 mg, 2.5 mg, 2.6 mg, 2.7 mg, 2.8 mg, 2.9 mg, 3.0 mg, 3.1 mg, 3.2 mg, 3.3 mg, 3.4 mg, 3.5 mg, 3.6 mg, 3.7 mg, 3.8 mg, 3.9 mg, 4.0 mg, 4.1 mg, 4.2 mg, 4.3 mg, 4.4 mg, 4.5 mg, 4.6 mg, 4.7 mg, 4.8 mg, 4.9 mg, or 5.0 mg, for instance, by oral administration. In some embodiments, the norethindrone acetate is administered to the patient at a dose of 1.0 mg, for instance, by oral administration. In some embodiments, the norethindrone acetate is administered to the patient at a dose of 0.5 mg, for instance, by oral administration. In some embodiments, the norethindrone acetate is administered to the patient at a dose of 0.1 mg, for instance, by oral administration.

The norethindrone acetate may be administered to the patient one or more times per day, week, or month. The norethindrone acetate may be administered to the patient, for example, at a dose of from about 0.05 mg/day to about 5.0 mg/day, such as at a dose of about 0.05 mg/day, 0.06 mg/day, 0.07 mg/day, 0.08 mg/day, 0.09 mg/day, 0.1 mg/day, 0.2 mg/day, 0.3 mg/day, 0.4 mg/day, 0.5 mg/day, 0.6 mg/day, 0.7 mg/day, 0.8 mg/day, 0.9 mg/day, 1.0 mg/day, 1.1 mg/day, 1.2 mg/day, 1.3 mg/day, 1.4 mg/day, 1.5 mg/day, 1.6 mg/day, 1.7 mg/day, 1.8 mg/day, 1.9 mg/day, 2.0 mg/day, 2.1 mg/day, 2.2 mg/day, 2.3 mg/day, 2.4 mg/day, 2.5 mg/day, 2.6 mg/day, 2.7 mg/day, 2.8 mg/day, 2.9 mg/day, 3.0 mg/day, 3.1 mg/day, 3.2 mg/day, 3.3 mg/day, 3.4 mg/day, 3.5 mg/day, 3.6 mg/day, 3.7 mg/day, 3.8 mg/day, 3.9 mg/day, 4.0 mg/day, 4.1 mg/day, 4.2 mg/day, 4.3 mg/day, 4.4 mg/day, 4.5 mg/day, 4.6 mg/day, 4.7 mg/day, 4.8 mg/day, 4.9 mg/day, or 5.0 mg/day, for instance, by oral administration. In some embodiments, the norethindrone acetate is administered to the patient at a dose of 1.0 mg/day, for instance, by oral administration. In some embodiments, the norethindrone acetate is administered to the patient at a dose of 0.5 mg/day, for instance, by oral administration. In some embodiments, the norethindrone acetate is administered to the patient at a dose of 0.1 mg/day, for instance, by oral administration.

In some embodiments, the progestin is progesterone. The progesterone may be administered to the patient, for example, at a dose of from about 50 mg to about 250 mg, such as a dose of about 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, 200 mg, 205 mg, 210 mg, 215 mg, 220 mg, 225 mg, 230 mg, 235 mg, 240 mg, 245 mg, or 250 mg, for instance, by oral administration. In some embodiments, the progesterone is administered to the patient at a dose of 200 mg, for instance, by oral administration. In some embodiments, the progesterone is administered to the patient at a dose of 100 mg, for instance, by oral administration.

The progesterone may be administered to the patient one or more times per day, week, or month. The progesterone may be administered to the patient, for example, at a dose of from about 50 mg/day to about 250 mg/day, such as a dose of about 50 mg/day, 55 mg/day, 60 mg/day, 65 mg/day, 70 mg/day, 75 mg/day, 80 mg/day, 85 mg/day, 90 mg/day, 95 mg/day, 100 mg/day, 105 mg/day, 110 mg/day, 115 mg/day, 120 mg/day, 125 mg/day, 130 mg/day, 135 mg/day, 140 mg/day, 145 mg/day, 150 mg/day, 155 mg/day, 160 mg/day, 165 mg/day, 170 mg/day, 175 mg/day, 180 mg/day, 185 mg/day, 190 mg/day, 195 mg/day, 200 mg/day, 205 mg/day, 210 mg/day, 215 mg/day, 220 mg/day, 225 mg/day, 230 mg/day, 235 mg/day, 240 mg/day, 245 mg/day, or 250 mg/day, for instance, by oral administration. In some embodiments, the progesterone is administered to the patient at a dose of 200 mg/day, for instance, by oral administration. In some embodiments, the progesterone is administered to the patient at a dose of 100 mg/day, for instance, by oral administration.

In some embodiments, the progestin is norgestimate. The norgestimate may be administered to the patient, for example, at a dose of from about 0.01 mg to about 2.0 mg, such as at a dose of about 0.01 mg, 0.02 mg, 0.03 mg, 0.04 mg, 0.05 mg, 0.06 mg, 0.07 mg, 0.08 mg, 0.09 mg, 0.1 mg, 0.2 mg, 0.3 mg, 0.4 mg, 0.5 mg, 0.6 mg, 0.7 mg, 0.8 mg, 0.9 mg, 1.0 mg, 1.1 mg, 1.2 mg, 1.3 mg, 1.4 mg, 1.5 mg, 1.6 mg, 1.7 mg, 1.8 mg, 1.9 mg, or 2.0 mg, for instance, by oral administration. In some embodiments, the norgestimate is administered to the patient at a dose of 0.09 mg, for instance, by oral administration.

The norgestimate may be administered to the patient one or more times per day, week, or month. The norgestimate may be administered to the patient, for example, at a dose of from about 0.01 mg/day to about 2.0 mg/day, such as at a dose of about 0.01 mg/day, 0.02 mg/day, 0.03 mg/day, 0.04 mg/day, 0.05 mg/day, 0.06 mg/day, 0.07 mg/day, 0.08 mg/day, 0.09 mg/day, 0.1 mg/day, 0.2 mg/day, 0.3 mg/day, 0.4 mg/day, 0.5 mg/day, 0.6 mg/day, 0.7 mg/day, 0.8 mg/day, 0.9 mg/day, 1.0 mg/day, 1.1 mg/day, 1.2 mg/day, 1.3 mg/day, 1.4 mg/day, 1.5 mg/day, 1.6 mg/day, 1.7 mg/day, 1.8 mg/day, 1.9 mg/day, or 2.0 mg/day, for instance, by oral administration. In some embodiments, the norgestimate is administered to the patient at a dose of 0.09 mg/day, for instance, by oral administration.

In some embodiments, the progestin is medroxyprogesterone. The medroxyprogesterone may be administered to the patient, for example, at a dose of from about 0.5 mg to about 10.0 mg, such as at a dose of about 0.5 mg, 0.6 mg, 0.7 mg, 0.8 mg, 0.9 mg, 1.0 mg, 1.1 mg, 1.2 mg, 1.3 mg, 1.4 mg, 1.5 mg, 1.6 mg, 1.7 mg, 1.8 mg, 1.9 mg, 2.0 mg, 2.1 mg, 2.2 mg, 2.3 mg, 2.4 mg, 2.5 mg, 2.6 mg, 2.7 mg, 2.8 mg, 2.9 mg, 3.0 mg, 3.1 mg, 3.2 mg, 3.3 mg, 3.4 mg, 3.5 mg, 3.6 mg, 3.7 mg, 3.8 mg, 3.9 mg, 4.0 mg, 4.1 mg, 4.2 mg, 4.3 mg, 4.4 mg, 4.5 mg, 4.6 mg, 4.7 mg, 4.8 mg, 4.9 mg, 5.0 mg, 5.1 mg, 5.2 mg, 5.3 mg, 5.4 mg, 5.5 mg, 5.6 mg, 5.7 mg, 5.8 mg, 5.9 mg, 6.0 mg, 6.1 mg, 6.2 mg, 6.3 mg, 6.4 mg, 6.5 mg, 6.6 mg, 6.7 mg, 6.8 mg, 6.9 mg, 7.0 mg, 7.1 mg, 7.2 mg, 7.3 mg, 7.4 mg, 7.5 mg, 7.6 mg, 7.7 mg, 7.8 mg, 7.9 mg, 8.0 mg, 8.1 mg, 8.2 mg, 8.3 mg, 8.4 mg, 8.5 mg, 8.6 mg, 8.7 mg, 8.8 mg, 8.9 mg, 9.0 mg, 9.1 mg, 9.2 mg, 9.3 mg, 9.4 mg, 9.5 mg, 9.6 mg, 9.7 mg, 9.8 mg, 9.9 mg, or 10.0 mg, for instance, by oral administration. In some embodiments, the medroxyprogesterone is administered to the patient at a dose of 5.0 mg, for instance, by oral administration. In some embodiments, the medroxyprogesterone is administered to the patient at a dose of 2.5 mg, for instance, by oral administration. In some embodiments, the medroxyprogesterone is administered to the patient at a dose of 1.5 mg, for instance, by oral administration.

The medroxyprogesterone may be administered to the patient one or more times per day, week, or month. The medroxyprogesterone may be administered to the patient, for example, at a dose of from about 0.5 mg/day to about 10.0 mg/day, such as at a dose of about 0.5 mg/day, 0.6 mg/day, 0.7 mg/day, 0.8 mg/day, 0.9 mg/day, 1.0 mg/day, 1.1 mg/day, 1.2 mg/day, 1.3 mg/day, 1.4 mg/day, 1.5 mg/day, 1.6 mg/day, 1.7 mg/day, 1.8 mg/day, 1.9 mg/day, 2.0 mg/day, 2.1 mg/day, 2.2 mg/day, 2.3 mg/day, 2.4 mg/day, 2.5 mg/day, 2.6 mg/day, 2.7 mg/day, 2.8 mg/day, 2.9 mg/day, 3.0 mg/day, 3.1 mg/day, 3.2 mg/day, 3.3 mg/day, 3.4 mg/day, 3.5 mg/day, 3.6 mg/day, 3.7 mg/day, 3.8 mg/day, 3.9 mg/day, 4.0 mg/day, 4.1 mg/day, 4.2 mg/day, 4.3 mg/day, 4.4 mg/day, 4.5 mg/day, 4.6 mg/day, 4.7 mg/day, 4.8 mg/day, 4.9 mg/day, 5.0 mg/day, 5.1 mg/day, 5.2 mg/day, 5.3 mg/day, 5.4 mg/day, 5.5 mg/day, 5.6 mg/day, 5.7 mg/day, 5.8 mg/day, 5.9 mg/day, 6.0 mg/day, 6.1 mg/day, 6.2 mg/day, 6.3 mg/day, 6.4 mg/day, 6.5 mg/day, 6.6 mg/day, 6.7 mg/day, 6.8 mg/day, 6.9 mg/day, 7.0 mg/day, 7.1 mg/day, 7.2 mg/day, 7.3 mg/day, 7.4 mg/day, 7.5 mg/day, 7.6 mg/day, 7.7 mg/day, 7.8 mg/day, 7.9 mg/day, 8.0 mg/day, 8.1 mg/day, 8.2 mg/day, 8.3 mg/day, 8.4 mg/day, 8.5 mg/day, 8.6 mg/day, 8.7 mg/day, 8.8 mg/day, 8.9 mg/day, 9.0 mg/day, 9.1 mg/day, 9.2 mg/day, 9.3 mg/day, 9.4 mg/day, 9.5 mg/day, 9.6 mg/day, 9.7 mg/day, 9.8 mg/day, 9.9 mg/day, or 10.0 mg/day, for instance, by oral administration. In some embodiments, the medroxyprogesterone is administered to the patient at a dose of 5.0 mg/day, for instance, by oral administration. In some embodiments, the medroxyprogesterone is administered to the patient at a dose of 2.5 mg/day, for instance, by oral administration. In some embodiments, the medroxyprogesterone is administered to the patient at a dose of 1.5 mg/day, for instance, by oral administration.

In some embodiments, the progestin is drospirenone. The drospirenone may be administered to the patient, for example, at a dose of from about 0.1 mg to about 1.0 mg, such as at a dose of about 0.1 mg, 0.2 mg, 0.3 mg, 0.4 mg, 0.5 mg, 0.6 mg, 0.7 mg, 0.8 mg, 0.9 mg, or 1.0 mg, for instance, by oral administration. In some embodiments, the drospirenone is administered to the patient at a dose of 0.5 mg, for instance, by oral administration. In some embodiments, the drospirenone is administered to the patient at a dose of 0.25 mg, for instance, by oral administration.

The drospirenone may be administered to the patient one or more times per day, week, or month. The drospirenone may be administered to the patient, for example, at a dose of from about 0.1 mg/day to about 1.0 mg/day, such as at a dose of about 0.1 mg/day, 0.2 mg/day, 0.3 mg/day, 0.4 mg/day, 0.5 mg/day, 0.6 mg/day, 0.7 mg/day, 0.8 mg/day, 0.9 mg/day, or 1.0 mg/day, for instance, by oral administration. In some embodiments, the drospirenone is administered to the patient at a dose of 0.5 mg/day, for instance, by oral administration. In some embodiments, the drospirenone is administered to the patient at a dose of 0.25 mg/day, for instance, by oral administration.

In some embodiments, the add-back therapy includes an estrogen and a progestin. In some embodiments, the add-back therapy includes β17-estradiol and norethindrone or a compound that is metabolized in vivo to produce norethindrone, such as an ester of norethindrone that is de-esterified in vivo to produce norethindrone, for instance, norethindrone acetate.

In some embodiments, the add-back therapy includes from about 0.75 mg to about 1.25 mg of β17-estradiol, e.g., administered orally, and from about 0.25 mg to about 0.75 mg of norethindrone or a compound that is metabolized in vivo to produce norethindrone, such as an ester of norethindrone that is de-esterified in vivo to produce norethindrone, for instance, norethindrone acetate, e.g., administered orally. In some embodiments, the add-back therapy includes 1.0 mg of β17-estradiol, e.g., administered orally, and 0.5 mg of norethindrone or a compound that is metabolized in vivo to produce norethindrone, such as an ester of norethindrone that is de-esterified in vivo to produce norethindrone, for instance, norethindrone acetate, e.g., administered orally. In some embodiments, the add-back therapy includes 1.0 mg of β17-estradiol, e.g., administered orally, and, in the same pharmaceutical composition, 0.5 mg of norethindrone or a compound that is metabolized in vivo to produce norethindrone, such as an ester of norethindrone that is de-esterified in vivo to produce norethindrone, for instance, norethindrone acetate, e.g., administered orally. In some embodiments, the add-back therapy includes 1.0 mg of β17-estradiol, e.g., administered orally, and, in a separate pharmaceutical composition, 0.5 mg of norethindrone or a compound that is metabolized in vivo to produce norethindrone, such as an ester of norethindrone that is de-esterified in vivo to produce norethindrone, for instance, norethindrone acetate, e.g., administered orally.

In some embodiments, the GnRH antagonist is a compound represented by formula (I), (II), or (III), herein, and is administered to the patient in a fixed-dose composition that contains about 50 mg, 75 mg, 100 mg, or 200 mg of the compound, from about 0.75 mg to about 1.25 mg of β17-estradiol, and from about 0.25 mg to about 0.75 mg of norethindrone or a compound that is metabolized in vivo to produce norethindrone, such as an ester of norethindrone that is de-esterified in vivo to produce norethindrone, for instance, norethindrone acetate. In some embodiments, the compound is administered to the patient in a fixed-dose composition that contains about 50 mg, 75 mg, 100 mg, or 200 mg of the compound, about 1.0 mg of β17-estradiol (e.g., 1.0 mg of β17-estradiol), and about 0.5 mg of norethindrone or a compound that is metabolized in vivo to produce norethindrone, such as an ester of norethindrone that is de-esterified in vivo to produce norethindrone, for instance, norethindrone acetate (e.g., 0.5 mg of norethindrone or a compound that is metabolized in vivo to produce norethindrone, such as an ester of norethindrone that is de-esterified in vivo to produce norethindrone, for instance, norethindrone acetate).

In some embodiments, the above fixed-dose composition is administered to the patient in one or more doses per 12 hours, 24 hours, 48 hours, 72 hours, week, month, or year, such as in from 1 to 10 doses per 12 hours (e.g., 1 dose every 12 hours, 2 doses every 12 hours, 3 doses every 12 hours, 4 doses every 12 hours, 5 doses every 12 hours, 6 doses every 12 hours, 7 doses every 12 hours, 8 doses every 12 hours, 9 doses every 12 hours, or 10 doses every 12 hours), from 1 to 10 doses per 24 hours (e.g., 1 dose every 24 hours, 2 doses every 24 hours, 3 doses every 24 hours, 4 doses every 24 hours, 5 doses every 24 hours, 6 doses every 24 hours, 7 doses every 24 hours, 8 doses every 24 hours, 9 doses every 24 hours, or 10 doses every 24 hours), from 1 to 10 doses per 48 hours (e.g., 1 dose every 48 hours, 2 doses every 48 hours, 3 doses every 48 hours, 4 doses every 48 hours, 5 doses every 48 hours, 6 doses every 48 hours, 7 doses every 48 hours, 8 doses every 48 hours, 9 doses every 48 hours, or 10 doses every 48 hours), from 1 to 10 doses per 72 hours (e.g., 1 dose every 72 hours, 2 doses every 72 hours, 3 doses every 72 hours, 4 doses every 72 hours, 5 doses every 72 hours, 6 doses every 72 hours, 7 doses every 72 hours, 8 doses every 72 hours, 9 doses every 72 hours, or 10 doses every 72 hours), from 1 to 10 doses per week (e.g., 1 dose every week, 2 doses every week, 3 doses every week, 4 doses every week, 5 doses every week, 6 doses every week, 7 doses every week, 8 doses every week, 9 doses every week, or 10 doses every week), or from 1 to 60 doses per month (e.g., from 30-60 doses per month, such as 1 time daily, 2 times daily, 3 times daily, 4 times daily, 5 times daily, 6 times daily, 7 times daily, 8 times daily, 9 times daily, 10 times daily, 7 times weekly, 8 times weekly, 9 times weekly, 10 times weekly, 11 times weekly, 12 times weekly, 13 times weekly, 14 times weekly, or more), among others. In some embodiments, the above fixed-dose composition is administered to the patient once daily.

In some embodiments, the add-back therapy includes from about 0.25 mg to about 0.75 mg of β17-estradiol, e.g., administered orally, and from about 0.05 mg to about 0.2 mg of norethindrone or a compound that is metabolized in vivo to produce norethindrone, such as an ester of norethindrone that is de-esterified in vivo to produce norethindrone, for instance, norethindrone acetate, e.g., administered orally. In some embodiments, the add-back therapy includes 0.5 mg of β17-estradiol, e.g., administered orally, and 0.1 mg of norethindrone or a compound that is metabolized in vivo to produce norethindrone, such as an ester of norethindrone that is de-esterified in vivo to produce norethindrone, for instance, norethindrone acetate, e.g., administered orally. In some embodiments, the add-back therapy includes 0.5 mg of β17-estradiol, e.g., administered orally, and, in the same pharmaceutical composition, 0.1 mg of norethindrone or a compound that is metabolized in vivo to produce norethindrone, such as an ester of norethindrone that is de-esterified in vivo to produce norethindrone, for instance, norethindrone acetate, e.g., administered orally. In some embodiments, the add-back therapy includes 0.5 mg of β17-estradiol, e.g., administered orally, and, in a separate pharmaceutical composition, 0.1 mg of norethindrone or a compound that is metabolized in vivo to produce norethindrone, such as an ester of norethindrone that is de-esterified in vivo to produce norethindrone, for instance, norethindrone acetate, e.g., administered orally.

In some embodiments, the GnRH antagonist is a compound represented by formula (I), (II), or (III), herein, and is administered to the patient in a fixed-dose composition that contains about 50 mg, 75 mg, 100 mg, or 200 mg of the compound, from about 0.25 mg to about 0.75 mg of β17-estradiol, and from about 0.05 mg to about 0.2 mg of norethindrone or a compound that is metabolized in vivo to produce norethindrone, such as an ester of norethindrone that is de-esterified in vivo to produce norethindrone, for instance, norethindrone acetate. In some embodiments, the compound is administered to the patient in a fixed-dose composition that contains about 50 mg, 75 mg, 100 mg, or 200 mg of the compound, about 0.5 mg of β17-estradiol (e.g., 0.5 mg of β17-estradiol), and about 0.1 mg of norethindrone or a compound that is metabolized in vivo to produce norethindrone, such as an ester of norethindrone that is de-esterified in vivo to produce norethindrone, for instance, norethindrone acetate (e.g., 0.1 mg of norethindrone or a compound that is metabolized in vivo to produce norethindrone, such as an ester of norethindrone that is de-esterified in vivo to produce norethindrone, for instance, norethindrone acetate).

In some embodiments, the above fixed-dose composition is administered to the patient in one or more doses per 12 hours, 24 hours, 48 hours, 72 hours, week, month, or year, such as in from 1 to 10 doses per 12 hours (e.g., 1 dose every 12 hours, 2 doses every 12 hours, 3 doses every 12 hours, 4 doses every 12 hours, 5 doses every 12 hours, 6 doses every 12 hours, 7 doses every 12 hours, 8 doses every 12 hours, 9 doses every 12 hours, or 10 doses every 12 hours), from 1 to 10 doses per 24 hours (e.g., 1 dose every 24 hours, 2 doses every 24 hours, 3 doses every 24 hours, 4 doses every 24 hours, 5 doses every 24 hours, 6 doses every 24 hours, 7 doses every 24 hours, 8 doses every 24 hours, 9 doses every 24 hours, or 10 doses every 24 hours), from 1 to 10 doses per 48 hours (e.g., 1 dose every 48 hours, 2 doses every 48 hours, 3 doses every 48 hours, 4 doses every 48 hours, 5 doses every 48 hours, 6 doses every 48 hours, 7 doses every 48 hours, 8 doses every 48 hours, 9 doses every 48 hours, or 10 doses every 48 hours), from 1 to 10 doses per 72 hours (e.g., 1 dose every 72 hours, 2 doses every 72 hours, 3 doses every 72 hours, 4 doses every 72 hours, 5 doses every 72 hours, 6 doses every 72 hours, 7 doses every 72 hours, 8 doses every 72 hours, 9 doses every 72 hours, or 10 doses every 72 hours), from 1 to 10 doses per week (e.g., 1 dose every week, 2 doses every week, 3 doses every week, 4 doses every week, 5 doses every week, 6 doses every week, 7 doses every week, 8 doses every week, 9 doses every week, or 10 doses every week), from 1 to 60 doses per month (e.g., from 30-60 doses per month, such as 1 time daily, 2 times daily, 3 times daily, 4 times daily, 5 times daily, 6 times daily, 7 times daily, 8 times daily, 9 times daily, 10 times daily, 7 times weekly, 8 times weekly, 9 times weekly, 10 times weekly, 11 times weekly, 12 times weekly, 13 times weekly, 14 times weekly, or more), among others. In some embodiments, the fixed-dose composition is administered to the patient once daily.

In some embodiments, the patient does not exhibit a reduction in BMD of greater than 5% following administration of the GnRH antagonist and the add-back therapy. In some embodiments, the patient does not exhibit a reduction in BMD of greater than 1% following administration of the GnRH antagonist and the add-back therapy. The add-back therapy may be formulated for oral administration. For instance, the add-back therapy may be formulated as a tablet, capsule, gel cap, powder, liquid solution, or liquid suspension. In some embodiments, the add-back therapy includes both an estrogen, such as β17-estradiol, and a progestin, such as norethindrone or norethindrone acetate. The estrogen and progestin may be administered separately or admixed in a single composition, such as a single tablet, capsule, gel cap, powder, liquid solution, or liquid suspension.

In some embodiments, the BMD is assessed by dual energy X-ray absorptiometry. In some embodiments, the BMD is assessed in the spine or femur of the patient.

In some embodiments, the GnRH antagonist is a compound represented by formula (I)

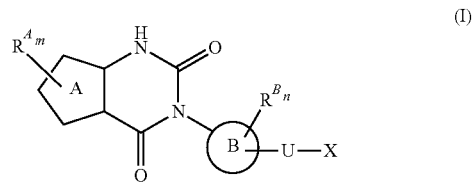

wherein ring A is a thiophene ring;
each $R^A$ is independently a halogen atom, a cyano group, a nitro group, an optionally substituted lower alkyl group, an optionally substituted lower alkenyl group, an optionally substituted lower alkynyl group, a hydroxyiminomethyl group, an optionally substituted sulfonyl group, an optionally substituted sulfinyl group, a tetrazolyl group, $OW^1$, $SW^1$, $COW^1$, $COOW^1$, $NHCOW^1$, $NHCONW^2W^3$, $NW^2W^3$, $CONW^2W^3$, or $SO_2NW^2W^3$, wherein $W^1$ to $W^3$ independently are a hydrogen atom or an optionally substituted lower alkyl group, or $W^2$ and $W^3$ may bind together with the neighboring nitrogen atom to form an optionally substituted cyclic amino group;
m is an integer from 0 to 3;
ring B is an aryl group or a monocyclic heteroaryl group;
each $R^B$ is independently a halogen atom, a cyano group, an optionally substituted lower alkyl group, $OW^4$, $COW^4$, $COOW^4$, or $CONW^5W^6$, wherein $W^4$ to $W^6$ independently are a hydrogen atom or an optionally substituted lower alkyl group, or $W^5$ and $W^6$ may bind together with the neighboring nitrogen atom to form an optionally substituted cyclic amino group;
n is an integer from 0 to 2;
U is a single bond;
X is a group represented by —S-L-Y, —O-L-Y, —CO-L-Y, or —SO$_2$-L-Y, wherein L is an optionally substituted lower alkylene group;
Y is a group represented by Z or —NW$^7$W$^8$, wherein W$^7$ and W$^8$ independently are a hydrogen atom, an optionally substituted lower alkyl group, or Z with the proviso that W$^7$ and W$^8$ are not simultaneously hydrogen atoms, or W$^7$ and W$^8$ may bind together with the neighboring nitrogen atom to form an optionally substituted cyclic amino group;
Z is an optionally fused and optionally substituted cycloalkyl group, an optionally fused and optionally substituted heterocycloalkyl group, an optionally fused and optionally substituted aryl group, or an optionally fused and optionally substituted heteroaryl group;

or a pharmaceutically acceptable salt thereof.

In some embodiments, the ring A is a thiophene ring represented by formula (A)

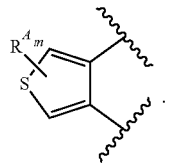

(A)

In some embodiments, m is 1 or 2. In some embodiments, m is 1. For instance, the ring A may be an optionally substituted thiophene ring represented by formula (B)

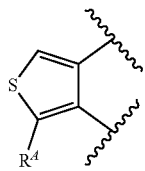

(B)

Each $R^A$ may independently be, for example, a halogen atom (e.g., fluorine, chlorine, bromine, or iodine), an optionally substituted lower alkyl group, $COOW^1$, or $CONW^2W^3$, wherein $W^1$ to $W^3$ independently are a hydrogen atom or an optionally substituted lower alkyl group, or $W^2$ and $W^3$ may bind together with the neighboring nitrogen atom to form an optionally substituted cyclic amino group. In some embodiments, each $R^A$ is COOH or pharmaceutically acceptable salt thereof.

In some embodiments, ring B is an optionally substituted benzene ring, pyridine ring, or thiophene ring. For instance, ring B may be represented by a formula selected from the group consisting of:

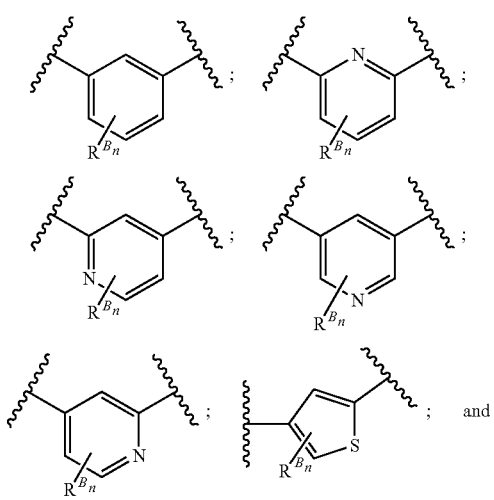

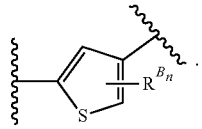

In some embodiments, n is 1 or 2. For instance, in some embodiments, n is 1. Ring B may be, for example, represented by a formula selected from the group consisting of:

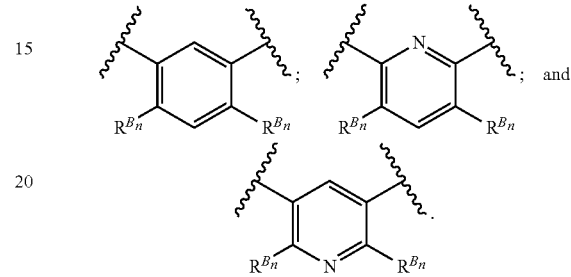

and

In some embodiments, each $R^B$ is independently a halogen atom, an optionally substituted lower alkyl group, or $OW^4$, wherein each $W^4$ is independently a hydrogen atom or an optionally substituted lower alkyl group. For instance, each $R^B$ may be independently a fluorine atom, chlorine atom, bromine atom, methyl group, or methoxy group.

In some embodiments, U is a single bond. X may be, for example, a group represented by —O-L-Y. L may be, for example, a methylene group. In some embodiments, Y is an optionally substituted benzene ring represented by formula (C)

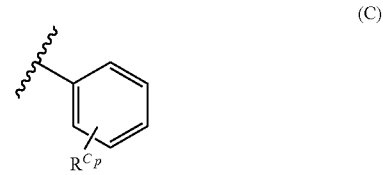

(C)

wherein each $R^C$ is independently a halogen atom, an optionally substituted lower alkyl group, or $OW^9$, wherein each $W^9$ is independently a hydrogen atom or an optionally substituted lower alkyl group; and p is an integer from 0 to 3.

In some embodiments, Y is a substituted benzene ring represented by formula (D)

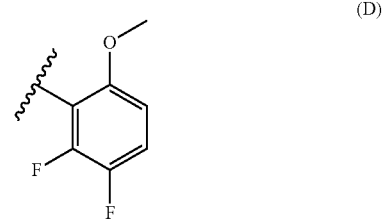 [SMILES: *c1c(OC)ccc(F)c1F]

(D)

In some embodiments, the compound is represented by formula (II)

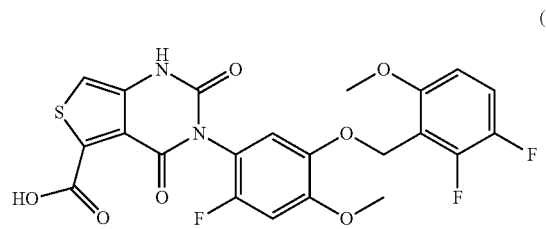

(II)

or a pharmaceutically acceptable salt thereof.

In some embodiments, the compound is the choline salt of the compound represented by formula (II), i.e., choline 3-[2-fluoro-5-(2,3-difluoro-6-methoxybenzyloxy)4-methoxyphenyl]-2,4-dioxo-1,2,3,4-tetrahydrothieno[3,4d]pyrimidine-5-carboxylate.

In some embodiments, the GnRH antagonist includes the compound represented by formula (II) in a crystalline state. In some embodiments, the compound exhibits characteristic X-ray powder diffraction peaks at about 7.1° 2θ, 11.5° 2θ, 19.4° 2θ, 20.3° 2θ, 21.5° 2θ, 22.0° 2θ, 22.6° 2θ, 23.5° 2θ, and 26.2° 2θ. In some embodiments, the compound exhibits $^{13}C$ solid-state nuclear magnetic resonance (NMR) peaks centered at about 155.8 ppm, 149.8 ppm, 145.3 ppm, 118.0 ppm, 113.7 ppm, 111.6 ppm, 110.3 ppm, 98.1 ppm, 69.8 ppm, 58.7 ppm, 57.1 ppm, and 55.5 ppm. In some embodiments, the compound exhibits $^{19}F$ solid-state NMR peaks centered at about −131.6 ppm, −145.2 ppm, and −151.8 ppm.

In some embodiments, the method includes administering from about 50 mg/day to about 200 mg/day (e.g., 50 mg/day, 55 mg/day, 60 mg/day, 65 mg/day, 70 mg/day, 75 mg/day, 80 mg/day, 85 mg/day, 90 mg/day, 95 mg/day, 100 mg/day, 110 mg/day, 115 mg/day, 120 mg/day, 125 mg/day, 130 mg/day, 135 mg/day, 140 mg/day, 145 mg/day, 150 mg/day, 155 mg/day, 160 mg/day, 165 mg/day, 170 mg/day, 175 mg/day, 180 mg/day, 185 mg/day, 190 mg/day, 195 mg/day, or 200 mg/day) of the compound represented by formula (I), or a pharmaceutically acceptable salt thereof, to the patient if the concentration of AMH in the sample isolated from the patient is above the AMH reference range.

In some embodiments, the method includes administering about 50 mg/day of the compound represented by formula (I), or a pharmaceutically acceptable salt thereof, to the patient if the concentration of AMH in the sample isolated from the patient is above the AMH reference range.

In some embodiments, the method includes administering about 75 mg/day of the compound represented by formula (I), or a pharmaceutically acceptable salt thereof, to the patient if the concentration of AMH in the sample isolated from the patient is above the AMH reference range.

In some embodiments, the method includes administering about 100 mg/day of the compound represented by formula (I), or a pharmaceutically acceptable salt thereof, to the patient if the concentration of AMH in the sample isolated from the patient is above the AMH reference range.

In some embodiments, the method includes administering about 200 mg/day of the compound represented by formula (I), or a pharmaceutically acceptable salt thereof, to the patient if the concentration of AMH in the sample isolated from the patient is above the AMH reference range.

In some embodiments, the method includes administering from 50 mg/day to about 200 mg/day (e.g., 50 mg/day, 55 mg/day, 60 mg/day, 65 mg/day, 70 mg/day, 75 mg/day, 80 mg/day, 85 mg/day, 90 mg/day, 95 mg/day, 100 mg/day, 110 mg/day, 115 mg/day, 120 mg/day, 125 mg/day, 130 mg/day, 135 mg/day, 140 mg/day, 145 mg/day, 150 mg/day, 155 mg/day, 160 mg/day, 165 mg/day, 170 mg/day, 175 mg/day, 180 mg/day, 185 mg/day, 190 mg/day, 195 mg/day, or 200 mg/day) of the compound represented by formula (II) to the patient if the concentration of AMH in the sample isolated from the patient is above the AMH reference range.

In some embodiments, the method includes administering about 50 mg/day of the compound represented by formula (II), or a pharmaceutically acceptable salt thereof, such as the choline salt thereof, to the patient if the concentration of AMH in the sample isolated from the patient is above the AMH reference range.

In some embodiments, the method includes administering about 75 mg/day of the compound represented by formula (II), or a pharmaceutically acceptable salt thereof, such as the choline salt thereof, to the patient if the concentration of AMH in the sample isolated from the patient is above the AMH reference range.

In some embodiments, the method includes administering about 100 mg/day of the compound represented by formula (II), or a pharmaceutically acceptable salt thereof, such as the choline salt thereof, to the patient if the concentration of AMH in the sample isolated from the patient is above the AMH reference range.

In some embodiments, the method includes administering about 200 mg/day of the compound represented by formula (II), or a pharmaceutically acceptable salt thereof, such as the choline salt thereof, to the patient if the concentration of AMH in the sample isolated from the patient is above the AMH reference range.

In some embodiments, the method includes administering from about 50 mg/day to about 200 mg/day (e.g., 50 mg/day, 55 mg/day, 60 mg/day, 65 mg/day, 70 mg/day, 75 mg/day, 80 mg/day, 85 mg/day, 90 mg/day, 95 mg/day, 100 mg/day, 110 mg/day, 115 mg/day, 120 mg/day, 125 mg/day, 130 mg/day, 135 mg/day, 140 mg/day, 145 mg/day, 150 mg/day, 155 mg/day, 160 mg/day, 165 mg/day, 170 mg/day, 175 mg/day, 180 mg/day, 185 mg/day, 190 mg/day, 195 mg/day, or 200 mg/day) of the compound represented by formula (I), or a pharmaceutically acceptable salt thereof, to the patient if the concentration of AMH in the sample isolated from the patient is below the AMH reference range.

In some embodiments, the method includes administering about 50 mg/day of the compound represented by formula (I), or a pharmaceutically acceptable salt thereof, to the patient if the concentration of AMH in the sample isolated from the patient is below the AMH reference range.

In some embodiments, the method includes administering about 75 mg/day of the compound represented by formula (I), or a pharmaceutically acceptable salt thereof, to the patient if the concentration of AMH in the sample isolated from the patient is below the AMH reference range.

In some embodiments, the method includes administering about 100 mg/day of the compound represented by formula (I), or a pharmaceutically acceptable salt thereof, to the patient if the concentration of AMH in the sample isolated from the patient is below the AMH reference range.

In some embodiments, the method includes administering about 200 mg/day of the compound represented by formula (I), or a pharmaceutically acceptable salt thereof, to the patient if the concentration of AMH in the sample isolated from the patient is below the AMH reference range.

In some embodiments, the method includes administering from 50 mg/day to about 200 mg/day (e.g., 50 mg/day, 55 mg/day, 60 mg/day, 65 mg/day, 70 mg/day, 75 mg/day, 80 mg/day, 85 mg/day, 90 mg/day, 95 mg/day, 100 mg/day, 110 mg/day, 115 mg/day, 120 mg/day, 125 mg/day, 130 mg/day, 135 mg/day, 140 mg/day, 145 mg/day, 150 mg/day, 155 mg/day, 160 mg/day, 165 mg/day, 170 mg/day, 175 mg/day, 180 mg/day, 185 mg/day, 190 mg/day, 195 mg/day, or 200 mg/day) of the compound represented by formula (II) to the patient if the concentration of AMH in the sample isolated from the patient is below the AMH reference range.

In some embodiments, the method includes administering about 50 mg/day of the compound represented by formula (II), or a pharmaceutically acceptable salt thereof, such as the choline salt thereof, to the patient if the concentration of AMH in the sample isolated from the patient is below the AMH reference range.

In some embodiments, the method includes administering about 75 mg/day of the compound represented by formula (II), or a pharmaceutically acceptable salt thereof, such as the choline salt thereof, to the patient if the concentration of AMH in the sample isolated from the patient is below the AMH reference range.

In some embodiments, the method includes administering about 100 mg/day of the compound represented by formula (II), or a pharmaceutically acceptable salt thereof, such as the choline salt thereof, to the patient if the concentration of AMH in the sample isolated from the patient is below the AMH reference range.

In some embodiments, the method includes administering about 200 mg/day of the compound represented by formula (II), or a pharmaceutically acceptable salt thereof, such as the choline salt thereof, to the patient if the concentration of AMH in the sample isolated from the patient is below the AMH reference range.

In some embodiments, the method includes administering from about 50 mg/day to about 200 mg/day (e.g., 50 mg/day, 55 mg/day, 60 mg/day, 65 mg/day, 70 mg/day, 75 mg/day, 80 mg/day, 85 mg/day, 90 mg/day, 95 mg/day, 100 mg/day, 110 mg/day, 115 mg/day, 120 mg/day, 125 mg/day, 130 mg/day, 135 mg/day, 140 mg/day, 145 mg/day, 150 mg/day, 155 mg/day, 160 mg/day, 165 mg/day, 170 mg/day, 175 mg/day, 180 mg/day, 185 mg/day, 190 mg/day, 195 mg/day, or 200 mg/day) of the compound represented by formula (I), or a pharmaceutically acceptable salt thereof, to the patient if the concentration of AMH in the sample isolated from the patient is within the AMH reference range.

In some embodiments, the method includes administering about 50 mg/day of the compound represented by formula (I), or a pharmaceutically acceptable salt thereof, to the patient if the concentration of AMH in the sample isolated from the patient is within the AMH reference range.

In some embodiments, the method includes administering about 75 mg/day of the compound represented by formula (I), or a pharmaceutically acceptable salt thereof, to the patient if the concentration of AMH in the sample isolated from the patient is within the AMH reference range.

In some embodiments, the method includes administering about 100 mg/day of the compound represented by formula (I), or a pharmaceutically acceptable salt thereof, to the patient if the concentration of AMH in the sample isolated from the patient is within the AMH reference range.

In some embodiments, the method includes administering about 200 mg/day of the compound represented by formula (I), or a pharmaceutically acceptable salt thereof, to the patient if the concentration of AMH in the sample isolated from the patient is within the AMH reference range.

In some embodiments, the method includes administering from 50 mg/day to about 200 mg/day (e.g., 50 mg/day, 55 mg/day, 60 mg/day, 65 mg/day, 70 mg/day, 75 mg/day, 80 mg/day, 85 mg/day, 90 mg/day, 95 mg/day, 100 mg/day, 110 mg/day, 115 mg/day, 120 mg/day, 125 mg/day, 130 mg/day, 135 mg/day, 140 mg/day, 145 mg/day, 150 mg/day, 155 mg/day, 160 mg/day, 165 mg/day, 170 mg/day, 175 mg/day, 180 mg/day, 185 mg/day, 190 mg/day, 195 mg/day, or 200 mg/day) of the compound represented by formula (II) to the patient if the concentration of AMH in the sample isolated from the patient is within the AMH reference range.

In some embodiments, the method includes administering about 50 mg/day of the compound represented by formula (II), or a pharmaceutically acceptable salt thereof, such as the choline salt thereof, to the patient if the concentration of AMH in the sample isolated from the patient is within the AMH reference range.

In some embodiments, the method includes administering about 75 mg/day of the compound represented by formula (II), or a pharmaceutically acceptable salt thereof, such as the choline salt thereof, to the patient if the concentration of AMH in the sample isolated from the patient is within the AMH reference range.

In some embodiments, the method includes administering about 100 mg/day of the compound represented by formula (II), or a pharmaceutically acceptable salt thereof, such as the choline salt thereof, to the patient if the concentration of AMH in the sample isolated from the patient is within the AMH reference range.

In some embodiments, the method includes administering about 200 mg/day of the compound represented by formula (II), or a pharmaceutically acceptable salt thereof, such as the choline salt thereof, to the patient if the concentration of AMH in the sample isolated from the patient is within the AMH reference range.

In some embodiments, the method includes administering from 40 to 225 mg/day (e.g., 40 mg/day, 45 mg/day, 50 mg/day, 55 mg/day, 60 mg/day, 65 mg/day, 70 mg/day, 75 mg/day, 80 mg/day, 85 mg/day, 90 mg/day, 95 mg/day, 100 mg/day, 125 mg/day, 150 mg/day, 175 mg/day, or 200 mg/day) of the compound represented by formula (I) to the patient if the concentration of AMH in the sample isolated from the patient is above the AMH reference range. In some embodiments, the method includes administering 50 mg/day, 75 mg/day, 100 mg/day, or 200 mg/day of the compound represented by formula (I) to the patient if the concentration of AMH in the sample isolated from the patient is above the AMH reference range. In some embodiments, the method includes administering from 40 to 225 mg/day (e.g., 40 mg/day, 45 mg/day, 50 mg/day, 55 mg/day, 60 mg/day, 65 mg/day, 70 mg/day, 75 mg/day, 80 mg/day, 85 mg/day, 90 mg/day, 95 mg/day, 100 mg/day, 125 mg/day, 150 mg/day, 175 mg/day, or 200 mg/day) of the compound represented by formula (II) to the patient if the concentration of AMH in the sample isolated from the patient is above the AMH reference range. In some embodiments, the method includes administering 50 mg/day, 75 mg/day, 100 mg/day, or 200 mg/day of the compound represented by formula (II) to the patient if the concentration of AMH in the sample isolated from the patient is above the AMH reference range. In some embodiments, the method includes administering from 40 to 225 mg/day (e.g., 40 mg/day, 45 mg/day, 50 mg/day, 55 mg/day, 60 mg/day, 65 mg/day, 70 mg/day, 75 mg/day, 80 mg/day, 85 mg/day, 90 mg/day, 95 mg/day, 100 mg/day, 125 mg/day, 150 mg/day, 175 mg/day, or 200 mg/day) of choline 3-[2-fluoro-5-(2,3-difluoro-6-methoxybenzyloxy)4-methoxyphenyl]-2,4-dioxo-1,2,3,4-tetrahydrothieno[3,4d]pyrimidine-5-carboxylate to the patient if the concentration of AMH in the sample isolated from the patient is above the AMH reference range. In some embodiments, the method includes administering 50 mg/day, 75 mg/day, 100 mg/day, or 200 mg/day of choline 3-[2-fluoro-5-(2,3-difluoro-6-methoxybenzyloxy)4-methoxyphenyl]-2,4-dioxo-1,2,3,4-tetrahydrothieno[3,4d]pyrimidine-5-carboxylate to the patient if the concentration of AMH in the sample isolated from the patient is above the AMH reference range.

In some embodiments, the method includes administering from 40 to 225 mg/day (e.g., 40 mg/day, 45 mg/day, 50 mg/day, 55 mg/day, 60 mg/day, 65 mg/day, 70 mg/day, 75 mg/day, 80 mg/day, 85 mg/day, 90 mg/day, 95 mg/day, 100 mg/day, 125 mg/day, 150 mg/day, 175 mg/day, or 200 mg/day) of the compound represented by formula (I) to the patient if the concentration of AMH in the sample isolated from the patient is below the AMH reference range. In some embodiments, the method includes administering 50 mg/day, 75 mg/day, 100 mg/day, or 200 mg/day of the compound represented by formula (I) to the patient if the concentration of AMH in the sample isolated from the patient is below the AMH reference range. In some embodiments, the method includes administering from 40 to 225 mg/day (e.g., 40 mg/day, 45 mg/day, 50 mg/day, 55 mg/day, 60 mg/day, 65 mg/day, 70 mg/day, 75 mg/day, 80 mg/day, 85 mg/day, 90 mg/day, 95 mg/day, 100 mg/day, 125 mg/day, 150 mg/day, 175 mg/day, or 200 mg/day) of the compound represented by formula (II) to the patient if the concentration of AMH in the sample isolated from the patient is below the AMH reference range. In some embodiments, the method includes administering 50 mg/day, 75 mg/day, 100 mg/day, or 200 mg/day of the compound represented by formula (II) to the patient if the concentration of AMH in the sample isolated from the patient is below the AMH reference range. In some embodiments, the method includes administering from 40 to 225 mg/day (e.g., 40 mg/day, 45 mg/day, 50 mg/day, 55 mg/day, 60 mg/day, 65 mg/day, 70 mg/day, 75 mg/day, 80 mg/day, 85 mg/day, 90 mg/day, 95 mg/day, 100 mg/day, 125 mg/day, 150 mg/day, 175 mg/day, or 200 mg/day) of choline 3-[2-fluoro-5-(2,3-difluoro-6-methoxybenzyloxy)4-methoxyphenyl]-2,4-dioxo-1,2,3,4-tetrahydrothieno[3,4d]pyrimidine-5-carboxylate to the patient if the concentration of AMH in the sample isolated from the patient is below the AMH reference range. In some embodiments, the method includes administering 50 mg/day, 75 mg/day, 100 mg/day, or 200 mg/day of choline 3-[2-fluoro-5-(2,3-difluoro-6-methoxybenzyloxy)4-methoxyphenyl]-2,4-dioxo-1,2,3,4-tetrahydrothieno[3,4d]pyrimidine-5-carboxylate to the patient if the concentration of AMH in the sample isolated from the patient is below the AMH reference range.

In some embodiments, the method includes administering from 40 to 225 mg/day (e.g., 40 mg/day, 45 mg/day, 50 mg/day, 55 mg/day, 60 mg/day, 65 mg/day, 70 mg/day, 75 mg/day, 80 mg/day, 85 mg/day, 90 mg/day, 95 mg/day, 100 mg/day, 125 mg/day, 150 mg/day, 175 mg/day, or 200 mg/day) of the compound represented by formula (I) to the patient if the concentration of AMH in the sample isolated from the patient is within the AMH reference range. In some embodiments, the method includes administering 50 mg/day, 75 mg/day, 100 mg/day, or 200 mg/day of the compound represented by formula (I) to the patient if the concentration of AMH in the sample isolated from the patient is within the AMH reference range. In some embodiments, the method includes administering from 40 to 225 mg/day (e.g., 40 mg/day, 45 mg/day, 50 mg/day, 55 mg/day, 60 mg/day, 65 mg/day, 70 mg/day, 75 mg/day, 80 mg/day, 85 mg/day, 90 mg/day, 95 mg/day, 100 mg/day, 125 mg/day, 150 mg/day, 175 mg/day, or 200 mg/day) of the compound represented by formula (II) to the patient if the concentration of AMH in the sample isolated from the patient is within the AMH reference range. In some embodiments, the method includes administering 50 mg/day, 75 mg/day, 100 mg/day, or 200 mg/day of the compound represented by formula (II) to the patient if the concentration of AMH in the sample isolated from the patient is within the AMH reference range. In some embodiments, the method includes administering from 40 to 225 mg/day (e.g., 40 mg/day, 45 mg/day, 50 mg/day, 55 mg/day, 60 mg/day, 65 mg/day, 70 mg/day, 75 mg/day, 80 mg/day, 85 mg/day, 90 mg/day, 95 mg/day, 100 mg/day, 125 mg/day, 150 mg/day, 175 mg/day, or 200 mg/day) of choline 3-[2-fluoro-5-(2,3-difluoro-6-methoxybenzyloxy)4-methoxyphenyl]-2,4-dioxo-1,2,3,4-tetrahydrothieno[3,4d]pyrimidine-5-carboxylate to the patient if the concentration of AMH in the sample isolated from the patient is within the AMH reference range. In some embodiments, the method includes administering 50 mg/day, 75 mg/day, 100 mg/day, or 200 mg/day of choline 3-[2-fluoro-5-(2,3-difluoro-6-methoxybenzyloxy)4-methoxyphenyl]-2,4-dioxo-1,2,3,4-tetrahydrothieno[3,4d]pyrimidine-5-carboxylate to the patient if the concentration of AMH in the sample isolated from the patient is within the AMH reference range.

In some embodiments, the GnRH antagonist is selected from the group consisting of elagolix, relugolix, ASP-1707, SKI2670, and BAY-784, or a derivative or variant thereof.

In some embodiments, the GnRH antagonist is elagolix or a derivative or variant thereof, such as a compound described in U.S. Pat. No. 7,056,927; 7,176,211; 7,419,983; 8,765,948; or 9,382,214; or in US Patent Application Publication No. 2014/0288031 or 2017/0056403, the disclosures of which are incorporated herein by reference in their entirety. In some embodiments, the method includes administering 150 mg/day or more (e.g., 150 mg/day, 155 mg/day, 160 mg/day, 165 mg/day, 170 mg/day, 175 mg/day, 180 mg/day, 185 mg/day, 190 mg/day, 195 mg/day, 200 mg/day, 205 mg/day, 210 mg/day, 215 mg/day, 220 mg/day, 225 mg/day, 230 mg/day, 235 mg/day, 240 mg/day, 245 mg/day, 250 mg/day, 255 mg/day, 260 mg/day, 265 mg/day, 270 mg/day, 275 mg/day, 280 mg/day, 285 mg/day, 290 mg/day, 295 mg/day, 300 mg/day, 305 mg/day, 310 mg/day, 315 mg/day, 320 mg/day, 325 mg/day, 330 mg/day, 335 mg/day, 340 mg/day, 345 mg/day, 350 mg/day, 355 mg/day, 360 mg/day, 365 mg/day, 370 mg/day, 375 mg/day, 380 mg/day, 385 mg/day, 390 mg/day, 395, 400 mg/day, or more) of elagolix to the patient if the concentration of AMH in the sample isolated from the patient is above the AMH reference range. In some embodiments, the method includes administering from 145 mg/day to 405 mg/day of elagolix to the patient if the concentration of AMH in the sample isolated from the patient is above the AMH reference range.

In some embodiments, the method includes administering more than 400 mg/day (e.g., 405 mg/day, 410 mg/day, 415 mg/day, 420 mg/day, 425 mg/day, 430 mg/day, 435 mg/day, 440 mg/day, 445 mg/day, 450 mg/day, 455 mg/day, 460 mg/day, 465 mg/day, 470 mg/day, 475 mg/day, 480 mg/day, 485 mg/day, 490 mg/day, 495 mg/day, 500 mg/day, 505 mg/day, 510 mg/day, 515 mg/day, 520 mg/day, 525 mg/day, 530 mg/day, 535 mg/day, 540 mg/day, 545 mg/day, 550 mg/day, 555 mg/day, 560 mg/day, 565 mg/day, 570 mg/day, 575 mg/day, 580 mg/day, 585 mg/day, 590 mg/day, 595 mg/day, 600 mg/day, 605 mg/day, 610 mg/day, 615 mg/day, 620 mg/day, 625 mg/day, 630 mg/day, 635 mg/day, 640 mg/day, 645 mg/day, 650 mg/day, 655 mg/day, 660 mg/day, 665 mg/day, 670 mg/day, 675 mg/day, 680 mg/day, 685 mg/day, 690 mg/day, 695 mg/day, 700 mg/day, or more) of elagolix to the patient if the concentration of AMH in the sample isolated from the patient is above the AMH reference range. In some embodiments, the method includes administering from 400 mg/day to 600 mg/day of elagolix to the patient if the concentration of AMH in the sample isolated from the patient is above the AMH reference range.

When administered at elevated doses (for instance, doses of 150 mg/day, 400 mg/day, or more) elagolix may be administered in combination with add-back therapy. The add-back therapy may be administered to the patient concurrently with the elagolix, prior to administration of the elagolix, or following administration of the elagolix.

In some embodiments, the add-back therapy includes an estrogen. In some embodiments, the estrogen is selected from the group consisting of β17-estradiol, ethinyl estradiol, and conjugated estrogens, such as conjugated equine estrogens.

In some embodiments, the estrogen is β17-estradiol. The β17-estradiol may be administered to the patient, for example, at a dose of from about 0.1 mg to about 2.5 mg, such as at a dose of about 0.1 mg, 0.2 mg, 0.3 mg, 0.4 mg, 0.5 mg, 0.6 mg, 0.7 mg, 0.8 mg, 0.9 mg, 1.0 mg, 1.1 mg, 1.2 mg, 1.3 mg, 1.4 mg, 1.5 mg, 1.6 mg, 1.7 mg, 1.8 mg, 1.9 mg, 2.0 mg, 2.1 mg, 2.2 mg, 2.3 mg, 2.4 mg, or 2.5 mg, for instance, by oral administration. In some embodiments, the β17-estradiol is administered to the patient at a dose of 1.0 mg, for instance, by oral administration. In some embodiments, the β17-estradiol is administered to the patient at a dose of 0.5 mg, for instance, by oral administration.

The β17-estradiol may be administered to the patient one or more times per day, week, or month. The β17-estradiol may be administered to the patient, for example, at a dose of from about 0.1 mg/day to about 2.5 mg/day, such as at a dose of about 0.1 mg/day, 0.2 mg/day, 0.3 mg/day, 0.4 mg/day, 0.5 mg/day, 0.6 mg/day, 0.7 mg/day, 0.8 mg/day, 0.9 mg/day, 1.0 mg/day, 1.1 mg/day, 1.2 mg/day, 1.3 mg/day, 1.4 mg/day, 1.5 mg/day, 1.6 mg/day, 1.7 mg/day, 1.8 mg/day, 1.9 mg/day, 2.0 mg/day, 2.1 mg/day, 2.2 mg/day, 2.3 mg/day, 2.4 mg/day, or 2.5 mg/day, for instance, by oral administration. In some embodiments, the β17-estradiol is administered to the patient at a dose of 1.0 mg/day, for instance, by oral administration. In some embodiments, the β17-estradiol is administered to the patient at a dose of 0.5 mg/day, for instance, by oral administration.

In some embodiments, the estrogen is ethinyl estradiol. The ethinyl estradiol may be administered to the patient, for example, at a dose of from about 1.0 µg to about 6.0 µg, such as at a dose of about 1.0 µg, 1.1 µg, 1.2 µg, 1.3 µg, 1.4 µg, 1.5 µg, 1.6 µg, 1.7 µg, 1.8 µg, 1.9 µg, 2.0 µg, 2.1 µg, 2.2 µg, 2.3 µg, 2.4 µg, 2.5 µg, 2.6 µg, 2.7 µg, 2.8 µg, 2.9 µg, 3.0 µg, 3.1 µg, 3.2 µg, 3.3 µg, 3.4 µg, 3.5 µg, 3.6 µg, 3.7 µg, 3.8 µg, 3.9 µg, 4.0 µg, 4.1 µg, 4.2 µg, 4.2 µg, 4.3 µg, 4.4 µg, 4.5 µg, 4.6 µg, 4.7 µg, 4.8 µg, 4.9 µg, 5.0 µg, 5.1 µg, 5.2 µg, 5.3 µg, 5.4 µg, 5.5 µg, 5.6 µg, 5.7 µg, 5.8 µg, 5.9 µg, or 6.0 µg, for instance, by oral administration. In some embodiments, the ethinyl estradiol is administered to the patient at a dose of 5.0 µg, for instance, by oral administration. In some embodiments, the ethinyl estradiol is administered to the patient at a dose of 2.5 µg, for instance, by oral administration.

The ethinyl estradiol may be administered to the patient one or more times per day, week, or month. The ethinyl estradiol may be administered to the patient, for example, at a dose of from about 1.0 µg/day to about 6.0 µg/day, such as at a dose of about 1.0 µg/day, 1.1 µg/day, 1.2 µg/day, 1.3 µg/day, 1.4 µg/day, 1.5 µg/day, 1.6 µg/day, 1.7 µg/day, 1.8 µg/day, 1.9 µg/day, 2.0 µg/day, 2.1 µg/day, 2.2 µg/day, 2.3 µg/day, 2.4 µg/day, 2.5 µg/day, 2.6 µg/day, 2.7 µg/day, 2.8 µg/day, 2.9 µg/day, 3.0 µg/day, 3.1 µg/day, 3.2 µg/day, 3.3 µg/day, 3.4 µg/day, 3.5 µg/day, 3.6 µg/day, 3.7 µg/day, 3.8 µg/day, 3.9 µg/day, 4.0 µg/day, 4.1 µg/day, 4.2 µg/day, 4.2 µg/day, 4.3 µg/day, 4.4 µg/day, 4.5 µg/day, 4.6 µg/day, 4.7 µg/day, 4.8 µg/day, 4.9 µg/day, 5.0 µg/day, 5.1 µg/day, 5.2 µg/day, 5.3 µg/day, 5.4 µg/day, 5.5 µg/day, 5.6 µg/day, 5.7 µg/day, 5.8 µg/day, 5.9 µg/day, or 6.0 µg/day, for instance, by oral administration. In some embodiments, the ethinyl estradiol is administered to the patient at a dose of 5.0 µg/day, for instance, by oral administration. In some embodiments, the ethinyl estradiol is administered to the patient at a dose of 2.5 µg/day, for instance, by oral administration.

In some embodiments, the estrogen is a conjugated estrogen, such as a conjugated equine estrogen. The conjugated estrogen may be administered to the patient, for example, at a dose of from about 0.1 mg to about 2.0 mg, such as at a dose of about 0.1 mg, 0.2 mg, 0.3 mg, 0.4 mg, 0.5 mg, 0.6 mg, 0.7 mg, 0.8 mg, 0.9 mg, 1.0 mg, 1.1 mg, 1.2 mg, 1.3 mg, 1.4 mg, 1.5 mg, 1.6 mg, 1.7 mg, 1.8 mg, 1.9 mg, or 2.0 mg, for instance, by oral administration. In some embodiments, the conjugated estrogen is administered to the patient at a dose of 0.625 mg, for instance, by oral administration. In some embodiments, the conjugated estrogen is administered to the patient at a dose of 0.45 mg, for instance, by oral administration. In some embodiments, the conjugated estrogen is administered to the patient at a dose of 0.3 mg, for instance, by oral administration.

The conjugated estrogen may be administered to the patient one or more times per day, week, or month. The conjugated estrogen may be administered to the patient, for example, at a dose of from about 0.1 mg/day to about 2.0 mg/day, such as at a dose of about 0.1 mg/day, 0.2 mg/day, 0.3 mg/day, 0.4 mg/day, 0.5 mg/day, 0.6 mg/day, 0.7 mg/day, 0.8 mg/day, 0.9 mg/day, 1.0 mg/day, 1.1 mg/day, 1.2 mg/day, 1.3 mg/day, 1.4 mg/day, 1.5 mg/day, 1.6 mg/day, 1.7 mg/day, 1.8 mg/day, 1.9 mg/day, or 2.0 mg/day, for instance, by oral administration. In some embodiments, the conjugated estrogen is administered to the patient at a dose of 0.625 mg/day, for instance, by oral administration. In some embodiments, the conjugated estrogen is administered to the patient at a dose of 0.45 mg/day, for instance, by oral administration. In some embodiments, the conjugated estrogen is administered to the patient at a dose of 0.3 mg/day, for instance, by oral administration.

In some embodiments, the add-back therapy includes a progestin. In some embodiments, the progestin is selected from the group consisting of norethindrone or an ester thereof, such as norethindrone acetate, or another agent such as progesterone, norgestimate, medroxyprogesterone, or drospirenone.

In some embodiments, the progestin is norethindrone or a compound that is metabolized in vivo to produce norethindrone, such as an ester of norethindrone that is de-esterified in vivo to produce norethindrone, for instance, norethindrone acetate.

In some embodiments, the progestin is norethindrone. The norethindrone may be administered to the patient, for example, at a dose of from about 0.05 mg to about 5.0 mg, such as at a dose of about 0.05 mg, 0.06 mg, 0.07 mg, 0.08 mg, 0.09 mg, 0.1 mg, 0.2 mg, 0.3 mg, 0.4 mg, 0.5 mg, 0.6 mg, 0.7 mg, 0.8 mg, 0.9 mg, 1.0 mg, 1.1 mg, 1.2 mg, 1.3 mg, 1.4 mg, 1.5 mg, 1.6 mg, 1.7 mg, 1.8 mg, 1.9 mg, 2.0 mg, 2.1 mg, 2.2 mg, 2.3 mg, 2.4 mg, 2.5 mg, 2.6 mg, 2.7 mg, 2.8 mg, 2.9 mg, 3.0 mg, 3.1 mg, 3.2 mg, 3.3 mg, 3.4 mg, 3.5 mg, 3.6 mg, 3.7 mg, 3.8 mg, 3.9 mg, 4.0 mg, 4.1 mg, 4.2 mg, 4.3 mg, 4.4 mg, 4.5 mg, 4.6 mg, 4.7 mg, 4.8 mg, 4.9 mg, or 5.0 mg, for instance, by oral administration. In some embodiments, the norethindrone is administered to the patient at a dose of 1.0 mg, for instance, by oral administration. In some embodiments, the norethindrone is administered to the patient at a dose of 0.5 mg, for instance, by oral administration. In some embodiments, the norethindrone is administered to the patient at a dose of 0.1 mg, for instance, by oral administration.

The norethindrone may be administered to the patient one or more times per day, week, or month. The norethindrone may be administered to the patient, for example, at a dose of from about 0.05 mg/day to about 5.0 mg/day, such as at a dose of about 0.05 mg/day, 0.06 mg/day, 0.07 mg/day, 0.08 mg/day, 0.09 mg/day, 0.1 mg/day, 0.2 mg/day, 0.3 mg/day, 0.4 mg/day, 0.5 mg/day, 0.6 mg/day, 0.7 mg/day, 0.8 mg/day, 0.9 mg/day, 1.0 mg/day, 1.1 mg/day, 1.2 mg/day, 1.3 mg/day, 1.4 mg/day, 1.5 mg/day, 1.6 mg/day, 1.7 mg/day, 1.8 mg/day, 1.9 mg/day, 2.0 mg/day, 2.1 mg/day, 2.2 mg/day, 2.3 mg/day, 2.4 mg/day, 2.5 mg/day, 2.6 mg/day, 2.7 mg/day, 2.8 mg/day, 2.9 mg/day, 3.0 mg/day, 3.1 mg/day, 3.2 mg/day, 3.3 mg/day, 3.4 mg/day, 3.5 mg/day, 3.6 mg/day, 3.7 mg/day, 3.8 mg/day, 3.9 mg/day, 4.0 mg/day, 4.1 mg/day, 4.2 mg/day, 4.3 mg/day, 4.4 mg/day, 4.5 mg/day, 4.6 mg/day, 4.7 mg/day, 4.8 mg/day, 4.9 mg/day, or 5.0 mg/day, for instance, by oral administration. In some embodiments, the norethindrone is administered to the patient at a dose of 1.0 mg/day, for instance, by oral administration. In some embodiments, the norethindrone is administered to the patient at a dose of 0.5 mg/day, for instance, by oral administration. In some embodiments, the norethindrone is administered to the patient at a dose of 0.1 mg/day, for instance, by oral administration.

In some embodiments, the progestin is norethindrone acetate. The norethindrone acetate may be administered to the patient, for example, at a dose of from about 0.05 mg to about 5.0 mg, such as at a dose of about 0.05 mg, 0.06 mg, 0.07 mg, 0.08 mg, 0.09 mg, 0.1 mg, 0.2 mg, 0.3 mg, 0.4 mg, 0.5 mg, 0.6 mg, 0.7 mg, 0.8 mg, 0.9 mg, 1.0 mg, 1.1 mg, 1.2 mg, 1.3 mg, 1.4 mg, 1.5 mg, 1.6 mg, 1.7 mg, 1.8 mg, 1.9 mg, 2.0 mg, 2.1 mg, 2.2 mg, 2.3 mg, 2.4 mg, 2.5 mg, 2.6 mg, 2.7 mg, 2.8 mg, 2.9 mg, 3.0 mg, 3.1 mg, 3.2 mg, 3.3 mg, 3.4 mg, 3.5 mg, 3.6 mg, 3.7 mg, 3.8 mg, 3.9 mg, 4.0 mg, 4.1 mg, 4.2 mg, 4.3 mg, 4.4 mg, 4.5 mg, 4.6 mg, 4.7 mg, 4.8 mg, 4.9 mg, or 5.0 mg, for instance, by oral administration. In some embodiments, the norethindrone acetate is administered to the patient at a dose of 1.0 mg/day, for instance, by oral administration. In some embodiments, the norethindrone acetate is administered to the patient at a dose of 0.5 mg/day, for instance, by oral administration. In some embodiments, the norethindrone acetate is administered to the patient at a dose of 0.1 mg, for instance, by oral administration.

The norethindrone acetate may be administered to the patient one or more times per day, week, or month. The norethindrone acetate may be administered to the patient, for example, at a dose of from about 0.05 mg/day to about 5.0 mg/day, such as at a dose of about 0.05 mg/day, 0.06 mg/day, 0.07 mg/day, 0.08 mg/day, 0.09 mg/day, 0.1 mg/day, 0.2 mg/day, 0.3 mg/day, 0.4 mg/day, 0.5 mg/day, 0.6 mg/day, 0.7 mg/day, 0.8 mg/day, 0.9 mg/day, 1.0 mg/day, 1.1 mg/day, 1.2 mg/day, 1.3 mg/day, 1.4 mg/day, 1.5 mg/day, 1.6 mg/day, 1.7 mg/day, 1.8 mg/day, 1.9 mg/day, 2.0 mg/day, 2.1 mg/day, 2.2 mg/day, 2.3 mg/day, 2.4 mg/day, 2.5 mg/day, 2.6 mg/day, 2.7 mg/day, 2.8 mg/day, 2.9 mg/day, 3.0 mg/day, 3.1 mg/day, 3.2 mg/day, 3.3 mg/day, 3.4 mg/day, 3.5 mg/day, 3.6 mg/day, 3.7 mg/day, 3.8 mg/day, 3.9 mg/day, 4.0 mg/day, 4.1 mg/day, 4.2 mg/day, 4.3 mg/day, 4.4 mg/day, 4.5 mg/day, 4.6 mg/day, 4.7 mg/day, 4.8 mg/day, 4.9 mg/day, or 5.0 mg/day, for instance, by oral administration. In some embodiments, the norethindrone acetate is administered to the patient at a dose of 1.0 mg/day, for instance, by oral administration. In some embodiments, the norethindrone acetate is administered to the patient at a dose of 0.5 mg/day, for instance, by oral administration. In some embodiments, the norethindrone acetate is administered to the patient at a dose of 0.1 mg/day, for instance, by oral administration.

In some embodiments, the progestin is progesterone. The progesterone may be administered to the patient, for example, at a dose of from about 50 mg to about 250 mg, such as a dose of about 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, 200 mg, 205 mg, 210 mg, 215 mg, 220 mg, 225 mg, 230 mg, 235 mg, 240 mg, 245 mg, or 250 mg, for instance, by oral administration. In some embodiments, the progesterone is administered to the patient at a dose of 200 mg, for instance, by oral administration. In some embodiments, the progesterone is administered to the patient at a dose of 100 mg, for instance, by oral administration.

The progesterone may be administered to the patient one or more times per day, week, or month. The progesterone may be administered to the patient, for example, at a dose of from about 50 mg/day to about 250 mg/day, such as a dose of about 50 mg/day, 55 mg/day, 60 mg/day, 65 mg/day, 70 mg/day, 75 mg/day, 80 mg/day, 85 mg/day, 90 mg/day, 95 mg/day, 100 mg/day, 105 mg/day, 110 mg/day, 115 mg/day, 120 mg/day, 125 mg/day, 130 mg/day, 135 mg/day, 140 mg/day, 145 mg/day, 150 mg/day, 155 mg/day, 160 mg/day, 165 mg/day, 170 mg/day, 175 mg/day, 180 mg/day, 185 mg/day, 190 mg/day, 195 mg/day, 200 mg/day, 205 mg/day, 210 mg/day, 215 mg/day, 220 mg/day, 225 mg/day, 230 mg/day, 235 mg/day, 240 mg/day, 245 mg/day, or 250 mg/day, for instance, by oral administration. In some embodiments, the progesterone is administered to the patient at a dose of 200 mg/day, for instance, by oral administration. In some embodiments, the progesterone is administered to the patient at a dose of 100 mg/day, for instance, by oral administration.

In some embodiments, the progestin is norgestimate. The norgestimate may be administered to the patient, for example, at a dose of from about 0.01 mg to about 2.0 mg, such as at a dose of about 0.01 mg, 0.02 mg, 0.03 mg, 0.04 mg, 0.05 mg, 0.06 mg, 0.07 mg, 0.08 mg, 0.09 mg, 0.1 mg, 0.2 mg, 0.3 mg, 0.4 mg, 0.5 mg, 0.6 mg, 0.7 mg, 0.8 mg, 0.9 mg, 1.0 mg, 1.1 mg, 1.2 mg, 1.3 mg, 1.4 mg, 1.5 mg, 1.6 mg, 1.7 mg, 1.8 mg, 1.9 mg, or 2.0 mg, for instance, by oral administration. In some embodiments, the norgestimate is administered to the patient at a dose of 0.09 mg, for instance, by oral administration.

The norgestimate may be administered to the patient one or more times per day, week, or month. The norgestimate may be administered to the patient, for example, at a dose of from about 0.01 mg/day to about 2.0 mg/day, such as at a dose of about 0.01 mg/day, 0.02 mg/day, 0.03 mg/day, 0.04 mg/day, 0.05 mg/day, 0.06 mg/day, 0.07 mg/day, 0.08 mg/day, 0.09 mg/day, 0.1 mg/day, 0.2 mg/day, 0.3 mg/day, 0.4 mg/day, 0.5 mg/day, 0.6 mg/day, 0.7 mg/day, 0.8 mg/day, 0.9 mg/day, 1.0 mg/day, 1.1 mg/day, 1.2 mg/day, 1.3 mg/day, 1.4 mg/day, 1.5 mg/day, 1.6 mg/day, 1.7 mg/day, 1.8 mg/day, 1.9 mg/day, or 2.0 mg/day, for instance, by oral administration. In some embodiments, the norgestimate is administered to the patient at a dose of 0.09 mg/day, for instance, by oral administration.

In some embodiments, the progestin is medroxyprogesterone. The medroxyprogesterone may be administered to the patient, for example, at a dose of from about 0.5 mg to about 10.0 mg, such as at a dose of about 0.5 mg, 0.6 mg, 0.7 mg, 0.8 mg, 0.9 mg, 1.0 mg, 1.1 mg, 1.2 mg, 1.3 mg, 1.4 mg, 1.5 mg, 1.6 mg, 1.7 mg, 1.8 mg, 1.9 mg, 2.0 mg, 2.1 mg, 2.2 mg, 2.3 mg, 2.4 mg, 2.5 mg, 2.6 mg, 2.7 mg, 2.8 mg, 2.9 mg, 3.0 mg, 3.1 mg, 3.2 mg, 3.3 mg, 3.4 mg, 3.5 mg, 3.6 mg, 3.7 mg, 3.8 mg, 3.9 mg, 4.0 mg, 4.1 mg, 4.2 mg, 4.3 mg, 4.4 mg, 4.5 mg, 4.6 mg, 4.7 mg, 4.8 mg, 4.9 mg, 5.0 mg, 5.1 mg, 5.2 mg, 5.3 mg, 5.4 mg, 5.5 mg, 5.6 mg, 5.7 mg, 5.8 mg, 5.9 mg, 6.0 mg, 6.1 mg, 6.2 mg, 6.3 mg, 6.4 mg, 6.5 mg, 6.6 mg, 6.7 mg, 6.8 mg, 6.9 mg, 7.0 mg, 7.1 mg, 7.2 mg, 7.3 mg, 7.4 mg, 7.5 mg, 7.6 mg, 7.7 mg, 7.8 mg, 7.9 mg, 8.0 mg, 8.1 mg, 8.2 mg, 8.3 mg, 8.4 mg, 8.5 mg, 8.6 mg, 8.7 mg, 8.8 mg, 8.9 mg, 9.0 mg, 9.1 mg, 9.2 mg, 9.3 mg, 9.4 mg, 9.5 mg, 9.6 mg, 9.7 mg, 9.8 mg, 9.9 mg, or 10.0 mg, for instance, by oral administration. In some embodiments, the medroxyprogesterone is administered to the patient at a dose of 5.0 mg, for instance, by oral administration. In some embodiments, the medroxyprogesterone is administered to the patient at a dose of 2.5 mg, for instance, by oral administration. In some embodiments, the medroxyprogesterone is administered to the patient at a dose of 1.5 mg, for instance, by oral administration.

The medroxyprogesterone may be administered to the patient one or more times per day, week, or month. The medroxyprogesterone may be administered to the patient, for example, at a dose of from about 0.5 mg/day to about 10.0 mg/day, such as at a dose of about 0.5 mg/day, 0.6 mg/day, 0.7 mg/day, 0.8 mg/day, 0.9 mg/day, 1.0 mg/day, 1.1 mg/day, 1.2 mg/day, 1.3 mg/day, 1.4 mg/day, 1.5 mg/day, 1.6 mg/day, 1.7 mg/day, 1.8 mg/day, 1.9 mg/day, 2.0 mg/day, 2.1 mg/day, 2.2 mg/day, 2.3 mg/day, 2.4 mg/day, 2.5 mg/day, 2.6 mg/day, 2.7 mg/day, 2.8 mg/day, 2.9 mg/day, 3.0 mg/day, 3.1 mg/day, 3.2 mg/day, 3.3 mg/day, 3.4 mg/day, 3.5 mg/day, 3.6 mg/day, 3.7 mg/day, 3.8 mg/day, 3.9 mg/day, 4.0 mg/day, 4.1 mg/day, 4.2 mg/day, 4.3 mg/day, 4.4 mg/day, 4.5 mg/day, 4.6 mg/day, 4.7 mg/day, 4.8 mg/day, 4.9 mg/day, 5.0 mg/day, 5.1 mg/day, 5.2 mg/day, 5.3 mg/day, 5.4 mg/day, 5.5 mg/day, 5.6 mg/day, 5.7 mg/day, 5.8 mg/day, 5.9 mg/day, 6.0 mg/day, 6.1 mg/day, 6.2 mg/day, 6.3 mg/day, 6.4 mg/day, 6.5 mg/day, 6.6 mg/day, 6.7 mg/day, 6.8 mg/day, 6.9 mg/day, 7.0 mg/day, 7.1 mg/day, 7.2 mg/day, 7.3 mg/day, 7.4 mg/day, 7.5 mg/day, 7.6 mg/day, 7.7 mg/day, 7.8 mg/day, 7.9 mg/day, 8.0 mg/day, 8.1 mg/day, 8.2 mg/day, 8.3 mg/day, 8.4 mg/day, 8.5 mg/day, 8.6 mg/day, 8.7 mg/day, 8.8 mg/day, 8.9 mg/day, 9.0 mg/day, 9.1 mg/day, 9.2 mg/day, 9.3 mg/day, 9.4 mg/day, 9.5 mg/day, 9.6 mg/day, 9.7 mg/day, 9.8 mg/day, 9.9 mg/day, or 10.0 mg/day, for instance, by oral administration. In some embodiments, the medroxyprogesterone is administered to the patient at a dose of 5.0 mg/day, for instance, by oral administration. In some embodiments, the medroxyprogesterone is administered to the patient at a dose of 2.5 mg/day, for instance, by oral administration. In some embodiments, the medroxyprogesterone is administered to the patient at a dose of 1.5 mg/day, for instance, by oral administration.

In some embodiments, the progestin is drospirenone. The drospirenone may be administered to the patient, for example, at a dose of from about 0.1 mg to about 1.0 mg, such as at a dose of about 0.1 mg, 0.2 mg, 0.3 mg, 0.4 mg, 0.5 mg, 0.6 mg, 0.7 mg, 0.8 mg, 0.9 mg, or 1.0 mg, for instance, by oral administration. In some embodiments, the drospirenone is administered to the patient at a dose of 0.5 mg, for instance, by oral administration. In some embodiments, the drospirenone is administered to the patient at a dose of 0.25 mg, for instance, by oral administration.

The drospirenone may be administered to the patient one or more times per day, week, or month. The drospirenone may be administered to the patient, for example, at a dose of from about 0.1 mg/day to about 1.0 mg/day, such as at a dose of about 0.1 mg/day, 0.2 mg/day, 0.3 mg/day, 0.4 mg/day, 0.5 mg/day, 0.6 mg/day, 0.7 mg/day, 0.8 mg/day, 0.9 mg/day, or 1.0 mg/day, for instance, by oral administration. In some embodiments, the drospirenone is administered to the patient at a dose of 0.5 mg/day, for instance, by oral administration. In some embodiments, the drospirenone is administered to the patient at a dose of 0.25 mg/day, for instance, by oral administration.

In some embodiments, the add-back therapy includes an estrogen and a progestin. In some embodiments, the add-back therapy includes β17-estradiol and norethindrone or a compound that is metabolized in vivo to produce norethindrone, such as an ester of norethindrone that is de-esterified in vivo to produce norethindrone, for instance, norethindrone acetate.

In some embodiments, the patient does not exhibit a reduction in BMD of greater than 5% following administration of the elagolix and the add-back therapy. In some embodiments, the patient does not exhibit a reduction in BMD of greater than 1% following administration of the elagolix and the add-back therapy. The add-back therapy may be formulated for oral administration. For instance, the add-back therapy may be formulated as a tablet, capsule, gel cap, powder, liquid solution, or liquid suspension. In some embodiments, the add-back therapy includes both an estrogen, such as ß17-estradiol, and a progestin, such as norethindrone or norethindrone acetate. The estrogen and progestin may be administered separately or admixed in a single composition, such as a single tablet, capsule, gel cap, powder, liquid solution, or liquid suspension.

In some embodiments, the method includes administering 400 mg/day, 150 mg/day, or less (e.g., 50 mg/day, 55 mg/day, 60 mg/day, 65 mg/day, 70 mg/day, 75 mg/day, 80 mg/day, 85 mg/day, 90 mg/day, 95 mg/day, 100 mg/day, 105 mg/day, 110 mg/day, 115 mg/day, 120 mg/day, 125 mg/day, 130 mg/day, 135 mg/day, 140 mg/day, or 145 mg/day) of elagolix to the patient if the concentration of AMH in the sample isolated from the patient is below the AMH reference range. In some embodiments, the method includes administering from 50 mg/day to 125 mg/day of elagolix to the patient if the concentration of AMH in the sample isolated from the patient is below the AMH reference range. In some embodiments, the method includes administering 100 mg/day of elagolix to the patient if the concentration of AMH in the sample isolated from the patient is below the AMH reference range.

In some embodiments, the method includes administering 400 mg/day or less (e.g., 50 mg/day, 55 mg/day, 60 mg/day, 65 mg/day, 70 mg/day, 75 mg/day, 80 mg/day, 85 mg/day, 90 mg/day, 95 mg/day, 100 mg/day, 105 mg/day, 110 mg/day, 115 mg/day, 120 mg/day, 125 mg/day, 130 mg/day, 135 mg/day, 140 mg/day, 145 mg/day, 150 mg/day, 155 mg/day, 160 mg/day, 165 mg/day, 170 mg/day, 175 mg/day, 180 mg/day, 185 mg/day, 190 mg/day, 195 mg/day, 200 mg/day, 205 mg/day, 210 mg/day, 215 mg/day, 220 mg/day, 225 mg/day, 230 mg/day, 235 mg/day, 240 mg/day, 245 mg/day, 250 mg/day, 255 mg/day, 260 mg/day, 265 mg/day, 270 mg/day, 275 mg/day, 280 mg/day, 285 mg/day, 290 mg/day, 295 mg/day, 300 mg/day, 305 mg/day, 310 mg/day, 315 mg/day, 320 mg/day, 325 mg/day, 330 mg/day, 335 mg/day, 340 mg/day, 345 mg/day, 350 mg/day, 355 mg/day, 360 mg/day, 365 mg/day, 370 mg/day, 375 mg/day, 380 mg/day, 385 mg/day, 390 mg/day, or 395 mg/day) of elagolix to the patient if the concentration of AMH in the sample isolated from the patient is below the AMH reference range. In some embodiments, the method includes administering from 150 mg/day to 375 mg/day of elagolix to the patient if the concentration of AMH in the sample isolated from the patient is below the AMH reference range. In some embodiments, the method includes administering 150 mg/day of elagolix to the patient if the concentration of AMH in the sample isolated from the patient is below the AMH reference range.

In some embodiments, the method includes administering from 150 mg/day to 400 mg/day (e.g., 150 mg/day, 155 mg/day, 160 mg/day, 165 mg/day, 170 mg/day, 175 mg/day, 180 mg/day, 185 mg/day, 190 mg/day, 195 mg/day, 200 mg/day, 205 mg/day, 210 mg/day, 215 mg/day, 220 mg/day, 225 mg/day, 230 mg/day, 235 mg/day, 240 mg/day, 245 mg/day, 250 mg/day, 255 mg/day, 260 mg/day, 265 mg/day, 270 mg/day, 275 mg/day, 280 mg/day, 285 mg/day, 290 mg/day, 295 mg/day, 300 mg/day, 305 mg/day, 310 mg/day, 315 mg/day, 320 mg/day, 325 mg/day, 330 mg/day, 335 mg/day, 340 mg/day, 345 mg/day, 350 mg/day, 355 mg/day, 360 mg/day, 365 mg/day, 370 mg/day, 375 mg/day, 380 mg/day, 385 mg/day, 390 mg/day, 395, or 400 mg/day) of elagolix to the patient if the concentration of AMH in the sample isolated from the patient is within the AMH reference range. In some embodiments, the method includes administering 150 mg/day of elagolix to the patient if the concentration of AMH in the sample isolated from the patient is within the AMH reference range. In some embodiments, the method includes administering 400 mg/day of elagolix to the patient if the concentration of AMH in the sample isolated from the patient is within the AMH reference range. For instance, the method may include administering 200 mg/day of the elagolix to the patient twice daily if the concentration of AMH in the sample isolated from the patient is within the AMH reference range.

In some embodiments, the GnRH antagonist is relugolix or a derivative or variant thereof, such as a compound described in U.S. Pat. No. 7,300,935; 8,058,280; 8,735,401; or 9,346,822; or in US Patent Application Publication No. 2015/0266891, the disclosures of which are incorporated herein by reference in their entirety. In some embodiments, the method includes administering 40 mg/day or more (e.g., from 40 mg/day to 150 mg/day or more, such as 45 mg/day, 50 mg/day, 55 mg/day, 60 mg/day, 65 mg/day, 70 mg/day, 75 mg/day, 80 mg/day, 85 mg/day, 90 mg/day, 95 mg/day, 100 mg/day, 105 mg/day, 110 mg/day, 115 mg/day, 120 mg/day, 125 mg/day, 130 mg/day, 135 mg/day, 140 mg/day, 145 mg/day, 150 mg/day, or more) of relugolix to the patient if the concentration of AMH in the sample isolated from the patient is above the AMH reference range. In some embodiments, the method includes administering from 50 mg/day to 75 mg/day of relugolix to the patient if the concentration of AMH in the sample isolated from the patient is above the AMH reference range.

In some embodiments, the method includes administering 40 mg/day or less (e.g., from 10 mg/day to 35 mg/day, such as 10 mg/day, 15 mg/day, 20 mg/day, 25 mg/day, 30 mg/day, or 35 mg/day) of relugolix to the patient if the concentration of AMH in the sample isolated from the patient is below the AMH reference range. In some embodiments, the method includes administering from 10 mg/day to 30 mg/day of relugolix to the patient if the concentration of AMH in the sample isolated from the patient is below the AMH reference range.

In some embodiments, the method includes administering from 35 mg/day to 45 mg/day (e.g., 35 mg/day, 40 mg/day, or 45 mg/day) of relugolix to the patient if the concentration of AMH in the sample isolated from the patient is within the AMH reference range. In some embodiments, the method includes administering 40 mg/day of relugolix to the patient if the concentration of AMH in the sample isolated from the patient is within the AMH reference range.

When administered at elevated doses (for instance, doses of 40 mg/day or more) relugolix may be administered in combination with add-back therapy. The add-back therapy may be administered to the patient concurrently with the relugolix, prior to administration of the relugolix, or following administration of the relugolix.

In some embodiments, the add-back therapy includes an estrogen. In some embodiments, the estrogen is selected from the group consisting of β17-estradiol, ethinyl estradiol, and conjugated estrogens, such as conjugated equine estrogens.

In some embodiments, the estrogen is β17-estradiol. The β17-estradiol may be administered to the patient, for example, at a dose of from about 0.1 mg to about 2.5 mg, such as at a dose of about 0.1 mg, 0.2 mg, 0.3 mg, 0.4 mg, 0.5 mg, 0.6 mg, 0.7 mg, 0.8 mg, 0.9 mg, 1.0 mg, 1.1 mg, 1.2 mg, 1.3 mg, 1.4 mg, 1.5 mg, 1.6 mg, 1.7 mg, 1.8 mg, 1.9 mg, 2.0 mg, 2.1 mg, 2.2 mg, 2.3 mg, 2.4 mg, or 2.5 mg, for instance, by oral administration. In some embodiments, the β17-estradiol is administered to the patient at a dose of 1.0 mg, for instance, by oral administration. In some embodiments, the β17-estradiol is administered to the patient at a dose of 0.5 mg, for instance, by oral administration.

The β17-estradiol may be administered to the patient one or more times per day, week, or month. The β17-estradiol may be administered to the patient, for example, at a dose of from about 0.1 mg/day to about 2.5 mg/day, such as at a dose of about 0.1 mg/day, 0.2 mg/day, 0.3 mg/day, 0.4 mg/day, 0.5 mg/day, 0.6 mg/day, 0.7 mg/day, 0.8 mg/day, 0.9 mg/day, 1.0 mg/day, 1.1 mg/day, 1.2 mg/day, 1.3 mg/day, 1.4 mg/day, 1.5 mg/day, 1.6 mg/day, 1.7 mg/day, 1.8 mg/day, 1.9 mg/day, 2.0 mg/day, 2.1 mg/day, 2.2 mg/day, 2.3 mg/day, 2.4 mg/day, or 2.5 mg/day, for instance, by oral administration. In some embodiments, the β17-estradiol is administered to the patient at a dose of 1.0 mg/day, for instance, by oral administration. In some embodiments, the β17-estradiol is administered to the patient at a dose of 0.5 mg/day, for instance, by oral administration.

In some embodiments, the estrogen is ethinyl estradiol. The ethinyl estradiol may be administered to the patient, for example, at a dose of from about 1.0 µg to about 6.0 µg, such as at a dose of about 1.0 µg, 1.1 µg, 1.2 µg, 1.3 µg, 1.4 µg, 1.5 µg, 1.6 µg, 1.7 µg, 1.8 µg, 1.9 µg, 2.0 µg, 2.1 µg, 2.2 µg, 2.3 µg, 2.4 µg, 2.5 µg, 2.6 µg, 2.7 µg, 2.8 µg, 2.9 µg, 3.0 µg, 3.1 µg, 3.2 µg, 3.3 µg, 3.4 µg, 3.5 µg, 3.6 µg, 3.7 µg, 3.8 µg, 3.9 µg, 4.0 µg, 4.1 µg, 4.2 µg, 4.2 µg, 4.3 µg, 4.4 µg, 4.5 µg, 4.6 µg, 4.7 µg, 4.8 µg, 4.9 µg, 5.0 µg, 5.1 µg, 5.2 µg, 5.3 µg, 5.4 µg, 5.5 µg, 5.6 µg, 5.7 µg, 5.8 µg, 5.9 µg, or 6.0 µg, for instance, by oral administration. In some embodiments, the ethinyl estradiol is administered to the patient at a dose of 5.0 µg, for instance, by oral administration. In some embodiments, the ethinyl estradiol is administered to the patient at a dose of 2.5 µg, for instance, by oral administration.

The ethinyl estradiol may be administered to the patient one or more times per day, week, or month. The ethinyl estradiol may be administered to the patient, for example, at a dose of from about 1.0 µg/day to about 6.0 µg/day, such as at a dose of about 1.0 µg/day, 1.1 µg/day, 1.2 µg/day, 1.3 µg/day, 1.4 µg/day, 1.5 µg/day, 1.6 µg/day, 1.7 µg/day, 1.8 µg/day, 1.9 µg/day, 2.0 µg/day, 2.1 µg/day, 2.2 µg/day, 2.3 µg/day, 2.4 µg/day, 2.5 µg/day, 2.6 µg/day, 2.7 µg/day, 2.8

μg/day, 2.9 μg/day, 3.0 μg/day, 3.1 μg/day, 3.2 μg/day, 3.3 μg/day, 3.4 μg/day, 3.5 μg/day, 3.6 μg/day, 3.7 μg/day, 3.8 μg/day, 3.9 μg/day, 4.0 μg/day, 4.1 μg/day, 4.2 μg/day, 4.2 μg/day, 4.3 μg/day, 4.4 μg/day, 4.5 μg/day, 4.6 μg/day, 4.7 μg/day, 4.8 μg/day, 4.9 μg/day, 5.0 μg/day, 5.1 μg/day, 5.2 μg/day, 5.3 μg/day, 5.4 μg/day, 5.5 μg/day, 5.6 μg/day, 5.7 μg/day, 5.8 μg/day, 5.9 μg/day, or 6.0 μg/day, for instance, by oral administration. In some embodiments, the ethinyl estradiol is administered to the patient at a dose of 5.0 μg/day, for instance, by oral administration. In some embodiments, the ethinyl estradiol is administered to the patient at a dose of 2.5 μg/day, for instance, by oral administration.

In some embodiments, the estrogen is a conjugated estrogen, such as a conjugated equine estrogen. The conjugated estrogen may be administered to the patient, for example, at a dose of from about 0.1 mg to about 2.0 mg, such as at a dose of about 0.1 mg, 0.2 mg, 0.3 mg, 0.4 mg, 0.5 mg, 0.6 mg, 0.7 mg, 0.8 mg, 0.9 mg, 1.0 mg, 1.1 mg, 1.2 mg, 1.3 mg, 1.4 mg, 1.5 mg, 1.6 mg, 1.7 mg, 1.8 mg, 1.9 mg, or 2.0 mg, for instance, by oral administration. In some embodiments, the conjugated estrogen is administered to the patient at a dose of 0.625 mg, for instance, by oral administration. In some embodiments, the conjugated estrogen is administered to the patient at a dose of 0.45 mg, for instance, by oral administration. In some embodiments, the conjugated estrogen is administered to the patient at a dose of 0.3 mg, for instance, by oral administration.

The conjugated estrogen may be administered to the patient one or more times per day, week, or month. The conjugated estrogen may be administered to the patient, for example, at a dose of from about 0.1 mg/day to about 2.0 mg/day, such as at a dose of about 0.1 mg/day, 0.2 mg/day, 0.3 mg/day, 0.4 mg/day, 0.5 mg/day, 0.6 mg/day, 0.7 mg/day, 0.8 mg/day, 0.9 mg/day, 1.0 mg/day, 1.1 mg/day, 1.2 mg/day, 1.3 mg/day, 1.4 mg/day, 1.5 mg/day, 1.6 mg/day, 1.7 mg/day, 1.8 mg/day, 1.9 mg/day, or 2.0 mg/day, for instance, by oral administration. In some embodiments, the conjugated estrogen is administered to the patient at a dose of 0.625 mg/day, for instance, by oral administration. In some embodiments, the conjugated estrogen is administered to the patient at a dose of 0.45 mg/day, for instance, by oral administration. In some embodiments, the conjugated estrogen is administered to the patient at a dose of 0.3 mg/day, for instance, by oral administration.

In some embodiments, the add-back therapy includes a progestin. In some embodiments, the progestin is selected from the group consisting of norethindrone or an ester thereof, such as norethindrone acetate, or another agent such as progesterone, norgestimate, medroxyprogesterone, or drospirenone.

In some embodiments, the progestin is norethindrone or a compound that is metabolized in vivo to produce norethindrone, such as an ester of norethindrone that is de-esterified in vivo to produce norethindrone, for instance, norethindrone acetate.

In some embodiments, the progestin is norethindrone. The norethindrone may be administered to the patient, for example, at a dose of from about 0.05 mg to about 5.0 mg, such as at a dose of about 0.05 mg, 0.06 mg, 0.07 mg, 0.08 mg, 0.09 mg, 0.1 mg, 0.2 mg, 0.3 mg, 0.4 mg, 0.5 mg, 0.6 mg, 0.7 mg, 0.8 mg, 0.9 mg, 1.0 mg, 1.1 mg, 1.2 mg, 1.3 mg, 1.4 mg, 1.5 mg, 1.6 mg, 1.7 mg, 1.8 mg, 1.9 mg, 2.0 mg, 2.1 mg, 2.2 mg, 2.3 mg, 2.4 mg, 2.5 mg, 2.6 mg, 2.7 mg, 2.8 mg, 2.9 mg, 3.0 mg, 3.1 mg, 3.2 mg, 3.3 mg, 3.4 mg, 3.5 mg, 3.6 mg, 3.7 mg, 3.8 mg, 3.9 mg, 4.0 mg, 4.1 mg, 4.2 mg, 4.3 mg, 4.4 mg, 4.5 mg, 4.6 mg, 4.7 mg, 4.8 mg, 4.9 mg, or 5.0 mg, for instance, by oral administration. In some embodiments, the norethindrone is administered to the patient at a dose of 1.0 mg, for instance, by oral administration. In some embodiments, the norethindrone is administered to the patient at a dose of 0.5 mg, for instance, by oral administration. In some embodiments, the norethindrone is administered to the patient at a dose of 0.1 mg, for instance, by oral administration.

The norethindrone may be administered to the patient one or more times per day, week, or month. The norethindrone may be administered to the patient, for example, at a dose of from about 0.05 mg/day to about 5.0 mg/day, such as at a dose of about 0.05 mg/day, 0.06 mg/day, 0.07 mg/day, 0.08 mg/day, 0.09 mg/day, 0.1 mg/day, 0.2 mg/day, 0.3 mg/day, 0.4 mg/day, 0.5 mg/day, 0.6 mg/day, 0.7 mg/day, 0.8 mg/day, 0.9 mg/day, 1.0 mg/day, 1.1 mg/day, 1.2 mg/day, 1.3 mg/day, 1.4 mg/day, 1.5 mg/day, 1.6 mg/day, 1.7 mg/day, 1.8 mg/day, 1.9 mg/day, 2.0 mg/day, 2.1 mg/day, 2.2 mg/day, 2.3 mg/day, 2.4 mg/day, 2.5 mg/day, 2.6 mg/day, 2.7 mg/day, 2.8 mg/day, 2.9 mg/day, 3.0 mg/day, 3.1 mg/day, 3.2 mg/day, 3.3 mg/day, 3.4 mg/day, 3.5 mg/day, 3.6 mg/day, 3.7 mg/day, 3.8 mg/day, 3.9 mg/day, 4.0 mg/day, 4.1 mg/day, 4.2 mg/day, 4.3 mg/day, 4.4 mg/day, 4.5 mg/day, 4.6 mg/day, 4.7 mg/day, 4.8 mg/day, 4.9 mg/day, or 5.0 mg/day, for instance, by oral administration. In some embodiments, the norethindrone is administered to the patient at a dose of 1.0 mg/day, for instance, by oral administration. In some embodiments, the norethindrone is administered to the patient at a dose of 0.5 mg/day, for instance, by oral administration. In some embodiments, the norethindrone is administered to the patient at a dose of 0.1 mg/day, for instance, by oral administration.

In some embodiments, the progestin is norethindrone acetate. The norethindrone acetate may be administered to the patient, for example, at a dose of from about 0.05 mg to about 5.0 mg, such as at a dose of about 0.05 mg, 0.06 mg, 0.07 mg, 0.08 mg, 0.09 mg, 0.1 mg, 0.2 mg, 0.3 mg, 0.4 mg, 0.5 mg, 0.6 mg, 0.7 mg, 0.8 mg, 0.9 mg, 1.0 mg, 1.1 mg, 1.2 mg, 1.3 mg, 1.4 mg, 1.5 mg, 1.6 mg, 1.7 mg, 1.8 mg, 1.9 mg, 2.0 mg, 2.1 mg, 2.2 mg, 2.3 mg, 2.4 mg, 2.5 mg, 2.6 mg, 2.7 mg, 2.8 mg, 2.9 mg, 3.0 mg, 3.1 mg, 3.2 mg, 3.3 mg, 3.4 mg, 3.5 mg, 3.6 mg, 3.7 mg, 3.8 mg, 3.9 mg, 4.0 mg, 4.1 mg, 4.2 mg, 4.3 mg, 4.4 mg, 4.5 mg, 4.6 mg, 4.7 mg, 4.8 mg, 4.9 mg, or 5.0 mg, for instance, by oral administration. In some embodiments, the norethindrone acetate is administered to the patient at a dose of 1.0 mg/day, for instance, by oral administration. In some embodiments, the norethindrone acetate is administered to the patient at a dose of 0.5 mg, for instance, by oral administration. In some embodiments, the norethindrone acetate is administered to the patient at a dose of 0.1 mg, for instance, by oral administration.

The norethindrone acetate may be administered to the patient one or more times per day, week, or month. The norethindrone acetate may be administered to the patient, for example, at a dose of from about 0.05 mg/day to about 5.0 mg/day, such as at a dose of about 0.05 mg/day, 0.06 mg/day, 0.07 mg/day, 0.08 mg/day, 0.09 mg/day, 0.1 mg/day, 0.2 mg/day, 0.3 mg/day, 0.4 mg/day, 0.5 mg/day, 0.6 mg/day, 0.7 mg/day, 0.8 mg/day, 0.9 mg/day, 1.0 mg/day, 1.1 mg/day, 1.2 mg/day, 1.3 mg/day, 1.4 mg/day, 1.5 mg/day, 1.6 mg/day, 1.7 mg/day, 1.8 mg/day, 1.9 mg/day, 2.0 mg/day, 2.1 mg/day, 2.2 mg/day, 2.3 mg/day, 2.4 mg/day, 2.5 mg/day, 2.6 mg/day, 2.7 mg/day, 2.8 mg/day, 2.9 mg/day, 3.0 mg/day, 3.1 mg/day, 3.2 mg/day, 3.3 mg/day, 3.4 mg/day, 3.5 mg/day, 3.6 mg/day, 3.7 mg/day, 3.8 mg/day, 3.9 mg/day, 4.0 mg/day, 4.1 mg/day, 4.2 mg/day, 4.3 mg/day, 4.4 mg/day, 4.5 mg/day, 4.6 mg/day, 4.7 mg/day, 4.8 mg/day, 4.9 mg/day, or 5.0 mg/day, for instance, by oral administration. In some embodiments, the norethindrone acetate is administered to the patient at a dose of 1.0 mg/day, for instance, by oral administration. In some embodiments, the norethindrone acetate is administered to the patient at a dose of 0.5 mg/day, for instance, by oral administration. In some embodiments, the norethindrone acetate is administered to the patient at a dose of 0.1 mg/day, for instance, by oral administration.

In some embodiments, the progestin is progesterone. The progesterone may be administered to the patient, for example, at a dose of from about 50 mg to about 250 mg, such as a dose of about 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, 200 mg, 205 mg, 210 mg, 215 mg, 220 mg, 225 mg, 230 mg, 235 mg, 240 mg, 245 mg, or 250 mg, for instance, by oral administration. In some embodiments, the progesterone is administered to the patient at a dose of 200 mg, for instance, by oral administration. In some embodiments, the progesterone is administered to the patient at a dose of 100 mg, for instance, by oral administration.

The progesterone may be administered to the patient one or more times per day, week, or month. The progesterone may be administered to the patient, for example, at a dose of from about 50 mg/day to about 250 mg/day, such as a dose of about 50 mg/day, 55 mg/day, 60 mg/day, 65 mg/day, 70 mg/day, 75 mg/day, 80 mg/day, 85 mg/day, 90 mg/day, 95 mg/day, 100 mg/day, 105 mg/day, 110 mg/day, 115 mg/day, 120 mg/day, 125 mg/day, 130 mg/day, 135 mg/day, 140 mg/day, 145 mg/day, 150 mg/day, 155 mg/day, 160 mg/day, 165 mg/day, 170 mg/day, 175 mg/day, 180 mg/day, 185 mg/day, 190 mg/day, 195 mg/day, 200 mg/day, 205 mg/day, 210 mg/day, 215 mg/day, 220 mg/day, 225 mg/day, 230 mg/day, 235 mg/day, 240 mg/day, 245 mg/day, or 250 mg/day, for instance, by oral administration. In some embodiments, the progesterone is administered to the patient at a dose of 200 mg/day, for instance, by oral administration. In some embodiments, the progesterone is administered to the patient at a dose of 100 mg/day, for instance, by oral administration.

In some embodiments, the progestin is norgestimate. The norgestimate may be administered to the patient, for example, at a dose of from about 0.01 mg to about 2.0 mg, such as at a dose of about 0.01 mg, 0.02 mg, 0.03 mg, 0.04 mg, 0.05 mg, 0.06 mg, 0.07 mg, 0.08 mg, 0.09 mg, 0.1 mg, 0.2 mg, 0.3 mg, 0.4 mg, 0.5 mg, 0.6 mg, 0.7 mg, 0.8 mg, 0.9 mg, 1.0 mg, 1.1 mg, 1.2 mg, 1.3 mg, 1.4 mg, 1.5 mg, 1.6 mg, 1.7 mg, 1.8 mg, 1.9 mg, or 2.0 mg, for instance, by oral administration. In some embodiments, the norgestimate is administered to the patient at a dose of 0.09 mg, for instance, by oral administration.

The norgestimate may be administered to the patient one or more times per day, week, or month. The norgestimate may be administered to the patient, for example, at a dose of from about 0.01 mg/day to about 2.0 mg/day, such as at a dose of about 0.01 mg/day, 0.02 mg/day, 0.03 mg/day, 0.04 mg/day, 0.05 mg/day, 0.06 mg/day, 0.07 mg/day, 0.08 mg/day, 0.09 mg/day, 0.1 mg/day, 0.2 mg/day, 0.3 mg/day, 0.4 mg/day, 0.5 mg/day, 0.6 mg/day, 0.7 mg/day, 0.8 mg/day, 0.9 mg/day, 1.0 mg/day, 1.1 mg/day, 1.2 mg/day, 1.3 mg/day, 1.4 mg/day, 1.5 mg/day, 1.6 mg/day, 1.7 mg/day, 1.8 mg/day, 1.9 mg/day, or 2.0 mg/day, for instance, by oral administration. In some embodiments, the norgestimate is administered to the patient at a dose of 0.09 mg/day, for instance, by oral administration.

In some embodiments, the progestin is medroxyprogesterone. The medroxyprogesterone may be administered to the patient, for example, at a dose of from about 0.5 mg to about 10.0 mg, such as at a dose of about 0.5 mg, 0.6 mg, 0.7 mg, 0.8 mg, 0.9 mg, 1.0 mg, 1.1 mg, 1.2 mg, 1.3 mg, 1.4 mg, 1.5 mg, 1.6 mg, 1.7 mg, 1.8 mg, 1.9 mg, 2.0 mg, 2.1 mg, 2.2 mg, 2.3 mg, 2.4 mg, 2.5 mg, 2.6 mg, 2.7 mg, 2.8 mg, 2.9 mg, 3.0 mg, 3.1 mg, 3.2 mg, 3.3 mg, 3.4 mg, 3.5 mg, 3.6 mg, 3.7 mg, 3.8 mg, 3.9 mg, 4.0 mg, 4.1 mg, 4.2 mg, 4.3 mg, 4.4 mg, 4.5 mg, 4.6 mg, 4.7 mg, 4.8 mg, 4.9 mg, 5.0 mg, 5.1 mg, 5.2 mg, 5.3 mg, 5.4 mg, 5.5 mg, 5.6 mg, 5.7 mg, 5.8 mg, 5.9 mg, 6.0 mg, 6.1 mg, 6.2 mg, 6.3 mg, 6.4 mg, 6.5 mg, 6.6 mg, 6.7 mg, 6.8 mg, 6.9 mg, 7.0 mg, 7.1 mg, 7.2 mg, 7.3 mg, 7.4 mg, 7.5 mg, 7.6 mg, 7.7 mg, 7.8 mg, 7.9 mg, 8.0 mg, 8.1 mg, 8.2 mg, 8.3 mg, 8.4 mg, 8.5 mg, 8.6 mg, 8.7 mg, 8.8 mg, 8.9 mg, 9.0 mg, 9.1 mg, 9.2 mg, 9.3 mg, 9.4 mg, 9.5 mg, 9.6 mg, 9.7 mg, 9.8 mg, 9.9 mg, or 10.0 mg, for instance, by oral administration. In some embodiments, the medroxyprogesterone is administered to the patient at a dose of 5.0 mg, for instance, by oral administration. In some embodiments, the medroxyprogesterone is administered to the patient at a dose of 2.5 mg, for instance, by oral administration. In some embodiments, the medroxyprogesterone is administered to the patient at a dose of 1.5 mg, for instance, by oral administration.

The medroxyprogesterone may be administered to the patient one or more times per day, week, or month. The medroxyprogesterone may be administered to the patient, for example, at a dose of from about 0.5 mg/day to about 10.0 mg/day, such as at a dose of about 0.5 mg/day, 0.6 mg/day, 0.7 mg/day, 0.8 mg/day, 0.9 mg/day, 1.0 mg/day, 1.1 mg/day, 1.2 mg/day, 1.3 mg/day, 1.4 mg/day, 1.5 mg/day, 1.6 mg/day, 1.7 mg/day, 1.8 mg/day, 1.9 mg/day, 2.0 mg/day, 2.1 mg/day, 2.2 mg/day, 2.3 mg/day, 2.4 mg/day, 2.5 mg/day, 2.6 mg/day, 2.7 mg/day, 2.8 mg/day, 2.9 mg/day, 3.0 mg/day, 3.1 mg/day, 3.2 mg/day, 3.3 mg/day, 3.4 mg/day, 3.5 mg/day, 3.6 mg/day, 3.7 mg/day, 3.8 mg/day, 3.9 mg/day, 4.0 mg/day, 4.1 mg/day, 4.2 mg/day, 4.3 mg/day, 4.4 mg/day, 4.5 mg/day, 4.6 mg/day, 4.7 mg/day, 4.8 mg/day, 4.9 mg/day, 5.0 mg/day, 5.1 mg/day, 5.2 mg/day, 5.3 mg/day, 5.4 mg/day, 5.5 mg/day, 5.6 mg/day, 5.7 mg/day, 5.8 mg/day, 5.9 mg/day, 6.0 mg/day, 6.1 mg/day, 6.2 mg/day, 6.3 mg/day, 6.4 mg/day, 6.5 mg/day, 6.6 mg/day, 6.7 mg/day, 6.8 mg/day, 6.9 mg/day, 7.0 mg/day, 7.1 mg/day, 7.2 mg/day, 7.3 mg/day, 7.4 mg/day, 7.5 mg/day, 7.6 mg/day, 7.7 mg/day, 7.8 mg/day, 7.9 mg/day, 8.0 mg/day, 8.1 mg/day, 8.2 mg/day, 8.3 mg/day, 8.4 mg/day, 8.5 mg/day, 8.6 mg/day, 8.7 mg/day, 8.8 mg/day, 8.9 mg/day, 9.0 mg/day, 9.1 mg/day, 9.2 mg/day, 9.3 mg/day, 9.4 mg/day, 9.5 mg/day, 9.6 mg/day, 9.7 mg/day, 9.8 mg/day, 9.9 mg/day, or 10.0 mg/day, for instance, by oral administration. In some embodiments, the medroxyprogesterone is administered to the patient at a dose of 5.0 mg/day, for instance, by oral administration. In some embodiments, the medroxyprogesterone is administered to the patient at a dose of 2.5 mg/day, for instance, by oral administration. In some embodiments, the medroxyprogesterone is administered to the patient at a dose of 1.5 mg/day, for instance, by oral administration.

In some embodiments, the progestin is drospirenone. The drospirenone may be administered to the patient, for example, at a dose of from about 0.1 mg to about 1.0 mg, such as at a dose of about 0.1 mg, 0.2 mg, 0.3 mg, 0.4 mg, 0.5 mg, 0.6 mg, 0.7 mg, 0.8 mg, 0.9 mg, or 1.0 mg, for instance, by oral administration. In some embodiments, the drospirenone is administered to the patient at a dose of 0.5 mg, for instance, by oral administration. In some embodiments, the drospirenone is administered to the patient at a dose of 0.25 mg, for instance, by oral administration.

The drospirenone may be administered to the patient one or more times per day, week, or month. The drospirenone may be administered to the patient, for example, at a dose of from about 0.1 mg/day to about 1.0 mg/day, such as at a dose of about 0.1 mg/day, 0.2 mg/day, 0.3 mg/day, 0.4 mg/day, 0.5 mg/day, 0.6 mg/day, 0.7 mg/day, 0.8 mg/day, 0.9 mg/day, or 1.0 mg/day, for instance, by oral administration. In some embodiments, the drospirenone is administered to the patient at a dose of 0.5 mg/day, for instance, by oral administration. In some embodiments, the drospirenone is administered to the patient at a dose of 0.25 mg/day, for instance, by oral administration.

In some embodiments, the add-back therapy includes an estrogen and a progestin. In some embodiments, the add-back therapy includes β17-estradiol and norethindrone or a compound that is metabolized in vivo to produce norethindrone, such as an ester of norethindrone that is de-esterified in vivo to produce norethindrone, for instance, norethindrone acetate.

In some embodiments, the patient does not exhibit a reduction in BMD of greater than 5% following administration of the relugolix and the add-back therapy. In some embodiments, the patient does not exhibit a reduction in BMD of greater than 1% following administration of the relugolix and the add-back therapy. The add-back therapy may be formulated for oral administration. For instance, the add-back therapy may be formulated as a tablet, capsule, gel cap, powder, liquid solution, or liquid suspension. In some embodiments, the add-back therapy includes both an estrogen, such as 617-estradiol, and a progestin, such as norethindrone or norethindrone acetate. The estrogen and progestin may be administered separately or admixed in a single composition, such as a single tablet, capsule, gel cap, powder, liquid solution, or liquid suspension.

In some embodiments, the GnRH antagonist is ASP-1707 or a derivative or variant thereof, such as a compound described in U.S. Pat. No. 6,960,591; 7,569,688; 7,960,562; or 9,527,818, the disclosures of which are incorporated herein by reference in their entirety. In some embodiments, the method includes administering 10 mg/day or more (e.g., from 15 mg/day to 100 mg/day or more, such as 15 mg/day, 20 mg/day, 25 mg/day, 30 mg/day, 35 mg/day, 40 mg/day, 45 mg/day, 50 mg/day, 55 mg/day, 60 mg/day, 65 mg/day, 70 mg/day, 75 mg/day, 80 mg/day, 85 mg/day, 90 mg/day, 95 mg/day, 100 mg/day, or more) of ASP-1707 to the patient if the concentration of AMH in the sample isolated from the patient is above the AMH reference range. In some embodiments, the method includes administering from 15 mg/day to 50 mg/day of ASP-1707 to the patient if the concentration of AMH in the sample isolated from the patient is above the AMH reference range.

In some embodiments, the method includes administering less than 10 mg/day (e.g., from 5 mg/day to 9 mg/day, such as 5 mg/day, 6 mg/day, 7 mg/day, 8 mg/day, or 9 mg/day) of ASP-1707 to the patient if the concentration of AMH in the sample isolated from the patient is below the AMH reference range. In some embodiments, the method includes administering from 5 mg/day to 7.5 mg/day of ASP-1707 to the patient if the concentration of AMH in the sample isolated from the patient is below the AMH reference range.

In some embodiments, the method includes administering from 7.5 mg/day to 15 mg/day (e.g., 7.5 mg/day, 10 mg/day, 12.5 mg/day, or 15 mg/day) of ASP-1707 to the patient if the concentration of AMH in the sample isolated from the patient is within the AMH reference range. In some embodiments, the method includes administering 10 mg/day of ASP-1707 to the patient if the concentration of AMH in the sample isolated from the patient is within the AMH reference range.

In some embodiments, the GnRH antagonist is BAY-784 or a derivative or variant thereof. The GnRH antagonist may be a compound described in US Patent Application Publication No. 2014/0357655 or 2016/0052936, the disclosures of which are incorporated herein by reference in their entirety.

When administered at elevated doses (for instance, doses of 40 mg/day or more) ASP-1707 and/or BAY-784 may be administered in combination with add-back therapy. The add-back therapy may be administered to the patient concurrently with the GnRH antagonist, prior to administration of the GnRH antagonist, or following administration of the GnRH antagonist.

In some embodiments, the add-back therapy includes an estrogen. In some embodiments, the estrogen is selected from the group consisting of β17-estradiol, ethinyl estradiol, and conjugated estrogens, such as conjugated equine estrogens.

In some embodiments, the estrogen is β17-estradiol. The β17-estradiol may be administered to the patient, for example, at a dose of from about 0.1 mg to about 2.5 mg, such as at a dose of about 0.1 mg, 0.2 mg, 0.3 mg, 0.4 mg, 0.5 mg, 0.6 mg, 0.7 mg, 0.8 mg, 0.9 mg, 1.0 mg, 1.1 mg, 1.2 mg, 1.3 mg, 1.4 mg, 1.5 mg, 1.6 mg, 1.7 mg, 1.8 mg, 1.9 mg, 2.0 mg, 2.1 mg, 2.2 mg, 2.3 mg, 2.4 mg, or 2.5 mg, for instance, by oral administration. In some embodiments, the β17-estradiol is administered to the patient at a dose of 1.0 mg, for instance, by oral administration. In some embodiments, the β17-estradiol is administered to the patient at a dose of 0.5 mg, for instance, by oral administration.

The β17-estradiol may be administered to the patient one or more times per day, week, or month. The β17-estradiol may be administered to the patient, for example, at a dose of from about 0.1 mg/day to about 2.5 mg/day, such as at a dose of about 0.1 mg/day, 0.2 mg/day, 0.3 mg/day, 0.4 mg/day, 0.5 mg/day, 0.6 mg/day, 0.7 mg/day, 0.8 mg/day, 0.9 mg/day, 1.0 mg/day, 1.1 mg/day, 1.2 mg/day, 1.3 mg/day, 1.4 mg/day, 1.5 mg/day, 1.6 mg/day, 1.7 mg/day, 1.8 mg/day, 1.9 mg/day, 2.0 mg/day, 2.1 mg/day, 2.2 mg/day, 2.3 mg/day, 2.4 mg/day, or 2.5 mg/day, for instance, by oral administration. In some embodiments, the β17-estradiol is administered to the patient at a dose of 1.0 mg/day, for instance, by oral administration. In some embodiments, the β17-estradiol is administered to the patient at a dose of 0.5 mg/day, for instance, by oral administration.

In some embodiments, the estrogen is ethinyl estradiol. The ethinyl estradiol may be administered to the patient, for example, at a dose of from about 1.0 μg to about 6.0 μg, such as at a dose of about 1.0 μg, 1.1 μg, 1.2 μg, 1.3 μg, 1.4 μg, 1.5 μg, 1.6 μg, 1.7 μg, 1.8 μg, 1.9 μg, 2.0 μg, 2.1 μg, 2.2 μg, 2.3 μg, 2.4 μg, 2.5 μg, 2.6 μg, 2.7 μg, 2.8 μg, 2.9 μg, 3.0 μg, 3.1 μg, 3.2 μg, 3.3 μg, 3.4 μg, 3.5 μg, 3.6 μg, 3.7 μg, 3.8 μg, 3.9 μg, 4.0 μg, 4.1 μg, 4.2 μg, 4.2 μg, 4.3 μg, 4.4 μg, 4.5 μg, 4.6 μg, 4.7 μg, 4.8 μg, 4.9 μg, 5.0 μg, 5.1 μg, 5.2 μg, 5.3 μg, 5.4 μg, 5.5 μg, 5.6 μg, 5.7 μg, 5.8 μg, 5.9 μg, or 6.0 μg, for instance, by oral administration. In some embodiments, the ethinyl estradiol is administered to the patient at a dose of 5.0 μg, for instance, by oral administration. In some embodiments, the ethinyl estradiol is administered to the patient at a dose of 2.5 μg, for instance, by oral administration.

The ethinyl estradiol may be administered to the patient one or more times per day, week, or month. The ethinyl estradiol may be administered to the patient, for example, at a dose of from about 1.0 μg/day to about 6.0 μg/day, such as at a dose of about 1.0 μg/day, 1.1 μg/day, 1.2 μg/day, 1.3 μg/day, 1.4 μg/day, 1.5 μg/day, 1.6 μg/day, 1.7 μg/day, 1.8 μg/day, 1.9 μg/day, 2.0 μg/day, 2.1 μg/day, 2.2 μg/day, 2.3

µg/day, 2.4 µg/day, 2.5 µg/day, 2.6 µg/day, 2.7 µg/day, 2.8 µg/day, 2.9 µg/day, 3.0 µg/day, 3.1 µg/day, 3.2 µg/day, 3.3 µg/day, 3.4 µg/day, 3.5 µg/day, 3.6 µg/day, 3.7 µg/day, 3.8 µg/day, 3.9 µg/day, 4.0 µg/day, 4.1 µg/day, 4.2 µg/day, 4.2 µg/day, 4.3 µg/day, 4.4 µg/day, 4.5 µg/day, 4.6 µg/day, 4.7 µg/day, 4.8 µg/day, 4.9 µg/day, 5.0 µg/day, 5.1 µg/day, 5.2 µg/day, 5.3 µg/day, 5.4 µg/day, 5.5 µg/day, 5.6 µg/day, 5.7 µg/day, 5.8 µg/day, 5.9 µg/day, or 6.0 µg/day, for instance, by oral administration. In some embodiments, the ethinyl estradiol is administered to the patient at a dose of 5.0 µg/day, for instance, by oral administration. In some embodiments, the ethinyl estradiol is administered to the patient at a dose of 2.5 µg/day, for instance, by oral administration.

In some embodiments, the estrogen is a conjugated estrogen, such as a conjugated equine estrogen. The conjugated estrogen may be administered to the patient, for example, at a dose of from about 0.1 mg to about 2.0 mg, such as at a dose of about 0.1 mg, 0.2 mg, 0.3 mg, 0.4 mg, 0.5 mg, 0.6 mg, 0.7 mg, 0.8 mg, 0.9 mg, 1.0 mg, 1.1 mg, 1.2 mg, 1.3 mg, 1.4 mg, 1.5 mg, 1.6 mg, 1.7 mg, 1.8 mg, 1.9 mg, or 2.0 mg, for instance, by oral administration. In some embodiments, the conjugated estrogen is administered to the patient at a dose of 0.625 mg, for instance, by oral administration. In some embodiments, the conjugated estrogen is administered to the patient at a dose of 0.45 mg, for instance, by oral administration. In some embodiments, the conjugated estrogen is administered to the patient at a dose of 0.3 mg, for instance, by oral administration.

The conjugated estrogen may be administered to the patient one or more times per day, week, or month. The conjugated estrogen may be administered to the patient, for example, at a dose of from about 0.1 mg/day to about 2.0 mg/day, such as at a dose of about 0.1 mg/day, 0.2 mg/day, 0.3 mg/day, 0.4 mg/day, 0.5 mg/day, 0.6 mg/day, 0.7 mg/day, 0.8 mg/day, 0.9 mg/day, 1.0 mg/day, 1.1 mg/day, 1.2 mg/day, 1.3 mg/day, 1.4 mg/day, 1.5 mg/day, 1.6 mg/day, 1.7 mg/day, 1.8 mg/day, 1.9 mg/day, or 2.0 mg/day, for instance, by oral administration. In some embodiments, the conjugated estrogen is administered to the patient at a dose of 0.625 mg/day, for instance, by oral administration. In some embodiments, the conjugated estrogen is administered to the patient at a dose of 0.45 mg/day, for instance, by oral administration. In some embodiments, the conjugated estrogen is administered to the patient at a dose of 0.3 mg/day, for instance, by oral administration.

In some embodiments, the add-back therapy includes a progestin. In some embodiments, the progestin is selected from the group consisting of norethindrone or an ester thereof, such as norethindrone acetate, or another agent such as progesterone, norgestimate, medroxyprogesterone, or drospirenone.

In some embodiments, the progestin is norethindrone or a compound that is metabolized in vivo to produce norethindrone, such as an ester of norethindrone that is de-esterified in vivo to produce norethindrone, for instance, norethindrone acetate.

In some embodiments, the progestin is norethindrone. The norethindrone may be administered to the patient, for example, at a dose of from about 0.05 mg to about 5.0 mg, such as at a dose of about 0.05 mg, 0.06 mg, 0.07 mg, 0.08 mg, 0.09 mg, 0.1 mg, 0.2 mg, 0.3 mg, 0.4 mg, 0.5 mg, 0.6 mg, 0.7 mg, 0.8 mg, 0.9 mg, 1.0 mg, 1.1 mg, 1.2 mg, 1.3 mg, 1.4 mg, 1.5 mg, 1.6 mg, 1.7 mg, 1.8 mg, 1.9 mg, 2.0 mg, 2.1 mg, 2.2 mg, 2.3 mg, 2.4 mg, 2.5 mg, 2.6 mg, 2.7 mg, 2.8 mg, 2.9 mg, 3.0 mg, 3.1 mg, 3.2 mg, 3.3 mg, 3.4 mg, 3.5 mg, 3.6 mg, 3.7 mg, 3.8 mg, 3.9 mg, 4.0 mg, 4.1 mg, 4.2 mg, 4.3 mg, 4.4 mg, 4.5 mg, 4.6 mg, 4.7 mg, 4.8 mg, 4.9 mg, or 5.0 mg, for instance, by oral administration. In some embodiments, the norethindrone is administered to the patient at a dose of 1.0 mg, for instance, by oral administration. In some embodiments, the norethindrone is administered to the patient at a dose of 0.5 mg, for instance, by oral administration. In some embodiments, the norethindrone is administered to the patient at a dose of 0.1 mg, for instance, by oral administration.

The norethindrone may be administered to the patient one or more times per day, week, or month. The norethindrone may be administered to the patient, for example, at a dose of from about 0.05 mg/day to about 5.0 mg/day, such as at a dose of about 0.05 mg/day, 0.06 mg/day, 0.07 mg/day, 0.08 mg/day, 0.09 mg/day, 0.1 mg/day, 0.2 mg/day, 0.3 mg/day, 0.4 mg/day, 0.5 mg/day, 0.6 mg/day, 0.7 mg/day, 0.8 mg/day, 0.9 mg/day, 1.0 mg/day, 1.1 mg/day, 1.2 mg/day, 1.3 mg/day, 1.4 mg/day, 1.5 mg/day, 1.6 mg/day, 1.7 mg/day, 1.8 mg/day, 1.9 mg/day, 2.0 mg/day, 2.1 mg/day, 2.2 mg/day, 2.3 mg/day, 2.4 mg/day, 2.5 mg/day, 2.6 mg/day, 2.7 mg/day, 2.8 mg/day, 2.9 mg/day, 3.0 mg/day, 3.1 mg/day, 3.2 mg/day, 3.3 mg/day, 3.4 mg/day, 3.5 mg/day, 3.6 mg/day, 3.7 mg/day, 3.8 mg/day, 3.9 mg/day, 4.0 mg/day, 4.1 mg/day, 4.2 mg/day, 4.3 mg/day, 4.4 mg/day, 4.5 mg/day, 4.6 mg/day, 4.7 mg/day, 4.8 mg/day, 4.9 mg/day, or 5.0 mg/day, for instance, by oral administration. In some embodiments, the norethindrone is administered to the patient at a dose of 1.0 mg/day, for instance, by oral administration. In some embodiments, the norethindrone is administered to the patient at a dose of 0.5 mg/day, for instance, by oral administration. In some embodiments, the norethindrone is administered to the patient at a dose of 0.1 mg/day, for instance, by oral administration.

In some embodiments, the progestin is norethindrone acetate. The norethindrone acetate may be administered to the patient, for example, at a dose of from about 0.05 mg to about 5.0 mg, such as at a dose of about 0.05 mg, 0.06 mg, 0.07 mg, 0.08 mg, 0.09 mg, 0.1 mg, 0.2 mg, 0.3 mg, 0.4 mg, 0.5 mg, 0.6 mg, 0.7 mg, 0.8 mg, 0.9 mg, 1.0 mg, 1.1 mg, 1.2 mg, 1.3 mg, 1.4 mg, 1.5 mg, 1.6 mg, 1.7 mg, 1.8 mg, 1.9 mg, 2.0 mg, 2.1 mg, 2.2 mg, 2.3 mg, 2.4 mg, 2.5 mg, 2.6 mg, 2.7 mg, 2.8 mg, 2.9 mg, 3.0 mg, 3.1 mg, 3.2 mg, 3.3 mg, 3.4 mg, 3.5 mg, 3.6 mg, 3.7 mg, 3.8 mg, 3.9 mg, 4.0 mg, 4.1 mg, 4.2 mg, 4.3 mg, 4.4 mg, 4.5 mg, 4.6 mg, 4.7 mg, 4.8 mg, 4.9 mg, or 5.0 mg, for instance, by oral administration. In some embodiments, the norethindrone acetate is administered to the patient at a dose of 1.0 mg/day, for instance, by oral administration. In some embodiments, the norethindrone acetate is administered to the patient at a dose of 0.5 mg, for instance, by oral administration. In some embodiments, the norethindrone acetate is administered to the patient at a dose of 0.1 mg, for instance, by oral administration.

The norethindrone acetate may be administered to the patient one or more times per day, week, or month. The norethindrone acetate may be administered to the patient, for example, at a dose of from about 0.05 mg/day to about 5.0 mg/day, such as at a dose of about 0.05 mg/day, 0.06 mg/day, 0.07 mg/day, 0.08 mg/day, 0.09 mg/day, 0.1 mg/day, 0.2 mg/day, 0.3 mg/day, 0.4 mg/day, 0.5 mg/day, 0.6 mg/day, 0.7 mg/day, 0.8 mg/day, 0.9 mg/day, 1.0 mg/day, 1.1 mg/day, 1.2 mg/day, 1.3 mg/day, 1.4 mg/day, 1.5 mg/day, 1.6 mg/day, 1.7 mg/day, 1.8 mg/day, 1.9 mg/day, 2.0 mg/day, 2.1 mg/day, 2.2 mg/day, 2.3 mg/day, 2.4 mg/day, 2.5 mg/day, 2.6 mg/day, 2.7 mg/day, 2.8 mg/day, 2.9 mg/day, 3.0 mg/day, 3.1 mg/day, 3.2 mg/day, 3.3 mg/day, 3.4 mg/day, 3.5 mg/day, 3.6 mg/day, 3.7 mg/day, 3.8 mg/day, 3.9 mg/day, 4.0 mg/day, 4.1 mg/day, 4.2 mg/day, 4.3 mg/day, 4.4 mg/day, 4.5 mg/day, 4.6 mg/day, 4.7 mg/day, 4.8 mg/day, 4.9 mg/day, or 5.0 mg/day, for instance, by oral administration. In some embodiments, the norethindrone acetate is administered to the patient at a dose of 1.0 mg/day, for instance, by oral administration. In some embodiments, the norethindrone acetate is administered to the patient at a dose of 0.5 mg/day, for instance, by oral administration. In some embodiments, the norethindrone acetate is administered to the patient at a dose of 0.1 mg/day, for instance, by oral administration.

In some embodiments, the progestin is progesterone. The progesterone may be administered to the patient, for example, at a dose of from about 50 mg to about 250 mg, such as a dose of about 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, 200 mg, 205 mg, 210 mg, 215 mg, 220 mg, 225 mg, 230 mg, 235 mg, 240 mg, 245 mg, or 250 mg, for instance, by oral administration. In some embodiments, the progesterone is administered to the patient at a dose of 200 mg, for instance, by oral administration. In some embodiments, the progesterone is administered to the patient at a dose of 100 mg, for instance, by oral administration.

The progesterone may be administered to the patient one or more times per day, week, or month. The progesterone may be administered to the patient, for example, at a dose of from about 50 mg/day to about 250 mg/day, such as a dose of about 50 mg/day, 55 mg/day, 60 mg/day, 65 mg/day, 70 mg/day, 75 mg/day, 80 mg/day, 85 mg/day, 90 mg/day, 95 mg/day, 100 mg/day, 105 mg/day, 110 mg/day, 115 mg/day, 120 mg/day, 125 mg/day, 130 mg/day, 135 mg/day, 140 mg/day, 145 mg/day, 150 mg/day, 155 mg/day, 160 mg/day, 165 mg/day, 170 mg/day, 175 mg/day, 180 mg/day, 185 mg/day, 190 mg/day, 195 mg/day, 200 mg/day, 205 mg/day, 210 mg/day, 215 mg/day, 220 mg/day, 225 mg/day, 230 mg/day, 235 mg/day, 240 mg/day, 245 mg/day, or 250 mg/day, for instance, by oral administration. In some embodiments, the progesterone is administered to the patient at a dose of 200 mg/day, for instance, by oral administration. In some embodiments, the progesterone is administered to the patient at a dose of 100 mg/day, for instance, by oral administration.

In some embodiments, the progestin is norgestimate. The norgestimate may be administered to the patient, for example, at a dose of from about 0.01 mg to about 2.0 mg, such as at a dose of about 0.01 mg, 0.02 mg, 0.03 mg, 0.04 mg, 0.05 mg, 0.06 mg, 0.07 mg, 0.08 mg, 0.09 mg, 0.1 mg, 0.2 mg, 0.3 mg, 0.4 mg, 0.5 mg, 0.6 mg, 0.7 mg, 0.8 mg, 0.9 mg, 1.0 mg, 1.1 mg, 1.2 mg, 1.3 mg, 1.4 mg, 1.5 mg, 1.6 mg, 1.7 mg, 1.8 mg, 1.9 mg, or 2.0 mg, for instance, by oral administration. In some embodiments, the norgestimate is administered to the patient at a dose of 0.09 mg, for instance, by oral administration.

The norgestimate may be administered to the patient one or more times per day, week, or month. The norgestimate may be administered to the patient, for example, at a dose of from about 0.01 mg/day to about 2.0 mg/day, such as at a dose of about 0.01 mg/day, 0.02 mg/day, 0.03 mg/day, 0.04 mg/day, 0.05 mg/day, 0.06 mg/day, 0.07 mg/day, 0.08 mg/day, 0.09 mg/day, 0.1 mg/day, 0.2 mg/day, 0.3 mg/day, 0.4 mg/day, 0.5 mg/day, 0.6 mg/day, 0.7 mg/day, 0.8 mg/day, 0.9 mg/day, 1.0 mg/day, 1.1 mg/day, 1.2 mg/day, 1.3 mg/day, 1.4 mg/day, 1.5 mg/day, 1.6 mg/day, 1.7 mg/day, 1.8 mg/day, 1.9 mg/day, or 2.0 mg/day, for instance, by oral administration. In some embodiments, the norgestimate is administered to the patient at a dose of 0.09 mg/day, for instance, by oral administration.

In some embodiments, the progestin is medroxyprogesterone. The medroxyprogesterone may be administered to the patient, for example, at a dose of from about 0.5 mg to about 10.0 mg, such as at a dose of about 0.5 mg, 0.6 mg, 0.7 mg, 0.8 mg, 0.9 mg, 1.0 mg, 1.1 mg, 1.2 mg, 1.3 mg, 1.4 mg, 1.5 mg, 1.6 mg, 1.7 mg, 1.8 mg, 1.9 mg, 2.0 mg, 2.1 mg, 2.2 mg, 2.3 mg, 2.4 mg, 2.5 mg, 2.6 mg, 2.7 mg, 2.8 mg, 2.9 mg, 3.0 mg, 3.1 mg, 3.2 mg, 3.3 mg, 3.4 mg, 3.5 mg, 3.6 mg, 3.7 mg, 3.8 mg, 3.9 mg, 4.0 mg, 4.1 mg, 4.2 mg, 4.3 mg, 4.4 mg, 4.5 mg, 4.6 mg, 4.7 mg, 4.8 mg, 4.9 mg, 5.0 mg, 5.1 mg, 5.2 mg, 5.3 mg, 5.4 mg, 5.5 mg, 5.6 mg, 5.7 mg, 5.8 mg, 5.9 mg, 6.0 mg, 6.1 mg, 6.2 mg, 6.3 mg, 6.4 mg, 6.5 mg, 6.6 mg, 6.7 mg, 6.8 mg, 6.9 mg, 7.0 mg, 7.1 mg, 7.2 mg, 7.3 mg, 7.4 mg, 7.5 mg, 7.6 mg, 7.7 mg, 7.8 mg, 7.9 mg, 8.0 mg, 8.1 mg, 8.2 mg, 8.3 mg, 8.4 mg, 8.5 mg, 8.6 mg, 8.7 mg, 8.8 mg, 8.9 mg, 9.0 mg, 9.1 mg, 9.2 mg, 9.3 mg, 9.4 mg, 9.5 mg, 9.6 mg, 9.7 mg, 9.8 mg, 9.9 mg, or 10.0 mg, for instance, by oral administration. In some embodiments, the medroxyprogesterone is administered to the patient at a dose of 5.0 mg, for instance, by oral administration. In some embodiments, the medroxyprogesterone is administered to the patient at a dose of 2.5 mg, for instance, by oral administration. In some embodiments, the medroxyprogesterone is administered to the patient at a dose of 1.5 mg, for instance, by oral administration.

The medroxyprogesterone may be administered to the patient one or more times per day, week, or month. The medroxyprogesterone may be administered to the patient, for example, at a dose of from about 0.5 mg/day to about 10.0 mg/day, such as at a dose of about 0.5 mg/day, 0.6 mg/day, 0.7 mg/day, 0.8 mg/day, 0.9 mg/day, 1.0 mg/day, 1.1 mg/day, 1.2 mg/day, 1.3 mg/day, 1.4 mg/day, 1.5 mg/day, 1.6 mg/day, 1.7 mg/day, 1.8 mg/day, 1.9 mg/day, 2.0 mg/day, 2.1 mg/day, 2.2 mg/day, 2.3 mg/day, 2.4 mg/day, 2.5 mg/day, 2.6 mg/day, 2.7 mg/day, 2.8 mg/day, 2.9 mg/day, 3.0 mg/day, 3.1 mg/day, 3.2 mg/day, 3.3 mg/day, 3.4 mg/day, 3.5 mg/day, 3.6 mg/day, 3.7 mg/day, 3.8 mg/day, 3.9 mg/day, 4.0 mg/day, 4.1 mg/day, 4.2 mg/day, 4.3 mg/day, 4.4 mg/day, 4.5 mg/day, 4.6 mg/day, 4.7 mg/day, 4.8 mg/day, 4.9 mg/day, 5.0 mg/day, 5.1 mg/day, 5.2 mg/day, 5.3 mg/day, 5.4 mg/day, 5.5 mg/day, 5.6 mg/day, 5.7 mg/day, 5.8 mg/day, 5.9 mg/day, 6.0 mg/day, 6.1 mg/day, 6.2 mg/day, 6.3 mg/day, 6.4 mg/day, 6.5 mg/day, 6.6 mg/day, 6.7 mg/day, 6.8 mg/day, 6.9 mg/day, 7.0 mg/day, 7.1 mg/day, 7.2 mg/day, 7.3 mg/day, 7.4 mg/day, 7.5 mg/day, 7.6 mg/day, 7.7 mg/day, 7.8 mg/day, 7.9 mg/day, 8.0 mg/day, 8.1 mg/day, 8.2 mg/day, 8.3 mg/day, 8.4 mg/day, 8.5 mg/day, 8.6 mg/day, 8.7 mg/day, 8.8 mg/day, 8.9 mg/day, 9.0 mg/day, 9.1 mg/day, 9.2 mg/day, 9.3 mg/day, 9.4 mg/day, 9.5 mg/day, 9.6 mg/day, 9.7 mg/day, 9.8 mg/day, 9.9 mg/day, or 10.0 mg/day, for instance, by oral administration. In some embodiments, the medroxyprogesterone is administered to the patient at a dose of 5.0 mg/day, for instance, by oral administration. In some embodiments, the medroxyprogesterone is administered to the patient at a dose of 2.5 mg/day, for instance, by oral administration. In some embodiments, the medroxyprogesterone is administered to the patient at a dose of 1.5 mg/day, for instance, by oral administration.

In some embodiments, the progestin is drospirenone. The drospirenone may be administered to the patient, for example, at a dose of from about 0.1 mg to about 1.0 mg, such as at a dose of about 0.1 mg, 0.2 mg, 0.3 mg, 0.4 mg, 0.5 mg, 0.6 mg, 0.7 mg, 0.8 mg, 0.9 mg, or 1.0 mg, for instance, by oral administration. In some embodiments, the drospirenone is administered to the patient at a dose of 0.5 mg, for instance, by oral administration. In some embodiments, the drospirenone is administered to the patient at a dose of 0.25 mg, for instance, by oral administration.

The drospirenone may be administered to the patient one or more times per day, week, or month. The drospirenone may be administered to the patient, for example, at a dose of from about 0.1 mg/day to about 1.0 mg/day, such as at a dose of about 0.1 mg/day, 0.2 mg/day, 0.3 mg/day, 0.4 mg/day, 0.5 mg/day, 0.6 mg/day, 0.7 mg/day, 0.8 mg/day, 0.9 mg/day, or 1.0 mg/day, for instance, by oral administration. In some embodiments, the drospirenone is administered to the patient at a dose of 0.5 mg/day, for instance, by oral administration. In some embodiments, the drospirenone is administered to the patient at a dose of 0.25 mg/day, for instance, by oral administration.

In some embodiments, the add-back therapy includes an estrogen and a progestin. In some embodiments, the add-back therapy includes β17-estradiol and norethindrone or a compound that is metabolized in vivo to produce norethindrone, such as an ester of norethindrone that is de-esterified in vivo to produce norethindrone, for instance, norethindrone acetate.

In some embodiments, the patient does not exhibit a reduction in BMD of greater than 5% following administration of the ASP-1707 or BAY-784 and the add-back therapy. In some embodiments, the patient does not exhibit a reduction in BMD of greater than 1% following administration of the ASP-1707 or BAY-784 and the add-back therapy. The add-back therapy may be formulated for oral administration. For instance, the add-back therapy may be formulated as a tablet, capsule, gel cap, powder, liquid solution, or liquid suspension. In some embodiments, the add-back therapy includes both an estrogen, such as β17-estradiol, and a progestin, such as norethindrone or norethindrone acetate. The estrogen and progestin may be administered separately or admixed in a single composition, such as a single tablet, capsule, gel cap, powder, liquid solution, or liquid suspension.

In some embodiments, the method includes orally administering the GnRH antagonist to the patient. In some embodiments, the method includes intravenously administering the GnRH antagonist to the patient.

In another aspect, the invention features a kit that contains the GnRH antagonist of any of the above aspects or embodiments of the invention. The kit may further contain one or more agents capable of detecting AMH and/or a package insert. The package insert may instruct a user of the kit to perform the method of any one of the above aspects or embodiments of the invention.

In some embodiments, the kit includes one or more agents capable of detecting a compound selected from the group consisting of E2, LH, and FSH. In some embodiments, the kit includes a thienopyrimidine GnRH antagonist, such as a compound represented by formula (II) or the choline salt thereof. In some embodiments, the kit includes a GnRH antagonist selected from the group consisting of elagolix, relugolix, ASP-1707, SKI2670, and BAY-784, or a derivative or variant thereof.

In another aspect, the invention features a method of treating endometriosis in a patient (e.g., a female human patient, such as a premenopausal female human patient). In another aspect, the invention features a method of reducing the concentration of E2, follicle-stimulating hormone (FSH), and/or luteinizing hormone (LH) in the blood of a patient (e.g., a female human patient, such as a premenopausal female human patient). In another aspect, the invention features a method of reducing pain (e.g., endometriosis-associated pain) in a patient (e.g., a female human patient, such as a premenopausal female human patient).

In any of the preceding aspects of the invention, the method may include the step of determining the concentration of E2 in a sample (e.g., a blood sample) isolated from the patient. In some embodiments, the concentration of E2 in a sample (e.g., a blood sample) isolated from the patient has previously been determined. The method may include:

a. comparing the concentration of E2 to an E2 reference range; and b. administering an increased dose of the GnRH antagonist to the patient if the concentration of E2 in the sample isolated from the patient is above the E2 reference range, or administering a decreased dose of the GnRH antagonist to the patient if the concentration of E2 in the sample isolated from the patient is below the E2 reference range.

In some embodiments, the method includes administering the originally dispensed dose of the GnRH antagonist to the patient if the concentration of E2 in the sample isolated from the patient is within the E2 reference range.

In some embodiments, the originally dispensed dose of the GnRH antagonist is from 10 to 500 mg/day (e.g., 10 mg/day, 15 mg/day, 20 mg/day, 25 mg/day, 30 mg/day, 35 mg/day, 40 mg/day, 45 mg/day, 50 mg/day, 55 mg/day, 60 mg/day, 65 mg/day, 70 mg/day, 75 mg/day, 80 mg/day, 85 mg/day, 90 mg/day, 95 mg/day, 100 mg/day, 105 mg/day, 110 mg/day, 115 mg/day, 120 mg/day, 125 mg/day, 130 mg/day, 135 mg/day, 140 mg/day, 145 mg/day, 150 mg/day, 155 mg/day, 160 mg/day, 165 mg/day, 170 mg/day, 175 mg/day, 180 mg/day, 185 mg/day, 190 mg/day, 195 mg/day, 200 mg/day, 205 mg/day, 210 mg/day, 215 mg/day, 220 mg/day, 225 mg/day, 230 mg/day, 235 mg/day, 240 mg/day, 245 mg/day, 250 mg/day, 255 mg/day, 260 mg/day, 265 mg/day, 270 mg/day, 275 mg/day, 280 mg/day, 285 mg/day, 290 mg/day, 295 mg/day, 300 mg/day, 305 mg/day, 310 mg/day, 315 mg/day, 320 mg/day, 325 mg/day, 330 mg/day, 335 mg/day, 340 mg/day, 345 mg/day, 350 mg/day, 355 mg/day, 360 mg/day, 365 mg/day, 370 mg/day, 375 mg/day, 380 mg/day, 385 mg/day, 390 mg/day, 395 mg/day, 400 mg/day, 405 mg/day, 410 mg/day, 415 mg/day, 420 mg/day, 425 mg/day, 430 mg/day, 435 mg/day, 440 mg/day, 445 mg/day, 450 mg/day, 455 mg/day, 460 mg/day, 465 mg/day, 470 mg/day, 475 mg/day, 480 mg/day, 485 mg/day, 490 mg/day, 495 mg/day, or 500 mg/day).

For instance, in some embodiments, the originally dispensed dose of the GnRH antagonist is 50 mg/day, 75 mg/day, 100 mg/day, or 200 mg/day and the GnRH antagonist is a compound represented by formula (I), such as a compound represented by formula (II) or the choline salt thereof.

In some embodiments, the originally dispensed dose of the GnRH antagonist is 150 mg/day and the GnRH antagonist is elagolix or a derivative or variant thereof, such as a compound described in U.S. Pat. No. 7,056,927; 7,176,211; 7,419,983; 8,765,948; or 9,382,214; or in US Patent Application Publication No. 2014/0288031 or 2017/0056403, the disclosures of which are incorporated herein by reference in their entirety. In some embodiments, the originally dispensed dose of the GnRH antagonist is 400 mg/day and the GnRH antagonist is elagolix or a derivative or variant thereof, such as a compound described in U.S. Pat. No. 7,056,927; 7,176,211; 7,419,983; 8,765,948; or 9,382,214; or in US Patent Application Publication No. 2014/0288031 or 2017/0056403, the disclosures of which are incorporated herein by reference in their entirety.

In some embodiments, the originally dispensed dose of the GnRH antagonist is 40 mg/day and the GnRH antagonist is relugolix or a derivative or variant thereof, such as a compound described in U.S. Pat. No. 7,300,935; 8,058,280; 8,735,401; or 9,346,822; or in US Patent Application Publication No. 2015/0266891, the disclosures of which are incorporated herein by reference in their entirety.

In some embodiments, the originally dispensed dose of the GnRH antagonist is 10 mg/day and the GnRH antagonist is ASP-1707 or a derivative or variant thereof, such as a compound described in U.S. Pat. No. 6,960,591; 7,569,688; 7,960,562; or 9,527,818, the disclosures of which are incorporated herein by reference in their entirety.

In another aspect, the invention provides a method of optimizing a dosing regimen for the treatment of endometriosis in a patient (e.g., a female human patient, such as a premenopausal female human patient) that is undergoing therapy with a GnRH antagonist. In another aspect, the invention provides a method of optimizing a dosing regimen for reducing the concentration of E2, follicle-stimulating hormone (FSH), and/or luteinizing hormone (LH) in the blood of a patient (e.g., a female human patient, such as a premenopausal female human patient) that is undergoing therapy with a GnRH antagonist. In another aspect, the invention provides a method of optimizing a dosing regimen for reducing pain (e.g., endometriosis-associated pain) in a patient (e.g., a female human patient, such as a premenopausal female human patient) that is undergoing therapy with a GnRH antagonist.

In any of the above aspects of the invention, the method may include the step of determining the concentration of E2 in a sample (e.g., a blood sample) isolated from the patient. In some embodiments, the concentration of E2 in a sample (e.g., a blood sample) isolated from the patient has previously been determined. The method may include:
a. comparing the concentration of E2 to an E2 reference range;
b. determining that the patient be administered an increased dose of a GnRH antagonist if the concentration of E2 in the sample isolated from the patient is above the E2 reference range, determining that the patient be administered a decreased dose of a GnRH antagonist if the concentration of E2 in the sample isolated from the patient is below the E2 reference range, or determining that the patient be administered the originally dispensed dose of the GnRH antagonist if the E2 concentration in the sample isolated from the patient is within the E2 reference range; and optionally
c. administering the GnRH antagonist to the patient at the dose determined in (b).

In some embodiments, the sample has been isolated from the patient between about 4 and about 36 weeks (e.g., about 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, or 36 week) following the start of the GnRH antagonist therapy. In some embodiments, the sample was isolated from the patient about 4 weeks following the start of the GnRH antagonist therapy. In some embodiments, the sample was isolated from the patient about 8 weeks following the start of the GnRH antagonist therapy. In some embodiments, the sample was isolated from the patient about 12 weeks following the start of GnRH antagonist therapy. In some embodiments, the sample was isolated from the patient about 24 weeks following the start of the GnRH antagonist therapy.

In some embodiments, the patient is administered the newly-determined dose of the GnRH antagonist between about 4 and about 36 weeks (e.g., about 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, or 36 week) following the start of the GnRH antagonist therapy. For example, the sample may be isolated from the patient about 4 weeks following the inception of the GnRH antagonist therapy, and the concentration of E2 in the sample can subsequently be compared to the E2 reference range to determine an appropriate GnRH dosage as described herein, and the patient may then be administered the newly-determined GnRH dosage either at about 4 weeks following the start of the GnRH antagonist therapy or at a later date, such as at about 12 weeks following the start of GnRH antagonist therapy. In some embodiments, the patient is administered the newly-determined GnRH antagonist dosage about 24 weeks following the inception of the GnRH antagonist therapy. In some embodiments, the sample is isolated from the patient about 8 weeks following the inception of the GnRH antagonist therapy, and the concentration of E2 in the sample is compared to the E2 reference range to determine an appropriate GnRH dosage as described herein. The patient may then be administered the newly-determined GnRH dosage either at about 8 weeks following the start of the GnRH antagonist therapy or at a later date, such as at about 12 weeks following the start of GnRH antagonist therapy. In some embodiments, the patient is administered the newly-determined GnRH antagonist dosage about 24 weeks following the inception of the GnRH antagonist therapy.

In some embodiments, the E2 reference range is from 20 to 50 pg/ml. Thus, it will be appreciated that an E2 concentration of less than 20 pg/ml (e.g., 1 pg/ml, 2 pg/ml, 3 pg/ml, 4 pg/ml, 5 pg/ml, 6 pg/ml, 7 pg/ml, 8 pg/ml, 9 pg/ml, 10 pg/ml, 11 pg/ml, 12 pg/ml, 13 pg/ml, 14 pg/ml, 15 pg/ml, 16 pg/ml, 17 pg/ml, 18 pg/ml, or 19 pg/ml) is considered below an E2 reference range of from 20 to 50 pg/ml. Likewise, an E2 concentration of greater than 50 pg/ml (e.g., 51 pg/ml, 52 pg/ml, 53 pg/ml, 54 pg/ml, 55 pg/ml, 60 pg/ml, 75 pg/ml, or greater) is considered above an E2 reference range of from 20 to 50 pg/ml.

In some embodiments, the method includes administering the GnRH antagonist to the patient in an amount sufficient to reduce or alleviate a symptom of the endometriosis, such as endometriosis-associated pain.

In some embodiments, the method includes administering the GnRH antagonist to the patient in an amount sufficient to reduce the serum concentration of E2 in the patient to between about 20 and about 50 pg/ml (e.g., to about 20 pg/ml, 25 pg/ml, 30 pg/ml, 35 pg/ml, 40 pg/ml, 45 pg/ml, or 50 pg/ml). In some embodiments, the serum concentration of E2 is reduced to between about 20 and about 50 pg/ml within about 4 to about 36 weeks of administering the GnRH antagonist to the patient (e.g., within about 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, or 36 weeks of administering the GnRH antagonist to the patient). In some embodiments, the serum concentration of E2 is reduced to between about 20 and about 50 pg/ml within about 4 weeks of administering the GnRH antagonist to the patient. In some embodiments, the serum concentration of E2 is reduced to between about 20 and about 50 pg/ml within about 12 weeks of administering the GnRH antagonist to the patient. In some embodiments, the serum concentration of E2 is reduced to between about 20 and about 50 pg/ml within about 24 weeks of administering the GnRH antagonist to the patient.

In some embodiments, the method includes administering the GnRH antagonist to the patient in an amount sufficient to reduce the serum concentration of follicle stimulating hormone (FSH) in the patient to between about 0.1 and about 10 mIU/ml (e.g., to about 0.1, 0.2, 0.3, 0.4, 0.5, 0.6, 0.7, 0.8, 0.9, 1, 2, 3, 4, 5, 6, 7, 8, 9, or 10 mIU/ml). In some embodiments, the serum concentration of FSH is reduced to between about 0.1 and about 10 mIU/mL within about 4 to about 36 weeks of administering the GnRH antagonist to the patient (e.g., within about 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, or 36 weeks of administering the GnRH antagonist to the patient). In some embodiments, the serum concentration of FSH is reduced to between about 0.1 and about 10 mIU/mL within about 4 weeks of administering the GnRH antagonist to the patient. In some embodiments, the serum concentration of FSH is reduced to between about 0.1 and about 10 mIU/mL within about 12 weeks of administering the GnRH antagonist to the patient. In some embodiments, the serum concentration of FSH is reduced to between about 0.1 and about 10 mIU/mL within about 24 weeks of administering the GnRH antagonist to the patient.

In some embodiments, the method includes administering the GnRH antagonist to the patient in an amount sufficient to reduce the serum concentration of luteinizing hormone (LH) in the patient to between about 0.1 and about 10 mIU/ml (e.g., to about 0.1, 0.2, 0.3, 0.4, 0.5, 0.6, 0.7, 0.8, 0.9, 1, 2, 3, 4, 5, 6, 7, 8, 9, or 10 mIU/ml). In some embodiments, the serum concentration of LH is reduced to between about 0.1 and about 10 mIU/mL within about 4 to about 36 weeks of administering the GnRH antagonist to the patient (e.g., within about 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, or 36 weeks of administering the GnRH antagonist to the patient). In some embodiments, the serum concentration of LH is reduced to between about 0.1 and about 10 mIU/mL within about 4 weeks of administering the GnRH antagonist to the patient. In some embodiments, the serum concentration of LH is reduced to between about 0.1 and about 10 mIU/mL within about 12 weeks of administering the GnRH antagonist to the patient. In some embodiments, the serum concentration of LH is reduced to between about 0.1 and about 10 mIU/mL within about 24 weeks of administering the GnRH antagonist to the patient.

In some embodiments, the method includes administering the GnRH antagonist to the patient in an amount sufficient to reduce endometriosis-associated pain experienced by the patient. In some embodiments, the endometriosis-associated pain is reduced within about 4 to about 36 weeks of administering the GnRH antagonist to the patient (e.g., within about 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, or 36 weeks of administering the GnRH antagonist to the patient). In some embodiments, the endometriosis-associated pain is reduced within about 4 weeks of administering the GnRH antagonist to the patient. In some embodiments, the endometriosis-associated pain is reduced within about 12 weeks of administering the GnRH antagonist to the patient. In some embodiments, the endometriosis-associated pain is reduced within about 24 weeks of administering the GnRH antagonist to the patient. In some embodiments, the endometriosis-associated pain is selected from the group consisting of pelvic pain, dyspareunia, and dyschezia.

In some embodiments, the endometriosis-associated pain is assessed by determining a Numerical Rating Score (NRS) for the patient. In some embodiments, the NRS is reduced by from about 1% to about 50% (e.g., by about 1%, 2%, 3%, 4%, 5%, 6%, 7%, 8%, 9%, 10%, 15%, 20%, 25%, 30%, 35%, 40%, 45%, or 50%). In some embodiments the NRS is reduced by about 30%.

In some embodiments, the endometriosis-associated pain is assessed by determining a Verbal Rating Score (VRS) for the patient. In some embodiments, the VRS is reduced by from about 1% to about 50% (e.g., by about 1%, 2%, 3%, 4%, 5%, 6%, 7%, 8%, 9%, 10%, 15%, 20%, 25%, 30%, 35%, 40%, 45%, or 50%). In some embodiments the VRS is reduced by about 30%.

In some embodiments, the method includes administering the GnRH antagonist to the patient in an amount sufficient to alleviate a symptom selected from the group consisting of dysmenorrhea, non-menstrual pelvic pain, and dyspareunia. In some embodiments, the symptom is alleviated within about 4 to about 36 weeks of administering the GnRH antagonist to the patient (e.g., within about 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, or 36 weeks of administering the GnRH antagonist to the patient). In some embodiments, the symptom is alleviated within about 4 weeks of administering the GnRH antagonist to the patient. In some embodiments, the symptom is alleviated within about 12 weeks of administering the GnRH antagonist to the patient. In some embodiments, the symptom is alleviated within about 24 weeks of administering the GnRH antagonist to the patient.

In some embodiments, the symptom is assessed by determining a Biberoglu and Behrman (B&B) scale score for the patient. In some embodiments, the B&B score is reduced by from about 1% to about 50% (e.g., by about 1%, 2%, 3%, 4%, 5%, 6%, 7%, 8%, 9%, 10%, 15%, 20%, 25%, 30%, 35%, 40%, 45%, or 50%).

In some embodiments, the method includes administering the GnRH antagonist to the patient in an amount sufficient to reduce an Endometriosis Health Profile-5 (EHP-5) score determined for the patient. In some embodiments, the EHP-5 score is reduced within about 4 to about 36 weeks of administering the GnRH antagonist to the patient (e.g., within about 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, or 36 weeks of administering the GnRH antagonist to the patient). In some embodiments, the EHP-5 score is reduced within about 4 weeks of administering the GnRH antagonist to the patient. In some embodiments, the EHP-5 score is reduced within about 12 weeks of administering the GnRH antagonist to the patient. In some embodiments, the EHP-5 score is reduced within about 24 weeks of administering the GnRH antagonist to the patient. In some embodiments, the EHP-5 score is reduced by from about 1% to about 50% (e.g., by about 1%, 2%, 3%, 4%, 5%, 6%, 7%, 8%, 9%, 10%, 15%, 20%, 25%, 30%, 35%, 40%, 45%, or 50%).

In some embodiments, the method includes administering the GnRH antagonist to the patient in an amount that does not cause a reduction in bone mineral density (BMD) in the patient of greater than 5%. In some embodiments, the method includes administering the GnRH antagonist to the patient in an amount that does not cause a reduction in BMD in the patient of greater than 1%.

In some embodiments, the method includes administering add-back therapy to the patient. In some embodiments, the add-back therapy is administered to the patient only if the dosage of the GnRH antagonist is increased in response to a finding that the E2 concentration in the sample isolated from the patient is greater than the E2 reference range. In some embodiments, the add-back therapy is administered to the patient regardless of whether the dose of the GnRH antagonist is increased, decreased, or remains the same upon evaluating the concentration of E2 in the sample obtained from the patient.

When administered, the add-back therapy may be administered to the patient concurrently with the GnRH antagonist, prior to administration of the GnRH antagonist, or following administration of the GnRH antagonist. In some embodiments, add-back therapy is administered as a fixed dose combination containing a GnRH antagonist, estrogen, and one or more additional agents, such as a progestin, in a single pharmaceutical composition. For instance, add-back therapy may be administered as a fixed dose combination of a GnRH antagonist, estrogen (e.g., in the form of E2) and a progestin (e.g., norethindrone or a compound that is metabolized in vivo to produce norethindrone, such as an ester of norethindrone that is de-esterified in vivo to produce norethindrone, for instance, norethindrone acetate) in the form of a single pharmaceutical composition, such as a single tablet, capsule, gel cap, powder, liquid solution, or liquid suspension.

In some embodiments, the add-back therapy includes an estrogen. In some embodiments, the estrogen is selected from the group consisting of β17-estradiol, ethinyl estradiol, and conjugated estrogens, such as conjugated equine estrogens.

In some embodiments, the estrogen is β17-estradiol. The β17-estradiol may be administered to the patient, for example, at a dose of from about 0.1 mg to about 2.5 mg, such as at a dose of about 0.1 mg, 0.2 mg, 0.3 mg, 0.4 mg, 0.5 mg, 0.6 mg, 0.7 mg, 0.8 mg, 0.9 mg, 1.0 mg, 1.1 mg, 1.2 mg, 1.3 mg, 1.4 mg, 1.5 mg, 1.6 mg, 1.7 mg, 1.8 mg, 1.9 mg, 2.0 mg, 2.1 mg, 2.2 mg, 2.3 mg, 2.4 mg, or 2.5 mg, for instance, by oral administration. In some embodiments, the β17-estradiol is administered to the patient at a dose of 1.0 mg, for instance, by oral administration. In some embodiments, the β17-estradiol is administered to the patient at a dose of 0.5 mg, for instance, by oral administration.

The β17-estradiol may be administered to the patient one or more times per day, week, or month. The β17-estradiol may be administered to the patient, for example, at a dose of from about 0.1 mg/day to about 2.5 mg/day, such as at a dose of about 0.1 mg/day, 0.2 mg/day, 0.3 mg/day, 0.4 mg/day, 0.5 mg/day, 0.6 mg/day, 0.7 mg/day, 0.8 mg/day, 0.9 mg/day, 1.0 mg/day, 1.1 mg/day, 1.2 mg/day, 1.3 mg/day, 1.4 mg/day, 1.5 mg/day, 1.6 mg/day, 1.7 mg/day, 1.8 mg/day, 1.9 mg/day, 2.0 mg/day, 2.1 mg/day, 2.2 mg/day, 2.3 mg/day, 2.4 mg/day, or 2.5 mg/day, for instance, by oral administration. In some embodiments, the β17-estradiol is administered to the patient at a dose of 1.0 mg/day, for instance, by oral administration. In some embodiments, the β17-estradiol is administered to the patient at a dose of 0.5 mg/day, for instance, by oral administration.

In some embodiments, the estrogen is ethinyl estradiol. The ethinyl estradiol may be administered to the patient, for example, at a dose of from about 1.0 μg to about 6.0 μg, such as at a dose of about 1.0 μg, 1.1 μg, 1.2 μg, 1.3 μg, 1.4 μg, 1.5 μg, 1.6 μg, 1.7 μg, 1.8 μg, 1.9 μg, 2.0 μg, 2.1 μg, 2.2 μg, 2.3 μg, 2.4 μg, 2.5 μg, 2.6 μg, 2.7 μg, 2.8 μg, 2.9 μg, 3.0 μg, 3.1 μg, 3.2 μg, 3.3 μg, 3.4 μg, 3.5 μg, 3.6 μg, 3.7 μg, 3.8 μg, 3.9 μg, 4.0 μg, 4.1 μg, 4.2 μg, 4.2 μg, 4.3 μg, 4.4 μg, 4.5 μg, 4.6 μg, 4.7 μg, 4.8 μg, 4.9 μg, 5.0 μg, 5.1 μg, 5.2 μg, 5.3 μg, 5.4 μg, 5.5 μg, 5.6 μg, 5.7 μg, 5.8 μg, 5.9 μg, or 6.0 μg, for instance, by oral administration. In some embodiments, the ethinyl estradiol is administered to the patient at a dose of 5.0 μg, for instance, by oral administration. In some embodiments, the ethinyl estradiol is administered to the patient at a dose of 2.5 μg, for instance, by oral administration.

The ethinyl estradiol may be administered to the patient one or more times per day, week, or month. The ethinyl estradiol may be administered to the patient, for example, at a dose of from about 1.0 μg/day to about 6.0 μg/day, such as at a dose of about 1.0 μg/day, 1.1 μg/day, 1.2 μg/day, 1.3 μg/day, 1.4 μg/day, 1.5 μg/day, 1.6 μg/day, 1.7 μg/day, 1.8 μg/day, 1.9 μg/day, 2.0 μg/day, 2.1 μg/day, 2.2 μg/day, 2.3 μg/day, 2.4 μg/day, 2.5 μg/day, 2.6 μg/day, 2.7 μg/day, 2.8 μg/day, 2.9 μg/day, 3.0 μg/day, 3.1 μg/day, 3.2 μg/day, 3.3 μg/day, 3.4 μg/day, 3.5 μg/day, 3.6 μg/day, 3.7 μg/day, 3.8 μg/day, 3.9 μg/day, 4.0 μg/day, 4.1 μg/day, 4.2 μg/day, 4.2 μg/day, 4.3 μg/day, 4.4 μg/day, 4.5 μg/day, 4.6 μg/day, 4.7 μg/day, 4.8 μg/day, 4.9 μg/day, 5.0 μg/day, 5.1 μg/day, 5.2 μg/day, 5.3 μg/day, 5.4 μg/day, 5.5 μg/day, 5.6 μg/day, 5.7 μg/day, 5.8 μg/day, 5.9 μg/day, or 6.0 μg/day, for instance, by oral administration. In some embodiments, the ethinyl estradiol is administered to the patient at a dose of 5.0 μg/day, for instance, by oral administration. In some embodiments, the ethinyl estradiol is administered to the patient at a dose of 2.5 μg/day, for instance, by oral administration.

In some embodiments, the estrogen is a conjugated estrogen, such as a conjugated equine estrogen. The conjugated estrogen may be administered to the patient, for example, at a dose of from about 0.1 mg to about 2.0 mg, such as at a dose of about 0.1 mg, 0.2 mg, 0.3 mg, 0.4 mg, 0.5 mg, 0.6 mg, 0.7 mg, 0.8 mg, 0.9 mg, 1.0 mg, 1.1 mg, 1.2 mg, 1.3 mg, 1.4 mg, 1.5 mg, 1.6 mg, 1.7 mg, 1.8 mg, 1.9 mg, or 2.0 mg, for instance, by oral administration. In some embodiments, the conjugated estrogen is administered to the patient at a dose of 0.625 mg, for instance, by oral administration. In some embodiments, the conjugated estrogen is administered to the patient at a dose of 0.45 mg, for instance, by oral administration. In some embodiments, the conjugated estrogen is administered to the patient at a dose of 0.3 mg, for instance, by oral administration.

The conjugated estrogen may be administered to the patient one or more times per day, week, or month. The conjugated estrogen may be administered to the patient, for example, at a dose of from about 0.1 mg/day to about 2.0 mg/day, such as at a dose of about 0.1 mg/day, 0.2 mg/day, 0.3 mg/day, 0.4 mg/day, 0.5 mg/day, 0.6 mg/day, 0.7 mg/day, 0.8 mg/day, 0.9 mg/day, 1.0 mg/day, 1.1 mg/day, 1.2 mg/day, 1.3 mg/day, 1.4 mg/day, 1.5 mg/day, 1.6 mg/day, 1.7 mg/day, 1.8 mg/day, 1.9 mg/day, or 2.0 mg/day, for instance, by oral administration. In some embodiments, the conjugated estrogen is administered to the patient at a dose of 0.625 mg/day, for instance, by oral administration. In some embodiments, the conjugated estrogen is administered to the patient at a dose of 0.45 mg/day, for instance, by oral administration. In some embodiments, the conjugated estrogen is administered to the patient at a dose of 0.3 mg/day, for instance, by oral administration.

In some embodiments, the add-back therapy includes a progestin. In some embodiments, the progestin is selected from the group consisting of norethindrone or an ester thereof, such as norethindrone acetate, or another agent such as progesterone, norgestimate, medroxyprogesterone, or drospirenone.

In some embodiments, the progestin is norethindrone or a compound that is metabolized in vivo to produce norethindrone, such as an ester of norethindrone that is de-esterified in vivo to produce norethindrone, for instance, norethindrone acetate.

In some embodiments, the progestin is norethindrone. The norethindrone may be administered to the patient, for example, at a dose of from about 0.05 mg to about 5.0 mg, such as at a dose of about 0.05 mg, 0.06 mg, 0.07 mg, 0.08 mg, 0.09 mg, 0.1 mg, 0.2 mg, 0.3 mg, 0.4 mg, 0.5 mg, 0.6 mg, 0.7 mg, 0.8 mg, 0.9 mg, 1.0 mg, 1.1 mg, 1.2 mg, 1.3 mg, 1.4 mg, 1.5 mg, 1.6 mg, 1.7 mg, 1.8 mg, 1.9 mg, 2.0 mg, 2.1 mg, 2.2 mg, 2.3 mg, 2.4 mg, 2.5 mg, 2.6 mg, 2.7 mg, 2.8 mg, 2.9 mg, 3.0 mg, 3.1 mg, 3.2 mg, 3.3 mg, 3.4 mg, 3.5 mg, 3.6 mg, 3.7 mg, 3.8 mg, 3.9 mg, 4.0 mg, 4.1 mg, 4.2 mg, 4.3 mg, 4.4 mg, 4.5 mg, 4.6 mg, 4.7 mg, 4.8 mg, 4.9 mg, or 5.0 mg, for instance, by oral administration. In some embodiments, the norethindrone is administered to the patient at a dose of 1.0 mg, for instance, by oral administration. In some embodiments, the norethindrone is administered to the patient at a dose of 0.5 mg, for instance, by oral administration. In some embodiments, the norethindrone is administered to the patient at a dose of 0.1 mg, for instance, by oral administration.

The norethindrone may be administered to the patient one or more times per day, week, or month. The norethindrone may be administered to the patient, for example, at a dose of from about 0.05 mg/day to about 5.0 mg/day, such as at a dose of about 0.05 mg/day, 0.06 mg/day, 0.07 mg/day, 0.08 mg/day, 0.09 mg/day, 0.1 mg/day, 0.2 mg/day, 0.3 mg/day, 0.4 mg/day, 0.5 mg/day, 0.6 mg/day, 0.7 mg/day, 0.8 mg/day, 0.9 mg/day, 1.0 mg/day, 1.1 mg/day, 1.2 mg/day, 1.3 mg/day, 1.4 mg/day, 1.5 mg/day, 1.6 mg/day, 1.7 mg/day, 1.8 mg/day, 1.9 mg/day, 2.0 mg/day, 2.1 mg/day, 2.2 mg/day, 2.3 mg/day, 2.4 mg/day, 2.5 mg/day, 2.6 mg/day, 2.7 mg/day, 2.8 mg/day, 2.9 mg/day, 3.0 mg/day, 3.1 mg/day, 3.2 mg/day, 3.3 mg/day, 3.4 mg/day, 3.5 mg/day, 3.6 mg/day, 3.7 mg/day, 3.8 mg/day, 3.9 mg/day, 4.0 mg/day, 4.1 mg/day, 4.2 mg/day, 4.3 mg/day, 4.4 mg/day, 4.5 mg/day, 4.6 mg/day, 4.7 mg/day, 4.8 mg/day, 4.9 mg/day, or 5.0 mg/day, for instance, by oral administration. In some embodiments, the norethindrone is administered to the patient at a dose of 1.0 mg/day, for instance, by oral administration. In some embodiments, the norethindrone is administered to the patient at a dose of 0.5 mg/day, for instance, by oral administration. In some embodiments, the norethindrone is administered to the patient at a dose of 0.1 mg/day, for instance, by oral administration.

In some embodiments, the progestin is norethindrone acetate. The norethindrone acetate may be administered to the patient, for example, at a dose of from about 0.05 mg to about 5.0 mg, such as at a dose of about 0.05 mg, 0.06 mg, 0.07 mg, 0.08 mg, 0.09 mg, 0.1 mg, 0.2 mg, 0.3 mg, 0.4 mg, 0.5 mg, 0.6 mg, 0.7 mg, 0.8 mg, 0.9 mg, 1.0 mg, 1.1 mg, 1.2 mg, 1.3 mg, 1.4 mg, 1.5 mg, 1.6 mg, 1.7 mg, 1.8 mg, 1.9 mg, 2.0 mg, 2.1 mg, 2.2 mg, 2.3 mg, 2.4 mg, 2.5 mg, 2.6 mg, 2.7 mg, 2.8 mg, 2.9 mg, 3.0 mg, 3.1 mg, 3.2 mg, 3.3 mg, 3.4 mg, 3.5 mg, 3.6 mg, 3.7 mg, 3.8 mg, 3.9 mg, 4.0 mg, 4.1 mg, 4.2 mg, 4.3 mg, 4.4 mg, 4.5 mg, 4.6 mg, 4.7 mg, 4.8 mg, 4.9 mg, or 5.0 mg, for instance, by oral administration. In some embodiments, the norethindrone acetate is administered to the patient at a dose of 1.0 mg/day, for instance, by oral administration. In some embodiments, the norethindrone acetate is administered to the patient at a dose of 0.5 mg, for instance, by oral administration. In some embodiments, the norethindrone acetate is administered to the patient at a dose of 0.1 mg, for instance, by oral administration.

The norethindrone acetate may be administered to the patient one or more times per day, week, or month. The norethindrone acetate may be administered to the patient, for example, at a dose of from about 0.05 mg/day to about 5.0 mg/day, such as at a dose of about 0.05 mg/day, 0.06 mg/day, 0.07 mg/day, 0.08 mg/day, 0.09 mg/day, 0.1 mg/day, 0.2 mg/day, 0.3 mg/day, 0.4 mg/day, 0.5 mg/day, 0.6 mg/day, 0.7 mg/day, 0.8 mg/day, 0.9 mg/day, 1.0 mg/day, 1.1 mg/day, 1.2 mg/day, 1.3 mg/day, 1.4 mg/day, 1.5 mg/day, 1.6 mg/day, 1.7 mg/day, 1.8 mg/day, 1.9 mg/day, 2.0 mg/day, 2.1 mg/day, 2.2 mg/day, 2.3 mg/day, 2.4 mg/day, 2.5 mg/day, 2.6 mg/day, 2.7 mg/day, 2.8 mg/day, 2.9 mg/day, 3.0 mg/day, 3.1 mg/day, 3.2 mg/day, 3.3 mg/day, 3.4 mg/day, 3.5 mg/day, 3.6 mg/day, 3.7 mg/day, 3.8 mg/day, 3.9 mg/day, 4.0 mg/day, 4.1 mg/day, 4.2 mg/day, 4.3 mg/day, 4.4 mg/day, 4.5 mg/day, 4.6 mg/day, 4.7 mg/day, 4.8 mg/day, 4.9 mg/day, or 5.0 mg/day, for instance, by oral administration. In some embodiments, the norethindrone acetate is administered to the patient at a dose of 1.0 mg/day, for instance, by oral administration. In some embodiments, the norethindrone acetate is administered to the patient at a dose of 0.5 mg/day, for instance, by oral administration. In some embodiments, the norethindrone acetate is administered to the patient at a dose of 0.1 mg/day, for instance, by oral administration.

In some embodiments, the progestin is progesterone. The progesterone may be administered to the patient, for example, at a dose of from about 50 mg to about 250 mg, such as a dose of about 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, 200 mg, 205 mg, 210 mg, 215 mg, 220 mg, 225 mg, 230 mg, 235 mg, 240 mg, 245 mg, or 250 mg, for instance, by oral administration. In some embodiments, the progesterone is administered to the patient at a dose of 200 mg, for instance, by oral administration. In some embodiments, the progesterone is administered to the patient at a dose of 100 mg, for instance, by oral administration.

The progesterone may be administered to the patient one or more times per day, week, or month. The progesterone may be administered to the patient, for example, at a dose of from about 50 mg/day to about 250 mg/day, such as a dose of about 50 mg/day, 55 mg/day, 60 mg/day, 65 mg/day, 70 mg/day, 75 mg/day, 80 mg/day, 85 mg/day, 90 mg/day, 95 mg/day, 100 mg/day, 105 mg/day, 110 mg/day, 115 mg/day, 120 mg/day, 125 mg/day, 130 mg/day, 135 mg/day, 140 mg/day, 145 mg/day, 150 mg/day, 155 mg/day, 160 mg/day, 165 mg/day, 170 mg/day, 175 mg/day, 180 mg/day, 185 mg/day, 190 mg/day, 195 mg/day, 200 mg/day, 205 mg/day, 210 mg/day, 215 mg/day, 220 mg/day, 225 mg/day, 230 mg/day, 235 mg/day, 240 mg/day, 245 mg/day, or 250 mg/day, for instance, by oral administration. In some embodiments, the progesterone is administered to the patient at a dose of 200 mg/day, for instance, by oral administration. In some embodiments, the progesterone is administered to the patient at a dose of 100 mg/day, for instance, by oral administration.

In some embodiments, the progestin is norgestimate. The norgestimate may be administered to the patient, for example, at a dose of from about 0.01 mg to about 2.0 mg, such as at a dose of about 0.01 mg, 0.02 mg, 0.03 mg, 0.04 mg, 0.05 mg, 0.06 mg, 0.07 mg, 0.08 mg, 0.09 mg, 0.1 mg, 0.2 mg, 0.3 mg, 0.4 mg, 0.5 mg, 0.6 mg, 0.7 mg, 0.8 mg, 0.9 mg, 1.0 mg, 1.1 mg, 1.2 mg, 1.3 mg, 1.4 mg, 1.5 mg, 1.6 mg, 1.7 mg, 1.8 mg, 1.9 mg, or 2.0 mg, for instance, by oral administration. In some embodiments, the norgestimate is administered to the patient at a dose of 0.09 mg, for instance, by oral administration.

The norgestimate may be administered to the patient one or more times per day, week, or month. The norgestimate may be administered to the patient, for example, at a dose of from about 0.01 mg/day to about 2.0 mg/day, such as at a dose of about 0.01 mg/day, 0.02 mg/day, 0.03 mg/day, 0.04 mg/day, 0.05 mg/day, 0.06 mg/day, 0.07 mg/day, 0.08 mg/day, 0.09 mg/day, 0.1 mg/day, 0.2 mg/day, 0.3 mg/day, 0.4 mg/day, 0.5 mg/day, 0.6 mg/day, 0.7 mg/day, 0.8 mg/day, 0.9 mg/day, 1.0 mg/day, 1.1 mg/day, 1.2 mg/day, 1.3 mg/day, 1.4 mg/day, 1.5 mg/day, 1.6 mg/day, 1.7 mg/day, 1.8 mg/day, 1.9 mg/day, or 2.0 mg/day, for instance, by oral administration. In some embodiments, the norgestimate is administered to the patient at a dose of 0.09 mg/day, for instance, by oral administration.

In some embodiments, the progestin is medroxyprogesterone. The medroxyprogesterone may be administered to the patient, for example, at a dose of from about 0.5 mg to about 10.0 mg, such as at a dose of about 0.5 mg, 0.6 mg, 0.7 mg, 0.8 mg, 0.9 mg, 1.0 mg, 1.1 mg, 1.2 mg, 1.3 mg, 1.4 mg, 1.5 mg, 1.6 mg, 1.7 mg, 1.8 mg, 1.9 mg, 2.0 mg, 2.1 mg, 2.2 mg, 2.3 mg, 2.4 mg, 2.5 mg, 2.6 mg, 2.7 mg, 2.8 mg, 2.9 mg, 3.0 mg, 3.1 mg, 3.2 mg, 3.3 mg, 3.4 mg, 3.5 mg, 3.6 mg, 3.7 mg, 3.8 mg, 3.9 mg, 4.0 mg, 4.1 mg, 4.2 mg, 4.3 mg, 4.4 mg, 4.5 mg, 4.6 mg, 4.7 mg, 4.8 mg, 4.9 mg, 5.0 mg, 5.1 mg, 5.2 mg, 5.3 mg, 5.4 mg, 5.5 mg, 5.6 mg, 5.7 mg, 5.8 mg, 5.9 mg, 6.0 mg, 6.1 mg, 6.2 mg, 6.3 mg, 6.4 mg, 6.5 mg, 6.6 mg, 6.7 mg, 6.8 mg, 6.9 mg, 7.0 mg, 7.1 mg, 7.2 mg, 7.3 mg, 7.4 mg, 7.5 mg, 7.6 mg, 7.7 mg, 7.8 mg, 7.9 mg, 8.0 mg, 8.1 mg, 8.2 mg, 8.3 mg, 8.4 mg, 8.5 mg, 8.6 mg, 8.7 mg, 8.8 mg, 8.9 mg, 9.0 mg, 9.1 mg, 9.2 mg, 9.3 mg, 9.4 mg, 9.5 mg, 9.6 mg, 9.7 mg, 9.8 mg, 9.9 mg, or 10.0 mg, for instance, by oral administration. In some embodiments, the medroxyprogesterone is administered to the patient at a dose of 5.0 mg, for instance, by oral administration. In some embodiments, the medroxyprogesterone is administered to the patient at a dose of 2.5 mg, for instance, by oral administration. In some embodiments, the medroxyprogesterone is administered to the patient at a dose of 1.5 mg, for instance, by oral administration.

The medroxyprogesterone may be administered to the patient one or more times per day, week, or month. The medroxyprogesterone may be administered to the patient, for example, at a dose of from about 0.5 mg/day to about 10.0 mg/day, such as at a dose of about 0.5 mg/day, 0.6 mg/day, 0.7 mg/day, 0.8 mg/day, 0.9 mg/day, 1.0 mg/day, 1.1 mg/day, 1.2 mg/day, 1.3 mg/day, 1.4 mg/day, 1.5 mg/day, 1.6 mg/day, 1.7 mg/day, 1.8 mg/day, 1.9 mg/day, 2.0 mg/day, 2.1 mg/day, 2.2 mg/day, 2.3 mg/day, 2.4 mg/day, 2.5 mg/day, 2.6 mg/day, 2.7 mg/day, 2.8 mg/day, 2.9 mg/day, 3.0 mg/day, 3.1 mg/day, 3.2 mg/day, 3.3 mg/day, 3.4 mg/day, 3.5 mg/day, 3.6 mg/day, 3.7 mg/day, 3.8 mg/day, 3.9 mg/day, 4.0 mg/day, 4.1 mg/day, 4.2 mg/day, 4.3 mg/day, 4.4 mg/day, 4.5 mg/day, 4.6 mg/day, 4.7 mg/day, 4.8 mg/day, 4.9 mg/day, 5.0 mg/day, 5.1 mg/day, 5.2 mg/day, 5.3 mg/day, 5.4 mg/day, 5.5 mg/day, 5.6 mg/day, 5.7 mg/day, 5.8 mg/day, 5.9 mg/day, 6.0 mg/day, 6.1 mg/day, 6.2 mg/day, 6.3 mg/day, 6.4 mg/day, 6.5 mg/day, 6.6 mg/day, 6.7 mg/day, 6.8 mg/day, 6.9 mg/day, 7.0 mg/day, 7.1 mg/day, 7.2 mg/day, 7.3 mg/day, 7.4 mg/day, 7.5 mg/day, 7.6 mg/day, 7.7 mg/day, 7.8 mg/day, 7.9 mg/day, 8.0 mg/day, 8.1 mg/day, 8.2 mg/day, 8.3 mg/day, 8.4 mg/day, 8.5 mg/day, 8.6 mg/day, 8.7 mg/day, 8.8 mg/day, 8.9 mg/day, 9.0 mg/day, 9.1 mg/day, 9.2 mg/day, 9.3 mg/day, 9.4 mg/day, 9.5 mg/day, 9.6 mg/day, 9.7 mg/day, 9.8 mg/day, 9.9 mg/day, or 10.0 mg/day, for instance, by oral administration. In some embodiments, the medroxyprogesterone is administered to the patient at a dose of 5.0 mg/day, for instance, by oral administration. In some embodiments, the medroxyprogesterone is administered to the patient at a dose of 2.5 mg/day, for instance, by oral administration. In some embodiments, the medroxyprogesterone is administered to the patient at a dose of 1.5 mg/day, for instance, by oral administration.

In some embodiments, the progestin is drospirenone. The drospirenone may be administered to the patient, for example, at a dose of from about 0.1 mg to about 1.0 mg, such as at a dose of about 0.1 mg, 0.2 mg, 0.3 mg, 0.4 mg, 0.5 mg, 0.6 mg, 0.7 mg, 0.8 mg, 0.9 mg, or 1.0 mg, for instance, by oral administration. In some embodiments, the drospirenone is administered to the patient at a dose of 0.5 mg, for instance, by oral administration. In some embodiments, the drospirenone is administered to the patient at a dose of 0.25 mg, for instance, by oral administration.

The drospirenone may be administered to the patient one or more times per day, week, or month. The drospirenone may be administered to the patient, for example, at a dose of from about 0.1 mg/day to about 1.0 mg/day, such as at a dose of about 0.1 mg/day, 0.2 mg/day, 0.3 mg/day, 0.4 mg/day, 0.5 mg/day, 0.6 mg/day, 0.7 mg/day, 0.8 mg/day, 0.9 mg/day, or 1.0 mg/day, for instance, by oral administration. In some embodiments, the drospirenone is administered to the patient at a dose of 0.5 mg/day, for instance, by oral administration. In some embodiments, the drospirenone is administered to the patient at a dose of 0.25 mg/day, for instance, by oral administration.

In some embodiments, the add-back therapy includes an estrogen and a progestin. In some embodiments, the add-back therapy includes β17-estradiol and norethindrone or a compound that is metabolized in vivo to produce norethindrone, such as an ester of norethindrone that is de-esterified in vivo to produce norethindrone, for instance, norethindrone acetate.

In some embodiments, the patient does not exhibit a reduction in BMD of greater than 5% following administration of the elagolix and the add-back therapy. In some embodiments, the patient does not exhibit a reduction in BMD of greater than 1% following administration of the elagolix and the add-back therapy. The add-back therapy may be formulated for oral administration. For instance, the add-back therapy may be formulated as a tablet, capsule, gel cap, powder, liquid solution, or liquid suspension. In some embodiments, the add-back therapy includes both an estrogen, such as 617-estradiol, and a progestin, such as norethindrone or norethindrone acetate. The estrogen and progestin may be administered separately or admixed in a single composition, such as a single tablet, capsule, gel cap, powder, liquid solution, or liquid suspension.

In some embodiments, the BMD is assessed by dual energy X-ray absorptiometry. In some embodiments, the BMD is assessed in the spine or femur of the patient.

In some embodiments, the GnRH antagonist is a compound represented by formula (I)

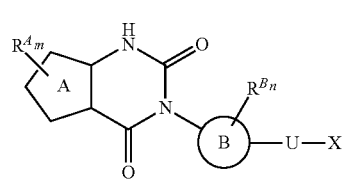
(I)

wherein ring A is a thiophene ring;
each $R^A$ is independently a halogen atom, a cyano group, a nitro group, an optionally substituted lower alkyl group, an optionally substituted lower alkenyl group, an optionally substituted lower alkynyl group, a hydroxyiminomethyl group, an optionally substituted sulfonyl group, an optionally substituted sulfinyl group, a tetrazolyl group, $OW^1$, $SW^1$, $COW^1$, $COOW^1$, $NHCOW^1$, $NHCONW^2W^3$, $NW^2W^3$, $CONW^2W^3$, or $SO_2NW^2W^3$, wherein $W^1$ to $W^3$ independently are a hydrogen atom or an optionally substituted lower alkyl group, or $W^2$ and $W^3$ may bind together with the neighboring nitrogen atom to form an optionally substituted cyclic amino group;
m is an integer from 0 to 3;
ring B is an aryl group or a monocyclic heteroaryl group;
each $R^B$ is independently a halogen atom, a cyano group, an optionally substituted lower alkyl group, $OW^4$, $COW^4$, $COOW^4$, or $CONW^5W^6$, wherein $W^4$ to $W^6$ independently are a hydrogen atom or an optionally substituted lower alkyl group, or $W^5$ and $W^6$ may bind together with the neighboring nitrogen atom to form an optionally substituted cyclic amino group;
n is an integer from 0 to 2;
U is a single bond;
X is a group represented by —S-L-Y, —O-L-Y, —CO-L-Y, or —SO$_2$-L-Y, wherein L is an optionally substituted lower alkylene group;
Y is a group represented by Z or —NW$^7$W$^8$, wherein W$^7$ and W$^8$ independently are a hydrogen atom, an optionally substituted lower alkyl group, or Z with the proviso that W$^7$ and W$^8$ are not simultaneously hydrogen atoms, or W$^7$ and W$^8$ may bind together with the neighboring nitrogen atom to form an optionally substituted cyclic amino group;
Z is an optionally fused and optionally substituted cycloalkyl group, an optionally fused and optionally substituted heterocycloalkyl group, an optionally fused and optionally substituted aryl group, or an optionally fused and optionally substituted heteroaryl group;
or a pharmaceutically acceptable salt thereof.

In some embodiments, the ring A is a thiophene ring represented by formula (A)

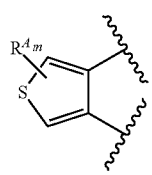
(A)

In some embodiments, m is 1 or 2. In some embodiments, m is 1. For instance, the ring A may be an optionally substituted thiophene ring represented by formula (B)

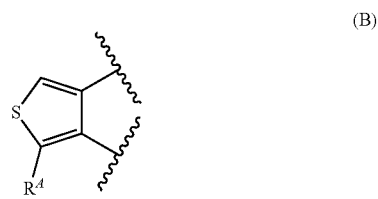
(B)

Each $R^A$ may independently be, for example, a halogen atom (e.g., fluorine, chlorine, bromine, or iodine), an optionally substituted lower alkyl group, $COOW^1$, or $CONW^2W^3$, wherein $W^1$ to $W^3$ independently are a hydrogen atom or an optionally substituted lower alkyl group, or $W^2$ and $W^3$ may bind together with the neighboring nitrogen atom to form an optionally substituted cyclic amino group. In some embodiments, each $R^A$ is COOH or pharmaceutically acceptable salt thereof.

In some embodiments, ring B is an optionally substituted benzene ring, pyridine ring, or thiophene ring. For instance, ring B may be represented by a formula selected from the group consisting of:

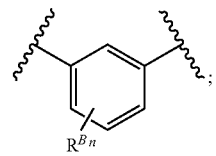

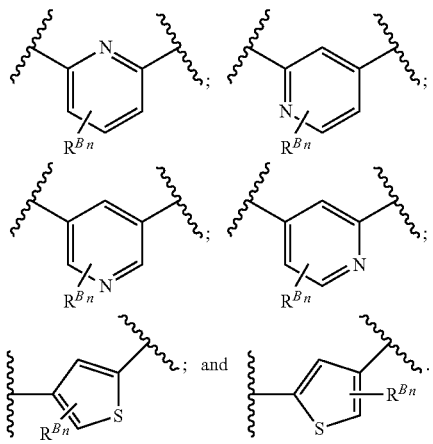

In some embodiments, n is 1 or 2. For instance, in some embodiments, n is 1. Ring B may be, for example, represented by a formula selected from the group consisting of:

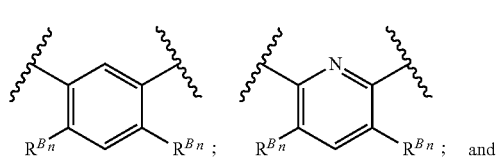

-continued

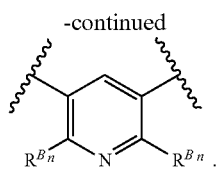

In some embodiments, each $R^B$ is independently a halogen atom, an optionally substituted lower alkyl group, or $OW^4$, wherein each $W^4$ is independently a hydrogen atom or an optionally substituted lower alkyl group. For instance, each $R^B$ may be independently a fluorine atom, chlorine atom, bromine atom, methyl group, or methoxy group.

In some embodiments, U is a single bond. X may be, for example, a group represented by —O-L-Y. L may be, for example, a methylene group. In some embodiments, Y is an optionally substituted benzene ring represented by formula (C)

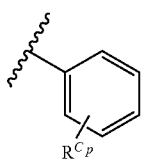

(C)

wherein each $R^C$ is independently a halogen atom, an optionally substituted lower alkyl group, or $OW^9$, wherein each $W^9$ is independently a hydrogen atom or an optionally substituted lower alkyl group; and
p is an integer from 0 to 3.

In some embodiments, Y is a substituted benzene ring represented by formula (D)

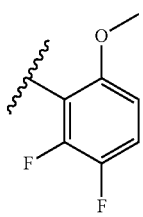

(D)

In some embodiments, the compound is represented by formula (II)

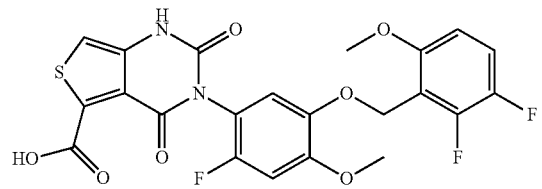

(II)

or a pharmaceutically acceptable salt thereof.

In some embodiments, the compound is the choline salt of the compound represented by formula (II), i.e., choline 3-[2-fluoro-5-(2,3-difluoro-6-methoxybenzyloxy)4-methoxyphenyl]-2,4-dioxo-1,2,3,4-tetrahydrothieno[3,4d]pyrimidine-5-carboxylate.

In some embodiments, the GnRH antagonist includes the compound represented by formula (II) in a crystalline state. In some embodiments, the compound exhibits characteristic X-ray powder diffraction peaks at about 7.1° 2θ, 11.5° 2θ, 19.4° 2θ, 20.3° 2θ, 21.5° 2θ, 22.0° 2θ, 22.6° 2θ, 23.5° 2θ, and 26.2° 2θ. In some embodiments, the compound exhibits $^{13}C$ solid-state NMR peaks centered at about 155.8 ppm, 149.8 ppm, 145.3 ppm, 118.0 ppm, 113.7 ppm, 111.6 ppm, 110.3 ppm, 98.1 ppm, 69.8 ppm, 58.7 ppm, 57.1 ppm, and 55.5 ppm. In some embodiments, the compound exhibits $^{19}F$ solid-state NMR peaks centered at about −131.6 ppm, −145.2 ppm, and −151.8 ppm.

In some embodiments, the method includes administering from 85 mg/day to 115 mg/day (e.g., 85 mg/day, 90 mg/day, 95 mg/day, 100 mg/day, 105 mg/day, 110 mg/day, or 115 mg/day) or more, such as from about 185 mg/day to about 215 mg/day (e.g., 185 mg/day, 190 mg/day, 195 mg/day, 200 mg/day, 205 mg/day, 210 mg/day, or 215 mg/day) of the compound represented by formula (I), formula (II), or a pharmaceutically acceptable salt thereof (e.g., choline 3-[2-fluoro-5-(2,3-difluoro-6-methoxybenzyloxy)4-methoxyphenyl]-2,4-dioxo-1,2,3,4-tetrahydrothieno[3,4d]pyrimidine-5-carboxylate) to the patient if the concentration of E2 in the sample isolated from the patient is within the E2 reference range. In some embodiments, the method includes administering from 60 to 90 mg/day (e.g., 60 mg/day, 65 mg/day, 70 mg/day, 75 mg/day, 80 mg/day, 85 mg/day, or 90 mg/day) of the compound represented by formula (I), formula (II), or a pharmaceutically acceptable salt thereof (e.g., choline 3-[2-fluoro-5-(2,3-difluoro-6-methoxybenzyloxy)4-methoxyphenyl]-2,4-dioxo-1,2,3,4-tetrahydrothieno[3,4d]pyrimidine-5-carboxylate) to the patient if the concentration of E2 in the sample isolated from the patient is within the E2 reference range. In some embodiments, the method includes administering from 35 to 65 mg/day (e.g., 35 mg/day, 40 mg/day, 45 mg/day, 45 mg/day, 50 mg/day, 55 mg/day, 60 mg/day, or 65 mg/day) of the compound represented by formula (I), formula (II), or a pharmaceutically acceptable salt thereof (e.g., choline 3-[2-fluoro-5-(2,3-difluoro-6-methoxybenzyloxy)4-methoxyphenyl]-2,4-dioxo-1,2,3,4-tetrahydrothieno[3,4d]pyrimidine-5-carboxylate) to the patient if the concentration of E2 in the sample isolated from the patient is within the E2 reference range.

In some embodiments, the method includes administering about 100 mg/day or about 200 mg/day of the compound represented by formula (I), formula (II), or a pharmaceutically acceptable salt thereof (e.g., choline 3-[2-fluoro-5-(2,3-difluoro-6-methoxybenzyloxy)4-methoxyphenyl]-2,4-dioxo-1,2,3,4-tetrahydrothieno[3,4d]pyrimidine-5-carboxylate) to the patient if the concentration of E2 in the sample isolated from the patient is within the E2 reference range. In some embodiments, the method includes administering about 75 mg/day of the compound represented by formula (I), formula (II), or a pharmaceutically acceptable salt thereof (e.g., choline 3-[2-fluoro-5-(2,3-difluoro-6-methoxybenzyloxy)4-methoxyphenyl]-2,4-dioxo-1,2,3,4-tetrahydrothieno[3,4d]pyrimidine-5-carboxylate) to the patient if the concentration of E2 in the sample isolated from the patient is within the E2 reference range. In some embodiments, the method includes administering about 50 mg/day of the compound represented by formula (I), formula (II), or a pharmaceutically acceptable salt thereof (e.g., choline 3-[2-fluoro-5-(2,3-difluoro-6-methoxybenzyloxy)4-methoxyphenyl]-2,4-dioxo-1,2,3,4-tetrahydrothieno[3,4d]pyrimidine-5-carboxylate) to the patient if the concentration of E2 in the sample isolated from the patient is within the E2 reference range.

In some embodiments, the method includes administering from 85 mg/day to 115 mg/day (e.g., 85 mg/day, 90 mg/day, 95 mg/day, 100 mg/day, 105 mg/day, 110 mg/day, or 115 mg/day) or more, such as from about 185 mg/day to about 215 mg/day (e.g., 185 mg/day, 190 mg/day, 195 mg/day, 200 mg/day, 205 mg/day, 210 mg/day, or 215 mg/day) of the compound represented by formula (I), formula (II), or a pharmaceutically acceptable salt thereof (e.g., choline 3-[2-fluoro-5-(2,3-difluoro-6-methoxybenzyloxy)4-methoxyphenyl]-2,4-dioxo-1,2,3,4-tetrahydrothieno[3,4d]pyrimidine-5-carboxylate) to the patient if the concentration of E2 in the sample isolated from the patient is above the E2 reference range. In some embodiments, the method includes administering from 60 to 90 mg/day (e.g., 60 mg/day, 65 mg/day, 70 mg/day, 75 mg/day, 80 mg/day, 85 mg/day, or 90 mg/day) of the compound represented by formula (I), formula (II), or a pharmaceutically acceptable salt thereof (e.g., choline 3-[2-fluoro-5-(2,3-difluoro-6-methoxybenzyloxy)4-methoxyphenyl]-2,4-dioxo-1,2,3,4-tetrahydrothieno[3,4d]pyrimidine-5-carboxylate) to the patient if the concentration of E2 in the sample isolated from the patient is above the E2 reference range. In some embodiments, the method includes administering from 35 to 65 mg/day (e.g., 35 mg/day, 40 mg/day, 45 mg/day, 45 mg/day, 50 mg/day, 55 mg/day, 60 mg/day, or 65 mg/day) of the compound represented by formula (I), formula (II), or a pharmaceutically acceptable salt thereof (e.g., choline 3-[2-fluoro-5-(2,3-difluoro-6-methoxybenzyloxy)4-methoxyphenyl]-2,4-dioxo-1,2,3,4-tetrahydrothieno[3,4d]pyrimidine-5-carboxylate) to the patient if the concentration of E2 in the sample isolated from the patient is above the E2 reference range.

In some embodiments, the method includes administering about 100 mg/day or about 200 mg/day of the compound represented by formula (I), formula (II), or a pharmaceutically acceptable salt thereof (e.g., choline 3-[2-fluoro-5-(2,3-difluoro-6-methoxybenzyloxy)4-methoxyphenyl]-2,4-dioxo-1,2,3,4-tetrahydrothieno[3,4d]pyrimidine-5-carboxylate) to the patient if the concentration of E2 in the sample isolated from the patient is above the E2 reference range. In some embodiments, the method includes administering about 75 mg/day of the compound represented by formula (I), formula (II), or a pharmaceutically acceptable salt thereof (e.g., choline 3-[2-fluoro-5-(2,3-difluoro-6-methoxybenzyloxy)4-methoxyphenyl]-2,4-dioxo-1,2,3,4-tetrahydrothieno[3,4d]pyrimidine-5-carboxylate) to the patient if the concentration of E2 in the sample isolated from the patient is above the E2 reference range. In some embodiments, the method includes administering about 50 mg/day of the compound represented by formula (I), formula (II), or a pharmaceutically acceptable salt thereof (e.g., choline 3-[2-fluoro-5-(2,3-difluoro-6-methoxybenzyloxy)4-methoxyphenyl]-2,4-dioxo-1,2,3,4-tetrahydrothieno[3,4d]pyrimidine-5-carboxylate) to the patient if the concentration of E2 in the sample isolated from the patient is above the E2 reference range.

In some embodiments, the method includes administering from 85 mg/day to 115 mg/day (e.g., 85 mg/day, 90 mg/day, 95 mg/day, 100 mg/day, 105 mg/day, 110 mg/day, or 115 mg/day) or more, such as from about 185 mg/day to about 215 mg/day (e.g., 185 mg/day, 190 mg/day, 195 mg/day, 200 mg/day, 205 mg/day, 210 mg/day, or 215 mg/day) of the compound represented by formula (I), formula (II), or a pharmaceutically acceptable salt thereof (e.g., choline 3-[2-fluoro-5-(2,3-difluoro-6-methoxybenzyloxy)4-methoxyphenyl]-2,4-dioxo-1,2,3,4-tetrahydrothieno[3,4d]pyrimidine-5-carboxylate) to the patient if the concentration of E2 in the sample isolated from the patient is below the E2 reference range. In some embodiments, the method includes administering from 60 to 90 mg/day (e.g., 60 mg/day, 65 mg/day, 70 mg/day, 75 mg/day, 80 mg/day, 85 mg/day, or 90 mg/day) of the compound represented by formula (I), formula (II), or a pharmaceutically acceptable salt thereof (e.g., choline 3-[2-fluoro-5-(2,3-difluoro-6-methoxybenzyloxy)4-methoxyphenyl]-2,4-dioxo-1,2,3,4-tetrahydrothieno[3,4d]pyrimidine-5-carboxylate) to the patient if the concentration of E2 in the sample isolated from the patient is below the E2 reference range. In some embodiments, the method includes administering from 35 to 65 mg/day (e.g., 35 mg/day, 40 mg/day, 45 mg/day, 45 mg/day, 50 mg/day, 55 mg/day, 60 mg/day, or 65 mg/day) of the compound represented by formula (I), formula (II), or a pharmaceutically acceptable salt thereof (e.g., choline 3-[2-fluoro-5-(2,3-difluoro-6-methoxybenzyloxy)4-methoxyphenyl]-2,4-dioxo-1,2,3,4-tetrahydrothieno[3,4d]pyrimidine-5-carboxylate) to the patient if the concentration of E2 in the sample isolated from the patient is below the E2 reference range.

In some embodiments, the method includes administering about 100 mg/day or about 200 mg/day of the compound represented by formula (I), formula (II), or a pharmaceutically acceptable salt thereof (e.g., choline 3-[2-fluoro-5-(2,3-difluoro-6-methoxybenzyloxy)4-methoxyphenyl]-2,4-dioxo-1,2,3,4-tetrahydrothieno[3,4d]pyrimidine-5-carboxylate) to the patient if the concentration of E2 in the sample isolated from the patient is below the E2 reference range. In some embodiments, the method includes administering about 75 mg/day of the compound represented by formula (I), formula (II), or a pharmaceutically acceptable salt thereof (e.g., choline 3-[2-fluoro-5-(2,3-difluoro-6-methoxybenzyloxy)4-methoxyphenyl]-2,4-dioxo-1,2,3,4-tetrahydrothieno[3,4d]pyrimidine-5-carboxylate) to the patient if the concentration of E2 in the sample isolated from the patient is below the E2 reference range. In some embodiments, the method includes administering about 50 mg/day of the compound represented by formula (I), formula (II), or a pharmaceutically acceptable salt thereof (e.g., choline 3-[2-fluoro-5-(2,3-difluoro-6-methoxybenzyloxy)4-methoxyphenyl]-2,4-dioxo-1,2,3,4-tetrahydrothieno[3,4d]pyrimidine-5-carboxylate) to the patient if the concentration of E2 in the sample isolated from the patient is below the E2 reference range.

In some embodiments, the GnRH antagonist is selected from the group consisting of elagolix, relugolix, ASP-1707, SKI2670, and BAY-784.

In some embodiments, the GnRH antagonist is elagolix or a derivative or variant thereof, such as a compound described in U.S. Pat. No. 7,056,927; 7,176,211; 7,419,983; 8,765,948; or 9,382,214; or in US Patent Application Publication No. 2014/0288031 or 2017/0056403, the disclosures of which are incorporated herein by reference in their entirety. In some embodiments, the method includes administering 150 mg/day or more (e.g., 155 mg/day, 160 mg/day, 165 mg/day, 170 mg/day, 175 mg/day, 180 mg/day, 185 mg/day, 190 mg/day, 195 mg/day, 200 mg/day, 205 mg/day, 210 mg/day, 215 mg/day, 220 mg/day, 225 mg/day, 230 mg/day, 235 mg/day, 240 mg/day, 245 mg/day, 250 mg/day, 255 mg/day, 260 mg/day, 265 mg/day, 270 mg/day, 275 mg/day, 280 mg/day, 285 mg/day, 290 mg/day, 295 mg/day, 300 mg/day, 305 mg/day, 310 mg/day, 315 mg/day, 320 mg/day, 325 mg/day, 330 mg/day, 335 mg/day, 340 mg/day, 345 mg/day, 350 mg/day, 355 mg/day, 360 mg/day, 365 mg/day, 370 mg/day, 375 mg/day, 380 mg/day, 385 mg/day, 390 mg/day, 395, 400 mg/day, or more) of elagolix to the patient if the concentration of E2 in the sample isolated from the patient is above the E2 reference range. In some embodiments, the method includes administering from 155 mg/day to 395 mg/day of elagolix to the patient if the concentration of E2 in the sample isolated from the patient is above the E2 reference range.

In some embodiments, the method includes administering 400 mg/day or more (e.g., 400 mg/day, 405 mg/day, 410 mg/day, 415 mg/day, 420 mg/day, 425 mg/day, 430 mg/day, 435 mg/day, 440 mg/day, 445 mg/day, 450 mg/day, 455 mg/day, 460 mg/day, 465 mg/day, 470 mg/day, 475 mg/day, 480 mg/day, 485 mg/day, 490 mg/day, 495 mg/day, 500 mg/day, 505 mg/day, 510 mg/day, 515 mg/day, 520 mg/day, 525 mg/day, 530 mg/day, 535 mg/day, 540 mg/day, 545 mg/day, 550 mg/day, 555 mg/day, 560 mg/day, 565 mg/day, 570 mg/day, 575 mg/day, 580 mg/day, 585 mg/day, 590 mg/day, 595 mg/day, 600 mg/day, 605 mg/day, 610 mg/day, 615 mg/day, 620 mg/day, 625 mg/day, 630 mg/day, 635 mg/day, 640 mg/day, 645 mg/day, 650 mg/day, 655 mg/day, 660 mg/day, 665 mg/day, 670 mg/day, 675 mg/day, 680 mg/day, 685 mg/day, 690 mg/day, 695 mg/day, 700 mg/day, or more) of elagolix to the patient if the concentration of E2 in the sample isolated from the patient is above the E2 reference range. In some embodiments, the method includes administering from 400 mg/day to 600 mg/day of elagolix to the patient if the concentration of E2 in the sample isolated from the patient is above the E2 reference range.

In some embodiments, the method includes administering 150 mg/day or less (e.g., 50 mg/day, 55 mg/day, 60 mg/day, 65 mg/day, 70 mg/day, 75 mg/day, 80 mg/day, 85 mg/day, 90 mg/day, 95 mg/day, 100 mg/day, 105 mg/day, 110 mg/day, 115 mg/day, 120 mg/day, 125 mg/day, 130 mg/day, 135 mg/day, 140 mg/day, 145 mg/day, or 150 mg/day) of elagolix to the patient if the concentration of E2 in the sample isolated from the patient is below the E2 reference range. In some embodiments, the method includes administering from 50 mg/day to 125 mg/day of elagolix to the patient if the concentration of E2 in the sample isolated from the patient is below the E2 reference range. In some embodiments, the method includes administering 100 mg/day of elagolix to the patient if the concentration of E2 in the sample isolated from the patient is below the E2 reference range.

In some embodiments, the method includes administering 400 mg/day or less (e.g., 50 mg/day, 55 mg/day, 60 mg/day, 65 mg/day, 70 mg/day, 75 mg/day, 80 mg/day, 85 mg/day, 90 mg/day, 95 mg/day, 100 mg/day, 105 mg/day, 110 mg/day, 115 mg/day, 120 mg/day, 125 mg/day, 130 mg/day, 135 mg/day, 140 mg/day, 145 mg/day, 150 mg/day, 155 mg/day, 160 mg/day, 165 mg/day, 170 mg/day, 175 mg/day, 180 mg/day, 185 mg/day, 190 mg/day, 195 mg/day, 200 mg/day, 205 mg/day, 210 mg/day, 215 mg/day, 220 mg/day, 225 mg/day, 230 mg/day, 235 mg/day, 240 mg/day, 245 mg/day, 250 mg/day, 255 mg/day, 260 mg/day, 265 mg/day, 270 mg/day, 275 mg/day, 280 mg/day, 285 mg/day, 290 mg/day, 295 mg/day, 300 mg/day, 305 mg/day, 310 mg/day, 315 mg/day, 320 mg/day, 325 mg/day, 330 mg/day, 335 mg/day, 340 mg/day, 345 mg/day, 350 mg/day, 355 mg/day, 360 mg/day, 365 mg/day, 370 mg/day, 375 mg/day, 380 mg/day, 385 mg/day, 390 mg/day, or 395 mg/day) of elagolix to the patient if the concentration of E2 in the sample isolated from the patient is below the E2 reference range. In some embodiments, the method includes administering from 150 mg/day to 375 mg/day of elagolix to the patient if the concentration of E2 in the sample isolated from the patient is below the E2 reference range. In some embodiments, the method includes administering 150 mg/day of elagolix to the patient if the concentration of E2 in the sample isolated from the patient is below the E2 reference range.

In some embodiments, the method includes administering from 150 mg/day to 400 mg/day (e.g., 150 mg/day, 155 mg/day, 160 mg/day, 165 mg/day, 170 mg/day, 175 mg/day, 180 mg/day, 185 mg/day, 190 mg/day, 195 mg/day, 200 mg/day, 205 mg/day, 210 mg/day, 215 mg/day, 220 mg/day, 225 mg/day, 230 mg/day, 235 mg/day, 240 mg/day, 245 mg/day, 250 mg/day, 255 mg/day, 260 mg/day, 265 mg/day, 270 mg/day, 275 mg/day, 280 mg/day, 285 mg/day, 290 mg/day, 295 mg/day, 300 mg/day, 305 mg/day, 310 mg/day, 315 mg/day, 320 mg/day, 325 mg/day, 330 mg/day, 335 mg/day, 340 mg/day, 345 mg/day, 350 mg/day, 355 mg/day, 360 mg/day, 365 mg/day, 370 mg/day, 375 mg/day, 380 mg/day, 385 mg/day, 390 mg/day, 395, or 400 mg/day) of elagolix to the patient if the concentration of E2 in the sample isolated from the patient is within the E2 reference range. In some embodiments, the method includes administering 150 mg/day of elagolix to the patient if the concentration of E2 in the sample isolated from the patient is within the E2 reference range. In some embodiments, the method includes administering 400 mg/day of elagolix to the patient if the concentration of E2 in the sample isolated from the patient is within the E2 reference range. For instance, the method may include administering 200 mg of elagolix to the patient twice daily if the concentration of E2 in the sample isolated from the patient is within the E2 reference range.

In some embodiments, the GnRH antagonist is relugolix or a derivative or variant thereof, such as a compound described in U.S. Pat. No. 7,300,935; 8,058,280; 8,735,401; or 9,346,822; or in US Patent Application Publication No. 2015/0266891, the disclosures of which are incorporated herein by reference in their entirety. In some embodiments, the method includes administering 40 mg/day or more (e.g., from 40 mg/day to 150 mg/day or more, such as 45 mg/day, 50 mg/day, 55 mg/day, 60 mg/day, 65 mg/day, 70 mg/day, 75 mg/day, 80 mg/day, 85 mg/day, 90 mg/day, 95 mg/day, 100 mg/day, 105 mg/day, 110 mg/day, 115 mg/day, 120 mg/day, 125 mg/day, 130 mg/day, 135 mg/day, 140 mg/day, 145 mg/day, 150 mg/day, or more) of relugolix to the patient if the concentration of E2 in the sample isolated from the patient is above the E2 reference range. In some embodiments, the method includes administering from 50 mg/day to 75 mg/day of relugolix to the patient if the concentration of E2 in the sample isolated from the patient is above the E2 reference range.

In some embodiments, the method includes administering 40 mg/day or less (e.g., from 10 mg/day to 40 mg/day, such as 10 mg/day, 15 mg/day, 20 mg/day, 25 mg/day, 30 mg/day, or 35 mg/day) of relugolix to the patient if the concentration of E2 in the sample isolated from the patient is below the E2 reference range. In some embodiments, the method includes administering from 10 mg/day to 35 mg/day of relugolix to the patient if the concentration of E2 in the sample isolated from the patient is below the E2 reference range.

In some embodiments, the method includes administering from 35 mg/day to 45 mg/day (e.g., 35 mg/day, 40 mg/day, or 45 mg/day) of relugolix to the patient if the concentration of E2 in the sample isolated from the patient is within the E2 reference range. In some embodiments, the method includes administering 40 mg/day of relugolix to the patient if the concentration of E2 in the sample isolated from the patient is within the E2 reference range.

In some embodiments, the GnRH antagonist is ASP-1707 or a derivative or variant thereof, such as a compound described in U.S. Pat. No. 6,960,591; 7,569,688; 7,960,562; or 9,527,818, the disclosures of which are incorporated herein by reference in their entirety. In some embodiments, the method includes administering 10 mg/day or more (e.g., from 15 mg/day to 100 mg/day or more, such as 15 mg/day, 20 mg/day, 25 mg/day, 30 mg/day, 35 mg/day, 40 mg/day, 45 mg/day, 50 mg/day, 55 mg/day, 60 mg/day, 65 mg/day, 70 mg/day, 75 mg/day, 80 mg/day, 85 mg/day, 90 mg/day, 95 mg/day, 100 mg/day, or more) of ASP-1707 to the patient if the concentration of E2 in the sample isolated from the patient is above the E2 reference range. In some embodiments, the method includes administering from 15 mg/day to 50 mg/day of ASP-1707 to the patient if the concentration of E2 in the sample isolated from the patient is above the E2 reference range.

In some embodiments, the method includes administering 10 mg/day or less (e.g., from 5 mg/day to 9 mg/day, such as 5 mg/day, 6 mg/day, 7 mg/day, 8 mg/day, or 9 mg/day) of ASP-1707 to the patient if the concentration of E2 in the sample isolated from the patient is below the E2 reference range. In some embodiments, the method includes administering from 5 mg/day to 7.5 mg/day of ASP-1707 to the patient if the concentration of E2 in the sample isolated from the patient is below the E2 reference range.

In some embodiments, the method includes administering from 7.5 mg/day to 15 mg/day (e.g., 7.5 mg/day, 10 mg/day, 12.5 mg/day, or 15 mg/day) of ASP-1707 to the patient if the concentration of E2 in the sample isolated from the patient is within the E2 reference range. In some embodiments, the method includes administering 10 mg/day of ASP-1707 to the patient if the concentration of E2 in the sample isolated from the patient is within the E2 reference range.

In some embodiments, the GnRH antagonist is BAY-784 or a derivative or variant thereof. The GnRH antagonist may be a compound described in US Patent Application Publication No. 2014/0357655 or 2016/0052936, the disclosures of which are incorporated herein by reference in their entirety.

In some embodiment s, the method includes orally administering the GnRH antagonist to the patient. In some embodiments, the method includes intravenously administering the GnRH antagonist to the patient.

In another aspect, the invention provides a kit that contains the GnRH antagonist of any of the above aspects or embodiments of the invention. The kit may further contain one or more agents capable of detecting E2 and/or a package insert. The package insert may instruct a user of the kit to perform the method of any one of the above aspects or embodiments of the invention.

In some embodiments, the kit contains one or more agents capable of detecting a compound selected from the group consisting of LH and FSH. In some embodiments, the kit includes a thienopyrimidine GnRH antagonist, such as a compound represented by formula (II) or the choline salt thereof. In some embodiments, the kit includes a GnRH antagonist selected from the group consisting of elagolix, relugolix, ASP-1707, SKI2670, and BAY-784, or a derivative or variant thereof.

In yet another aspect, the invention features a method of treating endometriosis in a patient (e.g., a female human patient, such as a premenopausal female human patient). In another aspect, the invention features a method of reducing the concentration of E2, follicle-stimulating hormone (FSH), and/or luteinizing hormone (LH) in the blood of a patient (e.g., a female human patient, such as a premenopausal female human patient). In another aspect, the invention features a method of reducing pain (e.g., endometriosis-associated pain) in a patient (e.g., a female human patient, such as a premenopausal female human patient). In these aspects, the method includes administering to the patient a compound represented by formula (I)

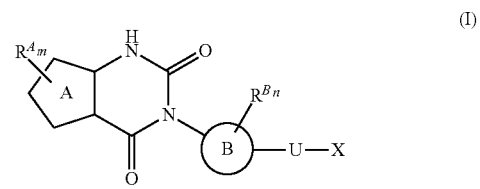

(I)

wherein ring A is a thiophene ring;

each $R^A$ is independently a halogen atom, a cyano group, a nitro group, an optionally substituted lower alkyl group, an optionally substituted lower alkenyl group, an optionally substituted lower alkynyl group, a hydroxyiminomethyl group, an optionally substituted sulfonyl group, an optionally substituted sulfinyl group, a tetrazolyl group, $OW^1$, $SW^1$, $COW^1$, $COOW^1$, $NHCOW^1$, $NHCONW^2W^3$, $NW^2W^3$, $CONW^2W^3$, or $SO_2NW^2W^3$, wherein $W^1$ to $W^3$ independently are a hydrogen atom or an optionally substituted lower alkyl group, or $W^2$ and $W^3$ may bind together with the neighboring nitrogen atom to form an optionally substituted cyclic amino group;

m is an integer from 0 to 3;

ring B is an aryl group or a monocyclic heteroaryl group;

each $R^B$ is independently a halogen atom, a cyano group, an optionally substituted lower alkyl group, $OW^4$, $COW^4$, $COOW^4$, or $CONW^5W^6$, wherein $W^4$ to $W^6$ independently are a hydrogen atom or an optionally substituted lower alkyl group, or $W^5$ and $W^6$ may bind together with the neighboring nitrogen atom to form an optionally substituted cyclic amino group;

n is an integer from 0 to 2;

U is a single bond;

X is a group represented by —S-L-Y, —O-L-Y, —CO-L-Y, or —SO$_2$-L-Y, wherein L is an optionally substituted lower alkylene group;

Y is a group represented by Z or —NW$^7$W$^8$, wherein W$^7$ and W$^8$ independently are a hydrogen atom, an optionally substituted lower alkyl group, or Z with the proviso that W$^7$ and W$^8$ are not simultaneously hydrogen atoms, or W$^7$ and W$^8$ may bind together with the neighboring nitrogen atom to form an optionally substituted cyclic amino group;

Z is an optionally fused and optionally substituted cycloalkyl group, an optionally fused and optionally substituted heterocycloalkyl group, an optionally fused and optionally substituted aryl group, or an optionally fused and optionally substituted heteroaryl group;

or a pharmaceutically acceptable salt thereof, in an amount of from about 25 mg per dose to about 300 mg per dose (e.g., in an amount of about 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, 200 mg, 205 mg, 210 mg, 215 mg, 220 mg, 225 mg, 230 mg, 235 mg, 240 mg, 245 mg, 250 mg, 255 mg, 260 mg, 265 mg, 270 mg, 275 mg, 280 mg, 285 mg, 290 mg, 295 mg, or 300 mg per dose). In some embodiments, the compound is administered in an amount of 50 mg per dose. In some embodiments, the compound is administered in an amount of 75 mg per dose. In some embodiments, the compound is administered in an amount of 100 mg per dose. In some embodiments, the compound is administered in an amount of 200 mg per dose.

In some embodiments, the compound is administered orally, for example, in the form of a tablet, capsule, gel cap, powder, liquid solution, or liquid suspension.

The compound may be administered to the patient in one or more doses per 12 hours, 24 hours, 48 hours, 72 hours, week, month, or year, such as in from 1 to 10 doses per 12 hours (e.g., 1 dose every 12 hours, 2 doses every 12 hours, 3 doses every 12 hours, 4 doses every 12 hours, 5 doses every 12 hours, 6 doses every 12 hours, 7 doses every 12 hours, 8 doses every 12 hours, 9 doses every 12 hours, or 10 doses every 12 hours), from 1 to 10 doses per 24 hours (e.g., 1 dose every 24 hours, 2 doses every 24 hours, 3 doses every 24 hours, 4 doses every 24 hours, 5 doses every 24 hours, 6 doses every 24 hours, 7 doses every 24 hours, 8 doses every 24 hours, 9 doses every 24 hours, or 10 doses every 24 hours), from 1 to 10 doses per 48 hours (e.g., 1 dose every 48 hours, 2 doses every 48 hours, 3 doses every 48 hours, 4 doses every 48 hours, 5 doses every 48 hours, 6 doses every 48 hours, 7 doses every 48 hours, 8 doses every 48 hours, 9 doses every 48 hours, or 10 doses every 48 hours), from 1 to 10 doses per 72 hours (e.g., 1 dose every 72 hours, 2 doses every 72 hours, 3 doses every 72 hours, 4 doses every 72 hours, 5 doses every 72 hours, 6 doses every 72 hours, 7 doses every 72 hours, 8 doses every 72 hours, 9 doses every 72 hours, or 10 doses every 72 hours), from 1 to 10 doses per week (e.g., 1 dose every week, 2 doses every week, 3 doses every week, 4 doses every week, 5 doses every week, 6 doses every week, 7 doses every week, 8 doses every week, 9 doses every week, or 10 doses every week), or from 1 to 60 doses per month (e.g., from 30-60 doses per month, such as 1 time daily, 2 times daily, 3 times daily, 4 times daily, 5 times daily, 6 times daily, 7 times daily, 8 times daily, 9 times daily, 10 times daily, 7 times weekly, 8 times weekly, 9 times weekly, 10 times weekly, 11 times weekly, 12 times weekly, 13 times weekly, 14 times weekly, or more), among others.

In some embodiments, the compound is administered to the patient in an amount of about 200 mg/day (e.g., 200 mg/day). In some embodiments, the compound is administered to the patient in an amount of about 400 mg every 48 hours (e.g., 400 mg every 48 hours). In some embodiments, the compound is administered to the patient in an amount of about 600 mg every 72 hours (e.g., 600 mg every 72 hours). In some embodiments, the compound is administered to the patient in an amount of about 1,400 mg/week (e.g., 1,400 mg/week).

In some embodiments, the compound is administered to the patient in an amount of about 100 mg every 12 hours (e.g., 100 mg every 12 hours), in an amount of about 50 mg every 6 hours (e.g., 50 mg every 6 hours), in an amount of about 33.33 mg every 4 hours (e.g., 33.33 mg every 4 hours), in an amount of about 25 mg every 3 hours (e.g., 25 mg every 3 hours), or the like, e.g., so as to achieve an amount of 200 mg/day.

In some embodiments, the compound is administered to the patient in an amount of about 100 mg/day (e.g., 100 mg/day). In some embodiments, the compound is administered to the patient in an amount of about 200 mg every 48 hours (e.g., 200 mg every 48 hours). In some embodiments, the compound is administered to the patient in an amount of about 300 mg every 72 hours (e.g., 300 mg every 72 hours). In some embodiments, the compound is administered to the patient in an amount of about 700 mg/week (e.g., 700 mg/week).

In some embodiments, the compound is administered to the patient in an amount of about 50 mg every 12 hours (e.g., 50 mg every 12 hours), in an amount of about 25 mg every 6 hours (e.g., 25 mg every 6 hours), in an amount of about 16.67 mg every 4 hours (e.g., 16.67 mg every 4 hours), in an amount of about 12.5 mg every 3 hours (e.g., 12.5 mg every 3 hours), or the like, e.g., so as to achieve an amount of 100 mg/day.

In some embodiments, the compound is administered to the patient in an amount of about 50 mg/day (e.g., 50 mg/day). In some embodiments, the compound is administered to the patient in an amount of about 100 mg every 48 hours (e.g., 100 mg every 48 hours). In some embodiments, the compound is administered to the patient in an amount of about 150 mg every 72 hours (e.g., 150 mg every 72 hours). In some embodiments, the compound is administered to the patient in an amount of about 350 mg/week (e.g., 350 mg/week).

In some embodiments, the compound is administered to the patient in an amount of about 25 mg every 12 hours (e.g., 25 mg every 12 hours), in an amount of about 12.5 mg every 6 hours (e.g., 12.5 mg every 6 hours), in an amount of about 8.33 mg every 4 hours (e.g., 8.33 mg every 4 hours), in an amount of about 6.25 mg every 3 hours (e.g., 6.25 mg every 3 hours), or the like, e.g., so as to achieve an amount of 50 mg/day.

In some embodiments, the compound is administered to the patient in an amount of about 75 mg/day (e.g., 75 mg/day). In some embodiments, the compound is administered to the patient in an amount of about 150 mg every 48 hours (e.g., 150 mg every 48 hours). In some embodiments, the compound is administered to the patient in an amount of about 225 mg every 72 hours (e.g., 225 mg every 72 hours). In some embodiments, the compound is administered to the patient in an amount of about 525 mg/week (e.g., 525 mg/week).

In some embodiments, the compound is administered to the patient in an amount of about 37.5 mg every 12 hours (e.g., 37.5 mg every 12 hours), in an amount of about 18.75 mg every 6 hours (e.g., 18.75 mg every 6 hours), in an amount of about 12.5 mg every 4 hours (e.g., 12.5 mg every 4 hours), in an amount of about 9.375 mg every 3 hours (e.g., 9.375 mg every 3 hours), or the like, e.g., so as to achieve an amount of 75 mg/day.

In some embodiments, the ring A is a thiophene ring represented by formula (A)

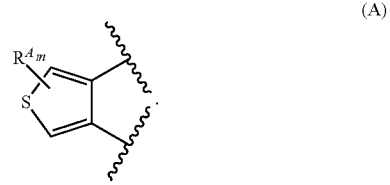

(A)

In some embodiments, m is 1 or 2. In some embodiments, m is 1. For instance, the ring A may be an optionally substituted thiophene ring represented by formula (B)

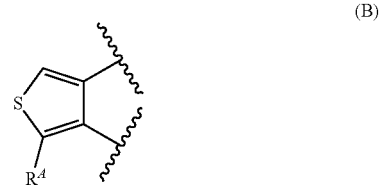

(B)

Each $R^A$ may independently be, for example, a halogen atom (e.g., fluorine, chlorine, bromine, or iodine), an optionally substituted lower alkyl group, $COOW^1$, or $CONW^2W^3$, wherein $W^1$ to $W^3$ independently are a hydrogen atom or an optionally substituted lower alkyl group, or $W^2$ and $W^3$ may bind together with the neighboring nitrogen atom to form an optionally substituted cyclic amino group. In some embodiments, each $R^A$ is COOH or pharmaceutically acceptable salt thereof.

In some embodiments, ring B is an optionally substituted benzene ring, pyridine ring, or thiophene ring. For instance, ring B may be represented by a formula selected from the group consisting of:

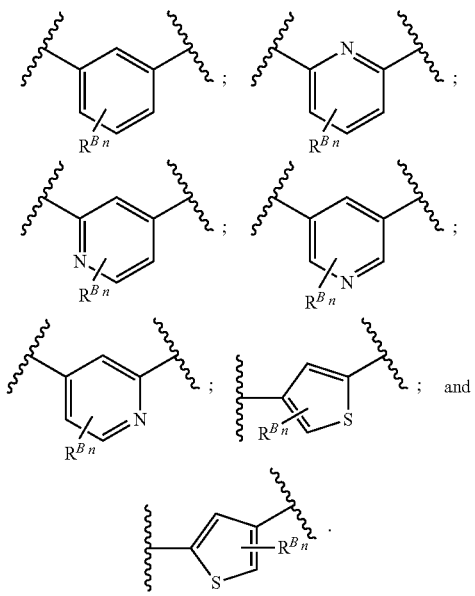

In some embodiments, n is 1 or 2. For instance, in some embodiments, n is 1. Ring B may be, for example, represented by a formula selected from the group consisting of:

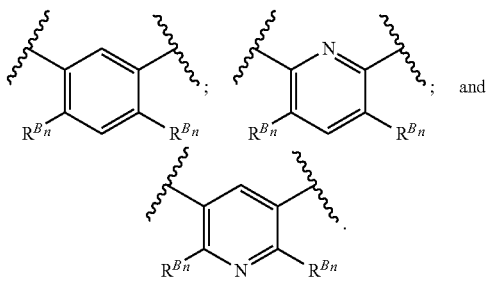

In some embodiments, each $R^B$ is independently a halogen atom, an optionally substituted lower alkyl group, or $OW^4$, wherein each $W^4$ is independently a hydrogen atom or an optionally substituted lower alkyl group. For instance, each $R^B$ may be independently a fluorine atom, chlorine atom, bromine atom, methyl group, or methoxy group.

In some embodiments, U is a single bond. X may be, for example, a group represented by —O-L-Y. L may be, for example, a methylene group. In some embodiments, Y is an optionally substituted benzene ring represented by formula (C)

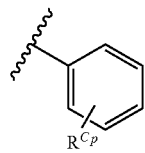

wherein each $R^C$ is independently a halogen atom, an optionally substituted lower alkyl group, or $OW^9$, wherein each $W^9$ is independently a hydrogen atom or an optionally substituted lower alkyl group; and p is an integer from 0 to 3.

In some embodiments, Y is a substituted benzene ring represented by formula (D)

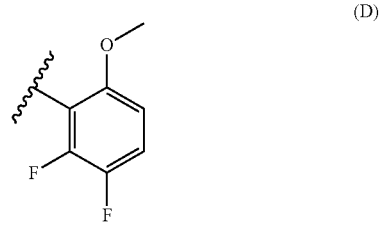 [SMILES: *c1c(OC)ccc(F)c1F]

In some embodiments, the compound is represented by formula (II)

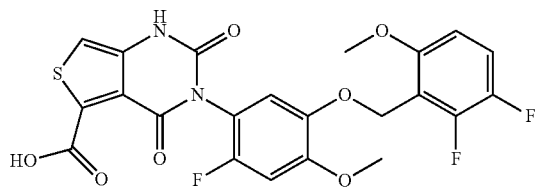

or a pharmaceutically acceptable salt thereof.

In some embodiments, the compound is the choline salt of the compound represented by formula (II), i.e., choline 3-[2-fluoro-5-(2,3-difluoro-6-methoxybenzyloxy)4-methoxyphenyl]-2,4-dioxo-1,2,3,4-tetrahydrothieno[3,4d]pyrimidine-5-carboxylate.

In some embodiments, the GnRH antagonist includes the compound represented by formula (II) in a crystalline state. In some embodiments, the compound exhibits characteristic X-ray powder diffraction peaks at about 7.1° 2θ, 11.5° 2θ, 19.4° 2θ, 20.3° 2θ, 21.5° 2θ, 22.0° 2θ, 22.6° 2θ, 23.5° 2θ, and 26.2° 2θ. In some embodiments, the compound exhibits $^{13}C$ solid-state NMR peaks centered at about 155.8 ppm, 149.8 ppm, 145.3 ppm, 118.0 ppm, 113.7 ppm, 111.6 ppm, 110.3 ppm, 98.1 ppm, 69.8 ppm, 58.7 ppm, 57.1 ppm, and 55.5 ppm. In some embodiments, the compound exhibits $^{19}F$ solid-state NMR peaks centered at about −131.6 ppm, −145.2 ppm, and −151.8 ppm.

In some embodiments, the method includes administering add-back therapy to the patient. The add-back therapy may be administered to the patient concurrently with the GnRH antagonist, prior to administration of the GnRH antagonist, or following administration of the GnRH antagonist. In some embodiments, add-back therapy is administered as a fixed dose combination containing a GnRH antagonist, estrogen, and one or more additional agents, such as a progestin, in a single pharmaceutical composition. For instance, add-back therapy may be administered as a fixed dose combination of a GnRH antagonist, estrogen (e.g., in the form of β17-estradiol, ethinyl estradiol, or a conjugated estrogen, such as a conjugated equine estrogen) and/or a progestin (e.g., norethindrone or a compound that is metabolized in vivo to produce norethindrone, such as an ester of norethindrone that is de-esterified in vivo to produce norethindrone, for instance, norethindrone acetate (also referred to herein as "NETA"), among other agents, such as progesterone, norgestimate, medroxyprogesterone, and drospirenone) in the form of a single pharmaceutical composition, such as a single tablet, capsule, gel cap, powder, liquid solution, or liquid suspension. In some embodiments, the add-back therapy is administered orally, transdermally, or intravaginally.

In some embodiments, the add-back therapy is administered to the patient in one or more doses per day, week, month, or year, such as daily, for example, from 1 to 10 times daily, or more (e.g., 1, 2, 3, 4, 5, 6, 7, 8, 9, 10, or more, times daily). In some embodiments, the add-back therapy is administered to the patient once daily, for example, concurrently with the GnRH antagonist. For example, the GnRH antagonist may be administered to the patient orally, and concurrently with oral administration of the GnRH antagonist, the add-back therapy may be administered to the patient orally, transdermally, or intravaginally. In some embodiments, the add-back therapy is administered to the patient in the form of a pharmaceutical composition that further includes the GnRH antagonist, such as a single tablet, capsule, gel cap, powder, liquid solution, or liquid suspension, for instance, as described above and herein.

In some embodiments, the add-back therapy is administered to the patient once daily, following administration of the compound. For example, the GnRH antagonist may be administered to the patient orally, and following oral administration of the GnRH antagonist, the add-back therapy may be administered to the patient orally, transdermally, or intravaginally.

In some embodiments, the add-back therapy is administered to the patient once daily, prior to administration of the compound. For example, the GnRH antagonist may be administered to the patient orally, and prior to oral administration of the GnRH antagonist, the add-back therapy may be administered to the patient orally, transdermally, or intravaginally.

In some embodiments, the add-back therapy includes an estrogen. In some embodiments, the estrogen is selected from the group consisting of β17-estradiol, ethinyl estradiol, and conjugated estrogens, such as conjugated equine estrogens.

In some embodiments, the estrogen is β17-estradiol. The β17-estradiol may be administered to the patient, for example, at a dose of from about 0.1 mg to about 2.5 mg, such as at a dose of about 0.1 mg, 0.2 mg, 0.3 mg, 0.4 mg, 0.5 mg, 0.6 mg, 0.7 mg, 0.8 mg, 0.9 mg, 1.0 mg, 1.1 mg, 1.2 mg, 1.3 mg, 1.4 mg, 1.5 mg, 1.6 mg, 1.7 mg, 1.8 mg, 1.9 mg, 2.0 mg, 2.1 mg, 2.2 mg, 2.3 mg, 2.4 mg, or 2.5 mg, for instance, by oral administration. In some embodiments, the β17-estradiol is administered to the patient at a dose of 1.0 mg, for instance, by oral administration. In some embodiments, the β17-estradiol is administered to the patient at a dose of 0.5 mg, for instance, by oral administration.

The β17-estradiol may be administered to the patient one or more times per day, week, or month. The β17-estradiol may be administered to the patient, for example, at a dose of from about 0.1 mg/day to about 2.5 mg/day, such as at a dose of about 0.1 mg/day, 0.2 mg/day, 0.3 mg/day, 0.4 mg/day, 0.5 mg/day, 0.6 mg/day, 0.7 mg/day, 0.8 mg/day, 0.9 mg/day, 1.0 mg/day, 1.1 mg/day, 1.2 mg/day, 1.3 mg/day, 1.4 mg/day, 1.5 mg/day, 1.6 mg/day, 1.7 mg/day, 1.8 mg/day, 1.9 mg/day, 2.0 mg/day, 2.1 mg/day, 2.2 mg/day, 2.3 mg/day, 2.4 mg/day, or 2.5 mg/day, for instance, by oral administration. In some embodiments, the β17-estradiol is administered to the patient at a dose of 1.0 mg/day, for instance, by oral administration. In some embodiments, the β17-estradiol is administered to the patient at a dose of 0.5 mg/day, for instance, by oral administration.

In some embodiments, the estrogen is ethinyl estradiol. The ethinyl estradiol may be administered to the patient, for example, at a dose of from about 1.0 µg to about 6.0 µg, such as at a dose of about 1.0 µg, 1.1 µg, 1.2 µg, 1.3 µg, 1.4 µg, 1.5 µg, 1.6 µg, 1.7 µg, 1.8 µg, 1.9 µg, 2.0 µg, 2.1 µg, 2.2 µg, 2.3 µg, 2.4 µg, 2.5 µg, 2.6 µg, 2.7 µg, 2.8 µg, 2.9 µg, 3.0 µg, 3.1 µg, 3.2 µg, 3.3 µg, 3.4 µg, 3.5 µg, 3.6 µg, 3.7 µg, 3.8 µg, 3.9 µg, 4.0 µg, 4.1 µg, 4.2 µg, 4.2 µg, 4.3 µg, 4.4 µg, 4.5 µg, 4.6 µg, 4.7 µg, 4.8 µg, 4.9 µg, 5.0 µg, 5.1 µg, 5.2 µg, 5.3 µg, 5.4 µg, 5.5 µg, 5.6 µg, 5.7 µg, 5.8 µg, 5.9 µg, or 6.0 µg, for instance, by oral administration. In some embodiments, the ethinyl estradiol is administered to the patient at a dose of 5.0 µg, for instance, by oral administration. In some embodiments, the ethinyl estradiol is administered to the patient at a dose of 2.5 µg, for instance, by oral administration.

The ethinyl estradiol may be administered to the patient one or more times per day, week, or month. The ethinyl estradiol may be administered to the patient, for example, at a dose of from about 1.0 µg/day to about 6.0 µg/day, such as at a dose of about 1.0 µg/day, 1.1 µg/day, 1.2 µg/day, 1.3 µg/day, 1.4 µg/day, 1.5 µg/day, 1.6 µg/day, 1.7 µg/day, 1.8 µg/day, 1.9 µg/day, 2.0 µg/day, 2.1 µg/day, 2.2 µg/day, 2.3 µg/day, 2.4 µg/day, 2.5 µg/day, 2.6 µg/day, 2.7 µg/day, 2.8 µg/day, 2.9 µg/day, 3.0 µg/day, 3.1 µg/day, 3.2 µg/day, 3.3 µg/day, 3.4 µg/day, 3.5 µg/day, 3.6 µg/day, 3.7 µg/day, 3.8 µg/day, 3.9 µg/day, 4.0 µg/day, 4.1 µg/day, 4.2 µg/day, 4.2 µg/day, 4.3 µg/day, 4.4 µg/day, 4.5 µg/day, 4.6 µg/day, 4.7 µg/day, 4.8 µg/day, 4.9 µg/day, 5.0 µg/day, 5.1 µg/day, 5.2 µg/day, 5.3 µg/day, 5.4 µg/day, 5.5 µg/day, 5.6 µg/day, 5.7 µg/day, 5.8 µg/day, 5.9 µg/day, or 6.0 µg/day, for instance, by oral administration. In some embodiments, the ethinyl estradiol is administered to the patient at a dose of 5.0 µg/day, for instance, by oral administration. In some embodiments, the ethinyl estradiol is administered to the patient at a dose of 2.5 µg/day, for instance, by oral administration.

In some embodiments, the estrogen is a conjugated estrogen, such as a conjugated equine estrogen. The conjugated estrogen may be administered to the patient, for example, at a dose of from about 0.1 mg to about 2.0 mg, such as at a dose of about 0.1 mg, 0.2 mg, 0.3 mg, 0.4 mg, 0.5 mg, 0.6 mg, 0.7 mg, 0.8 mg, 0.9 mg, 1.0 mg, 1.1 mg, 1.2 mg, 1.3 mg, 1.4 mg, 1.5 mg, 1.6 mg, 1.7 mg, 1.8 mg, 1.9 mg, or 2.0 mg, for instance, by oral administration. In some embodiments, the conjugated estrogen is administered to the patient at a dose of 0.625 mg, for instance, by oral administration. In some embodiments, the conjugated estrogen is administered to the patient at a dose of 0.45 mg, for instance, by oral administration. In some embodiments, the conjugated estrogen is administered to the patient at a dose of 0.3 mg, for instance, by oral administration.

The conjugated estrogen may be administered to the patient one or more times per day, week, or month. The conjugated estrogen may be administered to the patient, for example, at a dose of from about 0.1 mg/day to about 2.0 mg/day, such as at a dose of about 0.1 mg/day, 0.2 mg/day, 0.3 mg/day, 0.4 mg/day, 0.5 mg/day, 0.6 mg/day, 0.7 mg/day, 0.8 mg/day, 0.9 mg/day, 1.0 mg/day, 1.1 mg/day, 1.2 mg/day, 1.3 mg/day, 1.4 mg/day, 1.5 mg/day, 1.6 mg/day, 1.7 mg/day, 1.8 mg/day, 1.9 mg/day, or 2.0 mg/day, for instance, by oral administration. In some embodiments, the conjugated estrogen is administered to the patient at a dose of 0.625 mg/day, for instance, by oral administration. In some embodiments, the conjugated estrogen is administered to the patient at a dose of 0.45 mg/day, for instance, by oral administration. In some embodiments, the conjugated estrogen is administered to the patient at a dose of 0.3 mg/day, for instance, by oral administration.

In some embodiments, the add-back therapy includes a progestin. In some embodiments, the progestin is selected from the group consisting of norethindrone or an ester thereof, such as norethindrone acetate, or another agent such as progesterone, norgestimate, medroxyprogesterone, or drospirenone.

In some embodiments, the progestin is norethindrone or a compound that is metabolized in vivo to produce norethindrone, such as an ester of norethindrone that is de-esterified in vivo to produce norethindrone, for instance, norethindrone acetate.

In some embodiments, the progestin is norethindrone. The norethindrone may be administered to the patient, for example, at a dose of from about 0.05 mg to about 5.0 mg, such as at a dose of about 0.05 mg, 0.06 mg, 0.07 mg, 0.08 mg, 0.09 mg, 0.1 mg, 0.2 mg, 0.3 mg, 0.4 mg, 0.5 mg, 0.6 mg, 0.7 mg, 0.8 mg, 0.9 mg, 1.0 mg, 1.1 mg, 1.2 mg, 1.3 mg, 1.4 mg, 1.5 mg, 1.6 mg, 1.7 mg, 1.8 mg, 1.9 mg, 2.0 mg, 2.1 mg, 2.2 mg, 2.3 mg, 2.4 mg, 2.5 mg, 2.6 mg, 2.7 mg, 2.8 mg, 2.9 mg, 3.0 mg, 3.1 mg, 3.2 mg, 3.3 mg, 3.4 mg, 3.5 mg, 3.6 mg, 3.7 mg, 3.8 mg, 3.9 mg, 4.0 mg, 4.1 mg, 4.2 mg, 4.3 mg, 4.4 mg, 4.5 mg, 4.6 mg, 4.7 mg, 4.8 mg, 4.9 mg, or 5.0 mg, for instance, by oral administration. In some embodiments, the norethindrone is administered to the patient at a dose of 1.0 mg, for instance, by oral administration. In some embodiments, the norethindrone is administered to the patient at a dose of 0.5 mg, for instance, by oral administration. In some embodiments, the norethindrone is administered to the patient at a dose of 0.1 mg, for instance, by oral administration.

The norethindrone may be administered to the patient one or more times per day, week, or month. The norethindrone may be administered to the patient, for example, at a dose of from about 0.05 mg/day to about 5.0 mg/day, such as at a dose of about 0.05 mg/day, 0.06 mg/day, 0.07 mg/day, 0.08 mg/day, 0.09 mg/day, 0.1 mg/day, 0.2 mg/day, 0.3 mg/day, 0.4 mg/day, 0.5 mg/day, 0.6 mg/day, 0.7 mg/day, 0.8 mg/day, 0.9 mg/day, 1.0 mg/day, 1.1 mg/day, 1.2 mg/day, 1.3 mg/day, 1.4 mg/day, 1.5 mg/day, 1.6 mg/day, 1.7 mg/day, 1.8 mg/day, 1.9 mg/day, 2.0 mg/day, 2.1 mg/day, 2.2 mg/day, 2.3 mg/day, 2.4 mg/day, 2.5 mg/day, 2.6 mg/day, 2.7 mg/day, 2.8 mg/day, 2.9 mg/day, 3.0 mg/day, 3.1 mg/day, 3.2 mg/day, 3.3 mg/day, 3.4 mg/day, 3.5 mg/day, 3.6 mg/day, 3.7 mg/day, 3.8 mg/day, 3.9 mg/day, 4.0 mg/day, 4.1 mg/day, 4.2 mg/day, 4.3 mg/day, 4.4 mg/day, 4.5 mg/day, 4.6 mg/day, 4.7 mg/day, 4.8 mg/day, 4.9 mg/day, or 5.0 mg/day, for instance, by oral administration. In some embodiments, the norethindrone is administered to the patient at a dose of 1.0 mg/day, for instance, by oral administration. In some embodiments, the norethindrone is administered to the patient at a dose of 0.5 mg/day, for instance, by oral administration. In some embodiments, the norethindrone is administered to the patient at a dose of 0.1 mg/day, for instance, by oral administration.

In some embodiments, the progestin is norethindrone acetate. The norethindrone acetate may be administered to the patient, for example, at a dose of from about 0.05 mg to about 5.0 mg, such as at a dose of about 0.05 mg, 0.06 mg, 0.07 mg, 0.08 mg, 0.09 mg, 0.1 mg, 0.2 mg, 0.3 mg, 0.4 mg, 0.5 mg, 0.6 mg, 0.7 mg, 0.8 mg, 0.9 mg, 1.0 mg, 1.1 mg, 1.2 mg, 1.3 mg, 1.4 mg, 1.5 mg, 1.6 mg, 1.7 mg, 1.8 mg, 1.9 mg, 2.0 mg, 2.1 mg, 2.2 mg, 2.3 mg, 2.4 mg, 2.5 mg, 2.6 mg, 2.7 mg, 2.8 mg, 2.9 mg, 3.0 mg, 3.1 mg, 3.2 mg, 3.3 mg, 3.4 mg, 3.5 mg, 3.6 mg, 3.7 mg, 3.8 mg, 3.9 mg, 4.0 mg, 4.1 mg, 4.2 mg, 4.3 mg, 4.4 mg, 4.5 mg, 4.6 mg, 4.7 mg, 4.8 mg, 4.9 mg, or 5.0 mg, for instance, by oral administration. In some embodiments, the norethindrone acetate is administered to the patient at a dose of 1.0 mg/day, for instance, by oral administration. In some embodiments, the norethindrone acetate is administered to the patient at a dose of 0.5 mg, for instance, by oral administration. In some embodiments, the norethindrone acetate is administered to the patient at a dose of 0.1 mg, for instance, by oral administration.

The norethindrone acetate may be administered to the patient one or more times per day, week, or month. The norethindrone acetate may be administered to the patient, for example, at a dose of from about 0.05 mg/day to about 5.0 mg/day, such as at a dose of about 0.05 mg/day, 0.06 mg/day, 0.07 mg/day, 0.08 mg/day, 0.09 mg/day, 0.1 mg/day, 0.2 mg/day, 0.3 mg/day, 0.4 mg/day, 0.5 mg/day, 0.6 mg/day, 0.7 mg/day, 0.8 mg/day, 0.9 mg/day, 1.0 mg/day, 1.1 mg/day, 1.2 mg/day, 1.3 mg/day, 1.4 mg/day, 1.5 mg/day, 1.6 mg/day, 1.7 mg/day, 1.8 mg/day, 1.9 mg/day, 2.0 mg/day, 2.1 mg/day, 2.2 mg/day, 2.3 mg/day, 2.4 mg/day, 2.5 mg/day, 2.6 mg/day, 2.7 mg/day, 2.8 mg/day, 2.9 mg/day, 3.0 mg/day, 3.1 mg/day, 3.2 mg/day, 3.3 mg/day, 3.4 mg/day, 3.5 mg/day, 3.6 mg/day, 3.7 mg/day, 3.8 mg/day, 3.9 mg/day, 4.0 mg/day, 4.1 mg/day, 4.2 mg/day, 4.3 mg/day, 4.4 mg/day, 4.5 mg/day, 4.6 mg/day, 4.7 mg/day, 4.8 mg/day, 4.9 mg/day, or 5.0 mg/day, for instance, by oral administration. In some embodiments, the norethindrone acetate is administered to the patient at a dose of 1.0 mg/day, for instance, by oral administration. In some embodiments, the norethindrone acetate is administered to the patient at a dose of 0.5 mg/day, for instance, by oral administration. In some embodiments, the norethindrone acetate is administered to the patient at a dose of 0.1 mg/day, for instance, by oral administration.

In some embodiments, the progestin is progesterone. The progesterone may be administered to the patient, for example, at a dose of from about 50 mg to about 250 mg, such as a dose of about 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, 200 mg, 205 mg, 210 mg, 215 mg, 220 mg, 225 mg, 230 mg, 235 mg, 240 mg, 245 mg, or 250 mg, for instance, by oral administration. In some embodiments, the progesterone is administered to the patient at a dose of 200 mg, for instance, by oral administration. In some embodiments, the progesterone is administered to the patient at a dose of 100 mg, for instance, by oral administration.

The progesterone may be administered to the patient one or more times per day, week, or month. The progesterone may be administered to the patient, for example, at a dose of from about 50 mg/day to about 250 mg/day, such as a dose of about 50 mg/day, 55 mg/day, 60 mg/day, 65 mg/day, 70 mg/day, 75 mg/day, 80 mg/day, 85 mg/day, 90 mg/day, 95 mg/day, 100 mg/day, 105 mg/day, 110 mg/day, 115 mg/day, 120 mg/day, 125 mg/day, 130 mg/day, 135 mg/day, 140 mg/day, 145 mg/day, 150 mg/day, 155 mg/day, 160 mg/day, 165 mg/day, 170 mg/day, 175 mg/day, 180 mg/day, 185 mg/day, 190 mg/day, 195 mg/day, 200 mg/day, 205 mg/day, 210 mg/day, 215 mg/day, 220 mg/day, 225 mg/day, 230 mg/day, 235 mg/day, 240 mg/day, 245 mg/day, or 250 mg/day, for instance, by oral administration. In some embodiments, the progesterone is administered to the patient at a dose of 200 mg/day, for instance, by oral administration. In some embodiments, the progesterone is administered to the patient at a dose of 100 mg/day, for instance, by oral administration.

In some embodiments, the progestin is norgestimate. The norgestimate may be administered to the patient, for example, at a dose of from about 0.01 mg to about 2.0 mg, such as at a dose of about 0.01 mg, 0.02 mg, 0.03 mg, 0.04 mg, 0.05 mg, 0.06 mg, 0.07 mg, 0.08 mg, 0.09 mg, 0.1 mg, 0.2 mg, 0.3 mg, 0.4 mg, 0.5 mg, 0.6 mg, 0.7 mg, 0.8 mg, 0.9 mg, 1.0 mg, 1.1 mg, 1.2 mg, 1.3 mg, 1.4 mg, 1.5 mg, 1.6 mg, 1.7 mg, 1.8 mg, 1.9 mg, or 2.0 mg, for instance, by oral administration. In some embodiments, the norgestimate is administered to the patient at a dose of 0.09 mg, for instance, by oral administration.

The norgestimate may be administered to the patient one or more times per day, week, or month. The norgestimate may be administered to the patient, for example, at a dose of from about 0.01 mg/day to about 2.0 mg/day, such as at a dose of about 0.01 mg/day, 0.02 mg/day, 0.03 mg/day, 0.04 mg/day, 0.05 mg/day, 0.06 mg/day, 0.07 mg/day, 0.08 mg/day, 0.09 mg/day, 0.1 mg/day, 0.2 mg/day, 0.3 mg/day, 0.4 mg/day, 0.5 mg/day, 0.6 mg/day, 0.7 mg/day, 0.8 mg/day, 0.9 mg/day, 1.0 mg/day, 1.1 mg/day, 1.2 mg/day, 1.3 mg/day, 1.4 mg/day, 1.5 mg/day, 1.6 mg/day, 1.7 mg/day, 1.8 mg/day, 1.9 mg/day, or 2.0 mg/day, for instance, by oral administration. In some embodiments, the norgestimate is administered to the patient at a dose of 0.09 mg/day, for instance, by oral administration.

In some embodiments, the progestin is medroxyprogesterone. The medroxyprogesterone may be administered to the patient, for example, at a dose of from about 0.5 mg to about 10.0 mg, such as at a dose of about 0.5 mg, 0.6 mg, 0.7 mg, 0.8 mg, 0.9 mg, 1.0 mg, 1.1 mg, 1.2 mg, 1.3 mg, 1.4 mg, 1.5 mg, 1.6 mg, 1.7 mg, 1.8 mg, 1.9 mg, 2.0 mg, 2.1 mg, 2.2 mg, 2.3 mg, 2.4 mg, 2.5 mg, 2.6 mg, 2.7 mg, 2.8 mg, 2.9 mg, 3.0 mg, 3.1 mg, 3.2 mg, 3.3 mg, 3.4 mg, 3.5 mg, 3.6 mg, 3.7 mg, 3.8 mg, 3.9 mg, 4.0 mg, 4.1 mg, 4.2 mg, 4.3 mg, 4.4 mg, 4.5 mg, 4.6 mg, 4.7 mg, 4.8 mg, 4.9 mg, 5.0 mg, 5.1 mg, 5.2 mg, 5.3 mg, 5.4 mg, 5.5 mg, 5.6 mg, 5.7 mg, 5.8 mg, 5.9 mg, 6.0 mg, 6.1 mg, 6.2 mg, 6.3 mg, 6.4 mg, 6.5 mg, 6.6 mg, 6.7 mg, 6.8 mg, 6.9 mg, 7.0 mg, 7.1 mg, 7.2 mg, 7.3 mg, 7.4 mg, 7.5 mg, 7.6 mg, 7.7 mg, 7.8 mg, 7.9 mg, 8.0 mg, 8.1 mg, 8.2 mg, 8.3 mg, 8.4 mg, 8.5 mg, 8.6 mg, 8.7 mg, 8.8 mg, 8.9 mg, 9.0 mg, 9.1 mg, 9.2 mg, 9.3 mg, 9.4 mg, 9.5 mg, 9.6 mg, 9.7 mg, 9.8 mg, 9.9 mg, or 10.0 mg, for instance, by oral administration. In some embodiments, the medroxyprogesterone is administered to the patient at a dose of 5.0 mg, for instance, by oral administration. In some embodiments, the medroxyprogesterone is administered to the patient at a dose of 2.5 mg, for instance, by oral administration. In some embodiments, the medroxyprogesterone is administered to the patient at a dose of 1.5 mg, for instance, by oral administration.

The medroxyprogesterone may be administered to the patient one or more times per day, week, or month. The medroxyprogesterone may be administered to the patient, for example, at a dose of from about 0.5 mg/day to about 10.0 mg/day, such as at a dose of about 0.5 mg/day, 0.6 mg/day, 0.7 mg/day, 0.8 mg/day, 0.9 mg/day, 1.0 mg/day, 1.1 mg/day, 1.2 mg/day, 1.3 mg/day, 1.4 mg/day, 1.5 mg/day, 1.6 mg/day, 1.7 mg/day, 1.8 mg/day, 1.9 mg/day, 2.0 mg/day, 2.1 mg/day, 2.2 mg/day, 2.3 mg/day, 2.4 mg/day, 2.5 mg/day, 2.6 mg/day, 2.7 mg/day, 2.8 mg/day, 2.9 mg/day, 3.0 mg/day, 3.1 mg/day, 3.2 mg/day, 3.3 mg/day, 3.4 mg/day, 3.5 mg/day, 3.6 mg/day, 3.7 mg/day, 3.8 mg/day, 3.9 mg/day, 4.0 mg/day, 4.1 mg/day, 4.2 mg/day, 4.3 mg/day, 4.4 mg/day, 4.5 mg/day, 4.6 mg/day, 4.7 mg/day, 4.8 mg/day, 4.9 mg/day, 5.0 mg/day, 5.1 mg/day, 5.2 mg/day, 5.3 mg/day, 5.4 mg/day, 5.5 mg/day, 5.6 mg/day, 5.7 mg/day, 5.8 mg/day, 5.9 mg/day, 6.0 mg/day, 6.1 mg/day, 6.2 mg/day, 6.3 mg/day, 6.4 mg/day, 6.5 mg/day, 6.6 mg/day, 6.7 mg/day, 6.8 mg/day, 6.9 mg/day, 7.0 mg/day, 7.1 mg/day, 7.2 mg/day, 7.3 mg/day, 7.4 mg/day, 7.5 mg/day, 7.6 mg/day, 7.7 mg/day, 7.8 mg/day, 7.9 mg/day, 8.0 mg/day, 8.1 mg/day, 8.2 mg/day, 8.3 mg/day, 8.4 mg/day, 8.5 mg/day, 8.6 mg/day, 8.7 mg/day, 8.8 mg/day, 8.9 mg/day, 9.0 mg/day, 9.1 mg/day, 9.2 mg/day, 9.3 mg/day, 9.4 mg/day, 9.5 mg/day, 9.6 mg/day, 9.7 mg/day, 9.8 mg/day, 9.9 mg/day, or 10.0 mg/day, for instance, by oral administration. In some embodiments, the medroxyprogesterone is administered to the patient at a dose of 5.0 mg/day, for instance, by oral administration. In some embodiments, the medroxyprogesterone is administered to the patient at a dose of 2.5 mg/day, for instance, by oral administration. In some embodiments, the medroxyprogesterone is administered to the patient at a dose of 1.5 mg/day, for instance, by oral administration.

In some embodiments, the progestin is drospirenone. The drospirenone may be administered to the patient, for example, at a dose of from about 0.1 mg to about 1.0 mg, such as at a dose of about 0.1 mg, 0.2 mg, 0.3 mg, 0.4 mg, 0.5 mg, 0.6 mg, 0.7 mg, 0.8 mg, 0.9 mg, or 1.0 mg, for instance, by oral administration. In some embodiments, the drospirenone is administered to the patient at a dose of 0.5 mg, for instance, by oral administration. In some embodiments, the drospirenone is administered to the patient at a dose of 0.25 mg, for instance, by oral administration.

The drospirenone may be administered to the patient one or more times per day, week, or month. The drospirenone may be administered to the patient, for example, at a dose of from about 0.1 mg/day to about 1.0 mg/day, such as at a dose of about 0.1 mg/day, 0.2 mg/day, 0.3 mg/day, 0.4 mg/day, 0.5 mg/day, 0.6 mg/day, 0.7 mg/day, 0.8 mg/day, 0.9 mg/day, or 1.0 mg/day, for instance, by oral administration. In some embodiments, the drospirenone is administered to the patient at a dose of 0.5 mg/day, for instance, by oral administration. In some embodiments, the drospirenone is administered to the patient at a dose of 0.25 mg/day, for instance, by oral administration.

In some embodiments, the add-back therapy includes an estrogen and a progestin. In some embodiments, the add-back therapy includes $\beta$17-estradiol and norethindrone or a compound that is metabolized in vivo to produce norethindrone, such as an ester of norethindrone that is de-esterified in vivo to produce norethindrone, for instance, norethindrone acetate.

In some embodiments, the add-back therapy includes from about 0.75 mg to about 1.25 mg of $\beta$17-estradiol, e.g., administered orally, and from about 0.25 mg to about 0.75 mg of norethindrone or a compound that is metabolized in vivo to produce norethindrone, such as an ester of norethindrone that is de-esterified in vivo to produce norethindrone, for instance, norethindrone acetate, e.g., administered orally. In some embodiments, the add-back therapy includes 1.0 mg of $\beta$17-estradiol, e.g., administered orally, and 0.5 mg of norethindrone or a compound that is metabolized in vivo to produce norethindrone, such as an ester of norethindrone that is de-esterified in vivo to produce norethindrone, for instance, norethindrone acetate, e.g., administered orally. In some embodiments, the add-back therapy includes 1.0 mg of $\beta$17-estradiol, e.g., administered orally, and, in the same pharmaceutical composition, 0.5 mg of norethindrone or a compound that is metabolized in vivo to produce norethindrone, such as an ester of norethindrone that is de-esterified in vivo to produce norethindrone, for instance, norethindrone acetate, e.g., administered orally. In some embodiments, the add-back therapy includes 1.0 mg of β17-estradiol, e.g., administered orally, and, in a separate pharmaceutical composition, 0.5 mg of norethindrone or a compound that is metabolized in vivo to produce norethindrone, such as an ester of norethindrone that is de-esterified in vivo to produce norethindrone, for instance, norethindrone acetate, e.g., administered orally.

In some embodiments, the compound is administered to the patient in a fixed-dose composition that contains about 200 mg of the compound (e.g., 200 mg of the compound), from about 0.75 mg to about 1.25 mg of β17-estradiol, and from about 0.25 mg to about 0.75 mg of norethindrone or a compound that is metabolized in vivo to produce norethindrone, such as an ester of norethindrone that is de-esterified in vivo to produce norethindrone, for instance, norethindrone acetate. In some embodiments, the compound is administered to the patient in a fixed-dose composition that contains about 200 mg of the compound (e.g., 200 mg of the compound), about 1.0 mg of β17-estradiol (e.g., 1.0 mg of β17-estradiol), and about 0.5 mg of norethindrone or a compound that is metabolized in vivo to produce norethindrone, such as an ester of norethindrone that is de-esterified in vivo to produce norethindrone, for instance, norethindrone acetate (e.g., 0.5 mg of norethindrone or a compound that is metabolized in vivo to produce norethindrone, such as an ester of norethindrone that is de-esterified in vivo to produce norethindrone, for instance, norethindrone acetate). In some embodiments, the compound is administered to the patient in a fixed-dose composition that contains 200 mg of the compound, 1.0 mg of β17-estradiol, and 0.5 mg of norethindrone acetate.

In some embodiments, the above fixed-dose composition is administered to the patient in one or more doses per 12 hours, 24 hours, 48 hours, 72 hours, week, month, or year, such as in from 1 to 10 doses per 12 hours (e.g., 1 dose every 12 hours, 2 doses every 12 hours, 3 doses every 12 hours, 4 doses every 12 hours, 5 doses every 12 hours, 6 doses every 12 hours, 7 doses every 12 hours, 8 doses every 12 hours, 9 doses every 12 hours, or 10 doses every 12 hours), from 1 to 10 doses per 24 hours (e.g., 1 dose every 24 hours, 2 doses every 24 hours, 3 doses every 24 hours, 4 doses every 24 hours, 5 doses every 24 hours, 6 doses every 24 hours, 7 doses every 24 hours, 8 doses every 24 hours, 9 doses every 24 hours, or 10 doses every 24 hours), from 1 to 10 doses per 48 hours (e.g., 1 dose every 48 hours, 2 doses every 48 hours, 3 doses every 48 hours, 4 doses every 48 hours, 5 doses every 48 hours, 6 doses every 48 hours, 7 doses every 48 hours, 8 doses every 48 hours, 9 doses every 48 hours, or 10 doses every 48 hours), from 1 to 10 doses per 72 hours (e.g., 1 dose every 72 hours, 2 doses every 72 hours, 3 doses every 72 hours, 4 doses every 72 hours, 5 doses every 72 hours, 6 doses every 72 hours, 7 doses every 72 hours, 8 doses every 72 hours, 9 doses every 72 hours, or 10 doses every 72 hours), from 1 to 10 doses per week (e.g., 1 dose every week, 2 doses every week, 3 doses every week, 4 doses every week, 5 doses every week, 6 doses every week, 7 doses every week, 8 doses every week, 9 doses every week, or 10 doses every week), or from 1 to 60 doses per month (e.g., from 30-60 doses per month, such as 1 time daily, 2 times daily, 3 times daily, 4 times daily, 5 times daily, 6 times daily, 7 times daily, 8 times daily, 9 times daily, 10 times daily, 7 times weekly, 8 times weekly, 9 times weekly, 10 times weekly, 11 times weekly, 12 times weekly, 13 times weekly, 14 times weekly, or more), among others. In some embodiments, the above fixed-dose composition is administered to the patient once daily.

In some embodiments, the add-back therapy includes from about 0.25 mg to about 0.75 mg of β17-estradiol, e.g., administered orally, and from about 0.05 mg to about 0.2 mg of norethindrone or a compound that is metabolized in vivo to produce norethindrone, such as an ester of norethindrone that is de-esterified in vivo to produce norethindrone, for instance, norethindrone acetate, e.g., administered orally. In some embodiments, the add-back therapy includes 0.5 mg of β17-estradiol, e.g., administered orally, and 0.1 mg of norethindrone or a compound that is metabolized in vivo to produce norethindrone, such as an ester of norethindrone that is de-esterified in vivo to produce norethindrone, for instance, norethindrone acetate, e.g., administered orally. In some embodiments, the add-back therapy includes 0.5 mg of β17-estradiol, e.g., administered orally, and, in the same pharmaceutical composition, 0.1 mg of norethindrone or a compound that is metabolized in vivo to produce norethindrone, such as an ester of norethindrone that is de-esterified in vivo to produce norethindrone, for instance, norethindrone acetate, e.g., administered orally. In some embodiments, the add-back therapy includes 0.5 mg of β17-estradiol, e.g., administered orally, and, in a separate pharmaceutical composition, 0.1 mg of norethindrone or a compound that is metabolized in vivo to produce norethindrone, such as an ester of norethindrone that is de-esterified in vivo to produce norethindrone, for instance, norethindrone acetate, e.g., administered orally.

In some embodiments, the compound is administered to the patient in a fixed-dose composition that contains about 200 mg of the compound (e.g., 200 mg of the compound), from about 0.25 mg to about 0.75 mg of β17-estradiol, and from about 0.05 mg to about 0.2 mg of norethindrone or a compound that is metabolized in vivo to produce norethindrone, such as an ester of norethindrone that is de-esterified in vivo to produce norethindrone, for instance, norethindrone acetate. In some embodiments, the compound is administered to the patient in a fixed-dose composition that contains about 200 mg of the compound (e.g., 200 mg of the compound), about 0.5 mg of β17-estradiol (e.g., 0.5 mg of β17-estradiol), and about 0.1 mg of norethindrone or a compound that is metabolized in vivo to produce norethindrone, such as an ester of norethindrone that is de-esterified in vivo to produce norethindrone, for instance, norethindrone acetate (e.g., 0.1 mg of norethindrone or a compound that is metabolized in vivo to produce norethindrone, such as an ester of norethindrone that is de-esterified in vivo to produce norethindrone, for instance, norethindrone acetate). In some embodiments, the compound is administered to the patient in a fixed-dose composition that contains 200 mg of the compound, 0.5 mg of β17-estradiol, and 0.1 mg of norethindrone acetate.

In some embodiments, the above fixed-dose composition is administered to the patient in one or more doses per 12 hours, 24 hours, 48 hours, 72 hours, week, month, or year, such as in from 1 to 10 doses per 12 hours (e.g., 1 dose every 12 hours, 2 doses every 12 hours, 3 doses every 12 hours, 4 doses every 12 hours, 5 doses every 12 hours, 6 doses every 12 hours, 7 doses every 12 hours, 8 doses every 12 hours, 9 doses every 12 hours, or 10 doses every 12 hours), from 1 to 10 doses per 24 hours (e.g., 1 dose every 24 hours, 2 doses every 24 hours, 3 doses every 24 hours, 4 doses every 24 hours, 5 doses every 24 hours, 6 doses every 24 hours, 7 doses every 24 hours, 8 doses every 24 hours, 9 doses every 24 hours, or 10 doses every 24 hours), from 1 to 10 doses per 48 hours (e.g., 1 dose every 48 hours, 2 doses every 48 hours, 3 doses every 48 hours, 4 doses every 48 hours, 5 doses every 48 hours, 6 doses every 48 hours, 7 doses every 48 hours, 8 doses every 48 hours, 9 doses every 48 hours, or 10 doses every 48 hours), from 1 to 10 doses per 72 hours (e.g., 1 dose every 72 hours, 2 doses every 72 hours, 3 doses every 72 hours, 4 doses every 72 hours, 5 doses every 72 hours, 6 doses every 72 hours, 7 doses every 72 hours, 8 doses every 72 hours, 9 doses every 72 hours, or 10 doses every 72 hours), from 1 to 10 doses per week (e.g., 1 dose every week, 2 doses every week, 3 doses every week, 4 doses every week, 5 doses every week, 6 doses every week, 7 doses every week, 8 doses every week, 9 doses every week, or 10 doses every week), from 1 to 60 doses per month (e.g., from 30-60 doses per month, such as 1 time daily, 2 times daily, 3 times daily, 4 times daily, 5 times daily, 6 times daily, 7 times daily, 8 times daily, 9 times daily, 10 times daily, 7 times weekly, 8 times weekly, 9 times weekly, 10 times weekly, 11 times weekly, 12 times weekly, 13 times weekly, 14 times weekly, or more), among others. In some embodiments, the fixed-dose composition is administered to the patient once daily.

In some embodiments, the patient exhibits a serum concentration of β17-estradiol that is greater than 20 pg/ml, greater than 30 pg/ml, greater than 40 pg/ml, or greater than 50 pg/ml prior to the administration of the compound to the patient. The serum concentration of β17-estradiol may be reduced to less than 50 pg/ml following administration of the compound to the patient. For instance, in some embodiments, the patient exhibits a serum concentration of β17-estradiol that is reduced to less than 50 pg/ml, less than 45 pg/ml, less than 40 pg/ml, less than 35 pg/ml, less than 30 pg/ml, less than 25 pg/ml, less than 20 pg/ml, less than 15 pg/ml, or less than 10 pg/ml following administration of the compound to the patient. In some embodiments, the patient exhibits a serum concentration of β17-estradiol that is reduced to less than 10 pg/ml to about 40 pg/ml, such as a serum concentration of β17-estradiol of 5 pg/ml, 10 pg/ml, 15 pg/ml, 20 pg/ml, 25 pg/ml, 30 pg/ml, 35 pg/ml, or 40 pg/ml. In some embodiments, the patient exhibits a serum concentration of β17-estradiol of from 5 pg/ml to 50 pg/ml following administration of the compound to the patient (e.g., a serum concentration of β17-estradiol of 5 pg/ml, 6 pg/ml, 7 pg/ml, 8 pg/ml, 9 pg/ml, 10 pg/ml, 11 pg/ml, 12 pg/ml, 13 pg/ml, 14 pg/ml, 15 pg/ml, 16 pg/ml, 17 pg/ml, 18 pg/ml, 19 pg/ml, 20 pg/ml, 21 pg/ml, 22 pg/ml, 23 pg/ml, 24 pg/ml, 25 pg/ml, 26 pg/ml, 27 pg/ml, 28 pg/ml, 29 pg/ml, 30 pg/ml, 31 pg/ml, 32 pg/ml, 33 pg/ml, 34 pg/ml, 35 pg/ml, 36 pg/ml, 37 pg/ml, 38 pg/ml, 39 pg/ml, 40 pg/ml, 41 pg/ml, 42 pg/ml, 43 pg/ml, 44 pg/ml, 45 pg/ml, 46 pg/ml, 47 pg/ml, 48 pg/ml, 49 pg/ml, or 50 pg/ml). In some embodiments, the patient exhibits a serum concentration of β17-estradiol of from 5 pg/ml to 20 pg/ml following administration of the compound to the patient (e.g., a serum concentration of β17-estradiol of 5 pg/ml, 6 pg/ml, 7 pg/ml, 8 pg/ml, 9 pg/ml, 10 pg/ml, 11 pg/ml, 12 pg/ml, 13 pg/ml, 14 pg/ml, 15 pg/ml, 16 pg/ml, 17 pg/ml, 18 pg/ml, 19 pg/ml, or 20 pg/ml). In some embodiments, the patient exhibits a serum concentration of β17-estradiol of from 5 pg/ml to 10 pg/ml following administration of the compound to the patient (e.g., a serum concentration of β17-estradiol of 5 pg/ml, 6 pg/ml, 7 pg/ml, 8 pg/ml, 9 pg/ml, or 10 pg/ml).

In some embodiments, the patient exhibits a serum concentration of β17-estradiol of less than 50 pg/ml, or within one of the ranges specified above, within about 1 to about 22 days of the first administration of the compound to the patient, such as within about 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, or 22 days, for example within about 8 days to about 15 days, of the first administration of the compound to the patient.

In some embodiments, the patient exhibits a serum concentration of β17-estradiol of less than 20 pg/ml, or within one of the ranges specified above, within about 1 to about 22 days of the first administration of the compound to the patient, such as within about 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, or 22 days, for example, within about 8 days to about 15 days, of the first administration of the compound to the patient.

In some embodiments, the patient exhibits a serum concentration of β17-estradiol of less than 10 pg/ml, or within one of the ranges specified above, within about 1 to about 22 days of the first administration of the compound to the patient, such as within about 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, or 22 days, for example, within about 8 days to about 15 days, of the first administration of the compound to the patient.

In some embodiments of any of the above-described aspects or embodiments of the invention, the GnRH antagonist, such as the compound represented by formula (I), (II), or a pharmaceutically acceptable salt thereof, such as the choline salt thereof, (e.g., and add-back therapy) is administered to the patient daily (e.g., once daily and/or in any of the above-specified doses per day) for one or more treatment cycles. In some embodiments, the GnRH antagonist (e.g., and add-back therapy) is administered to the patient daily (e.g., once daily and/or in any of the above-specified doses per day) for one or more treatment cycles, each lasting for a period of about 4-72 weeks, or longer. For instance, the GnRH antagonist (e.g., and add-back therapy) may be administered to the patient daily (e.g., once daily and/or in any of the above-specified doses per day) for one or more treatment cycles, each lasting about 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, 36 weeks, 37 weeks, 38 weeks, 39 weeks, 40 weeks, 41 weeks, 42 weeks, 43 weeks, 44 weeks, 45 weeks, 46 weeks, 47 weeks, 48 weeks, 49 weeks, 50 weeks, 51 weeks, 52 weeks, 53 weeks, 54 weeks, 55 weeks, 56 weeks, 57 weeks, 58 weeks, 59 weeks, 60 weeks, 61 weeks, 62 weeks, 63 weeks, 64 weeks, 65 weeks, 66 weeks, 67 weeks, 68 weeks, 69 weeks, 70 weeks, 71 weeks, 72 weeks, or more.

In some embodiments, the GnRH antagonist (e.g., and add-back therapy) is administered to the patient for one or more treatment cycles, each lasting for a period of about 4-64 weeks. For instance, the GnRH antagonist (e.g., and add-back therapy) may be administered to the patient daily (e.g., once daily and/or in any of the above-specified doses per day) for one or more treatment cycles, each lasting about 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, 36 weeks, 37 weeks, 38 weeks, 39 weeks, 40 weeks, 41 weeks, 42 weeks, 43 weeks, 44 weeks, 45 weeks, 46 weeks, 47 weeks, 48 weeks, 49 weeks, 50 weeks, 51 weeks, 52 weeks, 53 weeks, 54 weeks, 55 weeks, 56 weeks, 57 weeks, 58 weeks, 59 weeks, 60 weeks, 61 weeks, 62 weeks, 63 weeks, or 64 weeks.

In some embodiments, the GnRH antagonist (e.g., and add-back therapy) is administered to the patient for one or more treatment cycles, each lasting for a period of about 4-52 weeks. For instance, the GnRH antagonist (e.g., and add-back therapy) may be administered to the patient daily (e.g., once daily and/or in any of the above-specified doses per day) for one or more treatment cycles, each lasting about 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, 36 weeks, 37 weeks, 38 weeks, 39 weeks, 40 weeks, 41 weeks, 42 weeks, 43 weeks, 44 weeks, 45 weeks, 46 weeks, 47 weeks, 48 weeks, 49 weeks, 50 weeks, 51 weeks, or 52 weeks.

In some embodiments, the GnRH antagonist (e.g., and add-back therapy) is administered to the patient for one or more treatment cycles, each lasting for a period of about 4-48 weeks. For instance, the GnRH antagonist (e.g., and add-back therapy) may be administered to the patient daily (e.g., once daily and/or in any of the above-specified doses per day) for one or more treatment cycles, each lasting about 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, 36 weeks, 37 weeks, 38 weeks, 39 weeks, 40 weeks, 41 weeks, 42 weeks, 43 weeks, 44 weeks, 45 weeks, 46 weeks, 47 weeks, or 48 weeks.

In some embodiments, the GnRH antagonist (e.g., and add-back therapy) is administered to the patient for one or more treatment cycles, each lasting for a period of about 4-24 weeks. For instance, the GnRH antagonist (e.g., and add-back therapy) may be administered to the patient daily (e.g., once daily and/or in any of the above-specified doses per day) for one or more treatment cycles, each lasting about 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, or 24 weeks.

In some embodiments, the GnRH antagonist (e.g., and add-back therapy) is administered to the patient for one or more treatment cycles, each lasting for a period of about 4-12 weeks. For instance, the GnRH antagonist (e.g., and add-back therapy) may be administered to the patient daily (e.g., once daily and/or in any of the above-specified doses per day) for one or more treatment cycles, each lasting about 4 weeks, 5 weeks, 6 weeks, 7 weeks, 8 weeks, 9 weeks, 10 weeks, 11 weeks, or 12 weeks.

In some embodiments, the GnRH antagonist (e.g., and add-back therapy) is administered to the patient for one or more treatment cycles (e.g., daily, such as once daily and/or in any of the above-specified doses per day), each treatment cycle lasting for a period of about 4 weeks. In some embodiments, the GnRH antagonist (e.g., and add-back therapy) is administered to the patient for one or more treatment cycles (e.g., daily, such as once daily and/or in any of the above-specified doses per day), each treatment cycle lasting for a period of about 6 weeks. In some embodiments, the GnRH antagonist (e.g., and add-back therapy) is administered to the patient for one or more treatment cycles (e.g., daily, such as once daily and/or in any of the above-specified doses per day), each treatment cycle lasting for a period of about 8 weeks. In some embodiments, the GnRH antagonist (e.g., and add-back therapy) is administered to the patient for one or more treatment cycles (e.g., daily, such as once daily and/or in any of the above-specified doses per day), each treatment cycle lasting for a period of about 12 weeks. In some embodiments, the GnRH antagonist (e.g., and add-back therapy) is administered to the patient for one or more treatment cycles (e.g., daily, such as once daily and/or in any of the above-specified doses per day), each treatment cycle lasting for a period of about 24 weeks. In some embodiments, the GnRH antagonist (e.g., and add-back therapy) is administered to the patient for one or more treatment cycles (e.g., daily, such as once daily and/or in any of the above-specified doses per day), each treatment cycle lasting for a period of about 36 weeks. In some embodiments, the GnRH antagonist (e.g., and add-back therapy) is administered to the patient for one or more treatment cycles (e.g., daily, such as once daily and/or in any of the above-specified doses per day), each treatment cycle lasting for a period of about 48 weeks. In some embodiments, the GnRH antagonist (e.g., and add-back therapy) is administered to the patient for one or more treatment cycles (e.g., daily, such as once daily and/or in any of the above-specified doses per day), each treatment cycle lasting for a period of about 52 weeks. In some embodiments, the GnRH antagonist (e.g., and add-back therapy) is administered to the patient for one or more treatment cycles (e.g., daily, such as once daily and/or in any of the above-specified doses per day), each treatment cycle lasting for a period of about 64 weeks. In some embodiments, the GnRH antagonist (e.g., and add-back therapy) is administered to the patient for one or more treatment cycles (e.g., daily, such as once daily and/or in any of the above-specified doses per day), each treatment cycle lasting for a period of about 72 weeks.

In another aspect, the invention features a kit that contains the compound of any of the preceding aspects or embodiments of the invention. The kit may further contain a package insert. The package insert may instruct a user of the kit to perform the method of any one of the above aspects or embodiments of the invention.

Definitions

As used herein, the term "about" refers to a value that is within 10% above or below the value being described.

As used herein, the term "add-back therapy" refers to the administration of estrogen during a treatment regimen, such as treatment with a GnRH antagonist (e.g., on the basis of a patient's AMH or E2 level as described herein), so as to counteract the side effects of excessive suppression of estradiol. Such side effects may include, for example, a reduction in bone mineral density (BMD). A patient's BMD may be assessed by dual energy X-ray absorptiometry, for instance, in the spine or femur of the patient. Add-back therapy may be administered to a patient according to the methods described herein so as to mitigate a reduction in BMD caused by the administration of a GnRH antagonist. For instance, add-back therapy may be administered to a patient undergoing GnRH antagonist therapy such that the patient does not exhibit a reduction in BMD of greater than 5% (e.g., no greater than 5%, 4%, 3%, 2%, 1%, 0.9%, 0.8%, 0.7%, 0.6%, 0.5%, 0.4%, 0.3%, 0.2%, 0.1%, or less).

Add-back therapy may include estrogen in the form of E2, and may include one or more additional agents, such as a progestin (e.g., norethindrone or a compound that is metabolized in vivo to produce norethindrone, such as an ester of norethindrone that is de-esterified in vivo to produce norethindrone, for instance, norethindrone acetate). Add-back therapy may be formulated for oral administration, such as in the form of a tablet, capsule, gel cap, powder, liquid solution, or liquid suspension. Add-back therapy may feature a co-formulation containing estrogen (e.g., in the form of E2) and an additional agent such as a progestin (e.g., norethindrone or a compound that is metabolized in vivo to produce norethindrone, such as an ester of norethindrone that is de-esterified in vivo to produce norethindrone, for instance, norethindrone acetate). For instance, add-back therapy may be administered to a patient in the form of a single tablet, capsule, gel cap, powder, liquid solution, or liquid suspension that contains both estrogen (e.g., in the form of E2) and a progestin (e.g., norethindrone or a compound that is metabolized in vivo to produce norethindrone, such as an ester of norethindrone that is de-esterified in vivo to produce norethindrone, for instance, norethindrone acetate). In some embodiments, add-back therapy is administered as a fixed dose combination containing a GnRH antagonist, estrogen, and one or more additional agents, such as a progestin, in a single pharmaceutical composition. For instance, add-back therapy may be administered as a fixed dose combination of a GnRH antagonist, estrogen (e.g., in the form of E2) and a progestin (e.g., norethindrone or a compound that is metabolized in vivo to produce norethindrone, such as an ester of norethindrone that is de-esterified in vivo to produce norethindrone, for instance, norethindrone acetate) in the form of a single pharmaceutical composition, such as a single tablet, capsule, gel cap, powder, liquid solution, or liquid suspension.

As used herein, the term "affinity" refers to the strength of a binding interaction between two molecules, such as a ligand and a receptor. The term "K", as used herein, is intended to refer to the inhibition constant of an antagonist for a particular molecule of interest, and can be expressed as a molar concentration (M). K values for antagonist-target interactions can be determined, e.g., using methods established in the art. Methods that can be used to determine the $K_i$ of an antagonist for a molecular target include competitive binding experiments, e.g., as described in U.S. Pat. No. 9,040,693. The term "$K_d$", as used herein, is intended to refer to the dissociation constant, which can be obtained, e.g., from the ratio of the rate constant for the dissociation of the two molecules ($k_d$) to the rate constant for the association of the two molecules ($k_a$) and is expressed as a molar concentration (M). $K_d$ values for receptor-ligand interactions can be determined, e.g., using methods established in the art. Methods that can be used to determine the $K_d$ of a receptor-ligand interaction include surface plasmon resonance, e.g., through the use of a biosensor system such as a BIACORE® system.

As used herein, the term "anti-Müllerian hormone reference range" or "AMH reference range" refers to a range of concentrations of AMH present within a mammalian subject (e.g., a human subject) or within a sample isolated there from that indicates that the subject is fertile or exhibits an ovarian reserve capable of supporting pregnancy. In some embodiments of the invention, the AMH reference range is from 15 to 35 pM (e.g., from 15 to 25 pM, from 20 to 30 pM, or from 25 to 35 pM, such as from 16 to 34 pM, from 17 to 33 pM, from 18 to 32 pM, from 19 to 31 pM, from 20-30 pM, from 21 to 29 pM, from 22 to 28 pM, from 23 to 27 pM, or from 24 to 26 pM).

As used herein, the term "β17-estradiol reference range" or "E2 reference range" refers to a range of concentrations of E2 present within a mammalian subject (e.g., a human subject) that has previously undergone treatment for endometriosis, e.g., with a GnRH antagonist, or within a sample isolated there from. An E2 reference range may be from, e.g., 20 to 50 pg/ml (e.g., from 20 to 40 pg/ml, from 30 to 50 pg/ml, or from 25 to 45 pg/ml, such as from 21 to 49 pg/ml, from 22 to 48 pg/ml, from 23 to 47 pg/ml, from 24 to 46 pg/ml, from 25 to 45 pg/ml, from 26 to 44 pg/ml, from 27 to 43 pg/ml, from 28 to 42 pg/ml, from 29 to 41 pg/ml, from 30 to 40 pg/ml, from 31 to 39 pm/ml, from 32 to 38 pg/ml, from 33 to 37 pg/ml, or from 34 to 36 pg/ml).

As used herein, the term "Biberoglu and Behrman scale" or "B&B scale" refers to a multi-point scale that can be used to indicate the severity of one or more symptoms experienced by patient suffering from endometriosis. A B&B score can be assessed by verbally prompting the patient to indicate the degree of function or quality of life being experienced. A B&B score can be used, e.g., to assess the severity of such symptoms as dysmenorrhea, dyspareunia, chronic pelvic pain, pelvic tenderness, and induration, among others. Methods of determining a B&B score are described in detail, e.g., in Vincent et al., Fertility and Sterility 93:62-67 (2010).

As used herein, the term "crystalline" or "crystalline form" means having a physical state that is a regular three-dimensional array of atoms, ions, molecules or molecular assemblies. Crystalline forms have lattice arrays of building blocks called asymmetric units that are arranged according to well-defined symmetries into unit cells that are repeated in three-dimensions. In contrast, the term "amorphous" or "amorphous form" refers to an unorganized (no orderly) structure. The physical state of a therapeutic compound may be determined by exemplary techniques such as x-ray diffraction, polarized light microscopy and/or differential scanning calorimetry.

As used herein, the term "dual energy X-ray absorptiometry" (DEXA) refers to a spectroscopic method of measuring bone mineral density in a patient (e.g., a human patient) in which X-ray radiation of two distinct frequencies are transmitted towards a target bone of the patient. The absorption of the transmitted radiation can subsequently be correlated with a measure of the bone mineral density within the target bone. Methods of determining bone mineral density using DEXA are described in detail, e.g., in Mazess et al., American Journal of Clinical Nutrition 51:1106-1112 (1990).

As used herein, the term "endogenous" describes a molecule (e.g., a polypeptide, nucleic acid, or cofactor) that is found naturally in a particular organism (e.g., a human) or in a particular location within an organism (e.g., an organ, a tissue, or a cell, such as a human cell).

As used herein, the term "Endometriosis Health Profile-5" or "EHP-5" refers to a questionnaire that can be used to evaluate quality of life in patient suffering from endometriosis. A score obtained from this questionnaire (i.e., an "EFP-5 score") may provide an indication of the patient's degree of pain, feeling of control and powerlessness, emotional well-being, social support, and/or self-image. The EHP-5 questionnaire and scores obtained there from are described in detail, e.g., in Renouvel et al., Journal de Gynécologie Obstétrique et Biologie de la Reproduction 38:404-410 (2009).

As used herein, the term "exogenous" describes a molecule (e.g., a polypeptide, nucleic acid, or cofactor) that is not found naturally in a particular organism (e.g., a human) or in a particular location within an organism (e.g., an organ, a tissue, or a cell, such as a human cell). Exogenous materials include those that are provided from an external source to an organism or to cultured matter extracted there from.

As used herein, the term "gonadotropin-releasing hormone antagonist" or "GnRH antagonist" refers to a compound capable of inhibiting the gonadotropin-releasing hormone receptor, e.g., such that release of one or more gonadotropins (such as follicle stimulating hormone and luteinizing hormone) is inhibited. GnRH antagonists for use with the compositions and methods of the invention include thieno[3,4d]pyrimidine derivatives and variants, such as those described in U.S. Pat. No. 9,040,693, the disclosure of which is incorporated herein by reference in its entirety. For instance, GnRH antagonists include 3-[2-fluoro-5-(2,3-difluoro-6-methoxybenzyloxy)4-methoxyphenyl]-2,4-dioxo-1, 2,3,4-tetrahydrothieno[3,4d]pyrimidine-5-carboxylic acid or the choline salt thereof, e.g., as described in U.S. Pat. No. 9,169,266, the disclosure of which is incorporated herein by reference in its entirety. Additional examples of GnRH antagonists include 2-phenylethylpyrimidine-2,4(1H,3H-dione derivatives and variants, such as those described in U.S. Pat. Nos. 7,056,927; 7,176,211; and 7,419,983; the disclosures of each of which are incorporated herein by reference in their entirety. Exemplary GnRH antagonists include elagolix, relugolix, ASP-1707, SK12670, and BAY-784, among others, such as those described herein.

As used herein, the term "$IC_{50}$" refers to the concentration of a substance (antagonist) that reduces the efficacy of a reference agonist or the constitutive activity of a biological target by 50%, e.g., as measured in a competitive ligand binding assay. Exemplary competitive ligand binding assays include competitive radioligand binding assays, competitive enzyme-linked immunosorbant assays (ELISA), and fluorescence anisotropy-based assays, among others known in the art.

As used herein, the term "Numerical Rating Score" (NRS) refers to a score within an 11-point numerical scale of 0-10 that indicates the degree of pain experienced by a patient. For instance, a score of 0 may indicate the patient is experiencing no pain, while scores from 1-3 may indicate that the patient is experiencing mild pain. A score of from 4-6 may indicate that the patient is experiencing moderate pain, and a score of from 7-10 may indicate that the patient is experiencing severe pain. Typically, to determine a NRS score, the patient is asked to indicate the level of pain currently being experienced, as well as the pain experienced at its most intense and least intense occurrences. Methods for determining a NRS are described in detail, e.g., in McCaffery et al., Pain: Clinical Manual for Nursing Practice. Baltimore (1993).

As used herein, the term "pharmaceutical composition" means a mixture containing a therapeutic compound to be administered to a subject, such as a mammal, e.g., a human, in order to prevent, treat or control a particular disease or condition affecting the mammal, such as endometriosis.

As used herein, the term "pharmaceutically acceptable" refers to those compounds, materials, compositions and/or dosage forms, which are suitable for contact with the tissues of a subject, such as a mammal (e.g., a human) without excessive toxicity, irritation, allergic response and other problem complications commensurate with a reasonable benefit/risk ratio.

As used herein, the term "sample" refers to a specimen (e.g., blood, blood component (e.g., serum or plasma), urine, saliva, amniotic fluid, cerebrospinal fluid, tissue (e.g., placental or dermal), pancreatic fluid, chorionic villus sample, and cells) isolated from a subject.

As used herein, the phrases "specifically binds" and "binds" refer to a binding reaction which is determinative of the presence of a particular protein in a heterogeneous population of proteins and other biological molecules that is recognized, e.g., by a ligand with particularity. A ligand (e.g., a protein, proteoglycan, or glycosaminoglycan) that specifically binds to a protein will bind to the protein, e.g., with a $K_D$ of less than 100 nM. For example, a ligand that specifically binds to a protein may bind to the protein with a $K_D$ of up to 100 nM (e.g., between 1 pM and 100 nM). A ligand that does not exhibit specific binding to a protein or a domain thereof may exhibit a $K_D$ of greater than 100 nM (e.g., greater than 200 nM, 300 nM, 400 nM, 500 nM, 600 nm, 700 nM, 800 nM, 900 nM, 1 µM, 100 µM, 500 µM, or 1 mM) for that particular protein or domain thereof. A variety of assay formats may be used to determine the affinity of a ligand for a specific protein. For example, solid-phase ELISA assays are routinely used to identify ligands that specifically bind a target protein. See, e.g., Harlow & Lane, Antibodies, A Laboratory Manual, Cold Spring Harbor Press, New York (1988) and Harlow & Lane, Using Antibodies, A Laboratory Manual, Cold Spring Harbor Press, New York (1999), for a description of assay formats and conditions that can be used to determine specific protein binding.

As used herein, the terms "subject" and "patient" are interchangeable and refer to an organism that receives treatment for a particular disease or condition as described herein (such as endometriosis) or that is diagnosed as having a disease or condition according to the methods described herein. Examples of subjects and patients include mammals, such as humans, receiving treatment for diseases or conditions, for example, endometriosis.

As used herein, the terms "treat" or "treatment" refer to therapeutic treatment, in which the object is to prevent or slow down (lessen) an undesired physiological change or disorder, such as the progression of endometriosis. Beneficial or desired clinical results include, but are not limited to, alleviation of symptoms, such as endometriosis-associated pain. Those in need of treatment include, e.g., female subjects already diagnosed as having endometriosis, as well as those prone to developing this condition. Indications of successful treatment of endometriosis include a finding that the patient exhibits a reduction in serum β17-estradiol concentration, for instance, of from an initial value that is greater than 50 pg/ml to a final value of from about 20 pg/ml to about 50 pg/ml (e.g., a final value of about 20 pg/ml, 25 pg/ml, 30 pg/ml, 35 pg/ml, 40 pg/ml, 45 pg/ml, or 50 pg/ml) or less, such as a value of from about 5 pg/ml to about 15 pg/ml (e.g., a final value of about 5 pg/ml, 6 pg/ml, 7 pg/ml, 8 pg/ml, 9 pg/ml, 10 pg/ml, 11 pg/ml, 12 pg/ml, 13 pg/ml, 14 pg/ml, or 15 pg/ml). Additional indicators of successful treatment of endometriosis include an observation that a patient experiences reduced levels of pain following treatment, for instance, with a GnRH antagonist described herein. Reduced pain may be detected using any one or more of the pain scales described herein or known in the art or known in the art.

As used herein, the term "Verbal Rating Score" (VRS) refers to a subjective multi-point scale used to indicate the level of pain being experienced by a patient undergoing therapy or that has previously undergone therapy for a disease or condition, such as endometriosis. The VRS may be a five-point scale and can be assessed by prompting the patient with one or more questions in order to determine the level of pain currently being experienced by the patient. Methods for assessing a VRS are described in detail, e.g., in Jensen et al., Journal of Pain and Symptom Management 41:1073-1093 (2011).

As used herein in the context of achieving a therapeutic effect within a certain time period of administering treatment to a subject, such as the administration of a GnRH antagonist to a subject having endometriosis, phrases such as "within about 4 weeks of said administering," "within about 8 weeks of said administering," "within about 12 weeks of said administering," "within about 24 weeks of said administering," "within about 36 weeks of said administering," and the like refer to the achievement of a therapeutic phenotype within about the indicated time period as measured from the date of the initial administration of the particular GnRH antagonist to the subject. Exemplary therapeutic phenotypes that may be achieved by administration of a GnRH antagonist to a subject suffering from endometriosis include reduced E2, LH, and/or FSH concentrations in the blood of the subject, as well as reduced endometriosis-associated pain. For instance, a subject is considered to exhibit a reduced E2, LH, or FSH level "within about 4 to about 36 weeks" of administering a GnRH antagonist to the subject according to a daily dosing schedule (e.g., 5 mg/day, 10 mg/day, 20 mg/day, 30 mg/day, 40 mg/day, 50 mg/day, 60 mg/day, 70 mg/day, 80 mg/day, 90 mg/day, 100 mg/day, 200 mg/day, 300 mg/day, 400 mg/day, or more, as described for various GnRH antagonists herein) if the subject presents with a diminished E2, LH, or FSH concentration, respectively (e.g., as assessed in a sample isolated from the subject), within about 4 weeks to about 36 weeks from the date of the first instance of administration of the GnRH antagonist to the subject. A subject may be administered, for example, a GnRH antagonist represented by formula (I), (II), or (III) described herein at a dosing schedule of, e.g., 50 mg/day, 75 mg/day, or 100 mg/day. The subject is considered to present with a therapeutic phenotype of interest, such as a reduced E2 level (e.g., an E2 level of from 20 pg/ml to 50 pg/ml) within about 4 weeks to about 36 weeks of administering the GnRH antagonist to the subject if the subject presents with the therapeutic phenotype of interest within about 4 weeks to about 36 weeks from the date of the first instance of administration of the GnRH antagonist represented by formula (I), (II), or (III) to the subject.

As used herein, the term "aryl" refers to an unsaturated aromatic carbocyclic group of from 6 to 14 carbon atoms having a single ring (e.g., optionally substituted phenyl) or multiple condensed rings (e.g., optionally substituted naphthyl). Exemplary aryl groups include phenyl, naphthyl, phenanthrenyl, and the like.

As used herein, the term "cycloalkyl" refers to a monocyclic cycloalkyl group having from 3 to 8 carbon atoms, such as cyclopropyl, cyclobutyl, cyclopentyl, cyclohexyl, cycloheptyl, cyclooctyl, and the like.

As used herein, the term "halogen atom" refers to a fluorine atom, a chlorine atom, a bromine atom, or an iodine atom.

As used herein, the term "heteroaryl" refers to a monocyclic heteroaromatic, or a bicyclic or a tricyclic fused-ring heteroaromatic group. Exemplary heteroaryl groups include optionally substituted pyridyl, pyrrolyl, furyl, thienyl, imidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, 1,3,4-triazinyl, 1,2,3-triazinyl, benzofuryl, [2,3-dihydro]benzofuryl, isobenzofuryl, benzothienyl, benzotriazolyl, isobenzothienyl, indolyl, isoindolyl, 3H-indolyl, benzimidazolyl, imidazo[1,2-a]pyridyl, benzothiazolyl, benzoxazolyl, quinolizinyl, quinazolinyl, pthalazinyl, quinoxalinyl, cinnolinyl, napthyridinyl, pyrido[3,4-b]pyridyl, pyrido[3,2-b]pyridyl, pyrido[4,3-b]pyridyl, quinolyl, isoquinolyl, tetrazolyl, 5,6,7,8-tetrahydroquinolyl, 5,6,7,8-tetrahydroisoquinolyl, purinyl, pteridinyl, carbazolyl, xanthenyl, benzoquinolyl, and the like.

As used herein, the term "heterocycloalkyl" refers to a 3 to 8-membered heterocycloalkyl group having 1 or more heteroatoms, such as a nitrogen atom, an oxygen atom, a sulfur atom, and the like, and optionally having 1 or 2 oxo groups such as pyrrolidinyl, piperidinyl, oxopiperidinyl, morpholinyl, piperazinyl, oxopiperazinyl, thiomorpholinyl, azepanyl, diazepanyl, oxazepanyl, thiazepanyl, dioxothiazepanyl, azokanyl, tetrahydrofuranyl, tetrahydropyranyl, and the like.

As used herein, the terms "lower alkyl" and "$C_{1-6}$ alkyl" refer to an optionally branched alkyl moiety having from 1 to 6 carbon atoms, such as methyl, ethyl, propyl, isopropyl, butyl, isobutyl, sec-butyl, tert-butyl, pentyl, isopentyl, neopentyl, tert-pentyl, hexyl, and the like.

As used herein, the term "lower alkylene" refers to an optionally branched alkylene group having from 1 to 6 carbon atoms, such as methylene, ethylene, methylmethylene, trimethylene, dimethylmethylene, ethylmethylene, methylethylene, propylmethylene, isopropylmethylene, dimethylethylene, butylmethylene, ethylmethylmethylene, pentamethylene, diethylmethylene, dimethyltrimethylene, hexamethylene, diethylethylene and the like.

As used herein, the term "lower alkenyl" refers to an optionally branched alkenyl moiety having from 2 to 6 carbon atoms, such as vinyl, allyl, 1-propenyl, isopropenyl, 1-butenyl, 2-butenyl, 2-methylallyl, and the like.

As used herein, the term "lower alkynyl" refers to an optionally branched alkynyl moiety having from 2 to 6 carbon atoms, such as ethynyl, 2-propynyl, and the like.

As used herein, the term "optionally fused" refers to a cyclic chemical group that may be fused with a ring system, such as cycloalkyl, heterocycloalkyl, aryl, or heteroaryl. Exemplary ring systems that may be fused to an optionally fused chemical group include, e.g., indolyl, isoindolyl, benzofuranyl, isobenzofuranyl, benzothiophenyl, benzoxazolyl, benzothiazolyl, benzoisoxazolyl, benzoisothiazolyl, indazolyl, benzimidazolyl, quinolinyl, isoquinolinyl, phthalazinyl, quinoxalinyl, quinazolinyl, cinnolinyl, indolizinyl, naphthyridinyl, pteridinyl, indanyl, naphtyl, 1,2,3,4-tetrahydronaphthyl, indolinyl, isoindolinyl, 2,3,4,5-tetrahydrobenzo[b]oxepinyl, 6,7,8,9-tetrahydro-5H-benzocycloheptenyl, chromanyl, and the like.

As used herein, the term "optionally substituted" refers to a chemical moiety that may have one or more (e.g., 1, 2, 3, 4, 5, 6, 7, 8, 9, 10, or more chemical substituents, such as lower alkyl, lower alkenyl, lower alkynyl, cycloalkyl, heterocyclolalkyl, aryl, alkylaryl, heteroaryl, alkylheteroaryl, amino, ammonium, acyl, acyloxy, acylamino, aminocarbonyl, alkoxycarbonyl, ureido, carbamate, sulfinyl, sulfonyl, alkoxy, sulfanyl, halogen, carboxy, trihalomethyl, cyano, hydroxy, mercapto, nitro, and the like. An optionally substituted chemical moiety may contain, e.g., neighboring substituents that have undergone ring closure, such as ring closure of vicinal functional substituents, thus forming, e.g., lactams, lactones, cyclic anhydrides, acetals, thioacetals, or aminals formed by ring closure, for instance, in order to generate protecting group.

As used herein, the term "sulfinyl" refers to the chemical moiety "—S(O)—R" in which R represents, e.g., hydrogen, aryl, heteroaryl, optionally substituted alkyl, optionally substituted alkenyl, or optionally substituted alkynyl.

As used herein, the term "sulfonyl" refers to the chemical moiety "—$SO_2$—R" in which R represents, e.g., hydrogen, aryl, heteroaryl, optionally substituted alkyl, optionally substituted alkenyl, or optionally substituted alkynyl.

DETAILED DESCRIPTION

Figure 1:
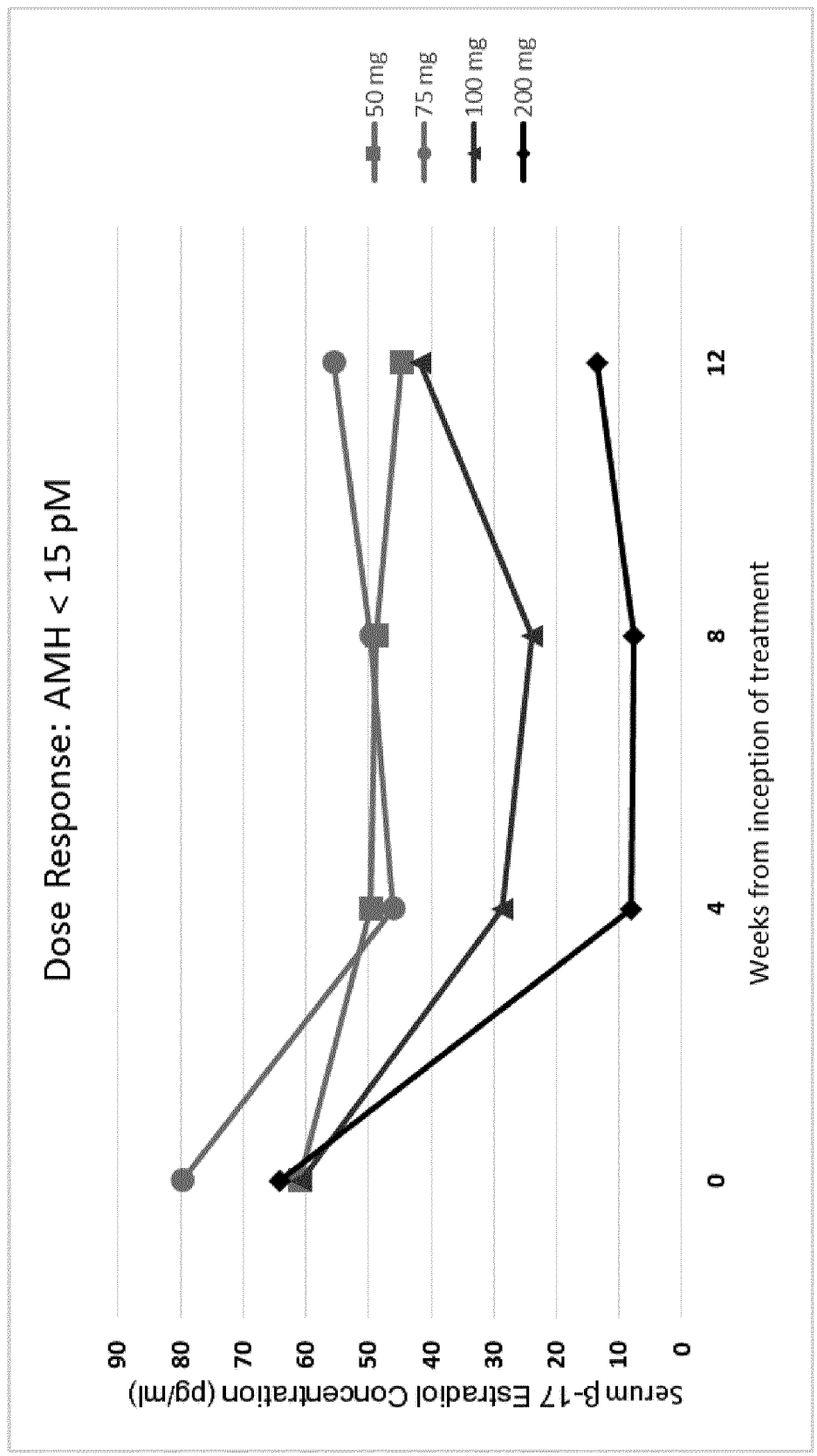
FIG. 1 is a graph showing the dose-dependent suppression of serum β17-estradiol (E2) in a series of human female patients suffering from endometriosis achieved by various daily doses of the GnRH antagonist represented by formula (III), herein (choline 3-[2-fluoro-5-(2,3-difluoro-6-methoxybenzyloxy)4-methoxyphenyl]-2,4-dioxo-1,2,3,4-tetrahydrothieno[3,4d]pyrimidine-5-carboxylate). The patients assessed in this group exhibited an initial serum concentration of anti-Müllerian hormone (AMH) of less than 15 pM. Values along the x-axis denote time, in weeks, from the inception of daily treatment with the GnRH antagonist at the indicated dosage. Values along the y-axis denote serum E2 concentration in pg/ml.

The invention provides compositions and methods for the treatment of endometriosis in a patient, such as a premenopausal female human patient, using gonadotropin-releasing hormone (GnRH) receptor antagonists. Using the compositions and methods described herein, a patient, such as a premenopausal female human patient, having endometriosis may be administered a GnRH antagonist, such as a compound of formula (I), (II), or a pharmaceutically acceptable salt thereof, such as choline 3-[2-fluoro-5-(2,3-difluoro-6-methoxybenzyloxy)4-methoxyphenyl]-2,4-dioxo-1,2,3,4-tetrahydrothieno[3,4d]pyrimidine-5-carboxylate, so as to treat this disease. Indicators of successful treatment include the alleviation of symptoms, such as endometriosis-associated pain, and a finding that the patient's serum concentration of β17-estradiol (E2) has decreased to within a range of from 20 pg/ml to 50 pg/ml, or less. Particularly, the GnRH antagonist represented by formula (I), (II), or a pharmaceutically acceptable salt thereof, such as choline 3-[2-fluoro-5-(2,3-difluoro-6-methoxybenzyloxy)4-methoxyphenyl]-2,4-dioxo-1,2,3,4-tetrahydrothieno[3,4d]pyrimidine-5-carboxylate, may be administered to a patient in an amount of from about 35 mg/day to about 215 mg/day, such as in an amount of 50 mg/day, 75 mg/day, 100 mg/day, or 200 mg/day, so as to treat the disease and induce the phenotypes described above. Using the compositions and methods described herein, the GnRH antagonist may be administered with or without add-back therapy. Add-back therapy, such as the combined use of an estrogen and progestin, may be administered to a patient in order to prevent a loss in bone mineral density that may otherwise be associated with reduced serum E2 concentrations.

The invention additionally features methods of treating endometriosis in a patient, such as a human patient, by administration of a GnRH antagonist to the patient in an amount that can be determined based on the concentration of anti-Müllerian hormone (AMH) and/or E2 in the patient or a sample (e.g., a serum sample) isolated therefrom. Using the methods of the invention, a physician of skill in the art can assess the concentration of AMH in a sample isolated from a patient in order to determine an optimal initial dosage of a GnRH antagonist to be administered to a patient suffering from endometriosis or prone to develop this condition. One may also use the patient's serum E2 concentration as a biomarker for determining whether the patient's dosage of the GnRH antagonist should be titrated up or down once treatment with the GnRH antagonist is underway.

Treatment of Endometriosis

GnRH antagonists, such as those described herein, represent a useful therapeutic paradigm for the treatment of endometriosis. By attenuating the release of FSH and LH from the anterior pituitary, GnRH antagonists can be used to suppress the production of estrogen, thereby reducing the aberrant growth of endometrial tissue. It has presently been discovered that effective treatment of endometriosis patients exhibiting elevated levels of endogenous AMH, such as a concentration in blood of beyond 35 pM, can be achieved by administration to such patients of an increased dosage of a GnRH antagonist as compared to the dose that would typically be prescribed or administered for the treatment of endometriosis. Examples of typical doses of certain GnRH antagonists for the treatment of endometriosis are described herein, for instance, in Table 1, below. According to the methods of the invention, if a determination is made that the concentration of AMH in a sample isolated from the patient is elevated, for example, beyond an AMH reference range (such as from 15 to 35 pM), a physician may determine that the patient should be administered a higher dosage of a GnRH antagonist relative to the dose of the GnRH antagonist that would normally be prescribed or administered to a patient for the treatment of endometriosis. Likewise, it has been presently discovered that effective treatment endometriosis in a patient exhibiting a reduced level of endogenous AMH, such as a blood concentration of AMH of less than 15 pM, can be achieved by administration to such patients of a decreased dosage of a GnRH antagonist as compared to the dose that would typically be prescribed or administered to a patient for the treatment of endometriosis. Thus, according to the methods described herein, if it is determined that the patient's endogenous AMH level is low, for instance, less than the lower bound of an AMH reference range (such as from 15 to 35 pM), the physician may determine that the patient should be administered a lower dosage of a GnRH antagonist relative to the dose of the GnRH antagonist that would normally be prescribed or administered to the patient for the treatment of endometriosis. It has further been presently discovered that optimal treatment of endometriosis in a patient exhibiting an endogenous AMH concentration that is within an AMH reference range, such as an AMH reference range of from 15 pM to 35 pM, can be achieved by administration to such patients of a dosage of a GnRH antagonist that would typically be prescribed or administered for the treatment of endometriosis. For instance, a determination that the patient's AMH level is within the particular AMH reference range of from 15 to 35 pM may indicate that the patient is to be administered an intermediate quantity of a GnRH antagonist, such as a quantity of a GnRH antagonist set forth in Table 1, below.

Using the methods of the invention, a physician may subsequently administer the GnRH antagonist to the patient by a suitable route, such as orally or intravenously, at the dosage identified based on the foregoing analysis.

TABLE 1

Examples of typically administered dosages of GnRH antagonists

| GnRH antagonist | Typically administered dosage for the treatment of endometriosis | Additional agent(s) administered in combination with GnRH antagonist |
| --- | --- | --- |
| Elagolix | 150 mg QD or 200 mg BID | — |
| Elagolix | Less than 150 mg QD or 200 mg BID | Rifampin or ketoconazole |
| Relugolix | 40 mg/day | — |
| ASP-1707 | 10 mg/day | — |

The present invention additionally features methods of optimizing a dosing regimen for a patient suffering from endometriosis and currently receiving GnRH antagonist treatment for the disease by assessing the patient's E2 level during the treatment and comparing the patient's E2 level to a prior measurement of the patient's E2 level, such as a measurement obtained prior to the initiation of therapy. According to the methods of the invention, a determination that the patient's E2 level has increased during the treatment period (e.g., is currently above an E2 reference range) may indicate that the patient is to be administered an elevated dosage of the GnRH antagonist. Similarly, a determination that the patient's E2 level has decreased during the treatment period (e.g., is currently below an E2 reference range) may indicate that the patient is to be administered a reduced dosage of the GnRH antagonist. A determination that the patient's E2 level has not changed or has remained within an E2 reference range during the treatment period may indicate that the patient is to be administered the originally dispensed dosage of the GnRH antagonist. Using the methods of the invention, a physician may subsequently administer the GnRH antagonist to the patient at the dosage identified based on the above analysis.

3-[2-fluoro-5-(2,3-difluoro-6-methoxybenzyloxy)4-methoxyphenyl]-2,4-dioxo-1,2,3,4-tetrahydrothieno[3,4d]pyrimidine-5-carboxylic acid (Compound II)

The invention is based in part on the discovery that 3-[2-fluoro-5-(2,3-difluoro-6-methoxybenzyloxy)4-methoxyphenyl]-2,4-dioxo-1,2,3,4-tetrahydrothieno[3,4d]pyrimidine-5-carboxylic acid, and the choline salt thereof, represented by formula (III), below) is an orally active, non-peptide GnRH antagonist. It has been shown to suppress the luteinizing hormone (LH) and β17-estradiol (E2) and to significantly reduce endometriosis-associated pain in Japanese women at doses between 50 and 200 mg daily with a good safety and tolerability profile.

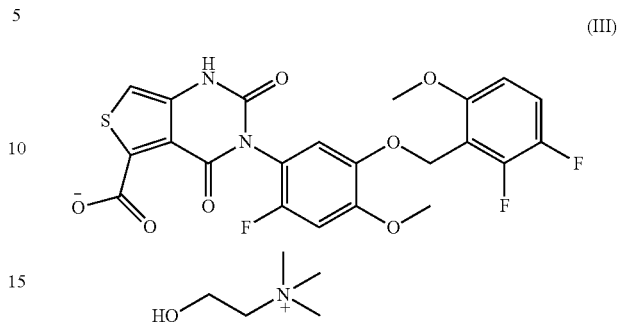

Compound (II) and the choline salt thereof (compound (III)) can be synthesized, for example, using the methodology described in WO 2014/042176, the disclosure of which is incorporated herein by reference in its entirety. An exemplary synthetic scheme that may be used for the preparation of compound (II) and the choline salt thereof is shown in Scheme 1, below.

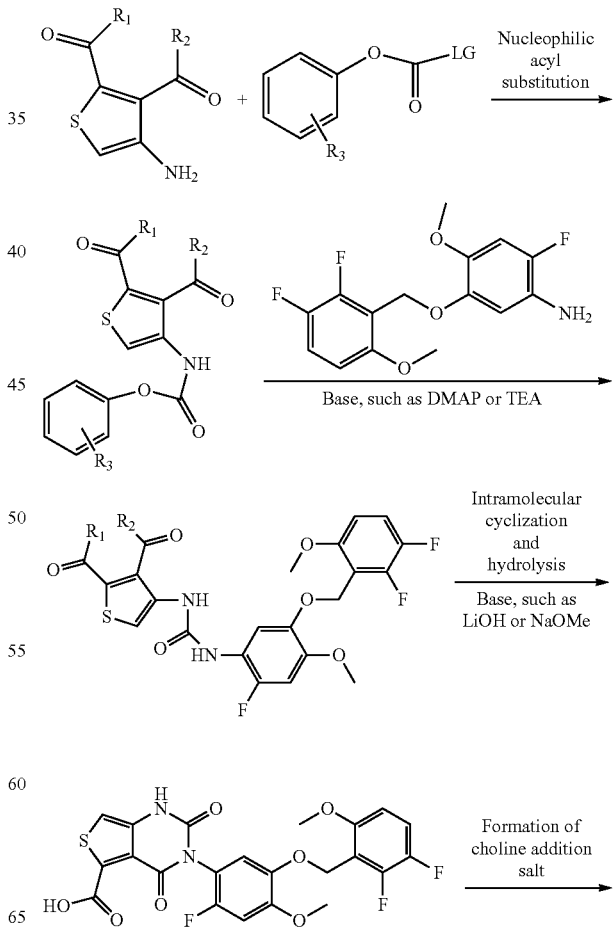

Scheme 1. Exemplary preparation of compound (II) and the choline salt thereof.

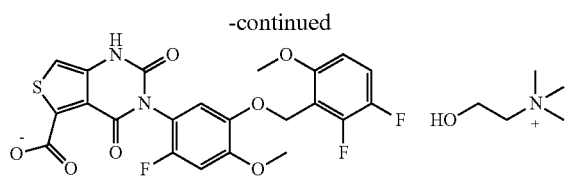

wherein $R^1$ and $R_2$ are each independently $C_{1-6}$ alkoxy groups; LG is a nucleofugal leaving group, such as chlorine or bromine, among others; $R_3$ represents an optional substituent, such as halogen, acyl group, $C_{1-6}$ alkyl group, or a nitro substituent; DMAP denotes N-dimethylaminopyridine; and TEA denotes trimethylamine.

Compound (II), as well as the choline salt thereof, exhibit a high affinity for human GnRH receptor (27.4 nM) and are capable of significantly suppressing serum LH concentration, E2 secretion, and the size of endometriotic lesions in various animal models of endometriosis. Using the methods of the invention, a physician of skill in the art can determine a dosing regimen for a patient suffering from endometriosis by analyzing the patient's AMH and/or E2 levels as described herein. Based on the levels of these endogenous substances, a physician of skill in the art may administer a thieno[3,4d]pyrimidine derivative represented by formula (I), above, such as compound (II) or the choline salt thereof (compound (III)) to the patient according to a dosing regimen of the invention.

For instance, according to the methods of the invention, a physician of skill in the art may assess a patient's AMH level, e.g., prior to the initiation of GnRH antagonist therapy. If a determination is made that the concentration of AMH in a sample isolated from the patient is elevated, e.g., with respect to an AMH reference range (such as from 15 to 35 pM), the physician may determine that the patient should be administered a higher dosage of a thieno[3,4d]pyrimidine derivative represented by formula (I), above, such as compound (II) or the choline salt thereof (e.g., from 75 to 225 mg/day, such as 75 mg/day, 80 mg/day, 85 mg/day, 90 mg/day, 95 mg/day, 100 mg/day, 105 mg/day, 110 mg/day, 115 mg/day, 120 mg/day, 125 mg/day, 130 mg/day, 135 mg/day, 140 mg/day, 145 mg/day, 150 mg/day, 155 mg/day, 160 mg/day, 165 mg/day, 170 mg/day, 175 mg/day, 180 mg/day, 185 mg/day, 190 mg/day, 195 mg/day, 200 mg/day, 205 mg/day, 210 mg/day, 215 mg/day, 220 mg/day, 225 mg/day, or more). For instance, an elevated AMH level relative to the AMH reference range may indicate that the patient is to be administered 75 mg/day, 100 mg/day, or 200 mg/day of a thieno[3,4d]pyrimidine derivative represented by formula (I), above, such as compound (II) or the choline salt thereof.

Likewise, if it is determined that the patient's AMH level is low, e.g., with respect to an AMH reference range (such as from 15 to 35 pM), the physician may determine that the patient should be administered a lower dosage of a thieno[3,4d]pyrimidine derivative represented by formula (I), above, such as compound (II) or the choline salt thereof (e.g., from about 35 mg/day to about 125 mg/day, such as about 35 mg/day, 40 mg/day, 45 mg/day, 50 mg/day, 55 mg/day, 60 mg/day, 65 mg/day, 70 mg/day, 75 mg/day, 80 mg/day, 85 mg/day, 90 mg/day, 95 mg/day, 100 mg/day, 105 mg/day, 110 mg/day, 115 mg/day, 120 mg/day, or 125 mg/day). For instance, a reduced AMH level relative to the AMH reference range may indicate that the patient is to be administered 50 mg/day, 75 mg/day, or 100 mg/day of a thieno[3,4d]pyrimidine derivative represented by formula (I), above, such as compound (II) or the choline salt thereof.

A determination that the patient's AMH level is within a particular AMH reference range (such as from 15 to 35 pM) may indicate that the patient is to be administered an intermediate quantity of a thieno[3,4d]pyrimidine derivative represented by formula (I), above, such as compound (II) or the choline salt thereof (e.g., from about 45 mg/day to about 215 mg/day, such as about 45 mg/day, 50 mg/day, 55 mg/day, 60 mg/day, 65 mg/day, 70 mg/day, 75 mg/day, 80 mg/day, 85 mg/day, 90 mg/day, 95 mg/day, 100 mg/day, 105 mg/day, 110 mg/day, 115 mg/day, 120 mg/day, 125 mg/day, 130 mg/day, 135 mg/day, 140 mg/day, 145 mg/day, 150 mg/day, 155 mg/day, 160 mg/day, 165 mg/day, 170 mg/day, 175 mg/day, 180 mg/day, 185 mg/day, 190 mg/day, 195 mg/day, 200 mg/day, 205 mg/day, 210 mg/day, or 215 mg/day). For instance, a patient AMH level that is within the AMH reference range may indicate that the patient is to be administered 50 mg/day, 75 mg/day, 100 mg/day, or 200 mg/day of a thieno[3,4d]pyrimidine derivative represented by formula (I), above, such as compound (II) or the choline salt thereof. Using the methods of the invention, a physician may subsequently administer the GnRH antagonist to the patient at the dosage identified based on the above analysis.

Additionally, using the methods of the invention a physician of skill in the art may optimize a dosing regimen of a thieno[3,4d]pyrimidine derivative represented by formula (I), above, such as compound (II) or the choline salt thereof, for a patient suffering from endometriosis and currently receiving GnRH antagonist treatment for the disease. The physician may assess the patient's E2 level during the treatment and compare the patient's E2 level to a prior measurement of the patient's E2 level, such as a measurement obtained prior to the initiation of therapy. According to the methods of the invention, a determination that the patient's E2 level has increased during the treatment period (e.g., is currently above an E2 reference range) may indicate that the patient is to be administered an elevated dosage of a thieno[3,4d]pyrimidine derivative represented by formula (I), above, such as compound (II) or the choline salt thereof (e.g., from 75 to 225 mg/day, such as 75 mg/day, 80 mg/day, 85 mg/day, 90 mg/day, 95 mg/day, 100 mg/day, 105 mg/day, 110 mg/day, 115 mg/day, 120 mg/day, 125 mg/day, 130 mg/day, 135 mg/day, 140 mg/day, 145 mg/day, 150 mg/day, 155 mg/day, 160 mg/day, 165 mg/day, 170 mg/day, 175 mg/day, 180 mg/day, 185 mg/day, 190 mg/day, 195 mg/day, 200 mg/day, 205 mg/day, 210 mg/day, 215 mg/day, 220 mg/day, 225 mg/day, or more). For instance, an elevated E2 level relative to the E2 reference range may indicate that the patient is to be administered 75 mg/day, 100 mg/day, or 200 mg/day of a thieno[3,4d]pyrimidine derivative represented by formula (I), above, such as compound (II) or the choline salt thereof.

Similarly, a determination that the patient's E2 level has decreased during the treatment period (e.g., is currently below an E2 reference range) may indicate that the patient is to be administered a reduced dosage of a thieno[3,4d] pyrimidine derivative represented by formula (I), above, such as compound (II) or the choline salt thereof (e.g., from about 35 mg/day to about 125 mg/day, such as about 35 mg/day, 40 mg/day, 45 mg/day, 50 mg/day, 55 mg/day, 60 mg/day, 65 mg/day, 70 mg/day, 75 mg/day, 80 mg/day, 85 mg/day, 90 mg/day, 95 mg/day, 100 mg/day, 105 mg/day, 110 mg/day, 115 mg/day, 120 mg/day, or 125 mg/day). For instance, a reduced E2 level relative to the E2 reference range may indicate that the patient is to be administered 50 mg/day, 75 mg/day, or 100 mg/day of a thieno[3,4d]pyrimidine derivative represented by formula (I), above, such as compound (II) or the choline salt thereof.

A determination that the patient's E2 level has not changed or has remained within an E2 reference range during the treatment period may indicate that the patient is to be administered the originally dispensed dosage of a thieno[3,4d]pyrimidine derivative represented by formula (I), above, such as compound (II) or the choline salt thereof (e.g., from about 45 mg/day to about 215 mg/day, such as about 45 mg/day, 50 mg/day, 55 mg/day, 60 mg/day, 65 mg/day, 70 mg/day, 75 mg/day, 80 mg/day, 85 mg/day, 90 mg/day, 95 mg/day, 100 mg/day, 105 mg/day, 110 mg/day, 115 mg/day, 120 mg/day, 125 mg/day, 130 mg/day, 135 mg/day, 140 mg/day, 145 mg/day, 150 mg/day, 155 mg/day, 160 mg/day, 165 mg/day, 170 mg/day, 175 mg/day, 180 mg/day, 185 mg/day, 190 mg/day, 195 mg/day, 200 mg/day, 205 mg/day, 210 mg/day, or 215 mg/day). For instance, a patient E2 level that is within the E2 reference range may indicate that the patient is to be administered 50 mg/day, 75 mg/day, 100 mg/day, or 200 mg/day of a thieno[3,4d] pyrimidine derivative represented by formula (I), above, such as compound (II) or the choline salt thereof.

Using the methods of the invention, a physician may subsequently administer the GnRH antagonist to the patient at the dosage identified based on the above analysis.

Elagolix

Additional GnRH antagonists that may be used in conjunction with the compositions and methods described herein include elagolix (4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethyl-amino)-butyric acid sodium salt), represented by formula (IV), below, as well as derivatives and variants thereof, such as a compound described in U.S. Pat. No. 7,056,927; 7,176,211; 7,419,983; 8,765,948; or 9,382,214; or in US Patent Application Publication No. 2014/0288031 or 2017/0056403, the disclosures of which are incorporated herein by reference in their entirety.

(IV)

Elagolix can be synthesized, for example, using the methodology described in U.S. Pat. No. 8,765,948, the disclosure of which is incorporated herein by reference in its entirety. An exemplary synthetic scheme that may be used for the preparation of elagolix is shown in Scheme 2, below.

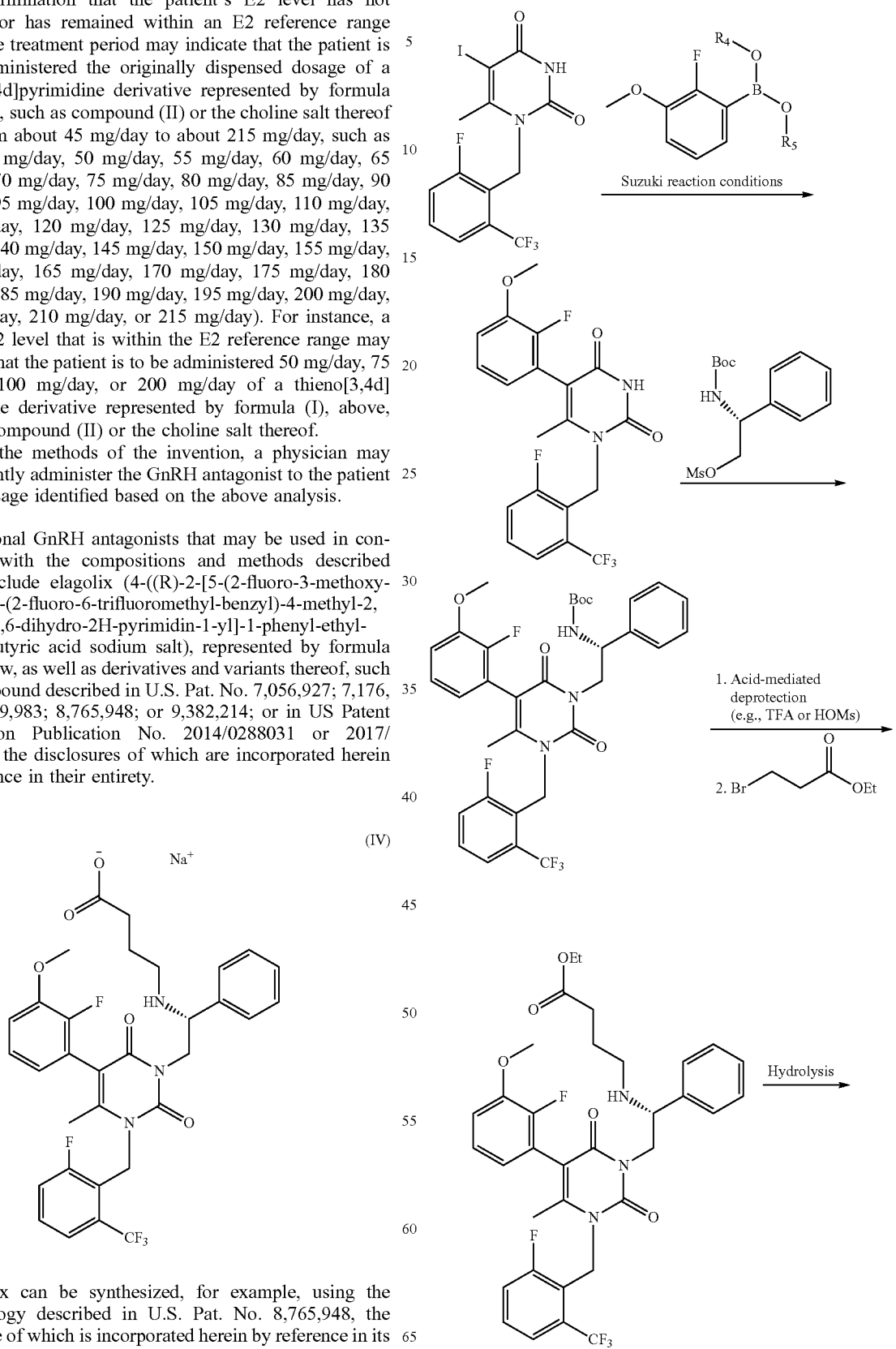

Scheme 2. Exemplary preparation of elagolix

-continued

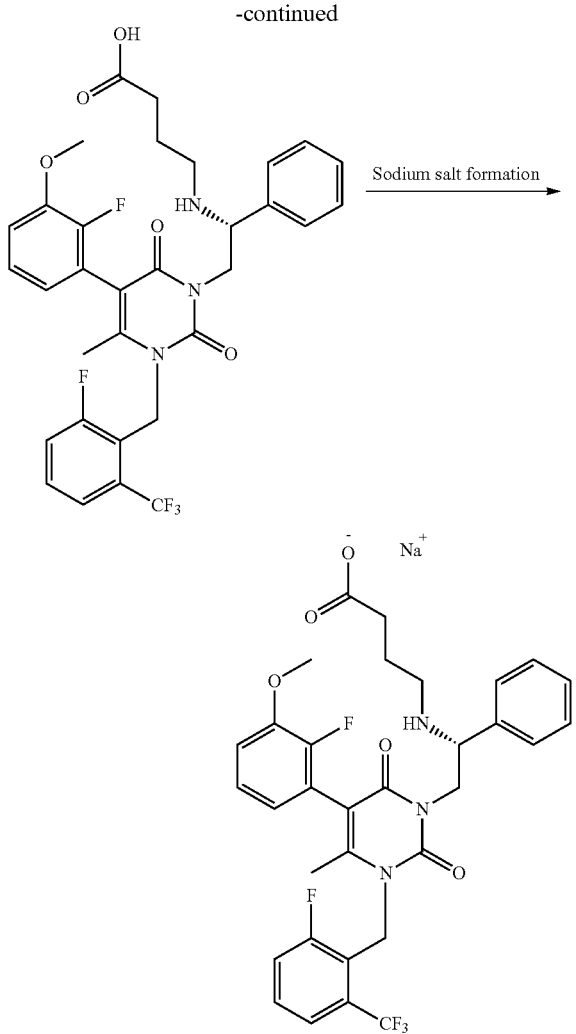

wherein $R_4$ and $R_5$ are each independently hydrogen or $C_{1-4}$ alkyl groups, or $R_4$ and $R_5$ combine to form a $C_{1-6}$ heterocycloalkyl ring, Boc denotes a tert-butoxycarbonyl protecting group; TFA denotes trifluoroacetic acid; and HOMs denotes methanesulfonic acid.

Typically prescribed or administered dosages of elagolix for the treatment of endometriosis include 150 mg/day and 400 mg/day (e.g., 200 mg BID) as set forth in Table 1, above. Reduced doses of elagolix may be administered to a patient when elagolix is provided in combination with a cytochrome P450 isoform 3A4 modulator, such as rifampin or ketoconazole (as described, for instance, in US Patent Application Publication No. 2017/0056403, the disclosure of which is incorporated herein by reference in its entirety). For instance, when administered in combination with rifampin or ketoconazole, elagolix may be administered to a patient at a dose that is reduced relative to 150 mg/day, such as a dose of 50 mg/day, 75 mg/day, 100 mg/day, or 125 mg/day. As another example, elagolix may be administered in combination with rifampin or ketoconazole at a dose that is reduced relative to 400 mg/day, such as a dose of 200 mg/day, 250 mg/day, 300 mg/day, or 350 mg/day.

It has presently been discovered that such low doses of elagolix may be used for the treatment of endometriosis when a patient exhibits a reduced concentration of AMH relative to an AMH reference range. For example, if a patient presents with an AMH concentration in a blood sample withdrawn from the patient of less than 15 pM, according to the methods described herein, the patient may be effectively treated with a reduced dosage of elagolix relative to that which would typically administered, e.g., as set forth in Table 1. For example, under these conditions, a patient may be administered a lower dose of elagolix, such as a dosage that is set forth in US Patent Application Publication No. 2017/0056403, such as a dose of 50 mg/day, 75 mg/day, 100 mg/day, or 125 mg/day, or a dose of 200 mg/day, 250 mg/day, 300 mg/day, or 350 mg/day.

Thus, using the methods of the invention, a physician of skill in the art can determine a dosing regimen for a patient suffering from endometriosis by analyzing the patient's AMH and/or E2 levels as described herein. Based on the levels of these endogenous substances, a physician of skill in the art may administer elagolix, or a derivative or variant thereof, to the patient according to a dosing regimen of the invention.

For instance, according to the methods of the invention, a physician of skill in the art may assess a patient's AMH level, e.g., prior to the initiation of GnRH antagonist therapy. If a determination is made that the concentration of AMH in a sample isolated from the patient is elevated, for instance, beyond an AMH reference range (such as from 15 to 35 pM), the physician may determine that the patient should be administered a higher dosage of elagolix or a derivative or variant thereof, such as a dosage of 150 mg/day or 400 mg/day or more (e.g., from 125 mg/day to 600 mg/day, such as 125 mg/day, 150 mg/day, 175 mg/day, 200 mg/day, 225 mg/day, 250 mg/day, 275 mg/day, 300 mg/day, 325 mg/day, 350 mg/day, 375 mg/day, 400 mg/day, 425 mg/day, 450 mg/day, 475 mg/day, 500 mg/day, 525 mg/day, 550 mg/day, 575 mg/day, or 600 mg/day, or more). For instance, an elevated AMH level relative to the AMH reference range may indicate that the patient is to be administered a dosage of elagolix of 150 mg/day, 400 mg/day, or more. Likewise, if it is determined that the patient's AMH level is low, e.g., with respect to an AMH reference range (such as from 15 to 35 pM), the physician may determine that the patient should be administered a lower dosage of elagolix, such as from 50 mg/day to 400 mg/day of elagolix or a derivative or variant thereof (e.g., 50 mg/day, 100 mg/day, 150 mg/day, 200 mg/day, 250 mg/day, 300 mg/day, 350 mg/day, or 400 mg/day). A determination that the patient's AMH level is within a particular AMH reference range (such as from 15 to 35 pM) may indicate that the patient is to be administered an intermediate quantity of elagolix or a derivative or variant thereof, such as 150 mg/day or 400 mg/day (e.g., 200 mg BID). For instance, a patient AMH level that is within the AMH reference range may indicate that the patient is to be administered 150 mg/day or 400 mg/day (e.g., 200 mg BID) of elagolix. Using the methods of the invention, a physician may subsequently administer the GnRH antagonist to the patient at the dosage identified based on the above analysis.

Additionally, using the methods of the invention a physician of skill in the art may optimize a dosing regimen of elagolix or a derivative or variant thereof for a patient suffering from endometriosis and currently receiving GnRH antagonist treatment for the disease. The physician may assess the patient's E2 level during the treatment and compare the patient's E2 level to a prior measurement of the patient's E2 level, such as a measurement obtained prior to the initiation of therapy. According to the methods of the invention, a determination that the patient's E2 level has increased during the treatment period (e.g., is currently above an E2 reference range) may indicate that the patient is to be administered an elevated dosage of elagolix or a derivative or variant thereof, such as a dosage of 150 mg/day or 400 mg/day or more (e.g., from 155 mg/day to 395 mg/day or from 400 mg/day to 600 mg/day). For instance, an elevated E2 level relative to the E2 reference range may indicate that the patient is to be administered a dosage greater than 150 mg/day or greater than 400 mg/day of elagolix. Similarly, a determination that the patient's E2 level has decreased during the treatment period (e.g., is currently below an E2 reference range) may indicate that the patient is to be administered a reduced dosage of elagolix or a derivative or variant thereof, such as from 50 mg/day to 125 mg/day of elagolix or a derivative or variant thereof. A determination that the patient's E2 level has not changed or has remained within an E2 reference range during the treatment period may indicate that the patient is to be administered the originally dispensed dosage of elagolix or a derivative or variant thereof, such as 150 mg/day or 400 mg/day (e.g., 200 mg BID). For instance, a patient E2 level that is within the E2 reference range may indicate that the patient is to be administered 150 mg/day or 400 mg/day (e.g., 200 mg BID) of elagolix. Using the methods of the invention, a physician may subsequently administer the GnRH antagonist to the patient at the dosage identified based on the above analysis.

disclosures of which are incorporated herein by reference in their entirety.

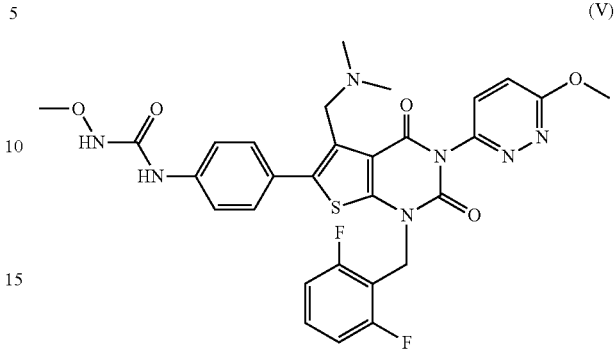

(V)

Relugolix can be synthesized, for example, using the methodology described in U.S. Pat. No. 8,765,948, the disclosure of which is incorporated herein by reference in its entirety. An exemplary one-pot synthetic scheme that may be used for the preparation of relugolix is shown in Scheme 3, below.

Scheme 3. Exemplary Preparation of Relugolix

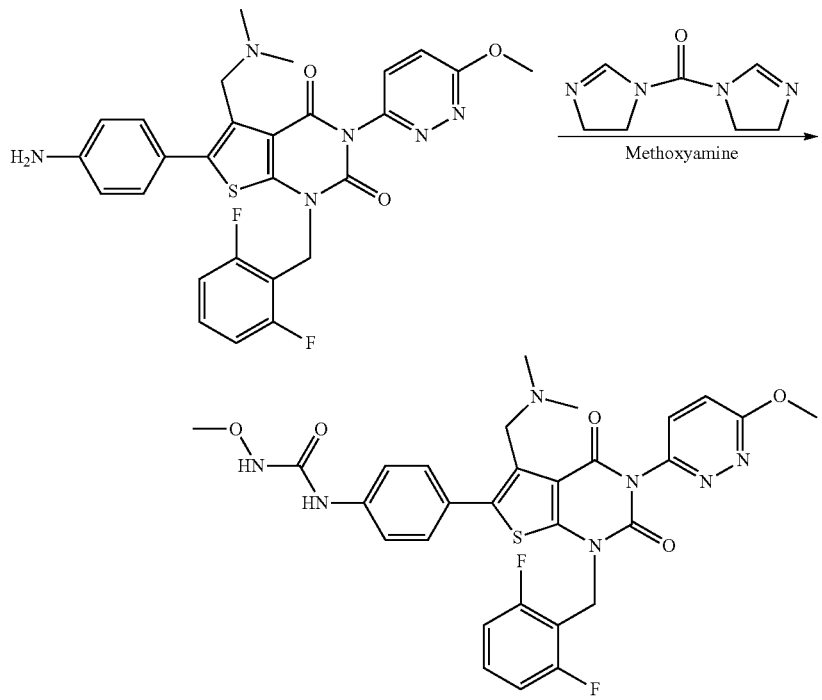

Relugolix

Additional GnRH antagonists that may be used in conjunction with the compositions and methods described herein include relugolix (1-{4-[1-(2,6-difluorobenzyl)-5-dimethylaminomethyl-3-(6-methoxypyridazin-3-yl)-2,4-dioxo-1,2,3,4-tetrahydrothieno[2,3-d]pyrimidin-6-yl]phenyl}-3-methoxyurea or a salt thereof), for instance, as represented by formula (V), below, as well as derivatives and variants thereof, such as a compound described in U.S. Pat. No. 7,300,935; 8,058,280; 8,735,401; or 9,346,822; or in US Patent Application Publication No. 2015/0266891, the Using the methods of the invention, a physician of skill in the art can determine a dosing regimen for a patient suffering from endometriosis by analyzing the patient's AMH and/or E2 levels as described herein. Based on the levels of these endogenous substances, a physician of skill in the art may administer relugolix, or a derivative or variant thereof, to the patient according to a dosing regimen of the invention.

For instance, according to the methods of the invention, a physician of skill in the art may assess a patient's AMH level, e.g., prior to the initiation of GnRH antagonist therapy. If a determination is made that the concentration of AMH in a sample isolated from the patient is elevated, for instance, beyond an AMH reference range (such as from 15 to 35 pM), the physician may determine that the patient should be administered a high dosage of relugolix or a derivative or variant thereof, such as a dosage that exceeds 40 mg/day (e.g., from 45 mg/day to 150 mg/day). For instance, an elevated AMH level relative to the AMH reference range may indicate that the patient is to be administered a dosage greater than 40 mg/day of relugolix. Likewise, if it is determined that the patient's AMH level is low, for instance, with respect to an AMH reference range (such as from 15 to 35 pM), the physician may determine that the patient should be administered a low dosage of relugolix, such as from 10 mg/day to 35 mg/day of relugolix or a derivative or variant thereof. For instance, a reduced AMH level relative to the AMH reference range may indicate that the patient is to be administered from 10 mg/day to 35 mg/day of relugolix. A determination that the patient's AMH level is within a particular AMH reference range (such as from 15 to 35 pM) may indicate that the patient is to be administered an intermediate quantity of relugolix or a derivative or variant thereof, such as 40 mg/day. For instance, a patient AMH level that is within the AMH reference range may indicate that the patient is to be administered 40 mg/day of relugolix. Using the methods of the invention, a physician may subsequently administer the GnRH antagonist to the patient at the dosage identified based on the above analysis.

Additionally, using the methods of the invention a physician of skill in the art may optimize a dosing regimen of relugolix or a derivative or variant thereof for a patient suffering from endometriosis and currently receiving GnRH antagonist treatment for the disease. The physician may assess the patient's E2 level during the treatment and compare the patient's E2 level to a prior measurement of the patient's E2 level, such as a measurement obtained prior to the initiation of therapy. According to the methods of the invention, a determination that the patient's E2 level has increased during the treatment period (e.g., is currently above an E2 reference range) may indicate that the patient is to be administered an elevated dosage of relugolix or a derivative or variant thereof, such as a dosage that exceeds 40 mg/day (e.g., from 45 mg/day to 150 mg/day). For instance, an elevated E2 level relative to the E2 reference range may indicate that the patient is to be administered a dosage greater than 40 mg/day of relugolix. Similarly, a determination that the patient's E2 level has decreased during the treatment period (e.g., is currently below an E2 reference range) may indicate that the patient is to be administered a reduced dosage of relugolix or a derivative or variant thereof, such as from 10 mg/day to 35 mg/day of relugolix or a derivative or variant thereof. For instance, a reduced E2 level relative to the E2 reference range may indicate that the patient is to be administered from 10 mg/day to 35 mg/day of relugolix. A determination that the patient's E2 level has not changed or has remained within an E2 reference range during the treatment period may indicate that the patient is to be administered the originally dispensed dosage of relugolix or a derivative or variant thereof, such as 40 mg/day. For instance, a patient E2 level that is within the E2 reference range may indicate that the patient is to be administered 40 mg/day of relugolix. Using the methods of the invention, a physician may subsequently administer the GnRH antagonist to the patient at the dosage identified based on the above analysis.

Methods of Assessing AMH and E2 Concentrations

Techniques for determining AMH and E2 concentrations within a patient or a sample isolated there from are known in the art. For instance, one of skill in the art can use an immunoassay, such as an enzymatic immunosorbant assay (ELISA) to quantify the concentration of AMH or E2 within a sample isolated from a patient (e.g., a blood sample isolated from the patient). Such techniques may employ anti-AMH and anti-E2 antibodies, examples of which are known in the art. For instance, immunoassays for the detection and quantification of AMH in a sample that generate a colorimetric or fluorescent signal (e.g., using antibodies conjugated to gold nanoparticles or fluorescent particles) are known in the art and are described in detail, e.g., in WO 2013/126517, the disclosure of which is incorporated herein by reference in its entirety. In such assays, the analytical signal generated (e.g., UV-Vis absorption, fluorescence, or chemiluminescence) is proportional to the approximate concentration of AMH in a sample.

Methods of determining E2 levels within a patient or a sample isolated there from are known in the art and may involve, e.g., competitive immunoassays in which E2 analogs compete with E2 for binding to an anti-E2 antibody. Such competitive binding assays are described in detail, e.g., in U.S. Pat. No. 6,201,141 and WO 1993/025672, the disclosures of which is incorporated herein by reference in its entirety.

In addition to the above, Pandey et al., (Clinica Chimica Acta 190:175-184 (1990)) have reported an ELISA-based E2 quantitation assay using the conjugate estradiol-6-(O-carboxymethyl)oxime linked to penicillinase with anti-estradiol antibody coated wells of a microtiter plate. Additionally, Maurel et al., (J. Immunolog. Methods 102:165-172 (1987)) have reported an E2-sensitive ELISA that utilizes an estradiol-6-(O-carboxymethyl)oxime conjugated to β-galactosidase. De Boever et al., (Clin. Chem. 32:1895-1900 (1986)) reported a chemiluminescence immunoassay for E2 quantification with a sensitivity limit of about 49 pg/mL and an assay time on the order of ninety minutes. De Lauzon et al., (J. Immunoassay 10:339-357 (1989)) reported a competitive enzyme immunoassay for E2 detection using microtiter plate wells coated with E2 coupled to bovine serum albumin (BSA). Alternatively, biotinylated anti-E2 antibodies may be utilized followed by a second incubation with avidin coupled to peroxidase. The disclosures of each of the foregoing references are incorporated herein by reference in their entirety.

Add-Back Therapy

Endogenous estrogens are largely responsible for the development and maintenance of the female reproductive system and secondary sexual characteristics. Although circulating estrogens exist in a dynamic equilibrium of metabolic interconversions, estradiol is the principal intracellular human estrogen and is substantially more potent than its metabolites, estrone and estriol, at the receptor level. The primary source of estrogen in normally cycling adult women is the ovarian follicle, which secretes 70 to 500 μg of estradiol daily, depending on the phase of the menstrual cycle. After menopause, most endogenous estrogen is produced by conversion of androstenedione, secreted by the adrenal cortex, to estrone by peripheral tissues. Thus, estrone and the sulfate conjugated form, estrone sulfate, are the most abundant circulating estrogens in postmenopausal women. Circulating estrogens modulate the pituitary secretion of the gonadotropins, LH and FSH, through a negative feedback mechanism. Estrogens act to reduce the elevated levels of these hormones seen in postmenopausal women.

Among the potential side-effects of GnRH antagonist therapy is a reduction in bone mineral density due to excessive depletion of estrogen (Newhall-Perry et al., American Journal of Obstetrics and Gynecology 173:824-

829 (1995)). Reductions in bone mineral density have led to the development of add-back therapy with estrogen and/or selected progestins that may be administered concurrently with GnRH antagonists for reducing such adverse symptoms and the risk of induced bone disease (Barbieri, American Journal of Obstetrics and Gynecology 166:740-745 (1992)).

Progestin compounds, such as norethindrone and esters thereof (e.g., norethindrone acetate), enhance cellular differentiation and generally oppose the actions of estrogens by decreasing estrogen receptor levels, increasing local metabolism of estrogens to less active metabolites, or inducing gene products that blunt cellular responses to estrogen. Progestins exert their effects in target cells by binding to specific progesterone receptors that interact with progesterone response elements in target genes. Progesterone receptors have been identified in the female reproductive tract, breast, pituitary, hypothalamus, and central nervous system. Progestins produce similar endometrial changes to those of the naturally occurring hormone progesterone. Progestins may be included in combination with estrogen in add-back therapy. For instance, according to the methods described herein, one can administer estrogen (e.g., E2) in conjunction with a progestin (e.g., norethindrone or an ester thereof, such as norethindrone acetate) to a patient undergoing GnRH antagonist therapy as to counteract the hypoestrogenemia that may be induced by the antagonist. In this way, add-back therapy can be used to mitigate or prevent potentially deleterious side effects, such as a reduction in bone mineral density.

Add-back therapy may be formulated for oral administration. For instance, add-back therapy administered in conjunction with the compositions and methods described herein may be formulated as a tablet, capsule, gel cap, powder, liquid solution, or liquid suspension. In some embodiments, the add-back therapy includes both an estrogen, such as β17-estradiol, and a progestin, such as norethindrone or norethindrone acetate. The estrogen and progestin may be administered separately or admixed in a single composition, such as a single tablet, capsule, gel cap, powder, liquid solution, or liquid suspension. For example, add-back therapy may feature a co-formulation containing estrogen (e.g., in the form of E2) and an additional agent such as a progestin (e.g., norethindrone or a compound that is metabolized in vivo to produce norethindrone, such as an ester of norethindrone that is de-esterified in vivo to produce norethindrone, for instance, norethindrone acetate). In some embodiments, add-back therapy is administered to a patient in the form of a single tablet, capsule, gel cap, powder, liquid solution, or liquid suspension that contains both estrogen (e.g., in the form of E2) and a progestin (e.g., norethindrone or a compound that is metabolized in vivo to produce norethindrone, such as an ester of norethindrone that is de-esterified in vivo to produce norethindrone, for instance, norethindrone acetate). In some embodiments, add-back therapy is administered as a fixed dose combination containing a GnRH antagonist, estrogen, and one or more additional agents, such as a progestin, in a single pharmaceutical composition. For instance, add-back therapy may be administered as a fixed dose combination of a GnRH antagonist, estrogen (e.g., in the form of E2) and a progestin (e.g., norethindrone or a compound that is metabolized in vivo to produce norethindrone, such as an ester of norethindrone that is de-esterified in vivo to produce norethindrone, for instance, norethindrone acetate) in the form of a single pharmaceutical composition, such as a single tablet, capsule, gel cap, powder, liquid solution, or liquid suspension.

Pharmaceutical Compositions

GnRH antagonists for use with the compositions and methods of the invention can be formulated into a pharmaceutical composition for administration to a subject, such as a female human subject, in a biologically compatible form suitable for administration in vivo. A pharmaceutical composition containing a GnRH antagonist (e.g., a compound represented by formula (I), above, such as compound (II) or a salt thereof, elagolix, relugolix, ASP-1707, SK12670, or BAY-784, or a derivative or variant thereof) may additionally contain a suitable diluent, carrier, or excipient. GnRH antagonists can be administered to a subject, for example, orally or by intravenous injection. Under ordinary conditions of storage and use, a pharmaceutical composition may contain a preservative, e.g., to prevent the growth of microorganisms. Conventional procedures and ingredients for the selection and preparation of suitable formulations are described, for example, in Remington: The Science and Practice of Pharmacy (2012, $22^{nd}$ ed.) and in The United States Pharmacopeia: The National Formulary (2015, USP 38 NF 33).

Pharmaceutical compositions may include sterile aqueous solutions, dispersions, or powders, e.g., for the extemporaneous preparation of sterile solutions or dispersions. In all cases the form may be sterilized using techniques known in the art and may be fluidized to the extent that may be easily administered to a subject in need of treatment.

A pharmaceutical composition may be administered to a subject, e.g., a human subject, alone or in combination with one or more pharmaceutically acceptable carriers, e.g., as described herein, the proportion of which may be determined by the solubility and/or chemical nature of the compound, chosen route of administration, and standard pharmaceutical practice.

Routes of Administration

The GnRH antagonists for use with the compositions and methods of the invention, such as the compounds of formula (I), (II), and pharmaceutically acceptable salts thereof (e.g., a choline salt thereof), may be administered to a patient orally, for example, in the form of a tablet, capsule, gel cap, powder, liquid solution, or liquid suspension. Other routes of administration may be used in conjunction with the GnRH antagonists described herein, such as intravenous administration, among others.

EXAMPLES

The following examples are put forth so as to provide those of ordinary skill in the art with a description of how the compositions and methods described herein may be used, made, and evaluated, and are intended to be purely exemplary of the invention and are not intended to limit the scope of what the inventors regards as their invention.

Example 1. Determining an Initial Dosage of a GnRH Antagonist for the Treatment of Endometriosis in a Human Subject Based on AMH Level Using the methods of the invention, a physician of skill in the art may assess a patient's AMH level prior to the initiation of GnRH antagonist therapy for the treatment of endometriosis. The GnRH antagonist to be administered to the patient may be a compound represented by formula (III), choline 3-[2-fluoro-5-(2,3-difluoro-6-methoxybenzyloxy)4-methoxyphenyl]-2,4-dioxo-1,2,3,4-tetrahydrothieno[3,4d]pyrimidine-5-carboxylate. A physician of skill in the art may withdraw blood from the patient and may subsequently perform or more analytical techniques, such as an immunoassay known in the art or described herein, in order to quantify the concentration of AMH in the blood sample isolated from the patient. If a determination is made that the concentration of AMH in the sample is elevated with respect to an AMH reference range of from 15 to 35 pM, the physician may determine that the patient should be administered a high dosage of compound (III), such as from 85 to 115 mg/day, e.g., 100 mg/day, or from 185 mg/day to 215 mg/day, e.g., 200 mg/day.

If the physician determines that the patient's AMH level is low with respect to the AMH reference range, the physician may determine that the patient be administered a low dosage of compound (III), such as from 35 to 65 mg/day, e.g., 50 mg/day.

A determination that the patient's AMH level is within the AMH reference range may indicate that the patient is to be administered an intermediate quantity of compound (III), such as from 60 to 90 mg/day, e.g., 75 mg/day.

Upon determining the initial dosage of the GnRH antagonist, the physician may administer the therapeutic compound to the patient, e.g., by oral or intravenous administration. The compound may be administered in conjunction with one or more carriers, diluents, or excipients known in the art or described herein.

Example 2. GnRH Antagonist Dose Titration for the Treatment of Endometriosis in a Human Subject Based on E2 Level Using the methods of the invention, a physician of skill in the art may assess the level of E2 in a patient that is currently undergoing GnRH antagonist therapy for the treatment of endometriosis in order to determine whether the patient should continue to be administered the same dosage of the GnRH antagonist or if the patient should be administered a different dosage of the GnRH antagonist in order to effectively alleviate one or more symptoms of endometriosis. The GnRH antagonist to be administered to the patient may be a compound represented by formula (III), choline 3-[2-fluoro-5-(2,3-difluoro-6-methoxybenzyloxy)4-methoxyphenyl]-2,4-dioxo-1,2,3,4-tetrahydrothieno[3,4d]pyrimidine-5-carboxylate. A physician of skill in the art may withdraw blood from the patient and may subsequently perform or more analytical techniques, such as an immunoassay known in the art or described herein, in order to quantify the concentration of E2 in the blood sample isolated from the patient. If a determination is made that the concentration of E2 in the sample is elevated with respect to the level of E2 in a sample from the patient that was withdrawn prior to the start of GnRH antagonist therapy, the physician may determine that the patient should be administered a higher dosage of compound (III), such as from 85 to 115 mg/day, e.g., 100 mg/day, or from 185 mg/day to 215 mg/day, e.g., 200 mg/day.

If the physician determines that the patient's E2 level is low with respect to the level of E2 in a sample from the patient that was withdrawn prior to the start of GnRH antagonist therapy, the physician may determine that the patient be administered a lower dosage of compound (III), such as from 35 to 65 mg/day, e.g., 50 mg/day.

A determination that the patient's E2 level is approximately the same as the level of E2 in a sample from the patient that was withdrawn prior to the start of GnRH antagonist therapy (e.g., within 1 pM, 2 pM, 3 pM, 4 pM, 5 pM, 6 pM, 7 pM, 8 pM, 9 pM, 10 pM, 11 pM, 12 pM, 13 pM, 14 pM, 15 pM, 16 pM, 17 pM, 18 pM, 19 pM, or 20 pM of the level of E2 in a sample from the patient that was withdrawn prior to the start of GnRH antagonist therapy) may indicate that the patient is to be administered the originally-dispensed quantity of compound (III), such as from 60 to 90 mg/day, e.g., 75 mg/day.

Upon determining the new dosage of the GnRH antagonist, the physician may administer the therapeutic compound to the patient, e.g., by oral or intravenous administration. The compound may be administered in conjunction with one or more carriers, diluents, or excipients known in the art or described herein.

Example 3. Administration of a GnRH Antagonist to Endometriosis Patients Presenting with Distinct AMH Levels In order to investigate the effects of GnRH antagonists, such as compound (I), (II), and pharmaceutically acceptable salts thereof, such as the choline salt thereof (compound (III)), on endometriosis patients presenting with distinct initial values of serum AMH, a series of experiments was conducted in which patients were divided into multiple treatment arms and orally administered either compound (III) or a placebo. Specifically, a series of n=327 human female patients having endometriosis were divided into five groups, and received either placebo, 50 mg/day of compound (III), 75 mg/day of compound (III), 100 mg/day of compound (III), or 200 mg/day of compound (III) by oral delivery. Treatment with the placebo or compound (III) at the doses specified above occurred continuously over a period of 12 weeks.

At various time points throughout these experiments, patients were evaluated for their serum E2 concentration. As described herein, an objective of endometriosis therapy utilizing a GnRH antagonist is to suppress serum E2 values to within a range of from about 20 pg/ml to about 50 pg/ml or lower. Alleviation of endometriosis symptoms correlates with a reduction of serum E2, and achieving serum E2 levels that are either within this range or below are indicators of successful endometriosis treatment.

Figure 2:
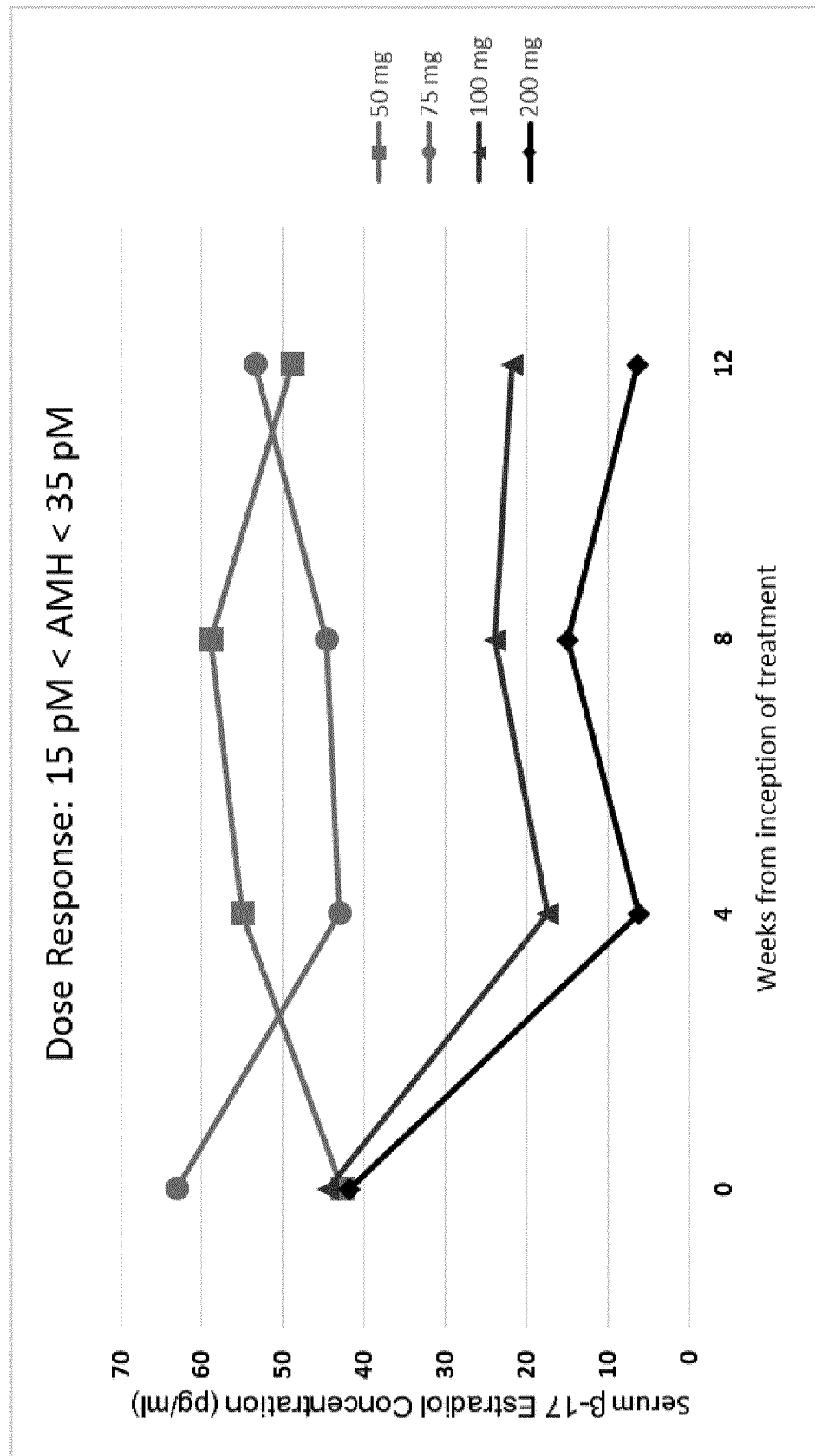
FIG. 2 is a graph showing the dose-dependent suppression of serum E2 in a series of human female patients suffering from endometriosis achieved by various daily doses of the GnRH antagonist represented by formula (III), herein (choline 3-[2-fluoro-5-(2,3-difluoro-6-methoxybenzyloxy)4-methoxyphenyl]-2,4-dioxo-1,2,3,4-tetrahydrothieno[3,4d]pyrimidine-5-carboxylate). The patients assessed in this group exhibited an initial serum concentration of AMH of from 15 pm to 35 pM. Values along the x-axis denote time, in weeks, from the inception of daily treatment with the GnRH antagonist at the indicated dosage. Values along the y-axis denote serum E2 concentration in pg/ml.

To analyze the response of patients presenting with different initial AMH serum concentrations, patients were further divided into groups based on initial AMH serum level. These groups included patients having initial AMH serum concentrations of less than 15 pM, from 15 pM to 35 pM, or greater than 35 pM prior to commencing treatment with the GnRH antagonist. The responsiveness of these groups of endometriosis patients to various daily dosages of compound (III) are shown in FIG. 1 (initial AMH values of less than 15 pM), FIG. 2 (initial AMH values of from 15 pM to 35 pM), and FIG. 3 (initial AMH values of greater than 35 pM).

Figure 3:
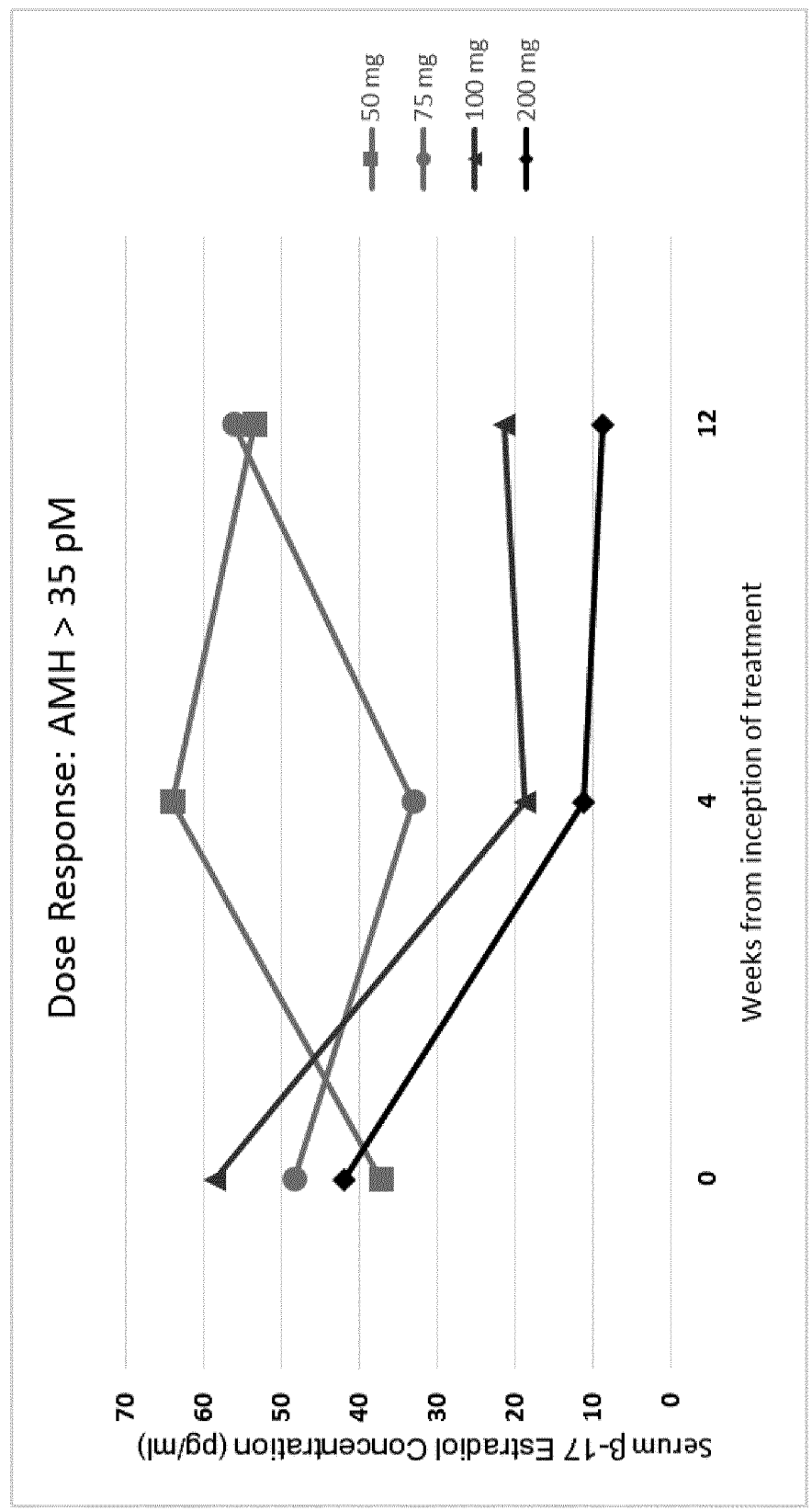
FIG. 3 is a graph showing the dose-dependent suppression of serum E2 in a series of human female patients suffering from endometriosis achieved by various daily doses of the GnRH antagonist represented by formula (III), herein (choline 3-[2-fluoro-5-(2,3-difluoro-6-methoxybenzyloxy)4-methoxyphenyl]-2,4-dioxo-1,2,3,4-tetrahydrothieno[3,4d]pyrimidine-5-carboxylate). The patients assessed in this group exhibited an initial serum concentration of AMH of greater than 35 pM. Values along the x-axis denote time, in weeks, from the inception of daily treatment with the GnRH antagonist at the indicated dosage. Values along the y-axis denote serum E2 concentration in pg/ml.

As these data demonstrate, patients presenting with lower initial serum AMH levels are generally responsive to lower dosages of the GnRH antagonist. This is manifest, for example, in the ability of a 50 mg/day treatment regimen using compound (III) to achieve a reduction in serum E2 concentration, and thus successfully treat endometriosis, over the course of the 12-week treatment period in patients presenting with initial AMH serum concentration of less than 15 pM (FIG. 1). In contrast, higher dosages, such as 100 mg/day and 200 mg/day, are generally required for suppression of serum E2 concentration in patients exhibiting higher initial serum AMH levels (FIG. 3).

Collectively, these data demonstrate that endometriosis patients presenting with elevated serum AMH levels generally require greater doses of a GnRH antagonist in order to lower serum E2 concentrations to therapeutic levels, while patients presenting with lower serum AMH levels can be successfully treated using lower quantities of a GnRH antagonist.

OTHER EMBODIMENTS

All publications, patents, and patent applications mentioned in this specification are incorporated herein by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the invention that come within known or customary practice within the art to which the invention pertains and may be applied to the essential features hereinbefore set forth, and follows in the scope of the claims.

Other embodiments are within the claims.

The invention claimed is:

1. A method of reducing endometriosis-associated pain in a female human patient having endometriosis, the method comprising administering to the patient a compound represented by formula (II)

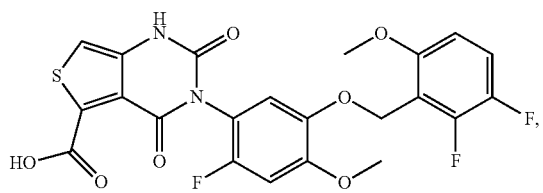

(II)

or a pharmaceutically acceptable salt thereof, in an amount of about 200 mg per day.

2. A method of treating endometriosis in a female human patient in need thereof, the method comprising administering to the patient a compound represented by formula (II)

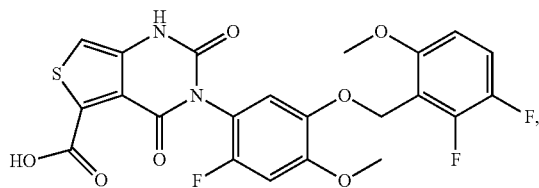

(II)

or a pharmaceutically acceptable salt thereof, in an amount of about 200 mg per day.

3. A method of reducing the concentration of β17-estradiol, follicle-stimulating hormone, and/or luteinizing hormone in a female human patient having endometriosis, the method comprising administering to the patient a compound represented by formula (II)

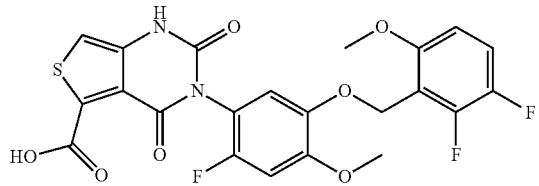

(II)

or a pharmaceutically acceptable salt thereof, in an amount of about 200 mg per day.

4. The method of claim 1, wherein the compound represented by formula (II) is administered to the patient in the form of the choline salt of formula (II).

5. The method of claim 1, wherein the compound is administered to the patient orally.

6. The method of claim 1, wherein the compound is administered to the patient once daily.

7. The method of claim 1, wherein the patient is further administered add-back therapy.

8. The method of claim 7, wherein the add-back therapy is administered to the patient once daily.

9. The method of claim 7, wherein the add-back therapy comprises an estrogen.

10. The method of claim 9, wherein the estrogen is β17-estradiol.

11. The method of claim 10, wherein the β17-estradiol is administered to the patient in an amount of about 1.0 mg per day.

12. The method of claim 7, wherein the add-back therapy comprises a progestin.

13. The method of claim 12, wherein the progestin is norethindrone acetate.

14. The method of claim 13, wherein the norethindrone acetate is administered to the patient in an amount of about 0.5 mg per day.

15. The method of claim 7, wherein the add-back therapy comprises about 1.0 mg of β17-estradiol and about 0.5 mg of norethindrone acetate.

16. The method of claim 15, wherein the add-back therapy is administered to the patient once daily.

17. A kit comprising a compound represented by formula (II)

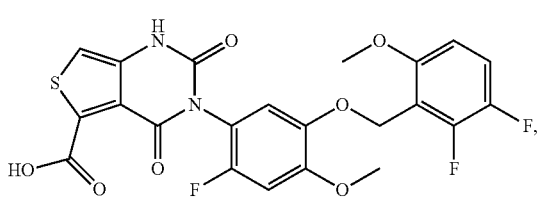

(II)

or a pharmaceutically acceptable salt thereof, in a unit dosage form of about 200 mg, and a package insert instructing a user of the kit to perform the method of claim 1.

18. A kit comprising a compound represented by formula (II)

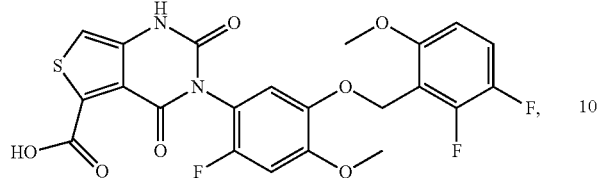

(II)

or a pharmaceutically acceptable salt thereof, in a unit dosage form of about 200 mg, and a package insert instructing a user of the kit to perform the method of claim 2.

19. A kit comprising a compound represented by formula (II)

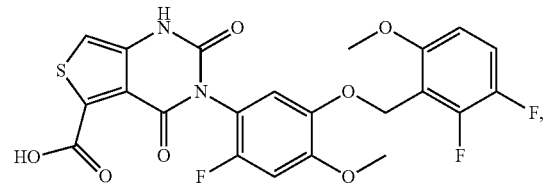

(II)

or a pharmaceutically acceptable salt thereof, in a unit dosage form of about 200 mg, and a package insert instructing a user of the kit to perform the method of claim 3.

20. The kit of claim 17, wherein the compound is present in the kit in the form of the choline salt of formula (II).

* * * * *

UNITED STATES PATENT AND TRADEMARK OFFICE
CERTIFICATE OF CORRECTION

PATENT NO. : 11,980,621 B2
APPLICATION NO. : 16/619776
DATED : May 14, 2024
INVENTOR(S) : Loumaye et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 661 days.

Signed and Sealed this
Sixth Day of May, 2025

Coke Morgan Stewart
*Acting Director of the United States Patent and Trademark Office*